(12) United States Patent
Li et al.

(10) Patent No.: US 12,152,060 B2
(45) Date of Patent: Nov. 26, 2024

(54) INTERLEUKIN-2 VARIANTS AND METHODS OF USES THEREOF

(71) Applicant: Cugene Inc, Waltham, MA (US)

(72) Inventors: Yue-Sheng Li, Thousand Oaks, CA (US); Lingyun Rui, Weston, MA (US); Jing Xu, Waltham, MA (US)

(73) Assignee: Cugene Inc., Waltham, MA (US)

( * ) Notice: Subject to any disclaimer, the term of this patent is extended or adjusted under 35 U.S.C. 154(b) by 0 days.

(21) Appl. No.: 18/224,440

(22) Filed: Jul. 20, 2023

(65) Prior Publication Data

US 2024/0059751 A1  Feb. 22, 2024

Related U.S. Application Data

(63) Continuation of application No. 17/254,098, filed as application No. PCT/US2019/038248 on Jun. 20, 2019.

(60) Provisional application No. 62/755,016, filed on Nov. 2, 2018, provisional application No. 62/689,055, filed on Jun. 22, 2018.

(51) Int. Cl.
*C07K 14/55* (2006.01)
*A61K 38/00* (2006.01)

(52) U.S. Cl.
CPC .............. *C07K 14/55* (2013.01); *A61K 38/00* (2013.01); *C07K 2319/01* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| | | |
|---|---|---|
| 6,955,807 B1 | 10/2005 | Shanafelt et al. |
| 7,112,660 B1 | 9/2006 | Domingues |
| 7,371,371 B2 | 5/2008 | Epstein et al. |
| 7,888,071 B2 | 2/2011 | Gillies et al. |
| 9,580,486 B2 | 2/2017 | Gavin et al. |
| 10,174,092 B1 | 1/2019 | Higginson-Scott et al. |
| 2003/0045474 A1 | 9/2003 | Gilles |
| 2003/0166163 A1* | 9/2003 | Gillies ............ C07K 14/55 435/325 |
| 2006/0269515 A1 | 11/2006 | Dennis-Mize |
| 2014/0294810 A1 | 10/2014 | Lowman |
| 2015/0218260 A1 | 8/2015 | Klein et al. |
| 2017/0044229 A1* | 2/2017 | Garcia ............ A61P 17/06 |
| 2017/0051029 A1 | 2/2017 | Greve |
| 2018/0125941 A1 | 5/2018 | Greve |
| 2019/0241638 A1 | 8/2019 | Bernett |

FOREIGN PATENT DOCUMENTS

| | | |
|---|---|---|
| WO | WO2010045193 | 4/2010 |
| WO | WO2015164815 | 10/2015 |
| WO | 2017220704 | 12/2017 |

OTHER PUBLICATIONS

Skolnick et al (Trends Biotechnol. Jan. 2000;18(1):34-9 (Year: 2000).*
Burgess et al. (J. Cell Biol. 111:2129-2138, 1990) (Year: 1990).*
Miosge (Proc Natl Acad Sci U S A. Sep. 15, 2015;112(37):E5189-98) (Year: 2015).*
Bork (Genome Research, 2000, 10:398-400) (Year: 2000).*
Kulmanov et al (Bioinformatics, 34(4), 2018, 660-668) (Year: 2018).*
Arenas-Ramirez N et al. Interleukin-2: Biology, Design and Application. Trends Immunol, 36(12): 763-777 (2015).
Baluna R et al. Evidence for a structural motif in toxins and interleukin-2 that may be responsible for binding to endothelial cells and initiating vascular leak syndrome. Proc Natl Acad Sci USA 96: 3957-3962 (1999).
Bell CJM et al. Sustained in vivo signaling by long-lived IL-2 induces prolonged increases of regulatory T cells. J Autoimmunity 56: 66-80 (2015).
Hezareh M et al. Effector Function Activities of a Panel of Mutants of a Broadly Neutralizing Antibody against Human Immunodeficiency Virus Type 1. J Virol 75: 12161-8 (2001).
Kosmaczewska A. Low-Dose Interleukin-2 Therapy: A Driver of an Imbalance between Immune Tolerance and Autoimmunity. Int J Mol Sci 15: 18574-18592 (2014).
PCT International Search Report—Written Opinion, Nov. 6, 2019.
Petersona LB et al. A long-lived IL-2 mutein that selectively activates and expands regulatory T cells as a therapy for autoimmune disease. J Autoimmunity 95: 1-14 (2018).

(Continued)

*Primary Examiner* — Brian Gangle
*Assistant Examiner* — Andrea K McCollum
(74) *Attorney, Agent, or Firm* — Craig A Crandall, APC; Craig A Crandall

(57) ABSTRACT

The present invention relates to polypeptides which share primary sequence with human Interleukin 2 (IL-2), except for several amino acids that have been mutated. One panel of IL-2 variants comprise mutations with impressive manufacturability that preferentially promotes the proliferation, survival, activation and/or function of immunosuppressive regulatory T cells (Tregs) (Treg: CD4+CD25+FoxP3+) over effector T cells and Natural Killer Cells (NK). cells. Also includes therapeutic uses of such IL-2 selective agent, used alone, or in combination with immune modulating agents or disease-tissue targeting antibody, protein or peptide to treat Treg cell-deficiency, various autoimmune and inflammatory disorders, organ transplantation and graft-versus-host disease. In another aspect the present invention relates to pharmaceutical compositions comprising the polypeptides disclosed. Finally, the present invention relates to the therapeutic use of the polypeptides and pharmaceutical compositions disclosed due to their selective modulating effect of the immune system on diseases like autoimmune and inflammatory disorders.

6 Claims, 33 Drawing Sheets

Specification includes a Sequence Listing.

(56) References Cited

OTHER PUBLICATIONS

Shanafelt AB et al. A T-cell-selective interleukin 2 mutein exhibits potent antitumor activity and is well tolerated in vivo. Nat Biotechnol 18(11):1197-202 (2000).
Shields RL et al. High resolution mapping of the binding site on human IgG1 for Fc gamma RI, Fc gamma RII, Fc gamma RIII, and FcRn and design of IgG1 variants with improved binding to the Fc gamma R. J Biol Chem 276(9):6591-604 (2001).
Spangler JB et al. Insights into Cytokine-Receptor Interactions from Cytokine Engineering. Annu Rev Immunol 33:139-167 (2015).
Wang X et al. Structure of the Quaternary Complex of Interleukin-2 with Its α, β, and γc Receptors. Science 310:1159-1163 (2005).
Bork, Genome Research, 10:398-400, 2000.
Burgess et al., J. Cell Biol, 11:2129-2138, 1990.
Fenton, Rheostat positions: A new classification of protein positions relevant to pharmacogenomics, Medicinal Chemistry Research, 29:1133-1146, 2000.
Guo, Protein tolerance to random amino acid change, PNAS, 101(25):9205-9210, 2004.
Kulmanov et al, Bioinformatics, 34(4):660-668, 2018.
Miosge, PNAS, 112(37):5189-5198, 2015.
Skolnick et al, Trends Biotechnol., 18(1):34-39, 2000.
Skrombolas et al., Expert Rev Clin Immunol., 10(2):207-217, 2014.

\* cited by examiner

FIG. 1A
P-0250
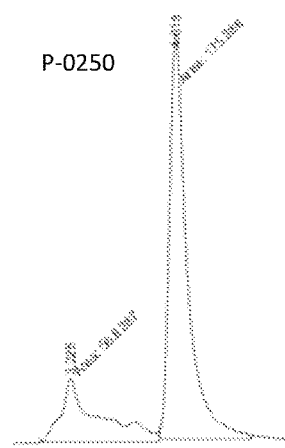
FIG. 1B
P-0318
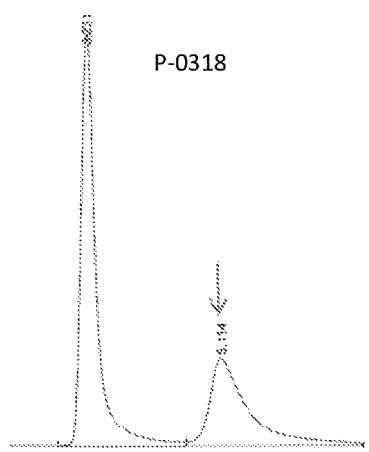
FIG. 1C
P-0317
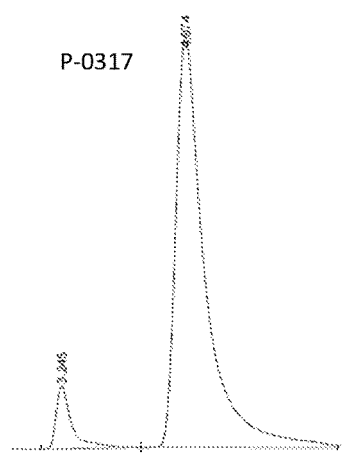
FIGS. 1A-1C

FIG. 1D
FIG. 1E
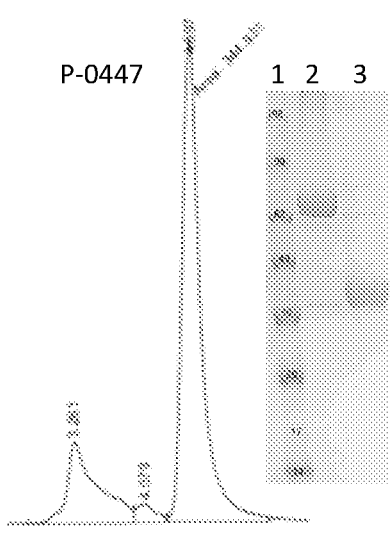
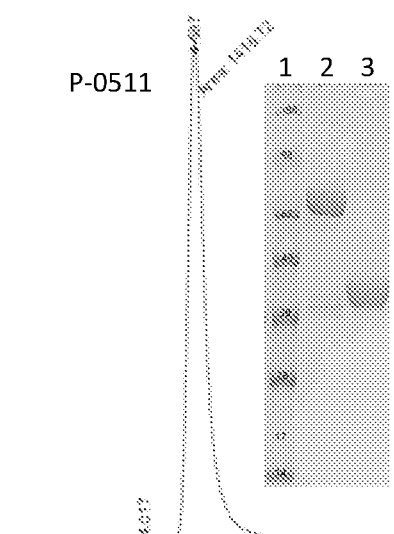
FIGS. 1D-1E

FIG. 2A
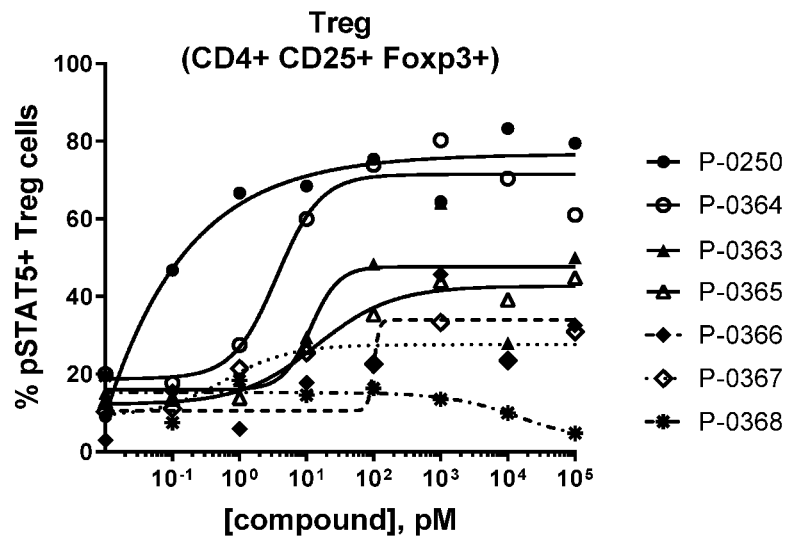
FIG. 2B
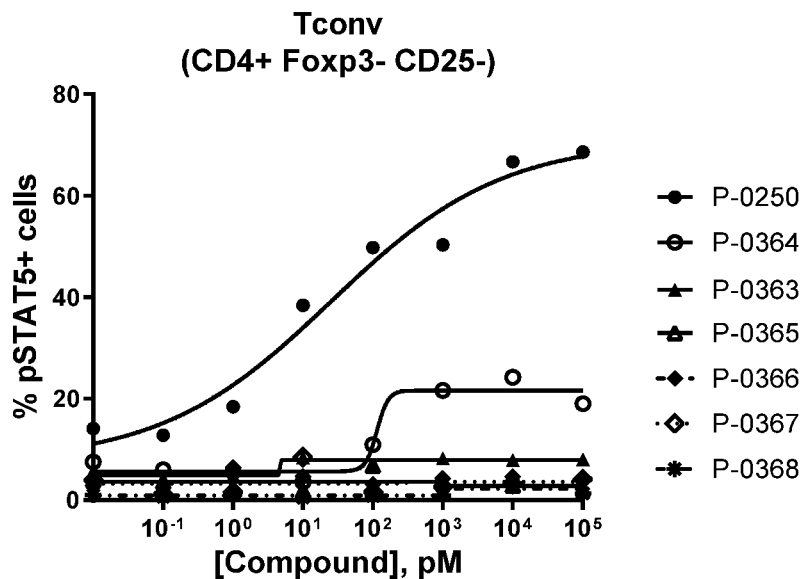
FIGS. 2A-2B

FIG. 3A
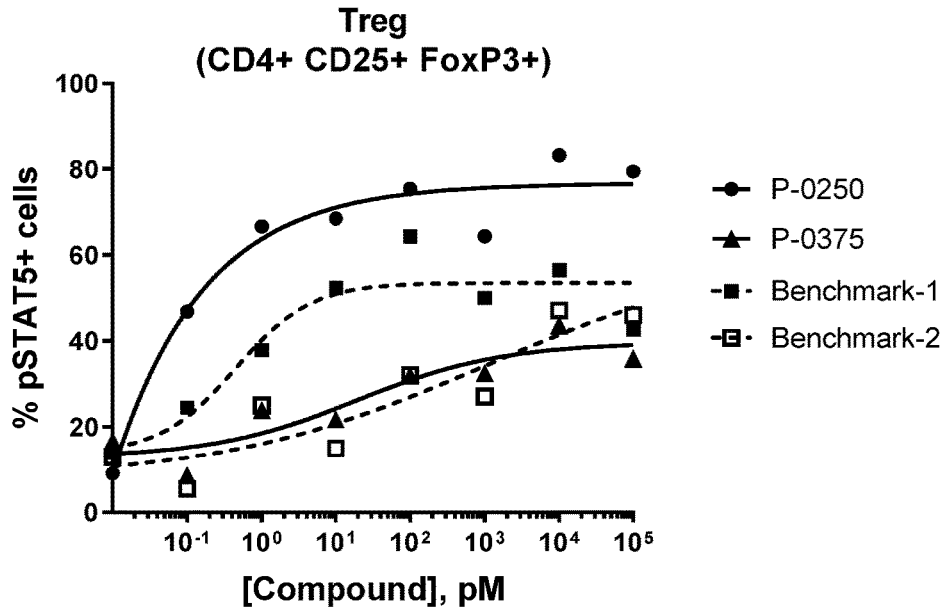
FIG. 3B
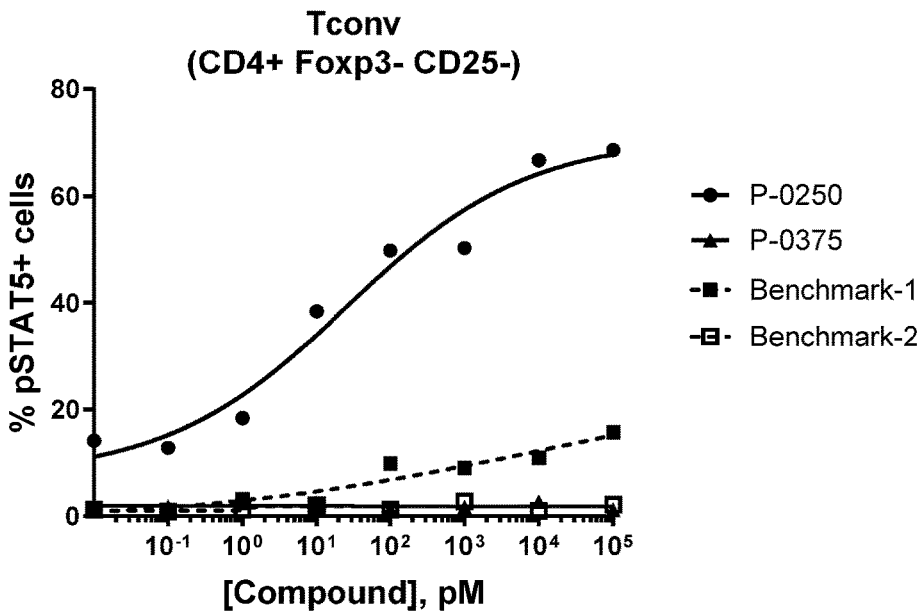
FIGS. 3A-3B

FIG. 4A
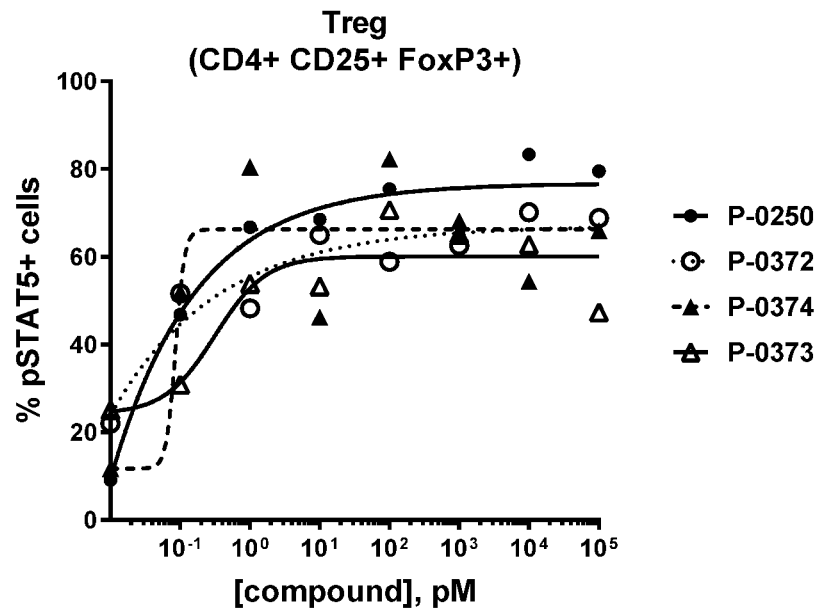
FIG. 4B
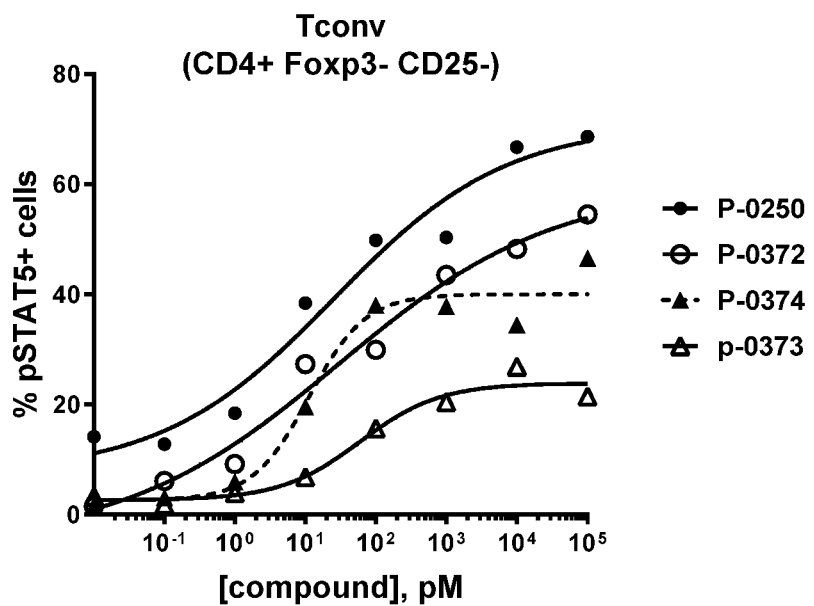
FIGS. 4A-4B

FIG. 4C
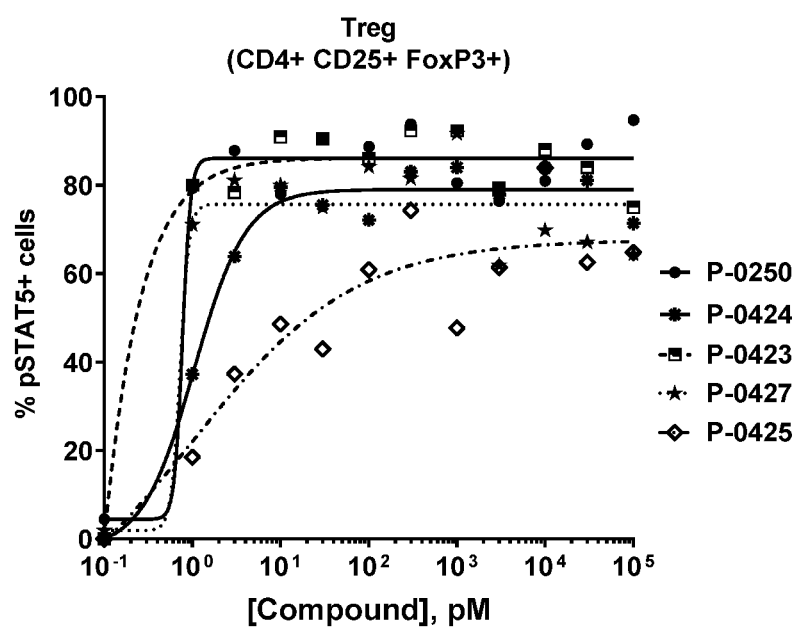
FIG. 4D
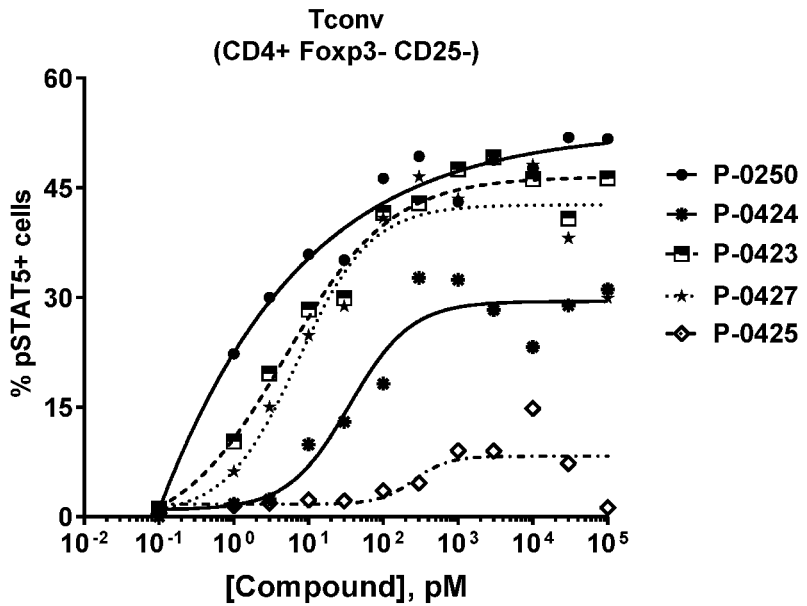
FIGS. 4C-4D

FIG. 5A
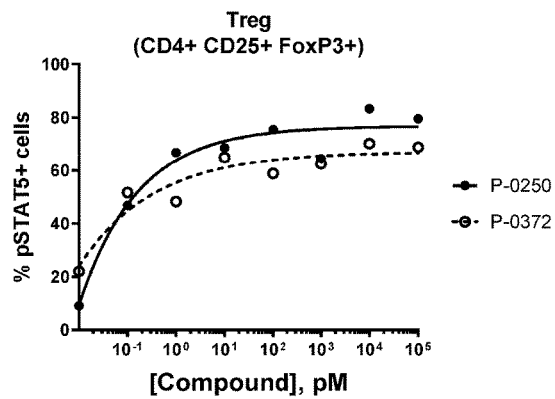
FIG. 5B
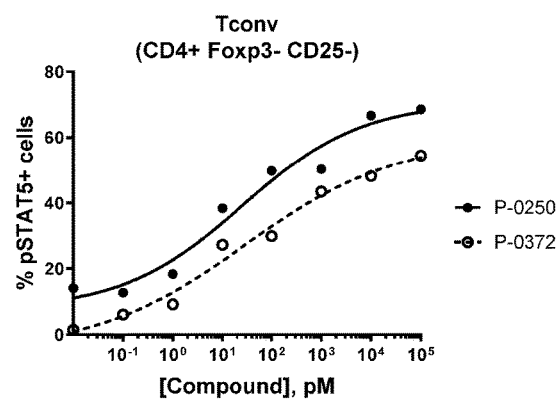
FIG. 5C
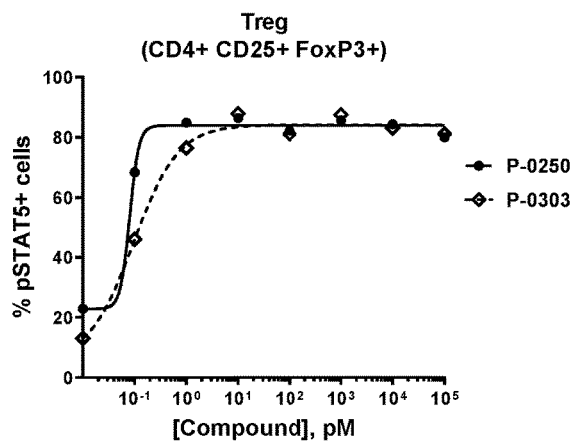
FIG. 5D
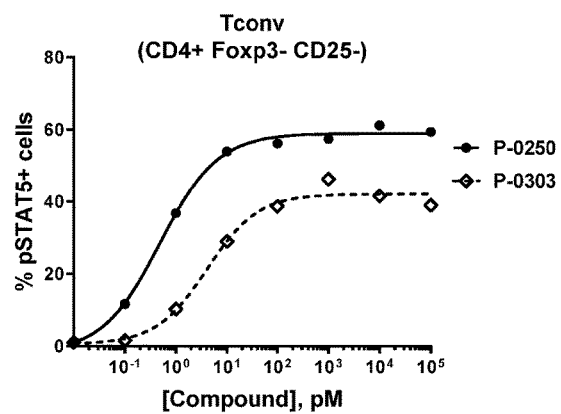
FIGS. 5A-5D FIG. 5E
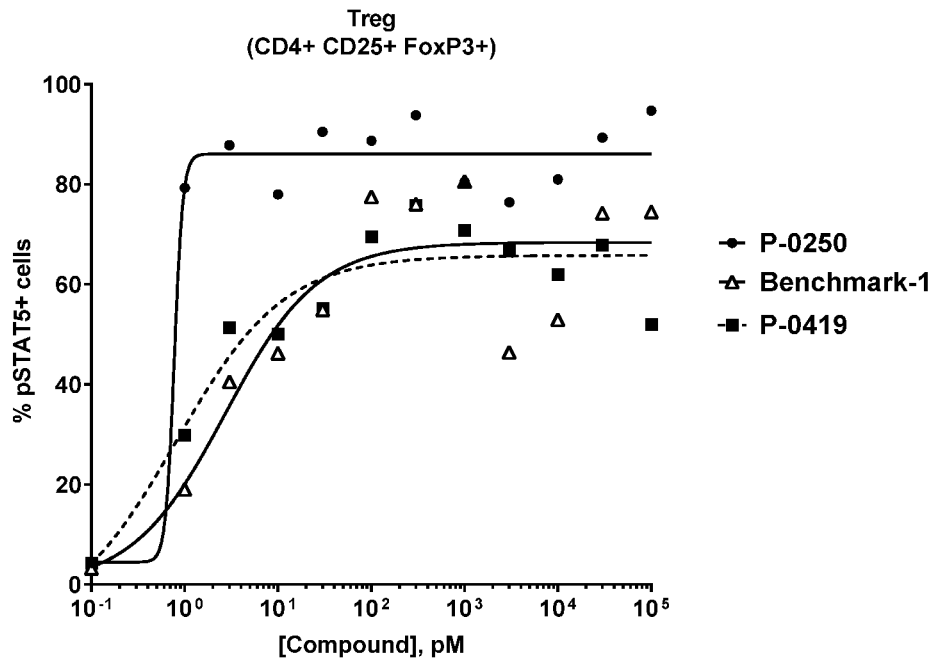
FIG. 5F
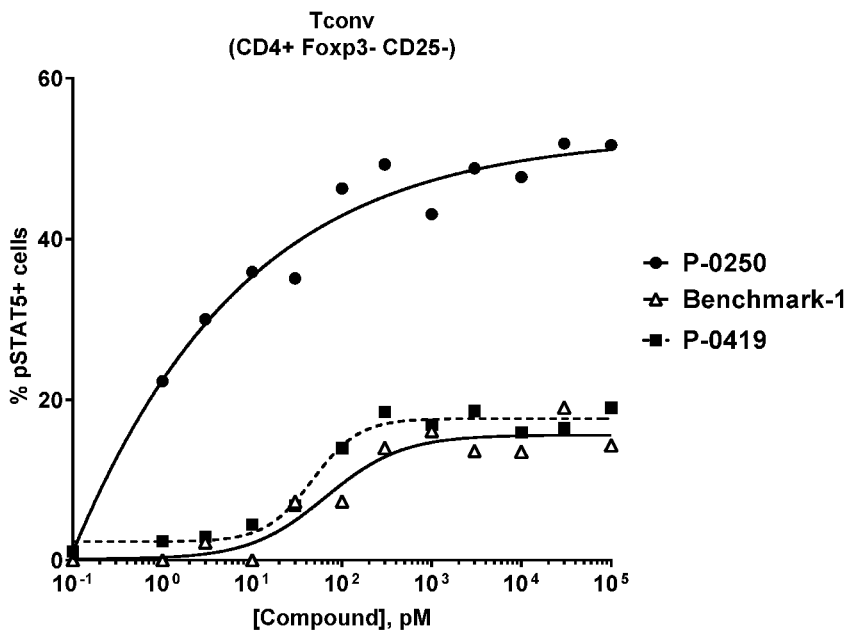
FIGS. 5E-5F FIG. 6A
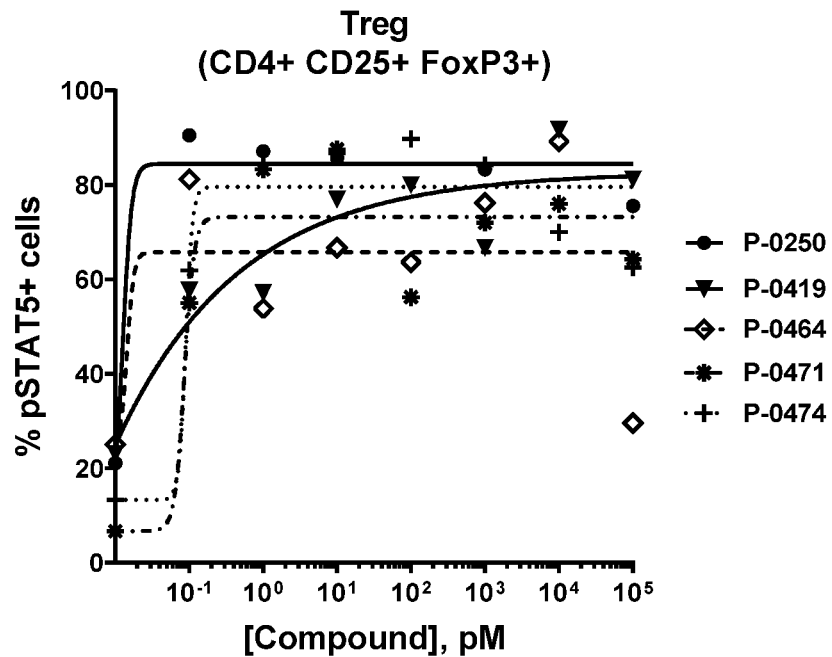
FIG. 6B
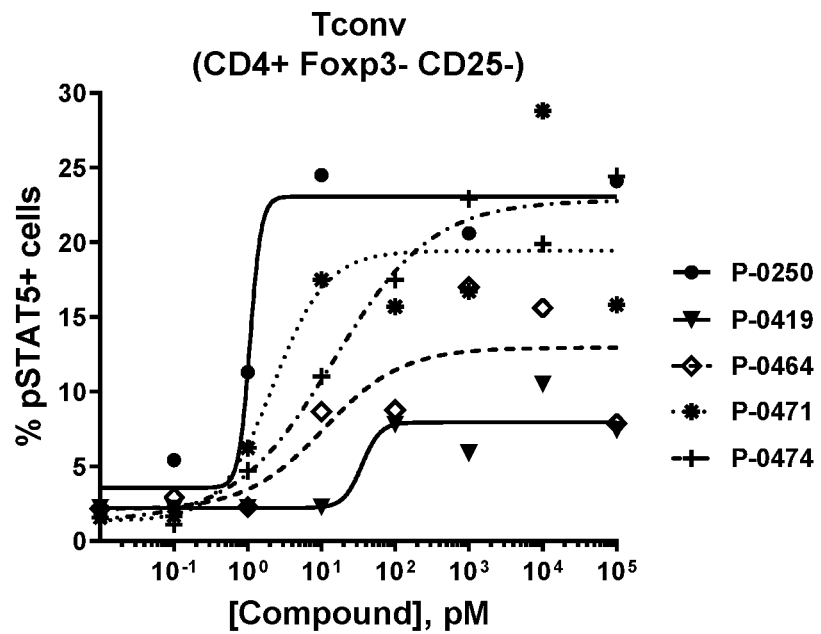
FIGS. 6A-6B FIG. 6C
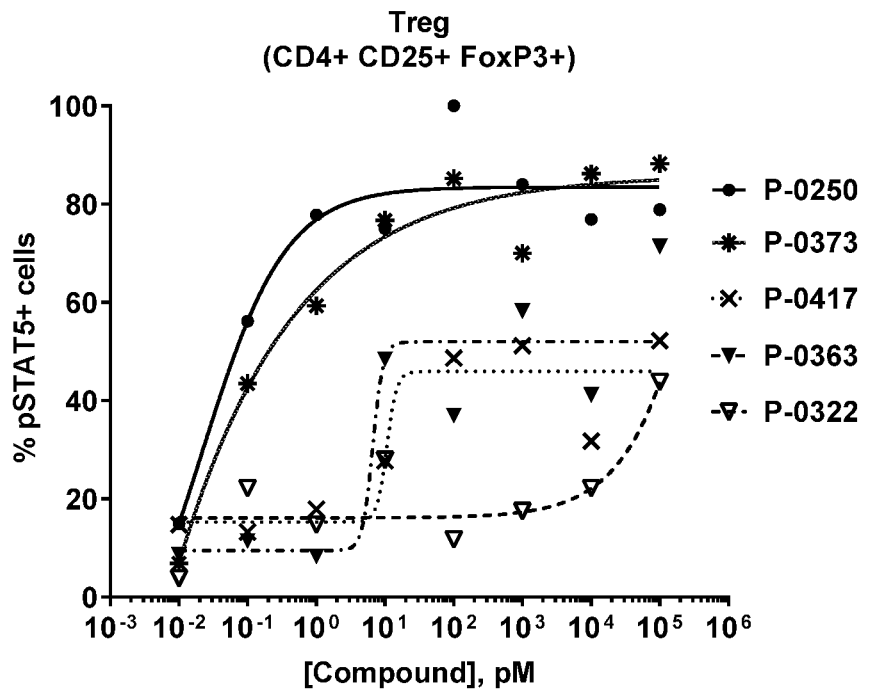
FIG. 6D
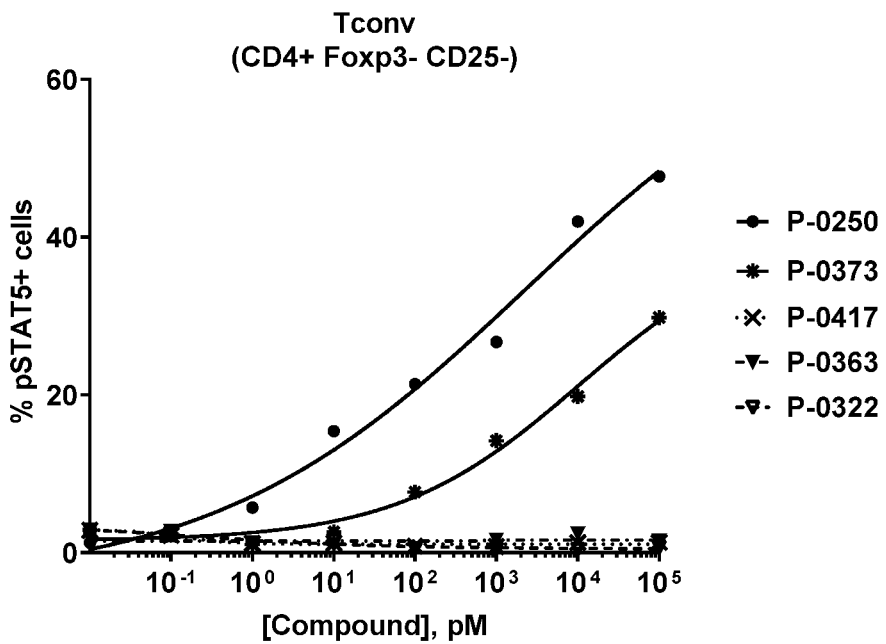
FIGS. 6C-6D

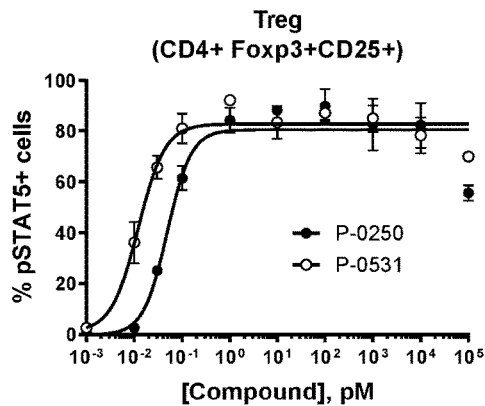
FIG. 8A
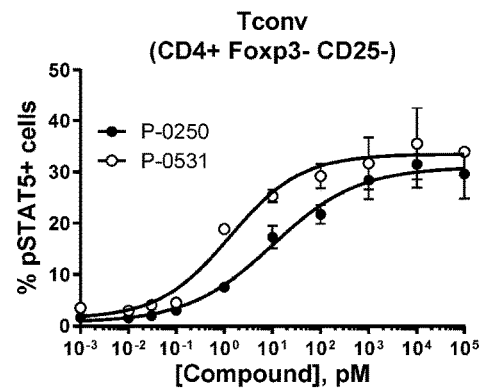
FIG. 8B
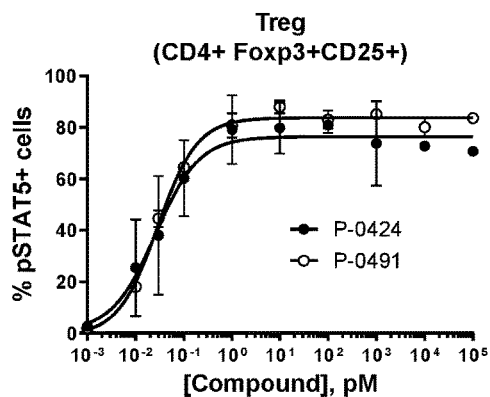
FIG. 8C
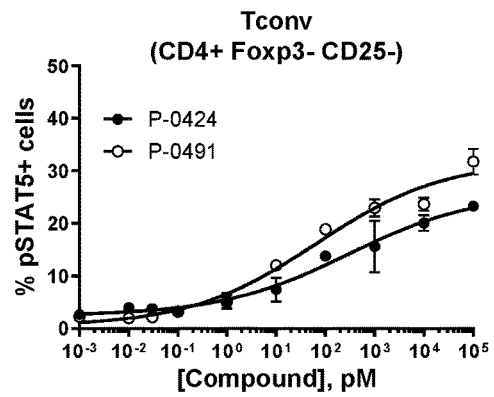
FIG. 8D
FIGS. 8A-8D FIG. 8E
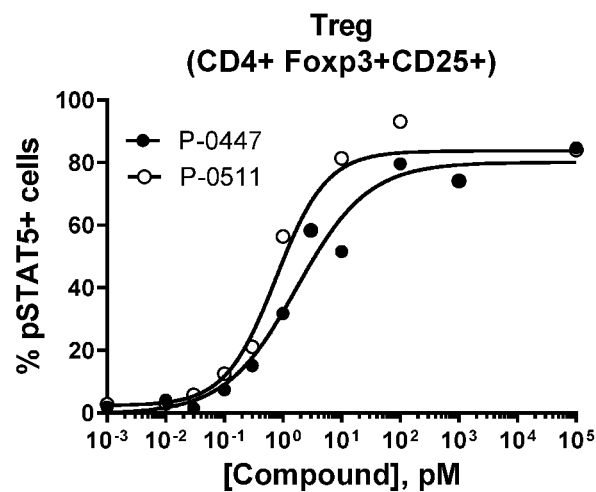
FIG. 8F
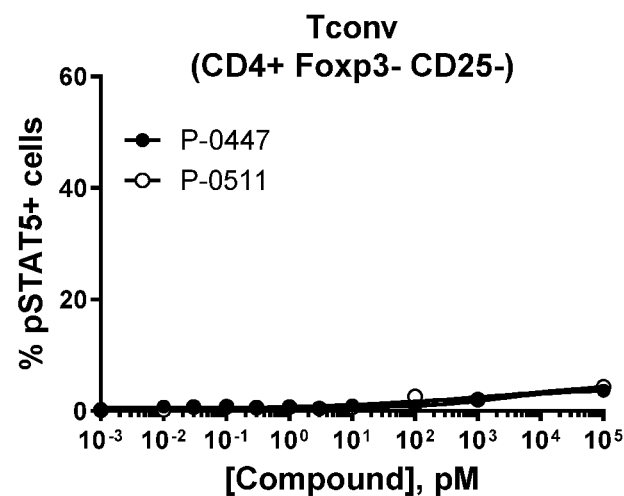
FIGS. 8E-8F FIG. 9A
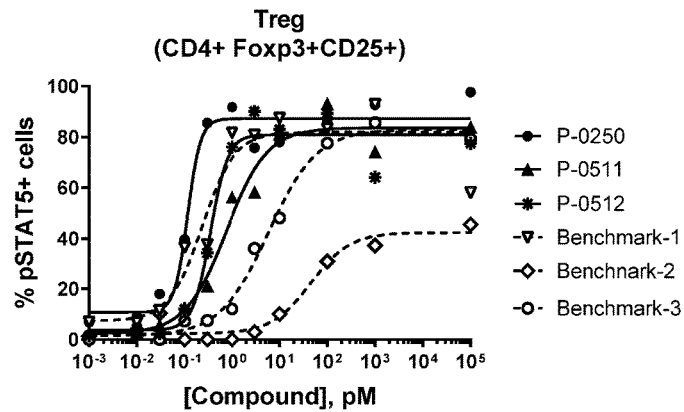
FIG. 9B
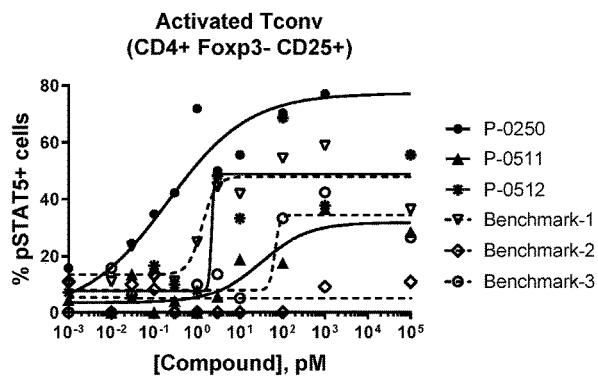
FIG. 9C
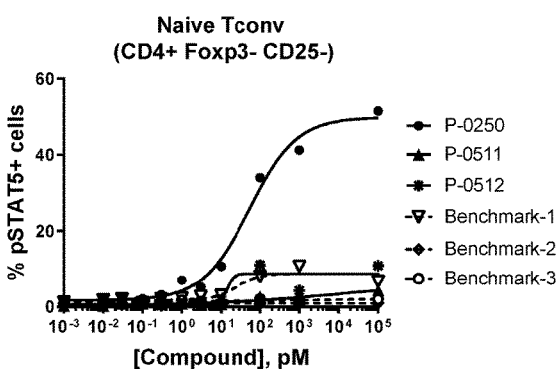
FIGS. 9A-9C FIG. 10A
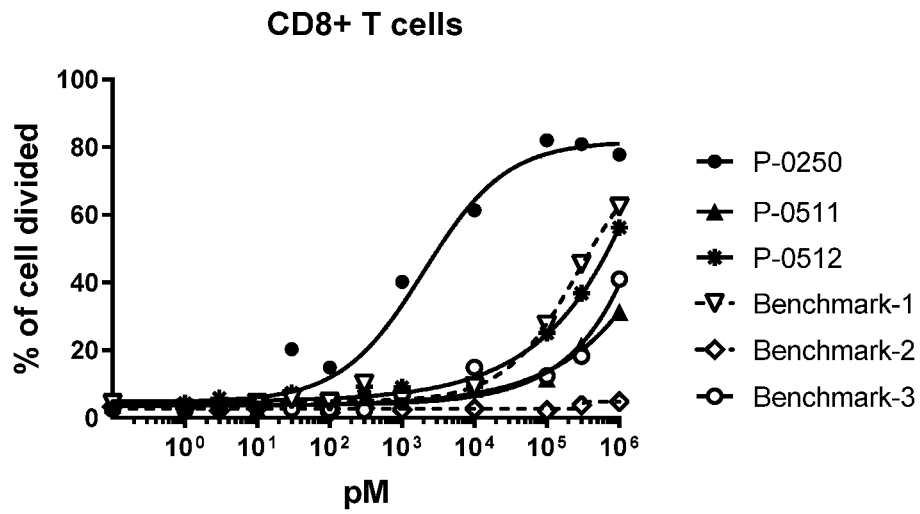
FIG. 10B
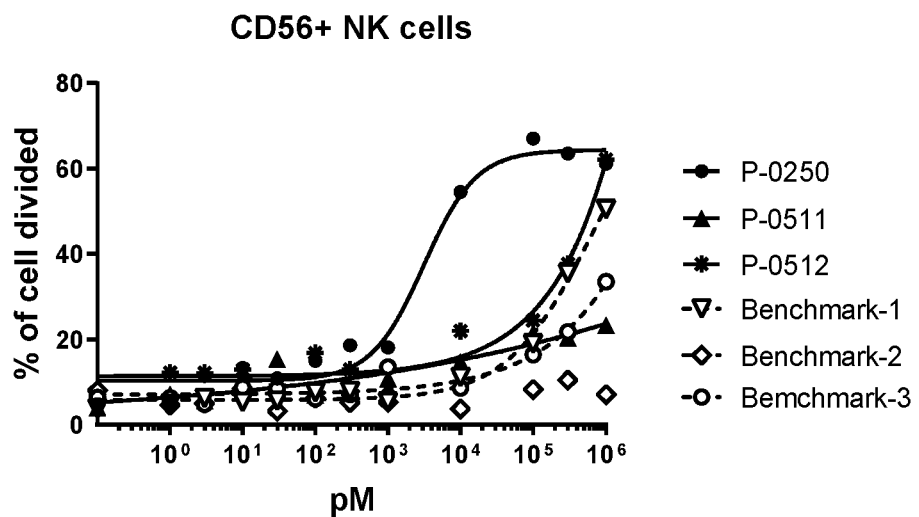
FIGS. 10A-10B FIG. 11A
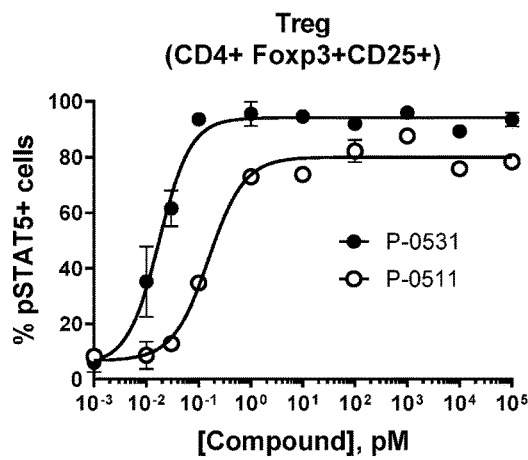
FIG. 11B
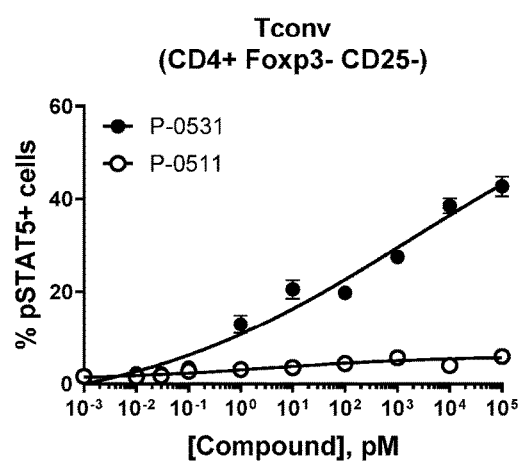
FIG. 11C
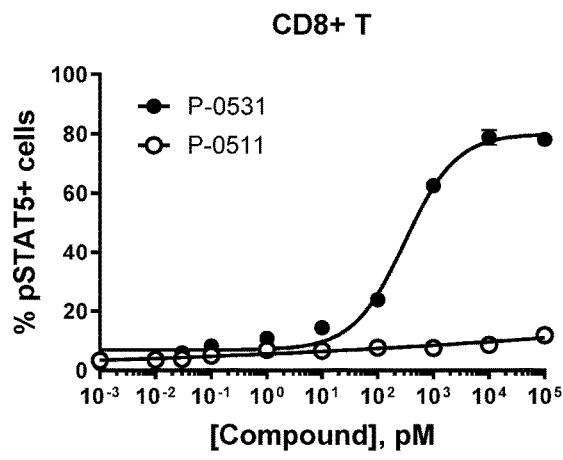
FIG. 11D
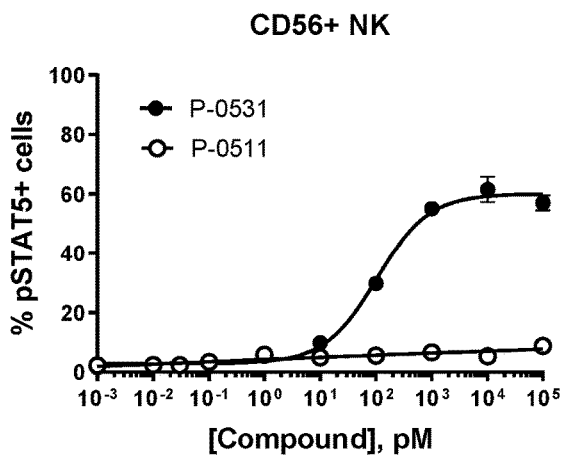
FIGS. 11A-11D FIG. 12A
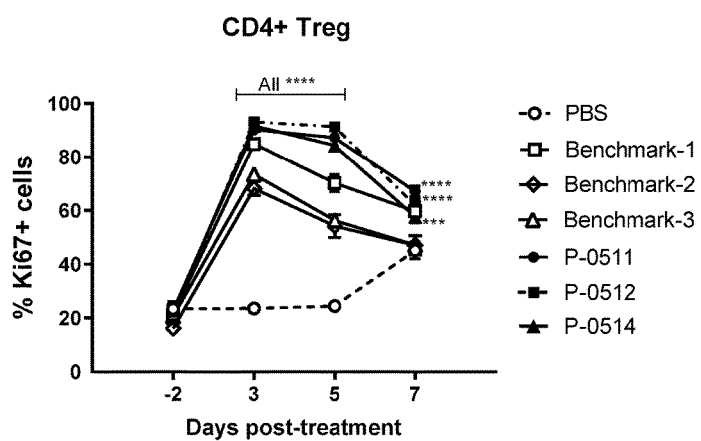
FIG. 12B
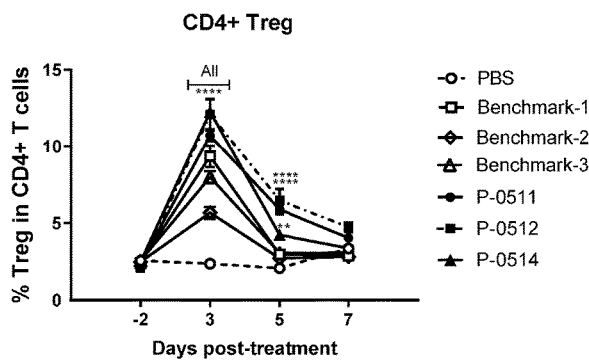
FIG. 12C
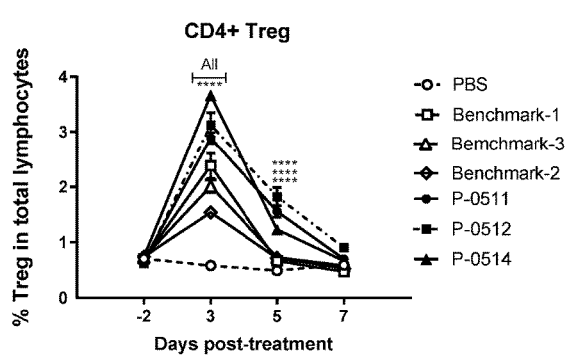
FIGS. 12A-12C FIG. 13A
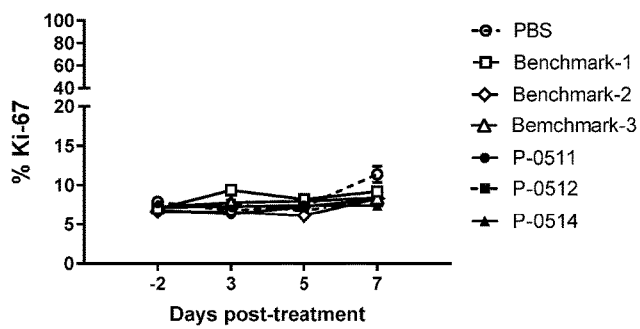
FIG. 13B
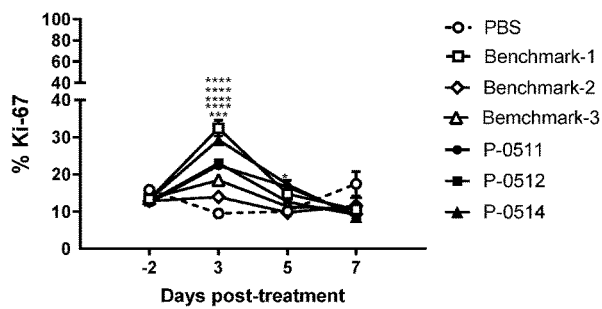
FIG. 13C
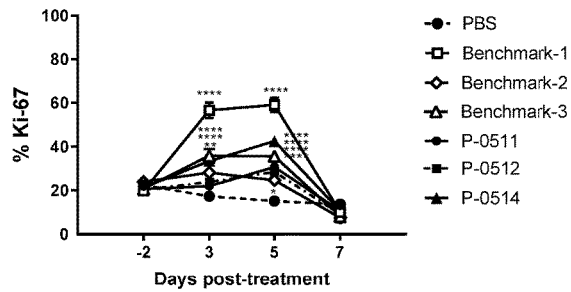
FIGS. 13A-13C

FIG. 15A
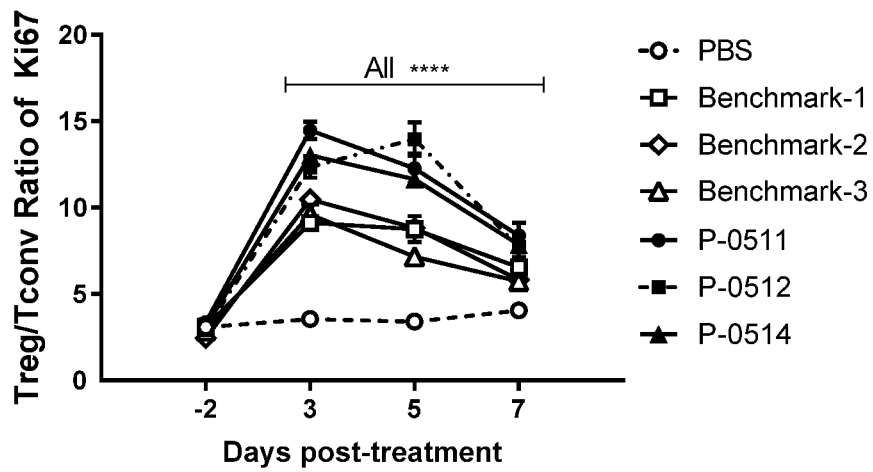
FIG. 15B
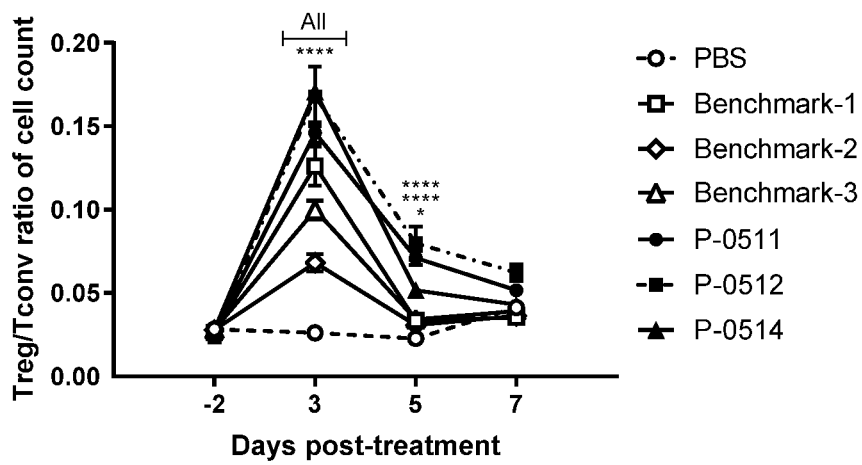
FIGS. 15A-15B

FIG. 16A
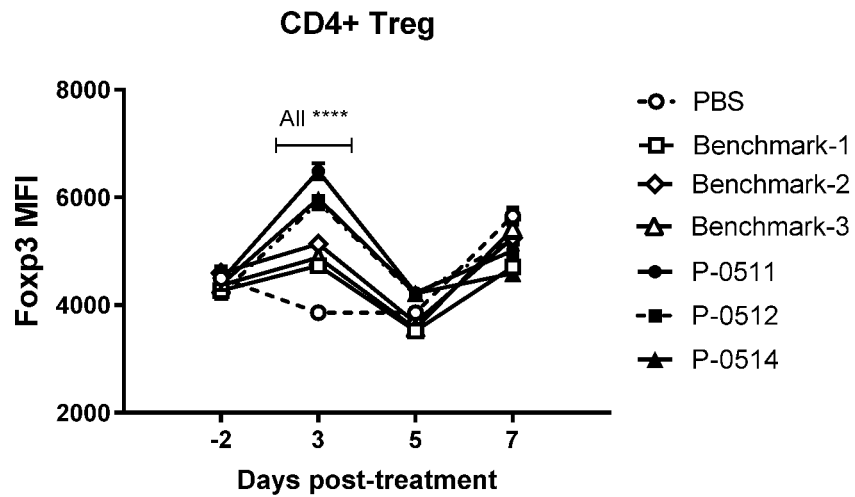
FIG. 16B
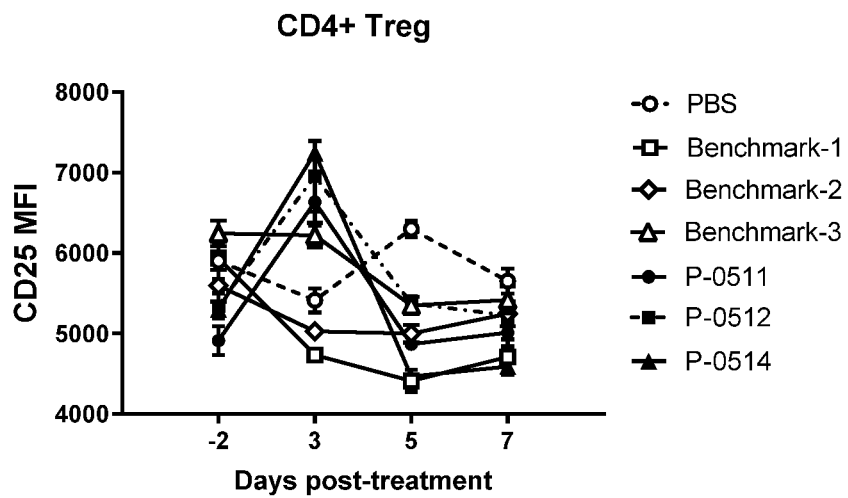
FIGS. 16A-16B

FIG. 17A
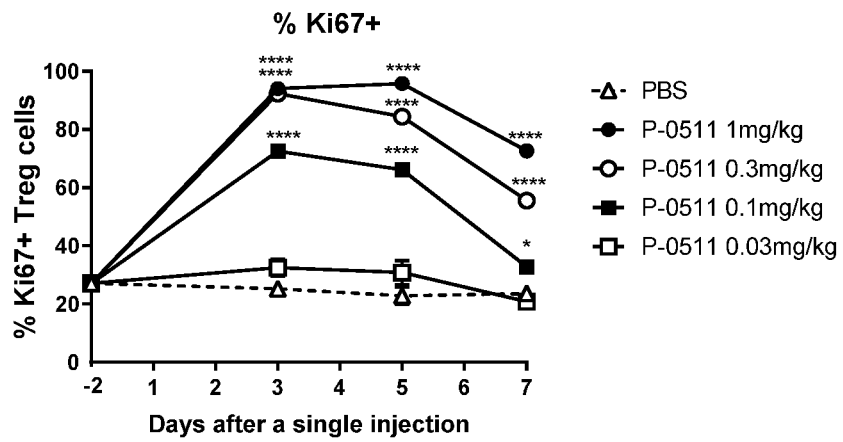
FIG. 17B
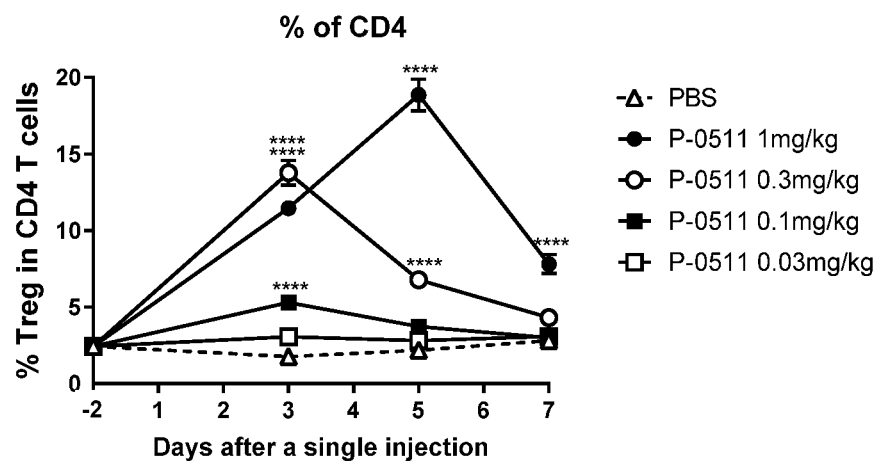
FIGS. 17A-17B

FIG. 17C
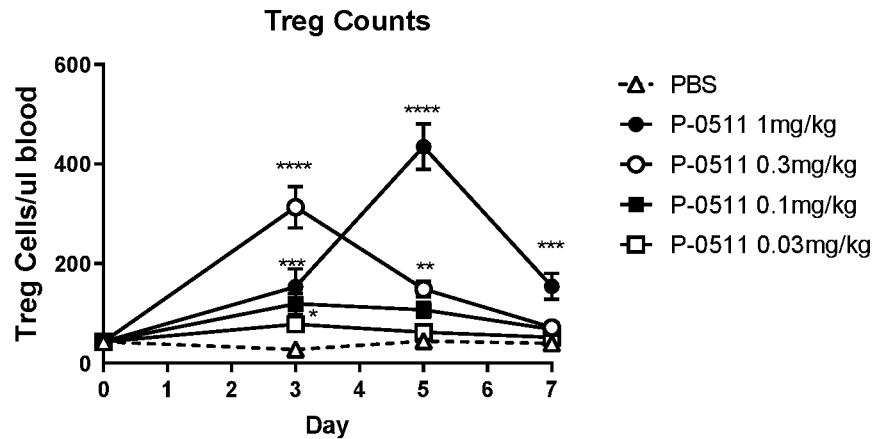
FIG. 17D
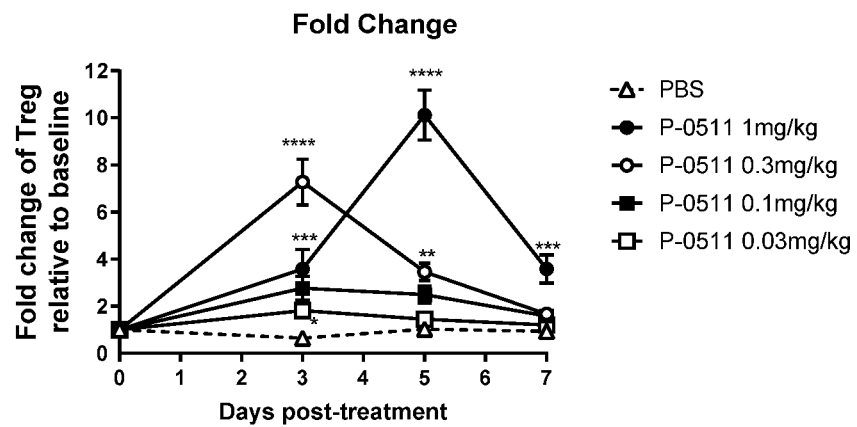
FIGS. 17C-17D

FIG. 18A
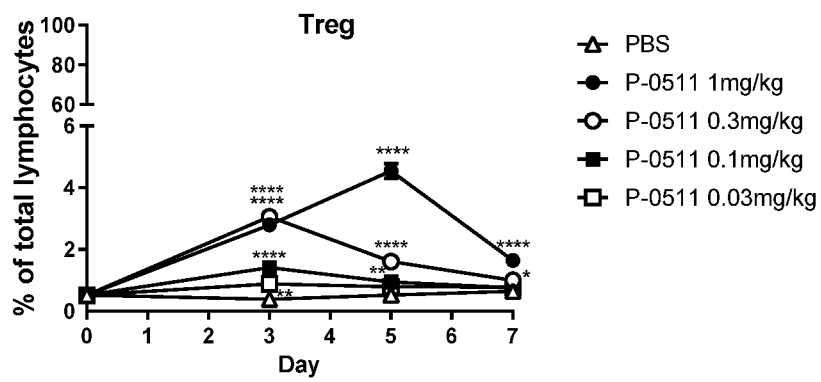
FIG. 18B
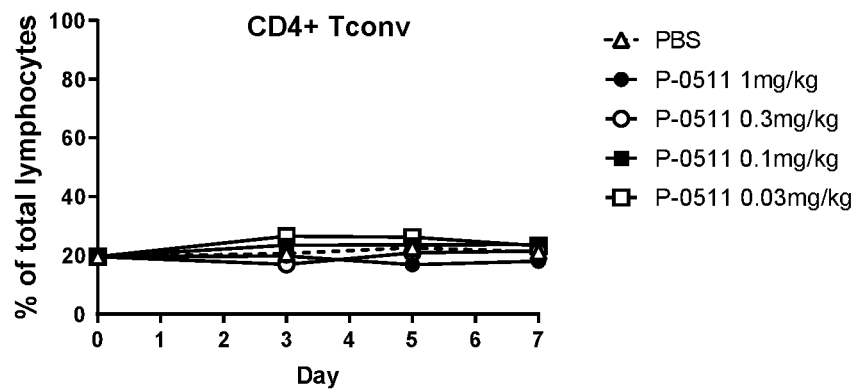
FIGS. 18A-18B

FIG. 18C
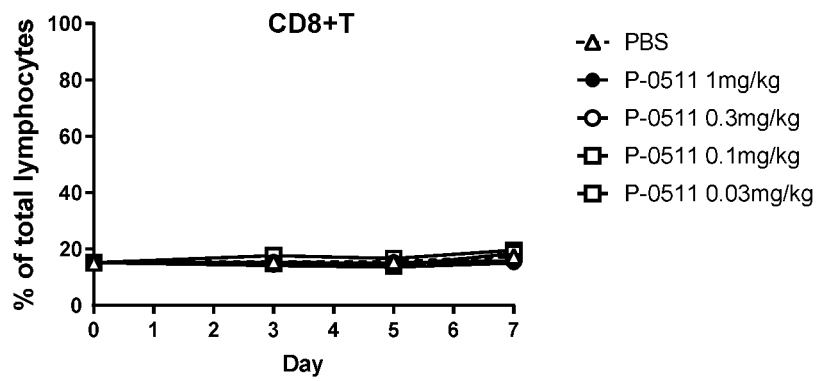
FIG. 18D
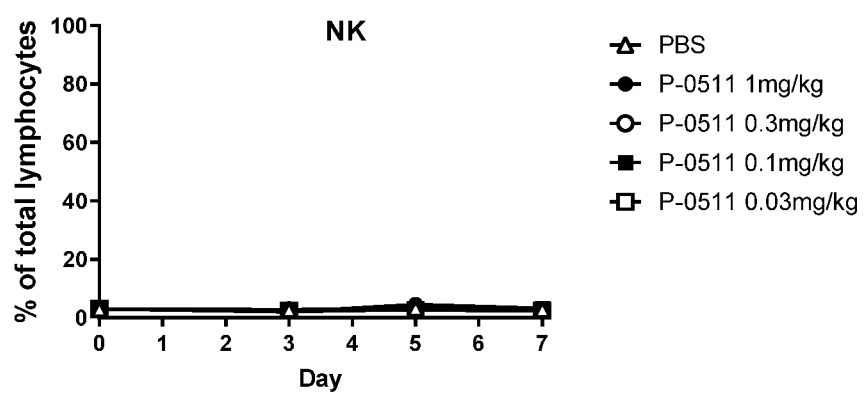
FIGS. 18C-18D

FIG. 19B
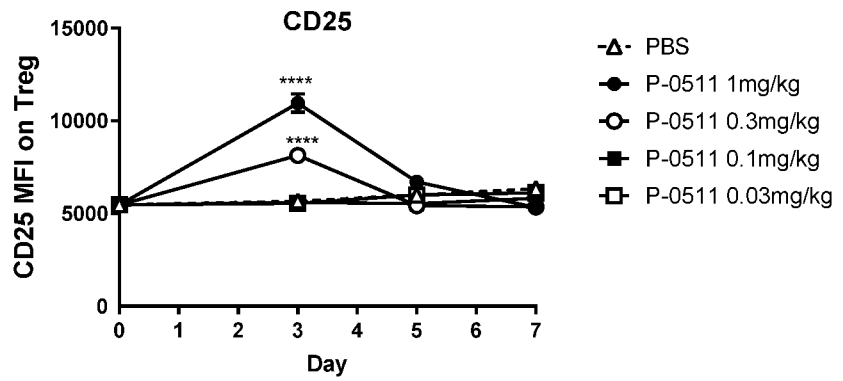
FIG. 19C
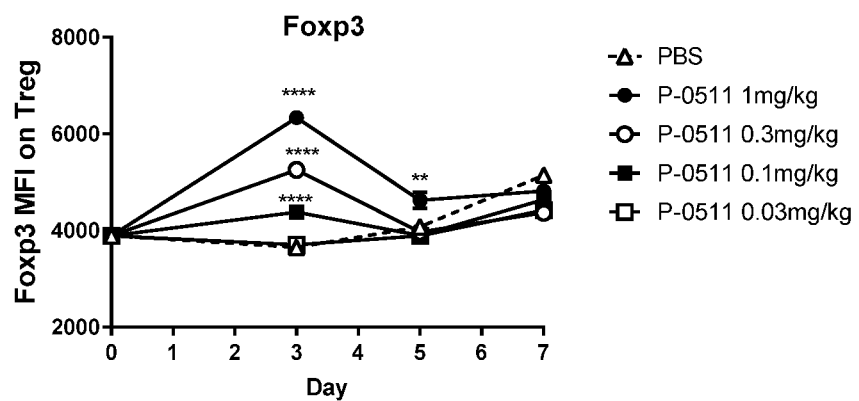
FIGS. 19B-19C

FIG. 20A
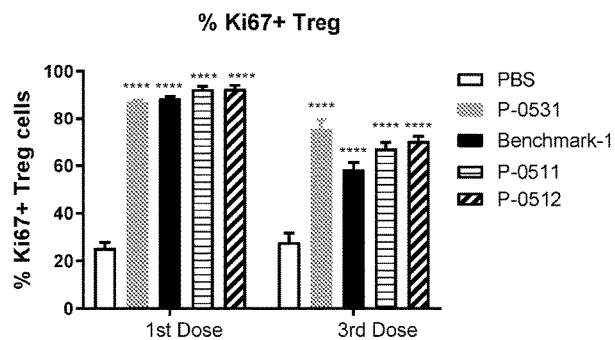
FIG. 20B
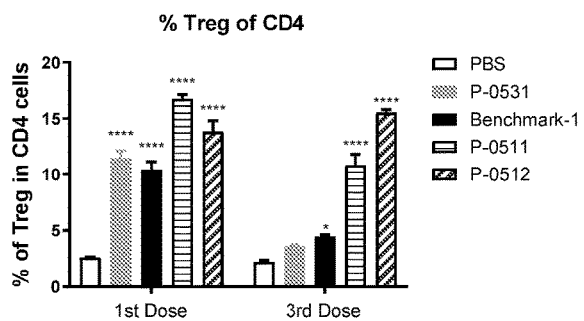
FIG. 20C
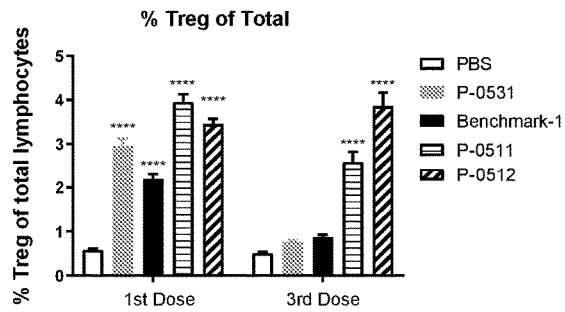
FIGS. 20A-20C FIG. 21A
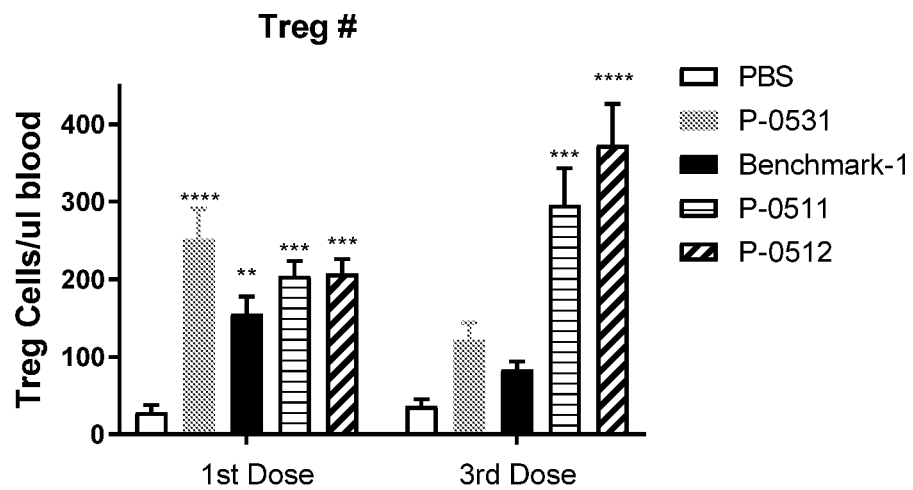
FIG. 21B
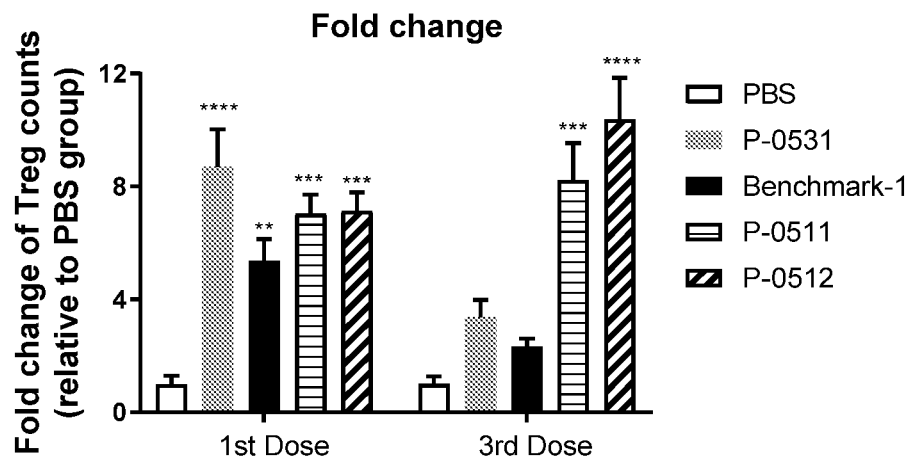
FIGS. 21A-21B FIG. 23A
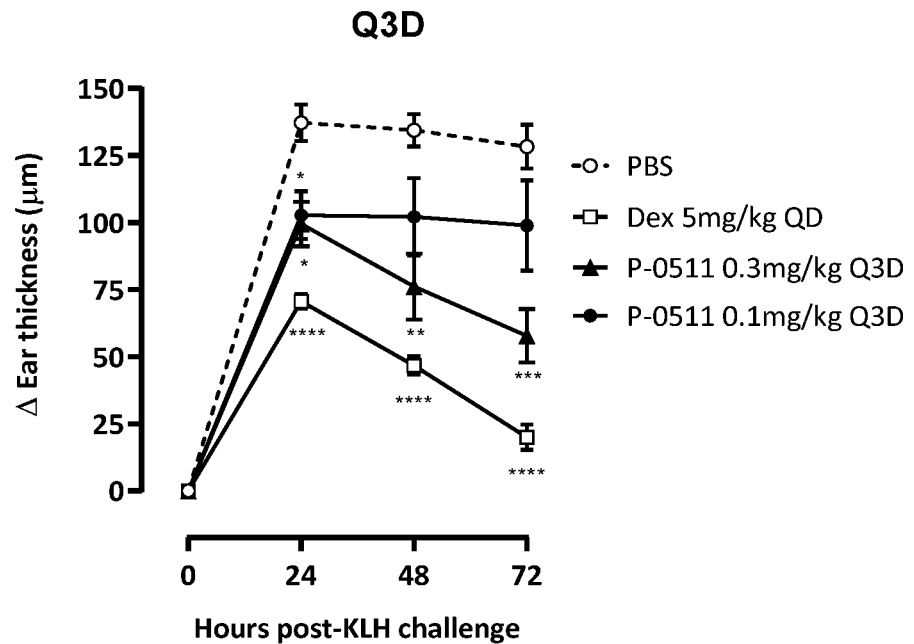
FIG. 23B
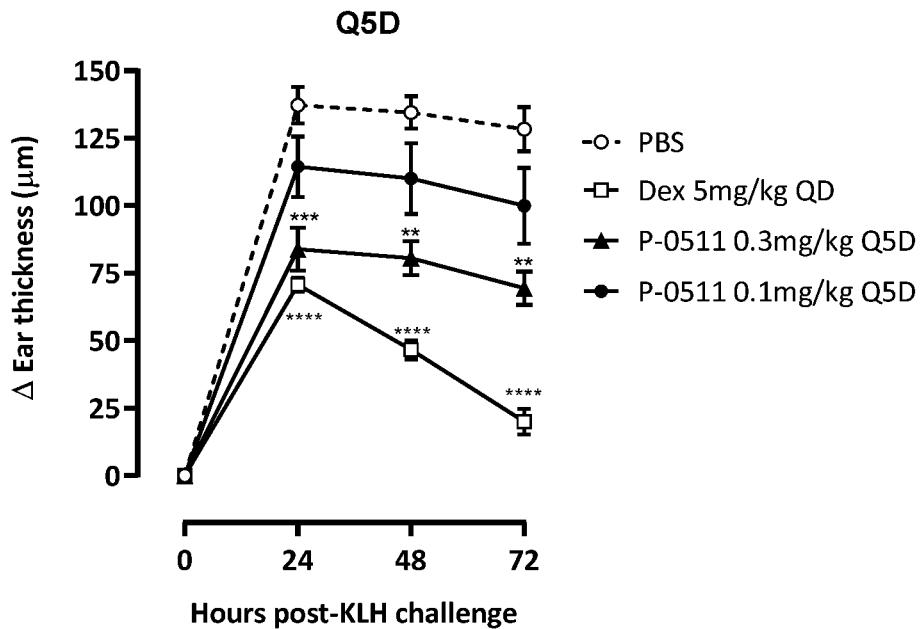
FIGS. 23A-23B

SEQUENCE LISTING

```
Sequence total quantity: 222
SEQ ID NO: 1                moltype = AA  length = 153
FEATURE                     Location/Qualifiers
source                      1..153
                            mol_type = protein
                            organism = Homo sapiens
SEQUENCE: 1
MYRMQLLSCI ALSLALVTNS APTSSSTKKT QLQLEHLLLD LQMILNGINN YKNPKLTRML  60
TFKFYMPKKA TELKHLQCLE EELKPLEEVL NLAQSKNFHL RPRDLISNIN VIVLELKGSE 120
TTFMCEYADE TATIVEFLNR WITFCQSIIS TLT                              153

SEQ ID NO: 2                moltype = AA  length = 133
FEATURE                     Location/Qualifiers
source                      1..133
                            mol_type = protein
                            organism = Homo sapiens
SEQUENCE: 2
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR 120
WITFCQSIIS TLT                                                    133

SEQ ID NO: 3                moltype = AA  length = 133
FEATURE                     Location/Qualifiers
source                      1..133
                            mol_type = protein
                            organism = Homo sapiens
SEQUENCE: 3
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR 120
WITFSQSIIS TLT                                                    133

SEQ ID NO: 4                moltype = AA  length = 133
FEATURE                     Location/Qualifiers
REGION                      1..133
                            note = IL-2 N88R variant sequence
source                      1..133
                            mol_type = protein
                            organism = synthetic construct
SEQUENCE: 4
APTSSSTKKT QLQLEHLLLD LQMILNGINN YKNPKLTRML TFKFYMPKKA TELKHLQCLE  60
EELKPLEEVL NLAQSKNFHL RPRDLISRIN VIVLELKGSE TTFMCEYADE TATIVEFLNR 120
WITFSQSIIS TLT                                                    133

SEQ ID NO: 5                moltype = AA  length = 133
FEATURE                     Location/Qualifiers
REGION                      1..133
                            note = IL-2 D20T variant sequence
source                      1..133
                            mol_type = protein
                            organism = synthetic construct
SEQUENCE: 5
APTSSSTKKT QLQLEHLLLT LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR 120
WITFSQSIIS TLT                                                    133

SEQ ID NO: 6                moltype = AA  length = 133
FEATURE                     Location/Qualifiers
REGION                      1..133
                            note = IL-2 D20E variant sequence
source                      1..133
                            mol_type = protein
                            organism = synthetic construct
SEQUENCE: 6
APTSSSTKKT QLQLEHLLLE LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR 120
WITFSQSIIS TLT                                                    133

SEQ ID NO: 7                moltype = AA  length = 133
FEATURE                     Location/Qualifiers
REGION                      1..133
                            note = IL-2 D20N variant sequence
source                      1..133
                            mol_type = protein
                            organism = synthetic construct
SEQUENCE: 7
APTSSSTKKT QLQLEHLLLN LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR 120
WITFSQSIIS TLT                                                    133
```

```
SEQ ID NO: 8              moltype = AA  length = 133
FEATURE                   Location/Qualifiers
REGION                    1..133
                          note = IL-2 D20Q variant sequence
source                    1..133
                          mol_type = protein
                          organism = synthetic construct
SEQUENCE: 8
APTSSSTKKT QLQLEHLLLQ LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFSQSIIS TLT                                                     133

SEQ ID NO: 9              moltype = AA  length = 133
FEATURE                   Location/Qualifiers
REGION                    1..133
                          note = IL-2 D20S variant sequence
source                    1..133
                          mol_type = protein
                          organism = synthetic construct
SEQUENCE: 9
APTSSSTKKT QLQLEHLLLS LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFSQSIIS TLT                                                     133

SEQ ID NO: 10             moltype = AA  length = 133
FEATURE                   Location/Qualifiers
REGION                    1..133
                          note = IL-2 D20Y variant sequence
source                    1..133
                          mol_type = protein
                          organism = synthetic construct
SEQUENCE: 10
APTSSSTKKT QLQLEHLLLY LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFSQSIIS TLT                                                     133

SEQ ID NO: 11             moltype = AA  length = 133
FEATURE                   Location/Qualifiers
REGION                    1..133
                          note = IL-2 D20I variant sequence
source                    1..133
                          mol_type = protein
                          organism = synthetic construct
SEQUENCE: 11
APTSSSTKKT QLQLEHLLLI LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFSQSIIS TLT                                                     133

SEQ ID NO: 12             moltype = AA  length = 133
FEATURE                   Location/Qualifiers
REGION                    1..133
                          note = IL-2 L19Y variant sequence
source                    1..133
                          mol_type = protein
                          organism = synthetic construct
SEQUENCE: 12
APTSSSTKKT QLQLEHLLYD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFSQSIIS TLT                                                     133

SEQ ID NO: 13             moltype = AA  length = 133
FEATURE                   Location/Qualifiers
REGION                    1..133
                          note = IL-2 L19N variant sequence
source                    1..133
                          mol_type = protein
                          organism = synthetic construct
SEQUENCE: 13
APTSSSTKKT QLQLEHLLND LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFSQSIIS TLT                                                     133

SEQ ID NO: 14             moltype = AA  length = 133
FEATURE                   Location/Qualifiers
REGION                    1..133
                          note = IL-2 L19R variant sequence
source                    1..133
                          mol_type = protein
```

```
                                organism = synthetic construct
SEQUENCE: 14
APTSSSTKKT QLQLEHLLRD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 15           moltype = AA  length = 133
FEATURE                 Location/Qualifiers
REGION                  1..133
                        note = IL-2 N88G variant sequence
source                  1..133
                        mol_type = protein
                        organism = synthetic construct
SEQUENCE: 15
APTSSSTKKT QLQLEHLLLD LQMILNGINN YKNPKLTRML TFKFYMPKKA TELKHLQCLE    60
EELKPLEEVL NLAQSKNFHL RPRDLISGIN VIVLELKGSE TTFMCEYADE TATIVEFLNR   120
WITFSQSIIS TLT                                                     133

SEQ ID NO: 16           moltype = AA  length = 133
FEATURE                 Location/Qualifiers
REGION                  1..133
                        note = IL-2 N88I variant sequence
source                  1..133
                        mol_type = protein
                        organism = synthetic construct
SEQUENCE: 16
APTSSSTKKT QLQLEHLLLD LQMILNGINN YKNPKLTRML TFKFYMPKKA TELKHLQCLE    60
EELKPLEEVL NLAQSKNFHL RPRDLISIIN VIVLELKGSE TTFMCEYADE TATIVEFLNR   120
WITFSQSIIS TLT                                                     133

SEQ ID NO: 17           moltype = AA  length = 133
FEATURE                 Location/Qualifiers
REGION                  1..133
                        note = IL-2 N88Q variant sequence
source                  1..133
                        mol_type = protein
                        organism = synthetic construct
SEQUENCE: 17
APTSSSTKKT QLQLEHLLLD LQMILNGINN YKNPKLTRML TFKFYMPKKA TELKHLQCLE    60
EELKPLEEVL NLAQSKNFHL RPRDLISQIN VIVLELKGSE TTFMCEYADE TATIVEFLNR   120
WITFSQSIIS TLT                                                     133

SEQ ID NO: 18           moltype = AA  length = 133
FEATURE                 Location/Qualifiers
REGION                  1..133
                        note = IL-2 N88E variant sequence
source                  1..133
                        mol_type = protein
                        organism = synthetic construct
SEQUENCE: 18
APTSSSTKKT QLQLEHLLLD LQMILNGINN YKNPKLTRML TFKFYMPKKA TELKHLQCLE    60
EELKPLEEVL NLAQSKNFHL RPRDLISEIN VIVLELKGSE TTFMCEYADE TATIVEFLNR   120
WITFSQSIIS TLT                                                     133

SEQ ID NO: 19           moltype = AA  length = 133
FEATURE                 Location/Qualifiers
REGION                  1..133
                        note = IL-2 N88T variant sequence
source                  1..133
                        mol_type = protein
                        organism = synthetic construct
SEQUENCE: 19
APTSSSTKKT QLQLEHLLLD LQMILNGINN YKNPKLTRML TFKFYMPKKA TELKHLQCLE    60
EELKPLEEVL NLAQSKNFHL RPRDLISTIN VIVLELKGSE TTFMCEYADE TATIVEFLNR   120
WITFSQSIIS TLT                                                     133

SEQ ID NO: 20           moltype = AA  length = 132
FEATURE                 Location/Qualifiers
REGION                  1..132
                        note = IL-2 N88M variant sequence
source                  1..132
                        mol_type = protein
                        organism = synthetic construct
SEQUENCE: 20
APTSSSTKKT QLQLEHLLLD LQMILNGINN YKNPKLTRML TFKFYMPKKA TELKHLQCLE    60
EELKPLEEVL NLAQSKNFHL RPRDLISMIN VIVLELKGSE TTFMCEYADE TATIVEFLNR   120
WITFSQSIIS TL                                                      132

SEQ ID NO: 21           moltype = AA  length = 133
```

```
FEATURE                 Location/Qualifiers
REGION                  1..133
                        note = IL-2 Q126E variant sequence
source                  1..133
                        mol_type = protein
                        organism = synthetic construct
SEQUENCE: 21
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR 120
WITFSESIIS TLT                                                   133

SEQ ID NO: 22           moltype = AA  length = 133
FEATURE                 Location/Qualifiers
REGION                  1..133
                        note = IL-2 Q126L variant sequence
source                  1..133
                        mol_type = protein
                        organism = synthetic construct
SEQUENCE: 22
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR 120
WITFSLSIIS TLT                                                   133

SEQ ID NO: 23           moltype = AA  length = 133
FEATURE                 Location/Qualifiers
REGION                  1..133
                        note = IL-2 Q126N variant sequence
source                  1..133
                        mol_type = protein
                        organism = synthetic construct
SEQUENCE: 23
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR 120
WITFSNSIIS TLT                                                   133

SEQ ID NO: 24           moltype = AA  length = 133
FEATURE                 Location/Qualifiers
REGION                  1..133
                        note = IL-2 Q126D variant sequence
source                  1..133
                        mol_type = protein
                        organism = synthetic construct
SEQUENCE: 24
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR 120
WITFSDSIIS TLT                                                   133

SEQ ID NO: 25           moltype = AA  length = 133
FEATURE                 Location/Qualifiers
REGION                  1..133
                        note = IL-2 Q126M variant sequence
source                  1..133
                        mol_type = protein
                        organism = synthetic construct
SEQUENCE: 25
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR 120
WITFSMSIIS TLT                                                   133

SEQ ID NO: 26           moltype = AA  length = 133
FEATURE                 Location/Qualifiers
REGION                  1..133
                        note = IL-2 D20I/N88G variant sequence
source                  1..133
                        mol_type = protein
                        organism = synthetic construct
SEQUENCE: 26
APTSSSTKKT QLQLEHLLLI LQMILNGINN YKNPKLTRML TFKFYMPKKA TELKHLQCLE  60
EELKPLEEVL NLAQSKNFHL RPRDLISGIN VIVLELKGSE TTFMCEYADE TATIVEFLNR 120
WITFSQSIIS TLT                                                   133

SEQ ID NO: 27           moltype = AA  length = 133
FEATURE                 Location/Qualifiers
REGION                  1..133
                        note = IL-2 D20I/N88R variant sequence
source                  1..133
                        mol_type = protein
                        organism = synthetic construct
SEQUENCE: 27
```

APTSSSTKKT QLQLEHLLLI LQMILNGINN YKNPKLTRML TFKFYMPKKA TELKHLQCLE  60
EELKPLEEVL NLAQSKNFHL RPRDLISRIN VIVLELKGSE TTFMCEYADE TATIVEFLNR 120
WITFSQSIIS TLT                                                   133

SEQ ID NO: 28           moltype = AA   length = 133
FEATURE                 Location/Qualifiers
REGION                  1..133
                        note = IL-2 D20T/N88R variant sequence
source                  1..133
                        mol_type = protein
                        organism = synthetic construct
SEQUENCE: 28
APTSSSTKKT QLQLEHLLLT LQMILNGINN YKNPKLTRML TFKFYMPKKA TELKHLQCLE  60
EELKPLEEVL NLAQSKNFHL RPRDLISRIN VIVLELKGSE TTFMCEYADE TATIVEFLNR 120
WITFSQSIIS TLT                                                   133

SEQ ID NO: 29           moltype = AA   length = 133
FEATURE                 Location/Qualifiers
REGION                  1..133
                        note = IL-2 D20I/N88I variant sequence
source                  1..133
                        mol_type = protein
                        organism = synthetic construct
SEQUENCE: 29
APTSSSTKKT QLQLEHLLLI LQMILNGINN YKNPKLTRML TFKFYMPKKA TELKHLQCLE  60
EELKPLEEVL NLAQSKNFHL RPRDLISIIN VIVLELKGSE TTFMCEYADE TATIVEFLNR 120
WITFSQSIIS TLT                                                   133

SEQ ID NO: 30           moltype = AA   length = 133
FEATURE                 Location/Qualifiers
REGION                  1..133
                        note = IL-2 D20T/Q126E variant sequence
source                  1..133
                        mol_type = protein
                        organism = synthetic construct
SEQUENCE: 30
APTSSSTKKT QLQLEHLLLT LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR 120
WITFSESIIS TLT                                                   133

SEQ ID NO: 31           moltype = AA   length = 133
FEATURE                 Location/Qualifiers
REGION                  1..133
                        note = IL-2 D20T/N88R/Q126E variant sequence
source                  1..133
                        mol_type = protein
                        organism = synthetic construct
SEQUENCE: 31
APTSSSTKKT QLQLEHLLLT LQMILNGINN YKNPKLTRML TFKFYMPKKA TELKHLQCLE  60
EELKPLEEVL NLAQSKNFHL RPRDLISRIN VIVLELKGSE TTFMCEYADE TATIVEFLNR 120
WITFSESIIS TLT                                                   133

SEQ ID NO: 32           moltype = AA   length = 133
FEATURE                 Location/Qualifiers
REGION                  1..133
                        note = IL-2 D20T/Q126L variant sequence
source                  1..133
                        mol_type = protein
                        organism = synthetic construct
SEQUENCE: 32
APTSSSTKKT QLQLEHLLLT LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR 120
WITFSLSIIS TLT                                                   133

SEQ ID NO: 33           moltype = AA   length = 133
FEATURE                 Location/Qualifiers
REGION                  1..133
                        note = IL-2 D20T/N88R/Q126L variant sequence
source                  1..133
                        mol_type = protein
                        organism = synthetic construct
SEQUENCE: 33
APTSSSTKKT QLQLEHLLLT LQMILNGINN YKNPKLTRML TFKFYMPKKA TELKHLQCLE  60
EELKPLEEVL NLAQSKNFHL RPRDLISRIN VIVLELKGSE TTFMCEYADE TATIVEFLNR 120
WITFSLSIIS TLT                                                   133

SEQ ID NO: 34           moltype = AA   length = 133
FEATURE                 Location/Qualifiers
REGION                  1..133

```
                        note = IL-2 L19N/Q126E variant sequence
source                  1..133
                        mol_type = protein
                        organism = synthetic construct
SEQUENCE: 34
APTSSSTKKT QLQLEHLLND LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSESIIS TLT                                                     133

SEQ ID NO: 35           moltype = AA  length = 133
FEATURE                 Location/Qualifiers
REGION                  1..133
                        note = IL-2 L19R/Q126E variant sequence
source                  1..133
                        mol_type = protein
                        organism = synthetic construct
SEQUENCE: 35
APTSSSTKKT QLQLEHLLRD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSESIIS TLT                                                     133

SEQ ID NO: 36           moltype = AA  length = 133
FEATURE                 Location/Qualifiers
REGION                  1..133
                        note = IL-2 L19Y/Q126E variant sequence
source                  1..133
                        mol_type = protein
                        organism = synthetic construct
SEQUENCE: 36
APTSSSTKKT QLQLEHLLYD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSESIIS TLT                                                     133

SEQ ID NO: 37           moltype = AA  length = 133
FEATURE                 Location/Qualifiers
REGION                  1..133
                        note = IL-2 L19Q variant sequence
source                  1..133
                        mol_type = protein
                        organism = synthetic construct
SEQUENCE: 37
APTSSSTKKT QLQLEHLLQD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 38           moltype = AA  length = 133
FEATURE                 Location/Qualifiers
REGION                  1..133
                        note = IL-2 L19H variant sequence
source                  1..133
                        mol_type = protein
                        organism = synthetic construct
SEQUENCE: 38
APTSSSTKKT QLQLEHLLHD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 39           moltype = AA  length = 133
FEATURE                 Location/Qualifiers
REGION                  1..133
                        note = IL-2 L19D variant sequence
source                  1..133
                        mol_type = protein
                        organism = synthetic construct
SEQUENCE: 39
APTSSSTKKT QLQLEHLLDD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 40           moltype = AA  length = 133
FEATURE                 Location/Qualifiers
REGION                  1..133
                        note = IL-2 L19P variant sequence
source                  1..133
                        mol_type = protein
                        organism = synthetic construct
SEQUENCE: 40
APTSSSTKKT QLQLEHLLPD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
```

```
WITFSQSIIS TLT                                                        133

SEQ ID NO: 41            moltype = AA  length = 133
FEATURE                  Location/Qualifiers
REGION                   1..133
                         note = IL-2 D20T/S125I/Q126K variant sequence
source                   1..133
                         mol_type = protein
                         organism = synthetic construct
SEQUENCE: 41
APTSSSTKKT QLQLEHLLLT LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFIKSIIS TLT                                                        133

SEQ ID NO: 42            moltype = AA  length = 133
FEATURE                  Location/Qualifiers
REGION                   1..133
                         note = IL-2 L19N/S125I/Q126K variant sequence
source                   1..133
                         mol_type = protein
                         organism = synthetic construct
SEQUENCE: 42
APTSSSTKKT QLQLEHLLND LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFIKSIIS TLT                                                        133

SEQ ID NO: 43            moltype = AA  length = 133
FEATURE                  Location/Qualifiers
REGION                   1..133
                         note = IL-2 L19R/S125I/Q126K variant sequence
source                   1..133
                         mol_type = protein
                         organism = synthetic construct
SEQUENCE: 43
APTSSSTKKT QLQLEHLLRD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFIKSIIS TLT                                                        133

SEQ ID NO: 44            moltype = AA  length = 226
FEATURE                  Location/Qualifiers
source                   1..226
                         mol_type = protein
                         organism = Homo sapiens
SEQUENCE: 44
DKTHTCPPCP APELLGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLTCLVK GFYPSDIAVE WESNGQPENN YKTTPPVLDS    180
DGSFFLYSKL TVDKSRWQQG NVFSCSVMHE ALHNHYTQKS LSLSPG                    226

SEQ ID NO: 45            moltype = AA  length = 226
FEATURE                  Location/Qualifiers
REGION                   1..226
                         note = Human IgG1-Fc with reduced/abolished effector
                           function
source                   1..226
                         mol_type = protein
                         organism = synthetic construct
SEQUENCE: 45
DKTHTCPPCP APEAAGAPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLTCLVK GFYPSDIAVE WESNGQPENN YKTTPPVLDS    180
DGSFFLYSKL TVDKSRWQQG NVFSCSVMHE ALHNHYTQKS LSLSPG                    226

SEQ ID NO: 46            moltype = AA  length = 226
FEATURE                  Location/Qualifiers
REGION                   1..226
                         note = Human IgG1-Fc reduced/abolished effector function
                           and with extended half-life
source                   1..226
                         mol_type = protein
                         organism = synthetic construct
SEQUENCE: 46
DKTHTCPPCP APEAAGGPSV FLFPPKPKDT LYITREPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSREEMTK NQVSLTCLVK GFYPSDIAVE WESNGQPENN YKTTPPVLDS    180
DGSFFLYSKL TVDKSRWQQG NVFSCSVMHE ALHNHYTQKS LSLSPG                    226

SEQ ID NO: 47            moltype = AA  length = 226
FEATURE                  Location/Qualifiers
```

```
REGION                  1..226
                        note = Human IgG1-Fc with reduced/abolished effector
                         function and extended half-life
source                  1..226
                        mol_type = protein
                        organism = synthetic construct
SEQUENCE: 47
DKTHTCPPCP APEAAGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHAHYTQKS LSLSPG                  226

SEQ ID NO: 48           moltype = AA   length = 12
FEATURE                 Location/Qualifiers
REGION                  1..12
                        note = Peptide linker sequence
source                  1..12
                        mol_type = protein
                        organism = synthetic construct
SEQUENCE: 48
GGGSGGGSGG GS                                                       12

SEQ ID NO: 49           moltype = AA   length = 4
FEATURE                 Location/Qualifiers
REGION                  1..4
                        note = Peptide linker sequence
source                  1..4
                        mol_type = protein
                        organism = synthetic construct
SEQUENCE: 49
GGGS                                                                4

SEQ ID NO: 50           moltype = AA   length = 13
FEATURE                 Location/Qualifiers
REGION                  1..13
                        note = Peptide linker sequence
source                  1..13
                        mol_type = protein
                        organism = synthetic construct
SEQUENCE: 50
GSSGGSGGSG GSG                                                      13

SEQ ID NO: 51           moltype = AA   length = 5
FEATURE                 Location/Qualifiers
REGION                  1..5
                        note = Peptide linker sequence
source                  1..5
                        mol_type = protein
                        organism = synthetic construct
SEQUENCE: 51
GSSGT                                                               5

SEQ ID NO: 52           moltype = AA   length = 14
FEATURE                 Location/Qualifiers
REGION                  1..14
                        note = Peptide linker sequence
source                  1..14
                        mol_type = protein
                        organism = synthetic construct
SEQUENCE: 52
GGGGSGGGGS GGGS                                                     14

SEQ ID NO: 53           moltype = AA   length = 17
FEATURE                 Location/Qualifiers
REGION                  1..17
                        note = Peptide linker sequence
source                  1..17
                        mol_type = protein
                        organism = synthetic construct
SEQUENCE: 53
AEAAAKEAAA KEAAAKA                                                  17

SEQ ID NO: 54           moltype = AA   length = 20
FEATURE                 Location/Qualifiers
REGION                  1..20
                        note = Peptide linker sequence
source                  1..20
                        mol_type = protein
                        organism = synthetic construct
```

```
SEQUENCE: 54
GGGGSGGGGS GGGGSGGGGS                                                    20

SEQ ID NO: 55          moltype = AA  length = 8
FEATURE                Location/Qualifiers
REGION                 1..8
                       note = Peptide linker sequence
source                 1..8
                       mol_type = protein
                       organism = synthetic construct
SEQUENCE: 55
GGGSGGGS                                                                  8

SEQ ID NO: 56          moltype =     length =
SEQUENCE: 56
000

SEQ ID NO: 57          moltype =     length =
SEQUENCE: 57
000

SEQ ID NO: 58          moltype = AA  length = 5
FEATURE                Location/Qualifiers
REGION                 1..5
                       note = Peptide linker sequence
source                 1..5
                       mol_type = protein
                       organism = synthetic construct
SEQUENCE: 58
GGGGS                                                                     5

SEQ ID NO: 59          moltype = AA  length = 4
FEATURE                Location/Qualifiers
REGION                 1..4
                       note = Peptide linker sequence
source                 1..4
                       mol_type = protein
                       organism = synthetic construct
SEQUENCE: 59
GGSG                                                                      4

SEQ ID NO: 60          moltype = AA  length = 4
FEATURE                Location/Qualifiers
REGION                 1..4
                       note = Peptide linker sequence
source                 1..4
                       mol_type = protein
                       organism = synthetic construct
SEQUENCE: 60
SGGG                                                                      4

SEQ ID NO: 61          moltype = AA  length = 4
FEATURE                Location/Qualifiers
REGION                 1..4
                       note = Peptide linker sequence
source                 1..4
                       mol_type = protein
                       organism = synthetic construct
SEQUENCE: 61
GSGS                                                                      4

SEQ ID NO: 62          moltype = AA  length = 6
FEATURE                Location/Qualifiers
REGION                 1..6
                       note = Peptide linker sequence
source                 1..6
                       mol_type = protein
                       organism = synthetic construct
SEQUENCE: 62
GSGSGS                                                                    6

SEQ ID NO: 63          moltype = AA  length = 8
FEATURE                Location/Qualifiers
REGION                 1..8
                       note = Peptide linker sequence
source                 1..8
                       mol_type = protein
                       organism = synthetic construct
SEQUENCE: 63
```

```
GSGSGSGS                                                                        8

SEQ ID NO: 64           moltype = AA  length = 10
FEATURE                 Location/Qualifiers
REGION                  1..10
                        note = Peptide linker sequence
source                  1..10
                        mol_type = protein
                        organism = synthetic construct
SEQUENCE: 64
GSGSGSGSGS                                                                      10

SEQ ID NO: 65           moltype = AA  length = 12
FEATURE                 Location/Qualifiers
REGION                  1..12
                        note = Peptide linker sequence
source                  1..12
                        mol_type = protein
                        organism = synthetic construct
SEQUENCE: 65
GSGSGSGSGS GS                                                                   12

SEQ ID NO: 66           moltype = AA  length = 10
FEATURE                 Location/Qualifiers
REGION                  1..10
                        note = Peptide linker sequence
source                  1..10
                        mol_type = protein
                        organism = synthetic construct
SEQUENCE: 66
GGGGSGGGGS                                                                      10

SEQ ID NO: 67           moltype = AA  length = 15
FEATURE                 Location/Qualifiers
REGION                  1..15
                        note = Peptide linker sequence
source                  1..15
                        mol_type = protein
                        organism = synthetic construct
SEQUENCE: 67
GGGGSGGGGS GGGGS                                                                15

SEQ ID NO: 68           moltype = AA  length = 165
FEATURE                 Location/Qualifiers
source                  1..165
                        mol_type = protein
                        organism = Homo sapiens
SEQUENCE: 68
ELCDDDPPEI PHATFKAMAY KEGTMLNCEC KRGFRRIKSG SLYMLCTGNS SHSSWDNQCQ    60
CTSSATRNTT KQVTPQPEEQ KERKTTEMQS PMQPVDQASL PGHCREPPPW ENEATERIYH    120
FVVGQMVYYQ CVQGYRALHR GPAESVCKMT HGKTRWTQPQ LICTG                    165

SEQ ID NO: 69           moltype = AA  length = 367
FEATURE                 Location/Qualifiers
REGION                  1..367
                        note = P-0250
source                  1..367
                        mol_type = protein
                        organism = synthetic construct
SEQUENCE: 69
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK    120
GQPREPQVYT LPPSRDELTK NQVSLTCLVK GFYPSDIAVE WESNGQPENN YKTTPPVLDS    180
DGSFFLYSKL TVDKSRWQQG NVFSCSVMHE ALHNHYTQKS LSLSPGGGGS GGGSAPTSSS    240
TKKTQLQLEH LLLDLQMILN GINNYKNPKL TRMLTFKFYM PKKATELKHL QCLEEELKPL    300
EEVLNLAQSK NFHLRPRDLI SNINIVLEL KGSETTFMCE YADETATIVE FLNRWITFSQ    360
SIISTLT                                                              367

SEQ ID NO: 70           moltype = AA  length = 371
FEATURE                 Location/Qualifiers
REGION                  1..371
                        note = P-0305
source                  1..371
                        mol_type = protein
                        organism = synthetic construct
SEQUENCE: 70
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFSQSIIS TLTAEAAAKE AAAKEAAAKA CPPCPAPEAA GAPSVFLFPP KPKDTLMISR    180
```

```
TPEVTCVVVD VSHEDPEVKF NWYVDGVEVH NAKTKPREEQ YNSTYRVVSV LTVLHQDWLN  240
GKEYKCKVSN KALPAPIEKT ISKAKGQPRE PQVYTLPPSR DELTKNQVSL TCLVKGFYPS  300
DIAVEWESNG QPENNYKTTP PVLDSDGSFF LYSKLTVDKS RWQQGNVFSC SVMHEALHNH  360
YTQKSLSLSP G                                                      371

SEQ ID NO: 71           moltype = AA   length = 367
FEATURE                 Location/Qualifiers
REGION                  1..367
                        note = P-0254
source                  1..367
                        mol_type = protein
                        organism = synthetic construct
SEQUENCE: 71
DKTHTCPPCP APEAAGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGSAPTSSS  240
TKKTQLQLEH LLLDLQMILN GINNYKNPKL TRMLTFKFYM PKKATELKHL QCLEEELKPL  300
EEVLNLAQSK NFHLRPRDLI SRINIVIVLEL KGSETTFMCE YADETATIVE FLNRWITFSQ  360
SIISTLT                                                           367

SEQ ID NO: 72           moltype = AA   length = 367
FEATURE                 Location/Qualifiers
REGION                  1..367
                        note = P-0363
source                  1..367
                        mol_type = protein
                        organism = synthetic construct
SEQUENCE: 72
DKTHTCPPCP APEAAGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGSAPTSSS  240
TKKTQLQLEH LLLTLQMILN GINNYKNPKL TRMLTFKFYM PKKATELKHL QCLEEELKPL  300
EEVLNLAQSK NFHLRPRDLI SNINIVIVLEL KGSETTFMCE YADETATIVE FLNRWITFSQ  360
SIISTLT                                                           367

SEQ ID NO: 73           moltype = AA   length = 367
FEATURE                 Location/Qualifiers
REGION                  1..367
                        note = P-0364
source                  1..367
                        mol_type = protein
                        organism = synthetic construct
SEQUENCE: 73
DKTHTCPPCP APEAAGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGSAPTSSS  240
TKKTQLQLEH LLLELQMILN GINNYKNPKL TRMLTFKFYM PKKATELKHL QCLEEELKPL  300
EEVLNLAQSK NFHLRPRDLI SNINIVIVLEL KGSETTFMCE YADETATIVE FLNRWITFSQ  360
SIISTLT                                                           367

SEQ ID NO: 74           moltype = AA   length = 367
FEATURE                 Location/Qualifiers
REGION                  1..367
                        note = P-0365
source                  1..367
                        mol_type = protein
                        organism = synthetic construct
SEQUENCE: 74
DKTHTCPPCP APEAAGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGSAPTSSS  240
TKKTQLQLEH LLLNLQMILN GINNYKNPKL TRMLTFKFYM PKKATELKHL QCLEEELKPL  300
EEVLNLAQSK NFHLRPRDLI SNINIVIVLEL KGSETTFMCE YADETATIVE FLNRWITFSQ  360
SIISTLT                                                           367

SEQ ID NO: 75           moltype = AA   length = 367
FEATURE                 Location/Qualifiers
REGION                  1..367
                        note = P-0366
source                  1..367
                        mol_type = protein
                        organism = synthetic construct
SEQUENCE: 75
DKTHTCPPCP APEAAGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
```

```
GQPREPQVYT LPPSRDELTK NQVSLTCLVK GFYPSDIAVE WESNGQPENN YKTTPPVLDS    180
DGSFFLYSKL TVDKSRWQQG NVFSCSVMHE ALHNHYTQKS LSLSPGGGGS GGGSAPTSSS    240
TKKTQLQLEH LLLQLQMILN GINNYKNPKL TRMLTFKFYM PKKATELKHL QCLEEELKPL    300
EEVLNLAQSK NFHLRPRDLI SNINIVLEL KGSETTFMCE YADETATIVE FLNRWITFSQ    360
SIISTLT                                                             367

SEQ ID NO: 76           moltype = AA  length = 367
FEATURE                 Location/Qualifiers
REGION                  1..367
                        note = P-0367
source                  1..367
                        mol_type = protein
                        organism = synthetic construct
SEQUENCE: 76
DKTHTCPPCP APEAAGAPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLTCLVK GFYPSDIAVE WESNGQPENN YKTTPPVLDS    180
DGSFFLYSKL TVDKSRWQQG NVFSCSVMHE ALHNHYTQKS LSLSPGGGGS GGGSAPTSSS    240
TKKTQLQLEH LLLSLQMILN GINNYKNPKL TRMLTFKFYM PKKATELKHL QCLEEELKPL    300
EEVLNLAQSK NFHLRPRDLI SNINIVLEL KGSETTFMCE YADETATIVE FLNRWITFSQ    360
SIISTLT                                                             367

SEQ ID NO: 77           moltype = AA  length = 367
FEATURE                 Location/Qualifiers
REGION                  1..367
                        note = P-0368
source                  1..367
                        mol_type = protein
                        organism = synthetic construct
SEQUENCE: 77
DKTHTCPPCP APEAAGAPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLTCLVK GFYPSDIAVE WESNGQPENN YKTTPPVLDS    180
DGSFFLYSKL TVDKSRWQQG NVFSCSVMHE ALHNHYTQKS LSLSPGGGGS GGGSAPTSSS    240
TKKTQLQLEH LLLYLQMILN GINNYKNPKL TRMLTFKFYM PKKATELKHL QCLEEELKPL    300
EEVLNLAQSK NFHLRPRDLI SNINIVLEL KGSETTFMCE YADETATIVE FLNRWITFSQ    360
SIISTLT                                                             367

SEQ ID NO: 78           moltype = AA  length = 367
FEATURE                 Location/Qualifiers
REGION                  1..367
                        note = P-0252
source                  1..367
                        mol_type = protein
                        organism = synthetic construct
SEQUENCE: 78
DKTHTCPPCP APEAAGAPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLTCLVK GFYPSDIAVE WESNGQPENN YKTTPPVLDS    180
DGSFFLYSKL TVDKSRWQQG NVFSCSVMHE ALHNHYTQKS LSLSPGGGGS GGGSAPTSSS    240
TKKTQLQLEH LLLILQMILN GINNYKNPKL TRMLTFKFYM PKKATELKHL QCLEEELKPL    300
EEVLNLAQSK NFHLRPRDLI SNINIVLEL KGSETTFMCE YADETATIVE FLNRWITFSQ    360
SIISTLT                                                             367

SEQ ID NO: 79           moltype = AA  length = 367
FEATURE                 Location/Qualifiers
REGION                  1..367
                        note = P-0372
source                  1..367
                        mol_type = protein
                        organism = synthetic construct
SEQUENCE: 79
DKTHTCPPCP APEAAGAPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLTCLVK GFYPSDIAVE WESNGQPENN YKTTPPVLDS    180
DGSFFLYSKL TVDKSRWQQG NVFSCSVMHE ALHNHYTQKS LSLSPGGGGS GGGSAPTSSS    240
TKKTQLQLEH LLYDLQMILN GINNYKNPKL TRMLTFKFYM PKKATELKHL QCLEEELKPL    300
EEVLNLAQSK NFHLRPRDLI SNINIVLEL KGSETTFMCE YADETATIVE FLNRWITFSQ    360
SIISTLT                                                             367

SEQ ID NO: 80           moltype = AA  length = 367
FEATURE                 Location/Qualifiers
REGION                  1..367
                        note = P-0373
source                  1..367
                        mol_type = protein
                        organism = synthetic construct
SEQUENCE: 80
DKTHTCPPCP APEAAGAPSV FLFPPKPKDT LMISRTPEVT CVVVDVSHED PEVKFNWYVD     60
```

```
GVEVHNAKTK PREEQYNSTY RVVSVLTVLH QDWLNGKEYK CKVSNKALPA PIEKTISKAK     120
GQPREPQVYT LPPSRDELTK NQVSLTCLVK GFYPSDIAVE WESNGQPENN YKTTPPVLDS     180
DGSFFLYSKL TVDKSRWQQG NVFSCSVMHE ALHNHYTQKS LSLSPGGGGS GGGSAPTSSS     240
TKKTQLQLEH LLNDLQMILN GINNYKNPKL TRMLTFKFYM PKKATELKHL QCLEEELKPL     300
EEVLNLAQSK NFHLRPRDLI SNINIVIVLEL KGSETTFMCE YADETATIVE FLNRWITFSQ    360
SIISTLT                                                               367

SEQ ID NO: 81            moltype = AA  length = 367
FEATURE                  Location/Qualifiers
REGION                   1..367
                         note = P-0374
source                   1..367
                         mol_type = protein
                         organism = synthetic construct
SEQUENCE: 81
DKTHTCPPCP APEAAGAPSV FLFPPKPKDT LMISRTPEVT CVVVDVSHED PEVKFNWYVD      60
GVEVHNAKTK PREEQYNSTY RVVSVLTVLH QDWLNGKEYK CKVSNKALPA PIEKTISKAK     120
GQPREPQVYT LPPSRDELTK NQVSLTCLVK GFYPSDIAVE WESNGQPENN YKTTPPVLDS     180
DGSFFLYSKL TVDKSRWQQG NVFSCSVMHE ALHNHYTQKS LSLSPGGGGS GGGSAPTSSS     240
TKKTQLQLEH LLRDLQMILN GINNYKNPKL TRMLTFKFYM PKKATELKHL QCLEEELKPL     300
EEVLNLAQSK NFHLRPRDLI SNINIVIVLEL KGSETTFMCE YADETATIVE FLNRWITFSQ    360
SIISTLT                                                               367

SEQ ID NO: 82            moltype = AA  length = 367
FEATURE                  Location/Qualifiers
REGION                   1..367
                         note = P-0253
source                   1..367
                         mol_type = protein
                         organism = synthetic construct
SEQUENCE: 82
DKTHTCPPCP APEAAGAPSV FLFPPKPKDT LMISRTPEVT CVVVDVSHED PEVKFNWYVD      60
GVEVHNAKTK PREEQYNSTY RVVSVLTVLH QDWLNGKEYK CKVSNKALPA PIEKTISKAK     120
GQPREPQVYT LPPSRDELTK NQVSLTCLVK GFYPSDIAVE WESNGQPENN YKTTPPVLDS     180
DGSFFLYSKL TVDKSRWQQG NVFSCSVMHE ALHNHYTQKS LSLSPGGGGS GGGSAPTSSS     240
TKKTQLQLEH LLLDLQMILN GINNYKNPKL TRMLTFKFYM PKKATELKHL QCLEEELKPL     300
EEVLNLAQSK NFHLRPRDLI SGINIVIVLEL KGSETTFMCE YADETATIVE FLNRWITFSQ    360
SIISTLT                                                               367

SEQ ID NO: 83            moltype = AA  length = 367
FEATURE                  Location/Qualifiers
REGION                   1..367
                         note = P-0302
source                   1..367
                         mol_type = protein
                         organism = synthetic construct
SEQUENCE: 83
DKTHTCPPCP APEAAGAPSV FLFPPKPKDT LMISRTPEVT CVVVDVSHED PEVKFNWYVD      60
GVEVHNAKTK PREEQYNSTY RVVSVLTVLH QDWLNGKEYK CKVSNKALPA PIEKTISKAK     120
GQPREPQVYT LPPSRDELTK NQVSLTCLVK GFYPSDIAVE WESNGQPENN YKTTPPVLDS     180
DGSFFLYSKL TVDKSRWQQG NVFSCSVMHE ALHNHYTQKS LSLSPGGGGS GGGSAPTSSS     240
TKKTQLQLEH LLLDLQMILN GINNYKNPKL TRMLTFKFYM PKKATELKHL QCLEEELKPL     300
EEVLNLAQSK NFHLRPRDLI SIINIVIVLEL KGSETTFMCE YADETATIVE FLNRWITFSQ    360
SIISTLT                                                               367

SEQ ID NO: 84            moltype = AA  length = 367
FEATURE                  Location/Qualifiers
REGION                   1..367
                         note = P-0375
source                   1..367
                         mol_type = protein
                         organism = synthetic construct
SEQUENCE: 84
DKTHTCPPCP APEAAGAPSV FLFPPKPKDT LMISRTPEVT CVVVDVSHED PEVKFNWYVD      60
GVEVHNAKTK PREEQYNSTY RVVSVLTVLH QDWLNGKEYK CKVSNKALPA PIEKTISKAK     120
GQPREPQVYT LPPSRDELTK NQVSLTCLVK GFYPSDIAVE WESNGQPENN YKTTPPVLDS     180
DGSFFLYSKL TVDKSRWQQG NVFSCSVMHE ALHNHYTQKS LSLSPGGGGS GGGSAPTSSS     240
TKKTQLQLEH LLLDLQMILN GINNYKNPKL TRMLTFKFYM PKKATELKHL QCLEEELKPL     300
EEVLNLAQSK NFHLRPRDLI SQINIVIVLEL KGSETTFMCE YADETATIVE FLNRWITFSQ    360
SIISTLT                                                               367

SEQ ID NO: 85            moltype = AA  length = 367
FEATURE                  Location/Qualifiers
REGION                   1..367
                         note = P-0376
source                   1..367
                         mol_type = protein
SEQUENCE: 85
```

```
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLDLQMILN GINNYKNPKL TRMLTFKFYM PKKATELKHL QCLEEELKPL   300
EEVLNLAQSK NFHLRPRDLI SEINVIVLEL KGSETTFMCE YADETATIVE FLNRWITFSQ   360
SIISTLT                                                            367

SEQ ID NO: 86           moltype = AA  length = 367
FEATURE                 Location/Qualifiers
REGION                  1..367
                        note = P-0377
source                  1..367
                        mol_type = protein
                        organism = synthetic construct
SEQUENCE: 86
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLDLQMILN GINNYKNPKL TRMLTFKFYM PKKATELKHL QCLEEELKPL   300
EEVLNLAQSK NFHLRPRDLI STINVIVLEL KGSETTFMCE YADETATIVE FLNRWITFSQ   360
SIISTLT                                                            367

SEQ ID NO: 87           moltype = AA  length = 367
FEATURE                 Location/Qualifiers
REGION                  1..367
                        note = P-0378
source                  1..367
                        mol_type = protein
                        organism = synthetic construct
SEQUENCE: 87
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLDLQMILN GINNYKNPKL TRMLTFKFYM PKKATELKHL QCLEEELKPL   300
EEVLNLAQSK NFHLRPRDLI SMINVIVLEL KGSETTFMCE YADETATIVE FLNRWITFSQ   360
SIISTLT                                                            367

SEQ ID NO: 88           moltype = AA  length = 367
FEATURE                 Location/Qualifiers
REGION                  1..367
                        note = P-0303
source                  1..367
                        mol_type = protein
                        organism = synthetic construct
SEQUENCE: 88
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSE   360
SIISTLT                                                            367

SEQ ID NO: 89           moltype = AA  length = 367
FEATURE                 Location/Qualifiers
REGION                  1..367
                        note = P-0304
source                  1..367
                        mol_type = protein
                        organism = synthetic construct
SEQUENCE: 89
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSL   360
SIISTLT                                                            367

SEQ ID NO: 90           moltype = AA  length = 367
FEATURE                 Location/Qualifiers
REGION                  1..367
                        note = P-0369
source                  1..367
                        mol_type = protein
                        organism = synthetic construct
```

```
SEQUENCE: 90
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSN   360
SIISTLT                                                            367

SEQ ID NO: 91           moltype = AA  length = 367
FEATURE                 Location/Qualifiers
REGION                  1..367
                        note = P-0370
source                  1..367
                        mol_type = protein
                        organism = synthetic construct
SEQUENCE: 91
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSD   360
SIISTLT                                                            367

SEQ ID NO: 92           moltype = AA  length = 367
FEATURE                 Location/Qualifiers
REGION                  1..367
                        note = P-0371
source                  1..367
                        mol_type = protein
                        organism = synthetic construct
SEQUENCE: 92
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSM   360
SIISTLT                                                            367

SEQ ID NO: 93           moltype = AA  length = 367
FEATURE                 Location/Qualifiers
REGION                  1..367
                        note = P-0251
source                  1..367
                        mol_type = protein
                        organism = synthetic construct
SEQUENCE: 93
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLILQMILN GINNYKNPKL TRMLTFKFYM PKKATELKHL QCLEEELKPL   300
EEVLNLAQSK NFHLRPRDLI SGINVIVLEL KGSETTFMCE YADETATIVE FLNRWITFSQ   360
SIISTLT                                                            367

SEQ ID NO: 94           moltype = AA  length = 367
FEATURE                 Location/Qualifiers
REGION                  1..367
                        note = P-0317
source                  1..367
                        mol_type = protein
                        organism = synthetic construct
SEQUENCE: 94
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLILQMILN GINNYKNPKL TRMLTFKFYM PKKATELKHL QCLEEELKPL   300
EEVLNLAQSK NFHLRPRDLI SRINVIVLEL KGSETTFMCE YADETATIVE FLNRWITFSQ   360
SIISTLT                                                            367

SEQ ID NO: 95           moltype = AA  length = 367
FEATURE                 Location/Qualifiers
REGION                  1..367
                        note = P-0318
source                  1..367
                        mol_type = protein
```

```
                        organism = synthetic construct
SEQUENCE: 95
DKTHTCPPCP APEAAGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGSAPTSSS  240
TKKTQLQLEH LLLILQMILN GINNYKNPKL TRMLTFKFYM PKKATELKHL QCLEEELKPL  300
EEVLNLAQSK NFHLRPRDLI SIINVIVLEL KGSETTFMCE YADETATIVE FLNRWITFSQ  360
SIISTLT                                                            367

SEQ ID NO: 96           moltype = AA   length = 367
FEATURE                 Location/Qualifiers
REGION                  1..367
                        note = P-0324
source                  1..367
                        mol_type = protein
                        organism = synthetic construct
SEQUENCE: 96
DKTHTCPPCP APEAAGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGSAPTSSS  240
TKKTQLQLEH LLLTLQMILN GINNYKNPKL TRMLTFKFYM PKKATELKHL QCLEEELKPL  300
EEVLNLAQSK NFHLRPRDLI SRINVIVLEL KGSETTFMCE YADETATIVE FLNRWITFSQ  360
SIISTLT                                                            367

SEQ ID NO: 97           moltype = AA   length = 367
FEATURE                 Location/Qualifiers
REGION                  1..367
                        note = P-0322
source                  1..367
                        mol_type = protein
                        organism = synthetic construct
SEQUENCE: 97
DKTHTCPPCP APEAAGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGSAPTSSS  240
TKKTQLQLEH LLLTLQMILN GINNYKNPKL TRMLTFKFYM PKKATELKHL QCLEEELKPL  300
EEVLNLAQSK NFHLRPRDLI SNINVIVLEL KGSETTFMCE YADETATIVE FLNRWITFSE  360
SIISTLT                                                            367

SEQ ID NO: 98           moltype = AA   length = 367
FEATURE                 Location/Qualifiers
REGION                  1..367
                        note = P-0323
source                  1..367
                        mol_type = protein
                        organism = synthetic construct
SEQUENCE: 98
DKTHTCPPCP APEAAGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGSAPTSSS  240
TKKTQLQLEH LLLTLQMILN GINNYKNPKL TRMLTFKFYM PKKATELKHL QCLEEELKPL  300
EEVLNLAQSK NFHLRPRDLI SNINVIVLEL KGSETTFMCE YADETATIVE FLNRWITFSL  360
SIISTLT                                                            367

SEQ ID NO: 99           moltype = AA   length = 367
FEATURE                 Location/Qualifiers
REGION                  1..367
                        note = P-0325
source                  1..367
                        mol_type = protein
                        organism = synthetic construct
SEQUENCE: 99
DKTHTCPPCP APEAAGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGSAPTSSS  240
TKKTQLQLEH LLLTLQMILN GINNYKNPKL TRMLTFKFYM PKKATELKHL QCLEEELKPL  300
EEVLNLAQSK NFHLRPRDLI SRINVIVLEL KGSETTFMCE YADETATIVE FLNRWITFSE  360
SIISTLT                                                            367

SEQ ID NO: 100          moltype = AA   length = 367
FEATURE                 Location/Qualifiers
REGION                  1..367
                        note = P-0326
source                  1..367
```

```
                            mol_type = protein
                            organism = synthetic construct
SEQUENCE: 100
DKTHTCPPCP APEAAGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGSAPTSSS  240
TKKTQLQLEH LLLTLQMILN GINNYKNPKL TRMLTFKFYM PKKATELKHL QCLEEELKPL  300
EEVLNLAQSK NFHLRPRDLI SRINVIVLEL KGSETTFMCE YADETATIVE FLNRWITFSL  360
SIISTLT                                                            367

SEQ ID NO: 101           moltype = AA  length = 367
FEATURE                  Location/Qualifiers
REGION                   1..367
                         note = P-0417
source                   1..367
                         mol_type = protein
                         organism = synthetic construct
SEQUENCE: 101
DKTHTCPPCP APEAAGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGSAPTSSS  240
TKKTQLQLEH LLNDLQMILN GINNYKNPKL TRMLTFKFYM PKKATELKHL QCLEEELKPL  300
EEVLNLAQSK NFHLRPRDLI SNINVIVLEL KGSETTFMCE YADETATIVE FLNRWITFSE  360
SIISTLT                                                            367

SEQ ID NO: 102           moltype = AA  length = 367
FEATURE                  Location/Qualifiers
REGION                   1..367
                         note = P-0418
source                   1..367
                         mol_type = protein
                         organism = synthetic construct
SEQUENCE: 102
DKTHTCPPCP APEAAGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGSAPTSSS  240
TKKTQLQLEH LLRDLQMILN GINNYKNPKL TRMLTFKFYM PKKATELKHL QCLEEELKPL  300
EEVLNLAQSK NFHLRPRDLI SNINVIVLEL KGSETTFMCE YADETATIVE FLNRWITFSE  360
SIISTLT                                                            367

SEQ ID NO: 103           moltype = AA  length = 367
FEATURE                  Location/Qualifiers
REGION                   1..367
                         note = P-0419
source                   1..367
                         mol_type = protein
                         organism = synthetic construct
SEQUENCE: 103
DKTHTCPPCP APEAAGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGSAPTSSS  240
TKKTQLQLEH LLYDLQMILN GINNYKNPKL TRMLTFKFYM PKKATELKHL QCLEEELKPL  300
EEVLNLAQSK NFHLRPRDLI SNINVIVLEL KGSETTFMCE YADETATIVE FLNRWITFSE  360
SIISTLT                                                            367

SEQ ID NO: 104           moltype = AA  length = 371
FEATURE                  Location/Qualifiers
REGION                   1..371
                         note = P-0416
source                   1..371
                         mol_type = protein
                         organism = synthetic construct
SEQUENCE: 104
APTSSSTKKT QLQLEHLLND LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFSQSIIS TLTAEAAAKE AAAKEAAAKA CPPCPAPEAA GAPSVFLFPP KPKDTLMISR  180
TPEVTCVVVD VSHEDPEVKF NWYVDGVEVH NAKTKPREEQ YNSTYRVVSV LTVLHQDWLN  240
GKEYKCKVSN KALPAPIEKT ISKAKGQPRE PQVYTLPPSR DELTKNQVSL TCLVKGFYPS  300
DIAVEWESNG QPENNYKTTP PVLDSDGSFF LYSKLTVDKS RWQQGNVFSC SVMHEALHNH  360
YTQKSLSLSP G                                                       371

SEQ ID NO: 105           moltype = AA  length = 371
FEATURE                  Location/Qualifiers
REGION                   1..371
                         note = P-0412
```

```
                            -continued source                    1..371
                          mol_type = protein
                          organism = synthetic construct
SEQUENCE: 105
APTSSSTKKT QLQLEHLLLE LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLTAEAAAKE AAAKEAAAKA CPPCPAPEAA GAPSVFLFPP KPKDTLMISR   180
TPEVTCVVVD VSHEDPEVKF NWYVDGVEVH NAKTKPREEQ YNSTYRVVSV LTVLHQDWLN   240
GKEYKCKVSN KALPAPIEKT ISKAKGQPRE PQVYTLPPSR DELTKNQVSL TCLVKGFYPS   300
DIAVEWESNG QPENNYKTTP PVLDSDGSFF LYSKLTVDKS RWQQGNVFSC SVMHEALHNH   360
YTQKSLSLSP G                                                       371

SEQ ID NO: 106            moltype = AA  length = 371
FEATURE                   Location/Qualifiers
REGION                    1..371
                          note = P-0306
source                    1..371
                          mol_type = protein
                          organism = synthetic construct
SEQUENCE: 106
APTSSSTKKT QLQLEHLLLI LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLTAEAAAKE AAAKEAAAKA CPPCPAPEAA GAPSVFLFPP KPKDTLMISR   180
TPEVTCVVVD VSHEDPEVKF NWYVDGVEVH NAKTKPREEQ YNSTYRVVSV LTVLHQDWLN   240
GKEYKCKVSN KALPAPIEKT ISKAKGQPRE PQVYTLPPSR DELTKNQVSL TCLVKGFYPS   300
DIAVEWESNG QPENNYKTTP PVLDSDGSFF LYSKLTVDKS RWQQGNVFSC SVMHEALHNH   360
YTQKSLSLSP G                                                       371

SEQ ID NO: 107            moltype = AA  length = 371
FEATURE                   Location/Qualifiers
REGION                    1..371
                          note = P-0319
source                    1..371
                          mol_type = protein
                          organism = synthetic construct
SEQUENCE: 107
APTSSSTKKT QLQLEHLLLI LQMILNGINN YKNPKLTRML TFKFYMPKKA TELKHLQCLE    60
EELKPLEEVL NLAQSKNFHL RPRDLISRIN VIVLELKGSE TTFMCEYADE TATIVEFLNR   120
WITFSQSIIS TLTAEAAAKE AAAKEAAAKA CPPCPAPEAA GAPSVFLFPP KPKDTLMISR   180
TPEVTCVVVD VSHEDPEVKF NWYVDGVEVH NAKTKPREEQ YNSTYRVVSV LTVLHQDWLN   240
GKEYKCKVSN KALPAPIEKT ISKAKGQPRE PQVYTLPPSR DELTKNQVSL TCLVKGFYPS   300
DIAVEWESNG QPENNYKTTP PVLDSDGSFF LYSKLTVDKS RWQQGNVFSC SVMHEALHNH   360
YTQKSLSLSP G                                                       371

SEQ ID NO: 108            moltype = AA  length = 133
FEATURE                   Location/Qualifiers
REGION                    1..133
                          note = IL-2 L19S variant sequence
source                    1..133
                          mol_type = protein
                          organism = synthetic construct
SEQUENCE: 108
APTSSSTKKT QLQLEHLLSD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 109            moltype = AA  length = 133
FEATURE                   Location/Qualifiers
REGION                    1..133
                          note = IL-2 L21S variant sequence
source                    1..133
                          mol_type = protein
                          organism = synthetic construct
SEQUENCE: 109
APTSSSTKKT QLQLEHLLLD SQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 110            moltype = AA  length = 133
FEATURE                   Location/Qualifiers
REGION                    1..133
                          note = IL-2 L21N variant sequence
source                    1..133
                          mol_type = protein
                          organism = synthetic construct
SEQUENCE: 110
APTSSSTKKT QLQLEHLLLD NQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133
```

```
SEQ ID NO: 111          moltype = AA  length = 133
FEATURE                 Location/Qualifiers
REGION                  1..133
                        note = IL-2 L21R variant sequence
source                  1..133
                        mol_type = protein
                        organism = synthetic construct
SEQUENCE: 111
APTSSSTKKT QLQLEHLLLD RQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFSQSIIS TLT                                                       133

SEQ ID NO: 112          moltype = AA  length = 133
FEATURE                 Location/Qualifiers
REGION                  1..133
                        note = IL-2 Q126K variant sequence
source                  1..133
                        mol_type = protein
                        organism = synthetic construct
SEQUENCE: 112
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFSKSIIS TLT                                                       133

SEQ ID NO: 113          moltype = AA  length = 133
FEATURE                 Location/Qualifiers
REGION                  1..133
                        note = IL-2 Q126H variant sequence
source                  1..133
                        mol_type = protein
                        organism = synthetic construct
SEQUENCE: 113
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFSHSIIS TLT                                                       133

SEQ ID NO: 114          moltype = AA  length = 133
FEATURE                 Location/Qualifiers
REGION                  1..133
                        note = IL-2 Q126Y variant sequence
source                  1..133
                        mol_type = protein
                        organism = synthetic construct
SEQUENCE: 114
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFSYSIIS TLT                                                       133

SEQ ID NO: 115          moltype = AA  length = 133
FEATURE                 Location/Qualifiers
REGION                  1..133
                        note = IL-2 S125E variant sequence
source                  1..133
                        mol_type = protein
                        organism = synthetic construct
SEQUENCE: 115
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFEQSIIS TLT                                                       133

SEQ ID NO: 116          moltype = AA  length = 133
FEATURE                 Location/Qualifiers
REGION                  1..133
                        note = IL-2 S125K variant sequence
source                  1..133
                        mol_type = protein
                        organism = synthetic construct
SEQUENCE: 116
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFKQSIIS TLT                                                       133

SEQ ID NO: 117          moltype = AA  length = 133
FEATURE                 Location/Qualifiers
REGION                  1..133
                        note = IL-2 S125H variant sequence
source                  1..133
                        mol_type = protein
```

```
                             organism = synthetic construct
SEQUENCE: 117
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFHQSIIS TLT                                                     133

SEQ ID NO: 118           moltype = AA  length = 133
FEATURE                  Location/Qualifiers
REGION                   1..133
                         note = IL-2 S125W variant sequence
source                   1..133
                         mol_type = protein
                         organism = synthetic construct
SEQUENCE: 118
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFWQSIIS TLT                                                     133

SEQ ID NO: 119           moltype = AA  length = 133
FEATURE                  Location/Qualifiers
REGION                   1..133
                         note = IL-2 S125I variant sequence
source                   1..133
                         mol_type = protein
                         organism = synthetic construct
SEQUENCE: 119
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFIQSIIS TLT                                                     133

SEQ ID NO: 120           moltype = AA  length = 133
FEATURE                  Location/Qualifiers
REGION                   1..133
                         note = IL-2 Q22N variant sequence
source                   1..133
                         mol_type = protein
                         organism = synthetic construct
SEQUENCE: 120
APTSSSTKKT QLQLEHLLLD LNMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 121           moltype = AA  length = 133
FEATURE                  Location/Qualifiers
REGION                   1..133
                         note = IL-2 Q22H variant sequence
source                   1..133
                         mol_type = protein
                         organism = synthetic construct
SEQUENCE: 121
APTSSSTKKT QLQLEHLLLD LHMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 122           moltype = AA  length = 133
FEATURE                  Location/Qualifiers
REGION                   1..133
                         note = IL-2 Q22K variant sequence
source                   1..133
                         mol_type = protein
                         organism = synthetic construct
SEQUENCE: 122
APTSSSTKKT QLQLEHLLLD LKMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 123           moltype = AA  length = 133
FEATURE                  Location/Qualifiers
REGION                   1..133
                         note = IL-2 Q22Y variant sequence
source                   1..133
                         mol_type = protein
                         organism = synthetic construct
SEQUENCE: 123
APTSSSTKKT QLQLEHLLLD LYMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 124           moltype = AA  length = 133
```

```
FEATURE                     Location/Qualifiers
REGION                      1..133
                            note = IL-2 Q22I variant sequence
source                      1..133
                            mol_type = protein
                            organism = synthetic construct
SEQUENCE: 124
APTSSSTKKT QLQLEHLLLD LIMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFSQSIIS TLT                                                    133

SEQ ID NO: 125              moltype = AA  length = 133
FEATURE                     Location/Qualifiers
REGION                      1..133
                            note = IL-2 L19H/Q126E variant sequence
source                      1..133
                            mol_type = protein
                            organism = synthetic construct
SEQUENCE: 125
APTSSSTKKT QLQLEHLLHD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFSESIIS TLT                                                    133

SEQ ID NO: 126              moltype = AA  length = 133
FEATURE                     Location/Qualifiers
REGION                      1..133
                            note = IL-2 L19Q/Q126E variant sequence
source                      1..133
                            mol_type = protein
                            organism = synthetic construct
SEQUENCE: 126
APTSSSTKKT QLQLEHLLQD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFSESIIS TLT                                                    133

SEQ ID NO: 127              moltype = AA  length = 133
FEATURE                     Location/Qualifiers
REGION                      1..133
                            note = IL-2 L19S/Q126E variant sequence
source                      1..133
                            mol_type = protein
                            organism = synthetic construct
SEQUENCE: 127
APTSSSTKKT QLQLEHLLSD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFSESIIS TLT                                                    133

SEQ ID NO: 128              moltype = AA  length = 133
FEATURE                     Location/Qualifiers
REGION                      1..133
                            note = IL-2 L19Y/Q126K variant sequence
source                      1..133
                            mol_type = protein
                            organism = synthetic construct
SEQUENCE: 128
APTSSSTKKT QLQLEHLLYD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFSKSIIS TLT                                                    133

SEQ ID NO: 129              moltype = AA  length = 133
FEATURE                     Location/Qualifiers
REGION                      1..133
                            note = IL-2 L19Y/Q126H variant sequence
source                      1..133
                            mol_type = protein
                            organism = synthetic construct
SEQUENCE: 129
APTSSSTKKT QLQLEHLLYD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFSHSIIS TLT                                                    133

SEQ ID NO: 130              moltype = AA  length = 133
FEATURE                     Location/Qualifiers
REGION                      1..133
                            note = IL-2 L19Y/Q126Y variant sequence
source                      1..133
                            mol_type = protein
                            organism = synthetic construct
SEQUENCE: 130
```

```
APTSSSTKKT QLQLEHLLYD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSYSIIS TLT                                                     133

SEQ ID NO: 131           moltype = AA   length = 133
FEATURE                  Location/Qualifiers
REGION                   1..133
                         note = IL-2 L19Y/S125E variant sequence
source                   1..133
                         mol_type = protein
                         organism = synthetic construct
SEQUENCE: 131
APTSSSTKKT QLQLEHLLYD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFEQSIIS TLT                                                     133

SEQ ID NO: 132           moltype = AA   length = 133
FEATURE                  Location/Qualifiers
REGION                   1..133
                         note = IL-2 L19Y/S125K variant sequence
source                   1..133
                         mol_type = protein
                         organism = synthetic construct
SEQUENCE: 132
APTSSSTKKT QLQLEHLLYD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFKQSIIS TLT                                                     133

SEQ ID NO: 133           moltype = AA   length = 133
FEATURE                  Location/Qualifiers
REGION                   1..133
                         note = IL-2 L19Y/S125H variant sequence
source                   1..133
                         mol_type = protein
                         organism = synthetic construct
SEQUENCE: 133
APTSSSTKKT QLQLEHLLYD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFHQSIIS TLT                                                     133

SEQ ID NO: 134           moltype = AA   length = 133
FEATURE                  Location/Qualifiers
REGION                   1..133
                         note = IL-2 L19Y/S125W variant sequence
source                   1..133
                         mol_type = protein
                         organism = synthetic construct
SEQUENCE: 134
APTSSSTKKT QLQLEHLLYD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFWQSIIS TLT                                                     133

SEQ ID NO: 135           moltype = AA   length = 133
FEATURE                  Location/Qualifiers
REGION                   1..133
                         note = IL-2 L19Y/S125I variant sequence
source                   1..133
                         mol_type = protein
                         organism = synthetic construct
SEQUENCE: 135
APTSSSTKKT QLQLEHLLYD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFIQSIIS TLT                                                     133

SEQ ID NO: 136           moltype = AA   length = 133
FEATURE                  Location/Qualifiers
REGION                   1..133
                         note = IL-2 L19Y/Q22N variant sequence
source                   1..133
                         mol_type = protein
                         organism = synthetic construct
SEQUENCE: 136
APTSSSTKKT QLQLEHLLYD LNMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 137           moltype = AA   length = 133
FEATURE                  Location/Qualifiers
REGION                   1..133
```

```
                        note = IL-2 L19Y/Q22H variant sequence
source                  1..133
                        mol_type = protein
                        organism = synthetic construct
SEQUENCE: 137
APTSSSTKKT QLQLEHLLYD LHMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFSQSIIS TLT                                                     133

SEQ ID NO: 138          moltype = AA   length = 133
FEATURE                 Location/Qualifiers
REGION                  1..133
                        note = IL-2 L19Y/Q22K variant sequence
source                  1..133
                        mol_type = protein
                        organism = synthetic construct
SEQUENCE: 138
APTSSSTKKT QLQLEHLLYD LKMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFSQSIIS TLT                                                     133

SEQ ID NO: 139          moltype = AA   length = 133
FEATURE                 Location/Qualifiers
REGION                  1..133
                        note = IL-2 L19Y/Q22Y variant sequence
source                  1..133
                        mol_type = protein
                        organism = synthetic construct
SEQUENCE: 139
APTSSSTKKT QLQLEHLLYD LYMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFSQSIIS TLT                                                     133

SEQ ID NO: 140          moltype = AA   length = 133
FEATURE                 Location/Qualifiers
REGION                  1..133
                        note = IL-2 L19Y/Q22I variant sequence
source                  1..133
                        mol_type = protein
                        organism = synthetic construct
SEQUENCE: 140
APTSSSTKKT QLQLEHLLYD LIMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFSQSIIS TLT                                                     133

SEQ ID NO: 141          moltype = AA   length = 133
FEATURE                 Location/Qualifiers
REGION                  1..133
                        note = IL-2 L19H/Q126K variant sequence
source                  1..133
                        mol_type = protein
                        organism = synthetic construct
SEQUENCE: 141
APTSSSTKKT QLQLEHLLHD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFSKSIIS TLT                                                     133

SEQ ID NO: 142          moltype = AA   length = 133
FEATURE                 Location/Qualifiers
REGION                  1..133
                        note = IL-2 L19H/S125I variant sequence
source                  1..133
                        mol_type = protein
                        organism = synthetic construct
SEQUENCE: 142
APTSSSTKKT QLQLEHLLHD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFIQSIIS TLT                                                     133

SEQ ID NO: 143          moltype = AA   length = 133
FEATURE                 Location/Qualifiers
REGION                  1..133
                        note = IL-2 L19D/S125I variant sequence
source                  1..133
                        mol_type = protein
                        organism = synthetic construct
SEQUENCE: 143
APTSSSTKKT QLQLEHLLDD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
```

```
WITFIQSIIS TLT                                                                 133

SEQ ID NO: 144          moltype = AA   length = 133
FEATURE                 Location/Qualifiers
REGION                  1..133
                        note = IL-2 D20E/S125I variant sequence
source                  1..133
                        mol_type = protein
                        organism = synthetic construct
SEQUENCE: 144
APTSSSTKKT QLQLEHLLLE LQMILNGINN YKNPKLTRML TFKFYMPKKA TELKHLQCLE              60
EELKPLEEVL NLAQSKNFHL RPRDLISNIN VIVLELKGSE TTFMCEYADE TATIVEFLNR             120
WITFIQSIIS TLT                                                               133

SEQ ID NO: 145          moltype = AA   length = 133
FEATURE                 Location/Qualifiers
REGION                  1..133
                        note = IL-2 D20T/S125I variant sequence
source                  1..133
                        mol_type = protein
                        organism = synthetic construct
SEQUENCE: 145
APTSSSTKKT QLQLEHLLLT LQMILNGINN YKNPKLTRML TFKFYMPKKA TELKHLQCLE              60
EELKPLEEVL NLAQSKNFHL RPRDLISNIN VIVLELKGSE TTFMCEYADE TATIVEFLNR             120
WITFIQSIIS TLT                                                               133

SEQ ID NO: 146          moltype = AA   length = 133
FEATURE                 Location/Qualifiers
REGION                  1..133
                        note = IL-2 L19Y/S125I/Q126E variant sequence
source                  1..133
                        mol_type = protein
                        organism = synthetic construct
SEQUENCE: 146
APTSSSTKKT QLQLEHLLYD LQMILNGINN YKNPKLTRML TFKFYMPKKA TELKHLQCLE              60
EELKPLEEVL NLAQSKNFHL RPRDLISNIN VIVLELKGSE TTFMCEYADE TATIVEFLNR             120
WITFIESIIS TLT                                                               133

SEQ ID NO: 147          moltype = AA   length = 367
FEATURE                 Location/Qualifiers
REGION                  1..367
                        note = P-0423
source                  1..367
                        mol_type = protein
                        organism = synthetic construct
SEQUENCE: 147
DKTHTCPPCP APEAAGAPSV FLFPPKPKDT LMISRTPEVT CVVVDVSHED PEVKFNWYVD              60
GVEVHNAKTK PREEQYNSTY RVVSVLTVLH QDWLNGKEYK CKVSNKALPA PIEKTISKAK             120
GQPREPQVYT LPPSRDELTK NQVSLTCLVK GFYPSDIAVE WESNGQPENN YKTTPPVLDS             180
DGSFFLYSKL TVDKSRWQQG NVFSCSVMHE ALHNHYTQKS LSLSPGGGGS GGGSAPTSSS             240
TKKTQLQLEH LLQDLQMILN GINNYKNPKL TRMLTFKFYM PKKATELKHL QCLEEELKPL             300
EEVLNLAQSK NFHLRPRDLI SNINVIVLEL KGSETTFMCE YADETATIVE FLNRWITFSQ             360
SIISTLT                                                                      367

SEQ ID NO: 148          moltype = AA   length = 367
FEATURE                 Location/Qualifiers
REGION                  1..367
                        note = P-0424
source                  1..367
                        mol_type = protein
                        organism = synthetic construct
SEQUENCE: 148
DKTHTCPPCP APEAAGAPSV FLFPPKPKDT LMISRTPEVT CVVVDVSHED PEVKFNWYVD              60
GVEVHNAKTK PREEQYNSTY RVVSVLTVLH QDWLNGKEYK CKVSNKALPA PIEKTISKAK             120
GQPREPQVYT LPPSRDELTK NQVSLTCLVK GFYPSDIAVE WESNGQPENN YKTTPPVLDS             180
DGSFFLYSKL TVDKSRWQQG NVFSCSVMHE ALHNHYTQKS LSLSPGGGGS GGGSAPTSSS             240
TKKTQLQLEH LLHDLQMILN GINNYKNPKL TRMLTFKFYM PKKATELKHL QCLEEELKPL             300
EEVLNLAQSK NFHLRPRDLI SNINVIVLEL KGSETTFMCE YADETATIVE FLNRWITFSQ             360
SIISTLT                                                                      367

SEQ ID NO: 149          moltype = AA   length = 367
FEATURE                 Location/Qualifiers
REGION                  1..367
                        note = P-0425
source                  1..367
                        mol_type = protein
                        organism = synthetic construct
SEQUENCE: 149
DKTHTCPPCP APEAAGAPSV FLFPPKPKDT LMISRTPEVT CVVVDVSHED PEVKFNWYVD              60
```

```
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLDDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSQ   360
SIISTLT                                                             367

SEQ ID NO: 150          moltype = AA  length = 367
FEATURE                 Location/Qualifiers
REGION                  1..367
                        note = P-0426
source                  1..367
                        mol_type = protein
                        organism = synthetic construct
SEQUENCE: 150
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLPDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSQ   360
SIISTLT                                                             367

SEQ ID NO: 151          moltype = AA  length = 367
FEATURE                 Location/Qualifiers
REGION                  1..367
                        note = P-0427
source                  1..367
                        mol_type = protein
                        organism = synthetic construct
SEQUENCE: 151
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLSDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSQ   360
SIISTLT                                                             367

SEQ ID NO: 152          moltype = AA  length = 367
FEATURE                 Location/Qualifiers
REGION                  1..367
                        note = P-0428
source                  1..367
                        mol_type = protein
                        organism = synthetic construct
SEQUENCE: 152
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLDSQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSQ   360
SIISTLT                                                             367

SEQ ID NO: 153          moltype = AA  length = 367
FEATURE                 Location/Qualifiers
REGION                  1..367
                        note = P-0429
source                  1..367
                        mol_type = protein
                        organism = synthetic construct
SEQUENCE: 153
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLDNQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSQ   360
SIISTLT                                                             367

SEQ ID NO: 154          moltype = AA  length = 367
FEATURE                 Location/Qualifiers
REGION                  1..367
                        note = P-0430
source                  1..367
                        mol_type = protein
                        organism = synthetic construct
SEQUENCE: 154
```

```
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLDRQMILN GINNYKNPKL TRMLTFKFYM PKKATELKHL QCLEEELKPL   300
EEVLNLAQSK NFHLRPRDLI SNINIVLEL  KGSETTFMCE YADETATIVE FLNRWITFSQ   360
SIISTLT                                                            367

SEQ ID NO: 155           moltype = AA  length = 367
FEATURE                  Location/Qualifiers
REGION                   1..367
                         note = P-0497
source                   1..367
                         mol_type = protein
                         organism = synthetic construct
SEQUENCE: 155
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLDLQMILN GINNYKNPKL TRMLTFKFYM PKKATELKHL QCLEEELKPL   300
EEVLNLAQSK NFHLRPRDLI SNINIVLEL  KGSETTFMCE YADETATIVE FLNRWITFSK   360
SIISTLT                                                            367

SEQ ID NO: 156           moltype = AA  length = 367
FEATURE                  Location/Qualifiers
REGION                   1..367
                         note = P-0498
source                   1..367
                         mol_type = protein
                         organism = synthetic construct
SEQUENCE: 156
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLDLQMILN GINNYKNPKL TRMLTFKFYM PKKATELKHL QCLEEELKPL   300
EEVLNLAQSK NFHLRPRDLI SNINIVLEL  KGSETTFMCE YADETATIVE FLNRWITFSH   360
SIISTLT                                                            367

SEQ ID NO: 157           moltype = AA  length = 367
FEATURE                  Location/Qualifiers
REGION                   1..367
                         note = P-0499
source                   1..367
                         mol_type = protein
                         organism = synthetic construct
SEQUENCE: 157
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLDLQMILN GINNYKNPKL TRMLTFKFYM PKKATELKHL QCLEEELKPL   300
EEVLNLAQSK NFHLRPRDLI SNINIVLEL  KGSETTFMCE YADETATIVE FLNRWITFSY   360
SIISTLT                                                            367

SEQ ID NO: 158           moltype = AA  length = 367
FEATURE                  Location/Qualifiers
REGION                   1..367
                         note = P-0500
source                   1..367
                         mol_type = protein
                         organism = synthetic construct
SEQUENCE: 158
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLDLQMILN GINNYKNPKL TRMLTFKFYM PKKATELKHL QCLEEELKPL   300
EEVLNLAQSK NFHLRPRDLI SNINIVLEL  KGSETTFMCE YADETATIVE FLNRWITFEQ   360
SIISTLT                                                            367

SEQ ID NO: 159           moltype = AA  length = 367
FEATURE                  Location/Qualifiers
REGION                   1..367
                         note = P-0501
source                   1..367
                         mol_type = protein
                         organism = synthetic construct
```

```
SEQUENCE: 159
DKTHTCPPCP APEAAGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGSAPTSSS  240
TKKTQLQLEH LLLDLQMILN GINNYKNPKL TRMLTFKFYM PKKATELKHL QCLEEELKPL  300
EEVLNLAQSK NFHLRPRDLI SNINVIVLEL KGSETTFMCE YADETATIVE FLNRWITFKQ  360
SIISTLT                                                            367

SEQ ID NO: 160         moltype = AA   length = 367
FEATURE                Location/Qualifiers
REGION                 1..367
                       note = P-0502
source                 1..367
                       mol_type = protein
                       organism = synthetic construct
SEQUENCE: 160
DKTHTCPPCP APEAAGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGSAPTSSS  240
TKKTQLQLEH LLLDLQMILN GINNYKNPKL TRMLTFKFYM PKKATELKHL QCLEEELKPL  300
EEVLNLAQSK NFHLRPRDLI SNINVIVLEL KGSETTFMCE YADETATIVE FLNRWITFHQ  360
SIISTLT                                                            367

SEQ ID NO: 161         moltype = AA   length = 367
FEATURE                Location/Qualifiers
REGION                 1..367
                       note = P-0503
source                 1..367
                       mol_type = protein
                       organism = synthetic construct
SEQUENCE: 161
DKTHTCPPCP APEAAGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGSAPTSSS  240
TKKTQLQLEH LLLDLQMILN GINNYKNPKL TRMLTFKFYM PKKATELKHL QCLEEELKPL  300
EEVLNLAQSK NFHLRPRDLI SNINVIVLEL KGSETTFMCE YADETATIVE FLNRWITFWQ  360
SIISTLT                                                            367

SEQ ID NO: 162         moltype = AA   length = 367
FEATURE                Location/Qualifiers
REGION                 1..367
                       note = P-0531
source                 1..367
                       mol_type = protein
                       organism = synthetic construct
SEQUENCE: 162
DKTHTCPPCP APEAAGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGSAPTSSS  240
TKKTQLQLEH LLLDLQMILN GINNYKNPKL TRMLTFKFYM PKKATELKHL QCLEEELKPL  300
EEVLNLAQSK NFHLRPRDLI SNINVIVLEL KGSETTFMCE YADETATIVE FLNRWITFIQ  360
SIISTLT                                                            367

SEQ ID NO: 163         moltype = AA   length = 367
FEATURE                Location/Qualifiers
REGION                 1..367
                       note = P-0505
source                 1..367
                       mol_type = protein
                       organism = synthetic construct
SEQUENCE: 163
DKTHTCPPCP APEAAGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGSAPTSSS  240
TKKTQLQLEH LLLDLNMILN GINNYKNPKL TRMLTFKFYM PKKATELKHL QCLEEELKPL  300
EEVLNLAQSK NFHLRPRDLI SNINVIVLEL KGSETTFMCE YADETATIVE FLNRWITFSQ  360
SIISTLT                                                            367

SEQ ID NO: 164         moltype = AA   length = 367
FEATURE                Location/Qualifiers
REGION                 1..367
                       note = P-0506
source                 1..367
                       mol_type = protein
```

```
                    organism = synthetic construct
SEQUENCE: 164
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLDLHMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSQ   360
SIISTLT                                                            367

SEQ ID NO: 165          moltype = AA  length = 367
FEATURE                 Location/Qualifiers
REGION                  1..367
                        note = P-0507
source                  1..367
                        mol_type = protein
                        organism = synthetic construct
SEQUENCE: 165
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLDLKMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSQ   360
SIISTLT                                                            367

SEQ ID NO: 166          moltype = AA  length = 367
FEATURE                 Location/Qualifiers
REGION                  1..367
                        note = P-0508
source                  1..367
                        mol_type = protein
                        organism = synthetic construct
SEQUENCE: 166
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLDLYMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSQ   360
SIISTLT                                                            367

SEQ ID NO: 167          moltype = AA  length = 367
FEATURE                 Location/Qualifiers
REGION                  1..367
                        note = P-0509
source                  1..367
                        mol_type = protein
                        organism = synthetic construct
SEQUENCE: 167
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLDLIMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSQ   360
SIISTLT                                                            367

SEQ ID NO: 168          moltype = AA  length = 367
FEATURE                 Location/Qualifiers
REGION                  1..367
                        note = P-0447
source                  1..367
                        mol_type = protein
                        organism = synthetic construct
SEQUENCE: 168
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLHDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSE   360
SIISTLT                                                            367

SEQ ID NO: 169          moltype = AA  length = 367
FEATURE                 Location/Qualifiers
REGION                  1..367
                        note = P-0448
source                  1..367
```

-continued

```
                        mol_type = protein
                        organism = synthetic construct
SEQUENCE: 169
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLQDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSE   360
SIISTLT                                                             367

SEQ ID NO: 170          moltype = AA  length = 367
FEATURE                 Location/Qualifiers
REGION                  1..367
                        note = P-0449
source                  1..367
                        mol_type = protein
                        organism = synthetic construct
SEQUENCE: 170
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLSDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSE   360
SIISTLT                                                             367

SEQ ID NO: 171          moltype = AA  length = 367
FEATURE                 Location/Qualifiers
REGION                  1..367
                        note = P-0464
source                  1..367
                        mol_type = protein
                        organism = synthetic construct
SEQUENCE: 171
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLYDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSK   360
SIISTLT                                                             367

SEQ ID NO: 172          moltype = AA  length = 367
FEATURE                 Location/Qualifiers
REGION                  1..367
                        note = P-0465
source                  1..367
                        mol_type = protein
                        organism = synthetic construct
SEQUENCE: 172
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLYDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSH   360
SIISTLT                                                             367

SEQ ID NO: 173          moltype = AA  length = 367
FEATURE                 Location/Qualifiers
REGION                  1..367
                        note = P-0466
source                  1..367
                        mol_type = protein
                        organism = synthetic construct
SEQUENCE: 173
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLYDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSY   360
SIISTLT                                                             367

SEQ ID NO: 174          moltype = AA  length = 367
FEATURE                 Location/Qualifiers
REGION                  1..367
                        note = P-0467
```

```
source                  1..367
                        mol_type = protein
                        organism = synthetic construct
SEQUENCE: 174
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLYDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFEQ   360
SIISTLT                                                            367

SEQ ID NO: 175          moltype = AA   length = 367
FEATURE                 Location/Qualifiers
REGION                  1..367
                        note = P-0468
source                  1..367
                        mol_type = protein
                        organism = synthetic construct
SEQUENCE: 175
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLYDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFKQ   360
SIISTLT                                                            367

SEQ ID NO: 176          moltype = AA   length = 367
FEATURE                 Location/Qualifiers
REGION                  1..367
                        note = P-0469
source                  1..367
                        mol_type = protein
                        organism = synthetic construct
SEQUENCE: 176
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLYDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFHQ   360
SIISTLT                                                            367

SEQ ID NO: 177          moltype = AA   length = 367
FEATURE                 Location/Qualifiers
REGION                  1..367
                        note = P-0470
source                  1..367
                        mol_type = protein
                        organism = synthetic construct
SEQUENCE: 177
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLYDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFWQ   360
SIISTLT                                                            367

SEQ ID NO: 178          moltype = AA   length = 367
FEATURE                 Location/Qualifiers
REGION                  1..367
                        note = P-0471
source                  1..367
                        mol_type = protein
                        organism = synthetic construct
SEQUENCE: 178
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLYDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFIQ   360
SIISTLT                                                            367

SEQ ID NO: 179          moltype = AA   length = 367
FEATURE                 Location/Qualifiers
REGION                  1..367
```

```
                        note = P-0472
source                  1..367
                        mol_type = protein
                        organism = synthetic construct
SEQUENCE: 179
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLYDLNMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSQ   360
SIISTLT                                                             367

SEQ ID NO: 180          moltype = AA  length = 367
FEATURE                 Location/Qualifiers
REGION                  1..367
                        note = P-0473
source                  1..367
                        mol_type = protein
                        organism = synthetic construct
SEQUENCE: 180
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLYDLHMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSQ   360
SIISTLT                                                             367

SEQ ID NO: 181          moltype = AA  length = 367
FEATURE                 Location/Qualifiers
REGION                  1..367
                        note = P-0474
source                  1..367
                        mol_type = protein
                        organism = synthetic construct
SEQUENCE: 181
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLYDLKMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSQ   360
SIISTLT                                                             367

SEQ ID NO: 182          moltype = AA  length = 367
FEATURE                 Location/Qualifiers
REGION                  1..367
                        note = P-0475
source                  1..367
                        mol_type = protein
                        organism = synthetic construct
SEQUENCE: 182
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLYDLYMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSQ   360
SIISTLT                                                             367

SEQ ID NO: 183          moltype = AA  length = 367
FEATURE                 Location/Qualifiers
REGION                  1..367
                        note = P-0476
source                  1..367
                        mol_type = protein
                        organism = synthetic construct
SEQUENCE: 183
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLYDLIMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSQ   360
SIISTLT                                                             367

SEQ ID NO: 184          moltype = AA  length = 367
FEATURE                 Location/Qualifiers
```

```
REGION                   1..367
                         note = P-0480
source                   1..367
                         mol_type = protein
                         organism = synthetic construct
SEQUENCE: 184
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLHDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFSK   360
SIISTLT                                                             367

SEQ ID NO: 185           moltype = AA  length = 367
FEATURE                  Location/Qualifiers
REGION                   1..367
                         note = P-0491
source                   1..367
                         mol_type = protein
                         organism = synthetic construct
SEQUENCE: 185
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLHDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFIQ   360
SIISTLT                                                             367

SEQ ID NO: 186           moltype = AA  length = 367
FEATURE                  Location/Qualifiers
REGION                   1..367
                         note = P-0492
source                   1..367
                         mol_type = protein
                         organism = synthetic construct
SEQUENCE: 186
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLDDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFIQ   360
SIISTLT                                                             367

SEQ ID NO: 187           moltype = AA  length = 367
FEATURE                  Location/Qualifiers
REGION                   1..367
                         note = P-0493
source                   1..367
                         mol_type = protein
                         organism = synthetic construct
SEQUENCE: 187
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLELQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFIQ   360
SIISTLT                                                             367

SEQ ID NO: 188           moltype = AA  length = 367
FEATURE                  Location/Qualifiers
REGION                   1..367
                         note = P-0494
source                   1..367
                         mol_type = protein
                         organism = synthetic construct
SEQUENCE: 188
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLTLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFIQ   360
SIISTLT                                                             367

SEQ ID NO: 189           moltype = AA  length = 367
```

```
FEATURE                 Location/Qualifiers
REGION                  1..367
                        note = P-0495
source                  1..367
                        mol_type = protein
                        organism = synthetic construct
SEQUENCE: 189
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLYDLQMILN GINNYKNPKL TRMLTFKFYM PKKATELKHL QCLEEELKPL   300
EEVLNLAQSK NFHLRPRDLI SNINIVIVLEL KGSETTFMCE YADETATIVE FLNRWITFIE   360
SIISTLT                                                              367

SEQ ID NO: 190          moltype = AA  length = 374
FEATURE                 Location/Qualifiers
REGION                  1..374
                        note = P-0496 (Benchmark-2)
source                  1..374
                        mol_type = protein
                        organism = synthetic construct
SEQUENCE: 190
APTSSSTKKT QLQLEHLLLD LQMILNGINN YKNPKLTRML TFKFYMPKKA TELKHLQCLE    60
EELKPLEEVL NLAQSKNFHL RPRDLISRIN VIVLELKGSE TTFMCEYADE TATIVEFLNR   120
WITFSQSIIS TLTGGGGSGG GGSGGGGSGG GGSCPPCPAP EAAGAPSVFL FPPKPKDTLM   180
ISRTPEVTCV VVDVSHEDPE VKFNWYVDGV EVHNAKTKPR EEQYNSTYRV VSVLTVLHQD   240
WLNGKEYKCK VSNKALPAPI EKTISKAKGQ PREPQVYTLP PSRDELTKNQ VSLTCLVKGF   300
YPSDIAVEWE SNGQPENNYK TTPPVLDSDG SFFLYSKLTV DKSRWQQGNV FSCSVMHEAL   360
HNHYTQKSLS LSPG                                                      374

SEQ ID NO: 191          moltype = AA  length = 367
FEATURE                 Location/Qualifiers
REGION                  1..367
                        note = Benchmark-1
source                  1..367
                        mol_type = protein
                        organism = synthetic construct
SEQUENCE: 191
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLLDLQMILN GINNYKNPKL TRMLTFKFYM PKKATELKHL QCLEEELKPL   300
EEVLNLAQSK NFHLRPRDLI SNINKIVLEL KGSETTFMCE YADETATIVE FLNRWITFSQ   360
SIISTLT                                                              367

SEQ ID NO: 192          moltype = AA  length = 367
FEATURE                 Location/Qualifiers
REGION                  1..367
                        note = Benchmark-3
source                  1..367
                        mol_type = protein
                        organism = synthetic construct
SEQUENCE: 192
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE LSLSPGGGGS GGGSAPTSSS               240
TKKTQLQLEH LLLDLQMILN GINNYKNPKL TRMLTFKFYM PKKATELKHL QCLEEELKPL   300
EEVLNLAQSK NFHLRPRDLI SDINVIVLEL KGSETTFMCE YADETATIVE FLNRWITFSQ   360
SIISTLT                                                              367

SEQ ID NO: 193          moltype = AA  length = 133
FEATURE                 Location/Qualifiers
REGION                  1..133
                        note = IL-2 L19H/S125I/Q126E variant sequence
source                  1..133
                        mol_type = protein
                        organism = synthetic construct
SEQUENCE: 193
APTSSSTKKT QLQLEHLLHD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFIESIIS TLT                                                       133

SEQ ID NO: 194          moltype = AA  length = 133
FEATURE                 Location/Qualifiers
REGION                  1..133
                        note = IL-2 L19H/S125I/Q126K variant sequence
```

```
                                          -continued source                    1..133
                          mol_type = protein
                          organism = synthetic construct
SEQUENCE: 194
APTSSSTKKT QLQLEHLLHD LQMILNGINN YKNPKLTRML TFKFYMPKKA TELKHLQCLE        60
EELKPLEEVL NLAQSKNFHL RPRDLISNIN VIVLELKGSE TTFMCEYADE TATIVEFLNR       120
WITFIKSIIS TLT                                                          133

SEQ ID NO: 195            moltype = AA   length = 133
FEATURE                   Location/Qualifiers
REGION                    1..133
                          note = IL-2 L19Q/Q126K variant sequence
source                    1..133
                          mol_type = protein
                          organism = synthetic construct
SEQUENCE: 195
APTSSSTKKT QLQLEHLLQD LQMILNGINN YKNPKLTRML TFKFYMPKKA TELKHLQCLE        60
EELKPLEEVL NLAQSKNFHL RPRDLISNIN VIVLELKGSE TTFMCEYADE TATIVEFLNR       120
WITFSKSIIS TLT                                                          133

SEQ ID NO: 196            moltype = AA   length = 133
FEATURE                   Location/Qualifiers
REGION                    1..133
                          note = IL-2 L19Q/S125I/Q126E variant sequence
source                    1..133
                          mol_type = protein
                          organism = synthetic construct
SEQUENCE: 196
APTSSSTKKT QLQLEHLLQD LQMILNGINN YKNPKLTRML TFKFYMPKKA TELKHLQCLE        60
EELKPLEEVL NLAQSKNFHL RPRDLISNIN VIVLELKGSE TTFMCEYADE TATIVEFLNR       120
WITFIESIIS TLT                                                          133

SEQ ID NO: 197            moltype = AA   length = 133
FEATURE                   Location/Qualifiers
REGION                    1..133
                          note = IL-2 L19Q/S125I/Q126K variant sequence
source                    1..133
                          mol_type = protein
                          organism = synthetic construct
SEQUENCE: 197
APTSSSTKKT QLQLEHLLQD LQMILNGINN YKNPKLTRML TFKFYMPKKA TELKHLQCLE        60
EELKPLEEVL NLAQSKNFHL RPRDLISNIN VIVLELKGSE TTFMCEYADE TATIVEFLNR       120
WITFIKSIIS TLT                                                          133

SEQ ID NO: 198            moltype = AA   length = 367
FEATURE                   Location/Qualifiers
REGION                    1..367
                          note = P-0511
source                    1..367
                          mol_type = protein
                          organism = synthetic construct
SEQUENCE: 198
DKTHTCPPCP APEAAGAPSV FLFPPKPKDT LMISRTPEVT CVVVDVSHED PEVKFNWYVD        60
GVEVHNAKTK PREEQYNSTY RVVSVLTVLH QDWLNGKEYK CKVSNKALPA PIEKTISKAK       120
GQPREPQVYT LPPSRDELTK NQVSLTCLVK GFYPSDIAVE WESNGQPENN YKTTPPVLDS       180
DGSFFLYSKL TVDKSRWQQG NVFSCSVMHE ALHNHYTQKS LSLSPGGGGS GGGSAPTSSS       240
TKKTQLQLEH LLHDLQMILN GINNYKNPKL TRMLTFKFYM PKKATELKHL QCLEEELKPL       300
EEVLNLAQSK NFHLRPRDLI SNINVIVLEL KGSETTFMCE YADETATIVE FLNRWITFIE       360
SIISTLT                                                                 367

SEQ ID NO: 199            moltype = AA   length = 367
FEATURE                   Location/Qualifiers
REGION                    1..367
                          note = P-0512
source                    1..367
                          mol_type = protein
                          organism = synthetic construct
SEQUENCE: 199
DKTHTCPPCP APEAAGAPSV FLFPPKPKDT LMISRTPEVT CVVVDVSHED PEVKFNWYVD        60
GVEVHNAKTK PREEQYNSTY RVVSVLTVLH QDWLNGKEYK CKVSNKALPA PIEKTISKAK       120
GQPREPQVYT LPPSRDELTK NQVSLTCLVK GFYPSDIAVE WESNGQPENN YKTTPPVLDS       180
DGSFFLYSKL TVDKSRWQQG NVFSCSVMHE ALHNHYTQKS LSLSPGGGGS GGGSAPTSSS       240
TKKTQLQLEH LLHDLQMILN GINNYKNPKL TRMLTFKFYM PKKATELKHL QCLEEELKPL       300
EEVLNLAQSK NFHLRPRDLI SNINVIVLEL KGSETTFMCE YADETATIVE FLNRWITFIK       360
SIISTLT                                                                 367

SEQ ID NO: 200            moltype = AA   length = 367
FEATURE                   Location/Qualifiers
REGION                    1..367
```

```
                    note = P-0513
source              1..367
                    mol_type = protein
                    organism = synthetic construct
SEQUENCE: 200
DKTHTCPPCP APEAAGAPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK 120
GQPREPQVYT LPPSRDELTK NQVSLTCLVK GFYPSDIAVE WESNGQPENN YKTTPPVLDS 180
DGSFFLYSKL TVDKSRWQQG NVFSCSVMHE ALHNHYTQKS LSLSPGGGGS GGGSAPTSSS 240
TKKTQLQLEH LLQDLQMILN GINNYKNPKL TRMLTFKFYM PKKATELKHL QCLEEELKPL 300
EEVLNLAQSK NFHLRPRDLI SNINVIVLEL KGSETTFMCE YADETATIVE FLNRWITFSK 360
SIISTLT                                                          367

SEQ ID NO: 201        moltype = AA  length = 367
FEATURE               Location/Qualifiers
REGION                1..367
                      note = P-0514
source                1..367
                      mol_type = protein
                      organism = synthetic construct
SEQUENCE: 201
DKTHTCPPCP APEAAGAPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK 120
GQPREPQVYT LPPSRDELTK NQVSLTCLVK GFYPSDIAVE WESNGQPENN YKTTPPVLDS 180
DGSFFLYSKL TVDKSRWQQG NVFSCSVMHE ALHNHYTQKS LSLSPGGGGS GGGSAPTSSS 240
TKKTQLQLEH LLQDLQMILN GINNYKNPKL TRMLTFKFYM PKKATELKHL QCLEEELKPL 300
EEVLNLAQSK NFHLRPRDLI SNINVIVLEL KGSETTFMCE YADETATIVE FLNRWITFIE 360
SIISTLT                                                          367

SEQ ID NO: 202        moltype = AA  length = 367
FEATURE               Location/Qualifiers
REGION                1..367
                      note = P-0515
source                1..367
                      mol_type = protein
                      organism = synthetic construct
SEQUENCE: 202
DKTHTCPPCP APEAAGAPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK 120
GQPREPQVYT LPPSRDELTK NQVSLTCLVK GFYPSDIAVE WESNGQPENN YKTTPPVLDS 180
DGSFFLYSKL TVDKSRWQQG NVFSCSVMHE ALHNHYTQKS LSLSPGGGGS GGGSAPTSSS 240
TKKTQLQLEH LLQDLQMILN GINNYKNPKL TRMLTFKFYM PKKATELKHL QCLEEELKPL 300
EEVLNLAQSK NFHLRPRDLI SNINVIVLEL KGSETTFMCE YADETATIVE FLNRWITFIK 360
SIISTLT                                                          367

SEQ ID NO: 203        moltype = AA  length = 367
FEATURE               Location/Qualifiers
REGION                1..367
                      note = P-0582
source                1..367
                      mol_type = protein
                      organism = synthetic construct
SEQUENCE: 203
DKTHTCPPCP APEAAGAPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK 120
GQPREPQVYT LPPSRDELTK NQVSLTCLVK GFYPSDIAVE WESNGQPENN YKTTPPVLDS 180
DGSFFLYSKL TVDKSRWQQG NVFSCSVMHE ALHNHYTQKS LSLSPGGGGS GGGSAPTSSS 240
TKKTQLQLEH LLLTLQMILN GINNYKNPKL TRMLTFKFYM PKKATELKHL QCLEEELKPL 300
EEVLNLAQSK NFHLRPRDLI SNINVIVLEL KGSETTFMCE YADETATIVE FLNRWITFIK 360
SIISTLT                                                          367

SEQ ID NO: 204        moltype = AA  length = 367
FEATURE               Location/Qualifiers
REGION                1..367
                      note = P-0583
source                1..367
                      mol_type = protein
                      organism = synthetic construct
SEQUENCE: 204
DKTHTCPPCP APEAAGAPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK 120
GQPREPQVYT LPPSRDELTK NQVSLTCLVK GFYPSDIAVE WESNGQPENN YKTTPPVLDS 180
DGSFFLYSKL TVDKSRWQQG NVFSCSVMHE ALHNHYTQKS LSLSPGGGGS GGGSAPTSSS 240
TKKTQLQLEH LLNDLQMILN GINNYKNPKL TRMLTFKFYM PKKATELKHL QCLEEELKPL 300
EEVLNLAQSK NFHLRPRDLI SNINVIVLEL KGSETTFMCE YADETATIVE FLNRWITFIK 360
SIISTLT                                                          367

SEQ ID NO: 205        moltype = AA  length = 367
FEATURE               Location/Qualifiers
```

```
REGION                     1..367
                           note = P-0584
source                     1..367
                           mol_type = protein
                           organism = synthetic construct
SEQUENCE: 205
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLRDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFIK   360
SIISTLT                                                             367

SEQ ID NO: 206             moltype = AA   length = 367
FEATURE                    Location/Qualifiers
REGION                     1..367
                           note = P-0585
source                     1..367
                           mol_type = protein
                           organism = synthetic construct
SEQUENCE: 206
DKTHTCPPCP APEAAGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSREEMTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLHDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFIE   360
SIISTLT                                                             367

SEQ ID NO: 207             moltype = AA   length = 367
FEATURE                    Location/Qualifiers
REGION                     1..367
                           note = P-0586
source                     1..367
                           mol_type = protein
                           organism = synthetic construct
SEQUENCE: 207
DKTHTCPPCP APEAAGGPSV FLFPPKPKDT LYITREPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSREEMTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGGS GGGSAPTSSS   240
TKKTQLQLEH LLHDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFIK   360
SIISTLT                                                             367

SEQ ID NO: 208             moltype = AA   length = 367
FEATURE                    Location/Qualifiers
REGION                     1..367
                           note = P-0616
source                     1..367
                           mol_type = protein
                           organism = synthetic construct
SEQUENCE: 208
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHAHYTQKS LSLSPGGGGS GGGSAPTSSS   240
TKKTQLQLEH LLHDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFIE   360
SIISTLT                                                             367

SEQ ID NO: 209             moltype = AA   length = 367
FEATURE                    Location/Qualifiers
REGION                     1..367
                           note = P-0672 Knob-Fc chain
source                     1..367
                           mol_type = protein
                           organism = synthetic construct
SEQUENCE: 209
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVCT LPPSREEMTK NQVSLWCLVK GFYPSDIAVE WESNGQPENN YKTTPPVLDS   180
DGSFFLYSKL TVDKSRWQQG NVFSCSVMHE ALHAHYTQKS LSLSPGGGGS GGGSAPTSSS   240
TKKTQLQLEH LLHDLQMILN GINNYKNPKL TRMLTFKFYM PKKATELKHL QCLEEELKPL   300
EEVLNLAQSK NFHLRPRDLI SNINVIVLEL KGSETTFMCE YADETATIVE FLNRWITFIE   360
SIISTLT                                                             367

SEQ ID NO: 210             moltype = AA   length = 374
```

```
FEATURE                 Location/Qualifiers
REGION                  1..374
                        note = P-0673 Knob-Fc chain
source                  1..374
                        mol_type = protein
                        organism = synthetic construct
SEQUENCE: 210
APTSSSTKKT QLQLEHLLHD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFIESIIS TLTGGGGSGG GGSGGGGSGG GGSCPPCPAP EAAGAPSVFL FPPKPKDTLM   180
ISRTPEVTCV VVDVSHEDPE VKFNWYVDGV EVHNAKTKPR EEQYNSTYRV VSVLTVLHQD   240
WLNGKEYKCK VSNKALPAPI EKTISKAKGQ PREPQVCTLP PSREEMTKNQ VSLWCLVKGF   300
YPSDIAVEWE SNGQPENNYK TTPPVLDSDG SFFLYSKLTV DKSRWQQGNV FSCSVMHEAL   360
HAHYTQKSLS LSPG                                                    374

SEQ ID NO: 211          moltype = AA   length = 374
FEATURE                 Location/Qualifiers
REGION                  1..374
                        note = P-0674
source                  1..374
                        mol_type = protein
                        organism = synthetic construct
SEQUENCE: 211
APTSSSTKKT QLQLEHLLHD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFIESIIS TLTGGGGSGG GGSGGGGSGG GGSCPPCPAP EAAGAPSVFL FPPKPKDTLM   180
ISRTPEVTCV VVDVSHEDPE VKFNWYVDGV EVHNAKTKPR EEQYNSTYRV VSVLTVLHQD   240
WLNGKEYKCK VSNKALPAPI EKTISKAKGQ PREPQVYTLP PSRDELTKNQ VSLTCLVKGF   300
YPSDIAVEWE SNGQPENNYK TTPPVLDSDG SFFLYSKLTV DKSRWQQGNV FSCSVMHEAL   360
HAHYTQKSLS LSPG                                                    374

SEQ ID NO: 212          moltype = AA   length = 226
FEATURE                 Location/Qualifiers
REGION                  1..226
                        note = Knob-Fc domain with extended in vivo half-life
source                  1..226
                        mol_type = protein
                        organism = synthetic construct
SEQUENCE: 212
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVCT LPPSREEMTK NQVSLWCLVK GFYPSDIAVE WESNGQPENN YKTTPPVLDS   180
DGSFFLYSKL TVDKSRWQQG NVFSCSVMHE ALHAHYTQKS LSLSPG                  226

SEQ ID NO: 213          moltype = AA   length = 226
FEATURE                 Location/Qualifiers
REGION                  1..226
                        note = Hole-Fc domain with extended in vivo half-life
source                  1..226
                        mol_type = protein
                        organism = synthetic construct
SEQUENCE: 213
DKTHTCPPCP APEAAGAPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPCREEMTK NQVSLSCAVK GFYPSDIAVE WESNGQPENN YKTTPPVLDS   180
DGSFFLVSKL TVDKSRWQQG NVFSCSVMHE ALHAHYTQKS LSLSPG                  226

SEQ ID NO: 214          moltype = DNA   length = 1158
FEATURE                 Location/Qualifiers
misc_feature            1..1158
                        note = P-0511
source                  1..1158
                        mol_type = other DNA
                        organism = synthetic construct
SEQUENCE: 214
atggagtttg ggctgagctg cttttttctt gtgctatttt aaaaggtgt ccagtgtgat     60
aagactcaca cttgccctcc atgcccagct ccagaggccg ctggcgctcc ttccgtcttt   120
ctgttcccac ctaagccaaa ggacactctc atgatctcaa ggacaccaga ggtcacatgc   180
gtcgtggtgg atgtgagcca cgaggaccca gaggtgaaat tcaactggta cgtggatgga   240
gtcgaggtcc acaacgccaa gacaaagcca agagaggaac agtacaattc cacatacaga   300
gtggtgtccg tgctgactgt gctgcatcaa gactggctga acggcaagga gtacaaatgc   360
aaggtcagca caaggccct cccagcccca atcgagaaga catttccaa ggccaagggg    420
cagcctaggg agccacaagt gtatactctg cctcctcta gggacgagct gacaaagaac   480
caagtgtctc tgacttgtct ggtgaagggc ttctacccta gcgacatcgc cgtggaatgg   540
gagtccaatg gacagccaga gaataactat aagactacac tccagtcct cgactccgac   600
ggaagcttct ttctgtactc caagctcact gtggataagt ctaggtggca acaaggcaac   660
gtcttcagct gtagcgtcat gcatgaggct ctccacaacc actacactca gaagtctctg   720
tctctgtccc ccgcggagg aggctccgga ggaggatccg ctcctacttc ctcctccact   780
aagaagacac agctccaact ggagcatctg ctccatgatc tgcagatgat tctgaacggc   840
```

```
attaacaact ataaaaatcc aaagctgact aggatgctga cttttaagtt ctacatgcca    900
aagaaagcca cagagctgaa acacctccag tgcctcgagg aagaactgaa gccactcgag    960
gaggtgctga acctcgccca gtccaagaat ttccatctga ggccaaggga tctgatcagc   1020
aacatcaacg tcattgtgct ggagctgaaa ggcagcgaga ctactttcat gtgcgagtac   1080
gccgatgaga cagctacaat cgtggagttc tcaataggg ggatcacatt catcgaaagc    1140
atcattagca cactgaca                                                 1158
```

| | | |
|---|---|---|
| SEQ ID NO: 215 | moltype = DNA length = 1158 | |
| FEATURE | Location/Qualifiers | |
| misc_feature | 1..1158 | |
| | note = P-0512 | |
| source | 1..1158 | |
| | mol_type = other DNA | |
| | organism = synthetic construct | |

```
SEQUENCE: 215
atggagtttg ggctgagctg gcttttttctt gtggctattt taaaaggtgt ccagtgtgat     60
aagactcaca cttgccctcc atgcccagct ccagaggccg ctggcgctcc ttccgtcttt    120
ctgttcccac ctaagccaaa ggacactctc atgatctcta ggacaccaga ggtcacatgc    180
gtcgtggtgg atgtgagcca cgaggaccca gaggtgaaat tcaactggta cgtggatgga    240
gtcgaggtcc acaacgccaa gacaaagcca agagaggaac agtacaattc cacatacaga    300
gtggtgtccg tgctgactgt gctgcatcaa gactggctga acggcaagga gtacaaatgc    360
aaggtcagca acaaggccct cccagccccc atcgagagaa caatttccaa ggccaaggc    420
cagcctaggg agccacaagt gtatactctg cctccttcta gggacgagct gacaaagaac    480
caagtgtctc tgacttgtct ggtgaagggc ttctacccta gcgacatcgc cgtggaatgg    540
gagtccaatg gacagccaga gaataactat aagactacac ctccagtcct cgactccgac    600
ggaagcttct ttctgtactc caagctcact gtggataagt ctaggtggca acaaggcaac    660
gtcttcagct gtagcgtcat gcatgaggct ctccacaacc actacactca gaagtctctg    720
tctctgtccc ccggcggagg aggctccgga ggaggatccg ctcctacttc ctcctccact    780
aagaagacac agctccaact ggagcatctg ctccatgatc tgcagatgat tctgaacgg    840
attaacaact ataaaatcc aaagctgact aggatgctga cttttaagtt ctacatgcca    900
aagaaagcca cagagctgaa acacctccag tgcctcgagg aagaactgaa gccactcgag    960
gaggtgctga acctcgccca gtccaagaat ttccatctga ggccaaggga tctgatcagc   1020
aacatcaacg tcattgtgct ggagctgaaa ggcagcgaga ctactttcat gtgcgagtac   1080
gccgatgaga cagctacaat cgtggagttc tcaataggg ggatcacatt catcaagagc    1140
atcattagca cactgaca                                                 1158
```

| | | |
|---|---|---|
| SEQ ID NO: 216 | moltype = DNA length = 1158 | |
| FEATURE | Location/Qualifiers | |
| misc_feature | 1..1158 | |
| | note = P-0514 | |
| source | 1..1158 | |
| | mol_type = other DNA | |
| | organism = synthetic construct | |

```
SEQUENCE: 216
atggagtttg ggctgagctg gcttttttctt gtggctattt taaaaggtgt ccagtgtgat     60
aagactcaca cttgccctcc atgcccagct ccagaggccg ctggcgctcc ttccgtcttt    120
ctgttcccac ctaagccaaa ggacactctc atgatctcta ggacaccaga ggtcacatgc    180
gtcgtggtgg atgtgagcca cgaggaccca gaggtgaaat tcaactggta cgtggatgga    240
gtcgaggtcc acaacgccaa gacaaagcca agagaggaac agtacaattc cacatacaga    300
gtggtgtccg tgctgactgt gctgcatcaa gactggctga acggcaagga gtacaaatgc    360
aaggtcagca acaaggccct cccagccccc atcgagagaa caatttccaa ggccaaggc    420
cagcctaggg agccacaagt gtatactctg cctccttcta gggacgagct gacaaagaac    480
caagtgtctc tgacttgtct ggtgaagggc ttctacccta gcgacatcgc cgtggaatgg    540
gagtccaatg gacagccaga gaataactat aagactacac ctccagtcct cgactccgac    600
ggaagcttct ttctgtactc caagctcact gtggataagt ctaggtggca acaaggcaac    660
gtcttcagct gtagcgtcat gcatgaggct ctccacaacc actacactca gaagtctctg    720
tctctgtccc ccggcggagg aggctccgga ggaggatccg ctcctacttc ctcctccact    780
aagaagacac agctccaact ggagcatctg ctccaggatc tgcagatgat tctgaacgg    840
attaacaact ataaaatcc aaagctgact aggatgctga cttttaagtt ctacatgcca    900
aagaaagcca cagagctgaa acacctccag tgcctcgagg aagaactgaa gccactcgag    960
gaggtgctga acctcgccca gtccaagaat ttccatctga ggccaaggga tctgatcagc   1020
aacatcaacg tcattgtgct ggagctgaaa ggcagcgaga ctactttcat gtgcgagtac   1080
gccgatgaga cagctacaat cgtggagttc tcaataggg ggatcacatt catcgaaagc    1140
atcattagca cactgaca                                                 1158
```

| | | |
|---|---|---|
| SEQ ID NO: 217 | moltype = DNA length = 1158 | |
| FEATURE | Location/Qualifiers | |
| misc_feature | 1..1158 | |
| | note = P-0582 | |
| source | 1..1158 | |
| | mol_type = other DNA | |
| | organism = synthetic construct | |

```
SEQUENCE: 217
atggagtttg ggctgagctg gcttttttctt gtggctattt taaaaggtgt ccagtgtgat     60
aagactcaca cttgccctcc atgcccagct ccagaggccg ctggcgctcc ttccgtcttt    120
ctgttcccac ctaagccaaa ggacactctc atgatctcta ggacaccaga ggtcacatgc    180
gtcgtggtgg atgtgagcca cgaggaccca gaggtgaaat tcaactggta cgtggatgga    240
gtcgaggtcc acaacgccaa gacaaagcca agagaggaac agtacaattc cacatacaga    300
gtggtgtccg tgctgactgt gctgcatcaa gactggctga acggcaagga gtacaaatgc    360
```

```
aaggtcagca acaaggccct cccagcccca atcgagaaga caatttccaa ggccaagggc  420
cagcctaggg agccacaagt gtatactctg cctccttcta gggacagagct gacaaagaac  480
caagtgtctc tgacttgtct ggtgaagggc ttctacccta gcgacatcgc cgtggaatgg  540
gagtccaatg gacagccaga gaataactat aagactacac ctccagtcct cgactccgac  600
ggaagcttct ttctgtactc caagctcact gtggataagt ctaggtggca acaaggcaac  660
gtcttcagct gtagcgtcat gcatgaggct ctccacaacc actacactca gaagtctctg  720
tctctgtccc ccggcggagg aggctccgga ggaggatccg ctcctacttc ctcctccact  780
aagaagacac agctccaact ggagcatctg ctcctgactc tgcagatgat tctgaacggc  840
attaacaact ataaaaatcc aaagctgact aggatgctga cttttaagtt ctacatgcca  900
aagaaagcca cagagctgaa acacctccag tgcctcgagg aagaactgaa gccactcgag  960
gaggtgctga acctcgccca gtccaagaat ttccatctga ggccaaggga tctgatcagc 1020
aacatcaacg tcattgtgct ggagctgaaa ggcagcgaga ctactttcat gtgcgagtac 1080
gccgatgaga cagctacaat cgtggagttc ctcaataggt ggatcacatt catcaagagc 1140
atcattagca cactgaca                                                1158

SEQ ID NO: 218           moltype = DNA   length = 1158
FEATURE                  Location/Qualifiers
misc_feature             1..1158
                         note = P-0583
source                   1..1158
                         mol_type = other DNA
                         organism = synthetic construct SEQUENCE: 218
atggagtttg ggctgagctg gcttttctt gtggctattt taaaaggtgt ccagtgtgat   60
aagactcaca cttgccctcc atgcccagct ccagaggccg ctggcgctcc ttccgtcttt  120
ctgttcccac ctaagccaaa ggacactctc atgatctcta ggacaccaga ggtcacatgc  180
gtcgtggtgg atgtgagcca cgaggaccca gaggtgaaat tcaactggta cgtggatgga  240
gtcgaggtcc acaacgccaa gacaaagcca agagaggaac agtacaattc cacatacaga  300
gtggtgtccg tgctgactgt gctgcatcaa gactggctga acggcaagga gtacaaatgc  360
aaggtcagca acaaggccct cccagcccca atcgagaaga caatttccaa ggccaagggc  420
cagcctaggg agccacaagt gtatactctg cctccttcta gggacgagct gacaaagaac  480
caagtgtctc tgacttgtct ggtgaagggc ttctacccta gcgacatcgc cgtggaatgg  540
gagtccaatg gacagccaga gaataactat aagactacac ctccagtcct cgactccgac  600
ggaagcttct ttctgtactc caagctcact gtggataagt ctaggtggca acaaggcaac  660
gtcttcagct gtagcgtcat gcatgaggct ctccacaacc actacactca gaagtctctg  720
tctctgtccc ccggcggagg aggctccgga ggaggatccg ctcctacttc ctcctccact  780
aagaagacac agctccaact ggagcatctg ctcaacgatc tgcagatgat tctgaacggc  840
attaacaact ataaaaatcc aaagctgact aggatgctga cttttaagtt ctacatgcca  900
aagaaagcca cagagctgaa acacctccag tgcctcgagg aagaactgaa gccactcgag  960
gaggtgctga acctcgccca gtccaagaat ttccatctga ggccaaggga tctgatcagc 1020
aacatcaacg tcattgtgct ggagctgaaa ggcagcgaga ctactttcat gtgcgagtac 1080
gccgatgaga cagctacaat cgtggagttc ctcaataggt ggatcacatt catcaagagc 1140
atcattagca cactgaca                                                1158

SEQ ID NO: 219           moltype = DNA   length = 1158
FEATURE                  Location/Qualifiers
misc_feature             1..1158
                         note = P-0584
source                   1..1158
                         mol_type = other DNA
                         organism = synthetic construct SEQUENCE: 219
atggagtttg ggctgagctg gcttttctt gtggctattt taaaaggtgt ccagtgtgat   60
aagactcaca cttgccctcc atgcccagct ccagaggccg ctggcgctcc ttccgtcttt  120
ctgttcccac ctaagccaaa ggacactctc atgatctcta ggacaccaga ggtcacatgc  180
gtcgtggtgg atgtgagcca cgaggaccca gaggtgaaat tcaactggta cgtggatgga  240
gtcgaggtcc acaacgccaa gacaaagcca agagaggaac agtacaattc cacatacaga  300
gtggtgtccg tgctgactgt gctgcatcaa gactggctga acggcaagga gtacaaatgc  360
aaggtcagca acaaggccct cccagcccca atcgagaaga caatttccaa ggccaagggc  420
cagcctaggg agccacaagt gtatactctg cctccttcta gggacgagct gacaaagaac  480
caagtgtctc tgacttgtct ggtgaagggc ttctacccta gcgacatcgc cgtggaatgg  540
gagtccaatg gacagccaga gaataactat aagactacac ctccagtcct cgactccgac  600
ggaagcttct ttctgtactc caagctcact gtggataagt ctaggtggca acaaggcaac  660
gtcttcagct gtagcgtcat gcatgaggct ctccacaacc actacactca gaagtctctg  720
tctctgtccc ccggcggagg aggctccgga ggaggatccg ctcctacttc ctcctccact  780
aagaagacac agctccaact ggagcatctg ctcaggatc tgcagatgat tctgaacggc  840
attaacaact ataaaaatcc aaagctgact aggatgctga cttttaagtt ctacatgcca  900
aagaaagcca cagagctgaa acacctccag tgcctcgagg aagaactgaa gccactcgag  960
gaggtgctga acctcgccca gtccaagaat ttccatctga ggccaaggga tctgatcagc 1020
aacatcaacg tcattgtgct ggagctgaaa ggcagcgaga ctactttcat gtgcgagtac 1080
gccgatgaga cagctacaat cgtggagttc ctcaataggt ggatcacatt catcaagagc 1140
atcattagca cactgaca                                                1158

SEQ ID NO: 220           moltype = DNA   length = 1158
FEATURE                  Location/Qualifiers
misc_feature             1..1158
                         note = P-0585
source                   1..1158
                         mol_type = other DNA
``` organism = synthetic construct
SEQUENCE: 220

```
atggagtttg ggctgagctg gcttttctt gtggctattt taaaaggtgt ccagtgtgat    60
aagactcaca cttgccctcc atgcccagct ccagaggccg ctggcggacc ttccgtcttt   120
ctgttcccac ctaagccaaa ggacactctc tacatcacaa gggaaccaga ggtcacatgc   180
gtcgtggtgg atgtgagcca cgaggaccca gaggtgaaat tcaactggta cgtggatgga   240
gtcgaggtcc acaacgccaa gacaaagcca agagaggaac agtacaattc cacatacaga   300
gtggtgtccg tgctgactgt gctgcatcaa gactggctga acggcaagga gtacaaatgc   360
aaggtcagca caaaggccct cccagcccca atcgagaaga caatttccaa ggccaagggc   420
cagcctaggg agccacaagt gtatactctg cctccttcta gggacgagct gacaaagaac   480
caagtgtctc tgacttgtct ggtgaagggc ttctacccta cgacatcgc cgtggaatgg   540
gagtccaatg gacagccaga gaataactat aagactacac ctccagtcct cgactccgac   600
ggaagcttct ttctgtactc caagctcact gtggataagt ctaggtggca caaggcaac   660
gtcttcagct gtagcgtcat gcatgaggct ctccacaacc actacactca gaagtctctg   720
tctctgtccc ccggcggagg aggctccgga ggaggatccg ctcctacttc ctcctccact   780
aagaagacac agctccaact ggagcatctg ctccatgatc tgcagatgat tctgaacggc   840
attaacaact ataaaaatcc aaagctgact aggatgctga cttttaagtt ctacatgcca   900
aagaaagcca cagagctgaa acacctccag tgcctcgagg aagaactgaa gccactcgag   960
gaggtgctga acctcgccca gtccaagaat ttccatctga ggccaaggga tctgatcagc  1020
aacatcaacg tcattgtgct ggagctgaaa ggcagcgaga ctactttcat gtgcgagtac  1080
gccgatgaga cagctacaat cgtggagttc ctcaataggt ggatcacatt catcgaaagc  1140
atcattagca cactgaca                                                1158
```

SEQ ID NO: 221        moltype = DNA   length = 1158
FEATURE              Location/Qualifiers
misc_feature        1..1158
                     note = P-0586
source                1..1158
                     mol_type = other DNA
                     organism = synthetic construct
SEQUENCE: 221

```
atggagtttg ggctgagctg gcttttctt gtggctattt taaaaggtgt ccagtgtgat    60
aagactcaca cttgccctcc atgcccagct ccagaggccg ctggcggacc ttccgtcttt   120
ctgttcccac ctaagccaaa ggacactctc tacatcacaa gggaaccaga ggtcacatgc   180
gtcgtggtgg atgtgagcca cgaggaccca gaggtgaaat tcaactggta cgtggatgga   240
gtcgaggtcc acaacgccaa gacaaagcca agagaggaac agtacaattc cacatacaga   300
gtggtgtccg tgctgactgt gctgcatcaa gactggctga acggcaagga gtacaaatgc   360
aaggtcagca caaaggccct cccagcccca atcgagaaga caatttccaa ggccaagggc   420
cagcctaggg agccacaagt gtatactctg cctccttcta gggacgagct gacaaagaac   480
caagtgtctc tgacttgtct ggtgaagggc ttctacccta cgacatcgc cgtggaatgg   540
gagtccaatg gacagccaga gaataactat aagactacac ctccagtcct cgactccgac   600
ggaagcttct ttctgtactc caagctcact gtggataagt ctaggtggca caaggcaac   660
gtcttcagct gtagcgtcat gcatgaggct ctccacaacc actacactca gaagtctctg   720
tctctgtccc ccggcggagg aggctccgga ggaggatccg ctcctacttc ctcctccact   780
aagaagacac agctccaact ggagcatctg ctccatgatc tgcagatgat tctgaacggc   840
attaacaact ataaaaatcc aaagctgact aggatgctga cttttaagtt ctacatgcca   900
aagaaagcca cagagctgaa acacctccag tgcctcgagg aagaactgaa gccactcgag   960
gaggtgctga acctcgccca gtccaagaat ttccatctga ggccaaggga tctgatcagc  1020
aacatcaacg tcattgtgct ggagctgaaa ggcagcgaga ctactttcat gtgcgagtac  1080
gccgatgaga cagctacaat cgtggagttc ctcaataggt ggatcacatt catcaagagc  1140
atcattagca cactgaca                                                1158
```

SEQ ID NO: 222        moltype = DNA   length = 1158
FEATURE              Location/Qualifiers
misc_feature        1..1158
                     note = P-0616
source                1..1158
                     mol_type = other DNA
                     organism = synthetic construct
SEQUENCE: 222

```
atggagtttg ggctgagctg gcttttctt gtggctattt taaaaggtgt ccagtgtgat    60
aagactcaca cttgccctcc atgcccagct ccagaggccg ctggcgctcc ttccgtcttt   120
ctgttcccac ctaagccaaa ggacactctc atgatctcta ggacaccaga ggtcacatgc   180
gtcgtggtgg atgtgagcca cgaggaccca gaggtgaaat tcaactggta cgtggatgga   240
gtcgaggtcc acaacgccaa gacaaagcca agagaggaac agtacaattc cacatacaga   300
gtggtgtccg tgctgactgt gctgcatcaa gactggctga acggcaagga gtacaaatgc   360
aaggtcagca caaaggccct cccagcccca atcgagaaga caatttccaa ggccaagggc   420
cagcctaggg agccacaagt gtatactctg cctccttcta gggacgagct gacaaagaac   480
caagtgtctc tgacttgtct ggtgaagggc ttctacccta cgacatcgc cgtggaatgg   540
gagtccaatg gacagccaga gaataactat aagactacac ctccagtcct cgactccgac   600
ggaagcttct ttctgtactc caagctcact gtggataagt ctaggtggca caaggcaac   660
gtcttcagct gtagcgtcat gcatgaggct ctccacgctc actacactca gaagtctctg   720
tctctgtccc ccggcggagg aggctccgga ggaggatccg ctcctacttc ctcctccact   780
aagaagacac agctccaact ggagcatctg ctccatgatc tgcagatgat tctgaacggc   840
```

-continued

```
attaacaact ataaaaatcc aaagctgact aggatgctga cttttaagtt ctacatgcca  900
aagaaagcca cagagctgaa acacctccag tgcctcgagg aagaactgaa gccactcgag  960
gaggtgctga acctcgccca gtccaagaat ttccatctga ggccaaggga tctgatcagc  1020
aacatcaacg tcattgtgct ggagctgaaa ggcagcgaga ctactttcat gtgcgagtac  1080
gccgatgaga cagctacaat cgtggagttc ctcaataggt ggatcacatt catcgaaagc  1140
atcattagca cactgaca                                                1158
```

INTERLEUKIN-2 VARIANTS AND METHODS OF USES THEREOF

RELATED PATENT APPLICATIONS

This application is a Continuation Application of U.S. application Ser. No. 17/254,098, filed Dec. 18, 2020, which is a U.S. National Stage Application pursuant to 35 U.S.C. § 371 of PCT/US2019/038248, filed Jun. 20, 2019, which claims benefit of U.S. Provisional Application No. 62/755,016, filed on Nov. 2, 2018, and U.S. Provisional Application No. 62/689,055, filed on Jun. 22, 2018, each incorporated in its entirety by reference herein.

REFERENCE TO AN ELECTRONIC SEQUENCE LISTING

The contents of the electronic sequence listing (CUGENE IL-2-AUTO.xml; Size: 325 Kilobytes; Date of Initial Creation: Jul. 17, 2023; Production Date: Jul. 20, 2023) is herein incorporated by reference in its entirety.

BACKGROUND ART

Interleukin 2 (IL-2) was the first growth factor described for T cells. Since its discovery it has been shown to promote proliferation and survival of T cells in vitro (Smith, K A. (1988) Science. 240, 1169-76) and the ability to boost immune response in the context of T viral infections (Blattman, J N, et al. (2003) Nat Med 9, 540-7) or vaccines (Fishman, M., et al. (2008) J Immunother. 31, 72-80, Kudo-Saito, C., et al. (2007) Cancer Immunol Immunother. 56, 1897-910; Lin, C T., et al. (2007) Immunol Lett. 114, 86-93).

IL-2 has been used in cancer therapy. Recombinant human IL-2 is an effective immunotherapy for metastatic melanoma and renal cancer, with durable responses in approximately 10% of patients. However short half-life and severe toxicity limits the optimal dosing of IL-2. Further, IL-2 also binds to its heterotrimeric receptor IL-2Rαβγ with greater affinity, which preferentially expands immunosuppressive regulatory T cells (Tregs) expressing high constitutive levels of IL-2Rα. Expansion of Tregs represents an undesirable effect of IL-2 for cancer immunotherapy. However, the capability of IL-2 to stimulate Treg cells even at low doses could be harnessed for the treatment of autoimmune and various inflammatory disorders.

Treg are central to immune system homeostasis and play a major role in maintaining peripheral immune tolerance by dampening (autoreactive) effector T cells. Multiple autoimmune and inflammatory diseases have been shown to have a deficiency of Treg cell numbers or Treg function. Consequently, there is great interest in the development of therapies that boost the numbers and/or function of Treg cells. One treatment approach for autoimmune diseases being investigated is employing low dose IL-2 to target Treg cells, because Treg cells respond to lower concentrations of IL-2 than many other immune cell types due to their high constitutive levels of IL-2Rα. (Klatzmann D, 2015 Nat Rev Immunol. 15:283-94). Clinical trials of low-dose IL-2 treatment of various GvHD (Koreth, J., et at., 2011, N Engl J Med., 365:2055-66) and HCV-associated autoimmune vasculitis patients (Saadoum, D., et al., 2011, N Engl J Med., 365:2067-77) have demonstrated increased Treg levels and signs of clinical efficacy. However, even these lower doses resulted in severe safety and tolerability issues. Therefore, there is need for an effective autoimmune/inflammatory disease therapy that can potentiate Treg cell numbers and function, that targets Treg cells more specifically than IL-2.

More recently, it was found that IL-2 could be modified to selectively stimulate either cytotoxic effector T cells or Treg cells. Various approaches have led to the generation of IL-2 variants with improved and selective immune stimulatory capacities (see, e.g., U.S. Pat. Nos. 7,186,804, 7,105,653, 6,955,807, 5,229,109, U.S. patent application No. 20050142106). In the current invention, IL-2 variants were designed to increase the capacity of this molecule to signal mainly by the high affinity receptor (alpha, beta and gamma chains) and not by the intermediate affinity receptor (beta and gamma chains). The basic idea was to promote signaling in Treg cells instead of signaling in effector T and NK cells, which were believed to be responsible for the observed toxic effects. Importantly, none of the prior art disclosures relates to variants of IL-2 that have greater therapeutic efficacy than the native IL-2 in vivo, based on their decreased ability to stimulate natural regulatory T cells. However, since the initial studies of the IL-2 variants, research in the field more fully established that Treg cells constitutively express high IL-2Rα (CD25) along with IL-2Rβ and γ_C, IL-2 variants as IL-2Rαβγ selective agonists should be selective for Treg cells.

In summary, IL-2 is a highly pleiotropic cytokine which is very relevant in the biological activity of different cell populations. This property makes the IL-2 an important node in the regulation of the immune response, making it an attractive target for therapies and complex immune modulation. Further, receptor subunit-biased IL-2 variants can be made to achieve IL-2 mediated selective immune modulation to promote the expansion and activity of regulatory T-cells (Treg) while minimizing helper and cytotoxic T effector (Teff) cells and led to lower levels of pro-inflammatory signaling molecules.

DISCLOSURE OF THE INVENTION

In one aspect, the present invention relates to the production of mutated variants of IL-2. These variants are characterized by their enhanced selectivity in stimulating Treg (T CD4+CD25+FoxP3+) cells over conventional CD4+ T cells, cytotoxic effective CD8+ T lymphocytes, and NK cells. Specifically, these variants will provide a practical solution to improve IL-2 therapy in autoimmune and inflammatory disorders. The present invention relates to polypeptide which share their primary sequence with the human IL-2, except for one to several amino acids that have been mutated. These variants have amino acid substitutions at positions corresponding to IL-2 interaction with IL-2Rβ and/or γ_C, and consequently these variants have reduced affinity for the IL-2Rβγ receptor complex and reduced or abolished ability to activate IL-2Rβγ-expressing cells but retain the ability to bind IL-2Rα and the ability to bind and activate the IL-2Rαβγ receptor complex. The present invention also includes therapeutic uses of these mutated variants for the treatment of autoimmune as well as various inflammatory disorders.

In one aspect, the present invention relates to the production of mutated variants of IL-2. These variants possess a combination of attributes with Treg-selective activity, reduced aggregation, increased expression, improved manufacturability and developability. These variants also provide improved protein biophysical properties and reduced immunogenic risk associated with IL-2 molecules. These variants provide a superior solution to improve IL-2 therapy and reduce toxicity in autoimmune and inflammatory disorders.

The present invention relates to polypeptide which share their primary sequence with the human IL-2, except for one to several amino acids that have been mutated.

In one aspect, the present invention relates to the production of mutated variants of IL-2, which are characterized by removing a proposed '$^{19}$LDL' motif resembling a component of bacterial toxins (Baluna R, Rizo et. al., Proc Natl Acad Sci 1999; 96:3957-62). This 'toxic motif' is responsible, in part, for direct vascular toxicity of IL-2. Mutations introduced to remove the critical residue, D20, or the flanking two residues of the toxin-like domain, are expected to eliminate the toxic motif and prevent endothelial cell damage and significantly reduce VLS. Significantly, as this motif is located at the interface with IL-2Rβ, the amino acid substitutions to this motif reduce their affinity for IL-2Rβ, and the resulting molecule would be expected to have two beneficial properties, including selectivity for activating Treg cells and reduced endothelial damage. The present invention relates to polypeptides which share their primary sequence with the human IL-2, except for one to several amino acids that have been mutated. The present invention also includes therapeutic uses of these mutated variants for therapy of Treg cell-deficient autoimmune and various inflammatory disorders.

The present invention allows for a substantial improvement of the current strategies of immunomodulation based on IL-2 in the therapy of autoimmune and various inflammatory disorders. Specifically, the replacement of the native IL-2 by the mutated variants described herein will result in CD25-biased selective stimulation of Treg cells. In various embodiments, the IL-2 variant (or mutant) comprises the sequence of the IL-2 variant (or mutant) derived from the sequence of the mature human IL-2 polypeptide as set forth in SEQ ID NO: 3. In various embodiments, the IL-2 variant functions as an IL-2 agonist. In various embodiments, the IL-2 variant functions as an IL-2 antagonist. In various embodiments, the IL-2 variants comprise the sequences set forth in SEQ ID NOS: 4-43, 108-146, and 193-197.

The present invention allows for a substantial improvement of the current strategies of immunomodulation based on IL-2 in the therapy of Treg cell-deficient autoimmune and various inflammatory disorders. Specifically, the replacement of the native IL-2 by the mutated variants described herein, will result in CD25-biased selective stimulation of Treg cells and is expected to eliminate the toxic motif and prevent endothelial cell damage and significantly reduce VLS. In various embodiments, the IL-2 variant (or mutant) comprises the sequence of the IL-2 variant (or mutant) derived from the sequence of the mature human IL-2 polypeptide as set forth in SEQ ID NO: 3. In various embodiments, the IL-2 variant functions as an IL-2 agonist. In various embodiments, the IL-2 variant functions as an IL-2 antagonist. In various embodiments, the IL-2 variants comprise SEQ ID NOS: 5-14, 26-43, 108-111, 125-146 and 193-197.

In another aspect, the IL-2 variants of the present invention are attached to at least one heterologous protein. In various embodiments, Il-2 variants are fused to at least one polypeptide that confers extended half-life on the fusion molecule. Such polypeptides include an IgG Fc or other polypeptides that bind to the neonatal Fcγ/receptor, human serum albumin, or polypeptides that bind to a protein having extended serum half-life, including IgGs, non-IgG immunoglobulin, proteins and non-protein agents, that have increased in vivo half-lives due to the presence of an IgG constant domain, or a portion thereof that binds the FcRn, having one or more amino acid modifications that increase the affinity of the constant domain or fragment for FcRn. Such proteins and molecules with increased half-lives have the advantage that smaller amounts and or less frequent dosing is required in the therapeutic, prophylactic or diagnostic use of such molecules (see, e.g., U.S. Pat. No. 7,658,921).

In various embodiments, the IL-2 variants can be linked to the N-terminus or the C-terminus of the heterologous protein.

In various embodiments, the IL-2 variant is fused to an IgG Fc molecule. In various embodiments, the Fc domain is a human IgG Fc domain. In various embodiments, the Fc domain is derived from the human IgG1 heavy chain constant domain sequence set forth in SEQ ID NO: 44. In various embodiments, the Fc domain is an Fc domain having the amino acid sequence set forth in SEQ ID NO: 45. In various embodiments, the Fc domain is an Fc domain having the amino acid sequence set forth in SEQ ID NO: 46. In various embodiments, the Fc domain is an Fc domain having the amino acid sequence set forth in SEQ ID NO: 47. In various embodiments, the Fc domain is derived from the human IgG2 heavy chain constant domain sequence. In various embodiments, the Fc domain is derived from the human IgG4 heavy chain constant domain sequence.

The term "Fc" refers to molecule or sequence comprising the sequence of a non-antigen-binding fragment of whole antibody, whether in monomeric or multimeric form. The original immunoglobulin source of the native Fc is preferably of human origin and may be any of the immunoglobulins disclosed in the art. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgA2). One example of a native Fc is a disulfide-bonded dimer resulting from papain digestion of an IgG (see Ellison et al. (1982), Nucleic Acids Res. 10:4071-9). The term "native Fc" as used herein is generic to the monomeric, dimeric, and multimeric forms. Fc domains containing binding sites for Protein A, Protein G, various Fc receptors and complement proteins.

In various embodiments, the term "Fc variant" refers to a molecule or sequence that is modified from a native Fc but still comprises a binding site for the salvage receptor, FcRn. International applications WO 97/34631 (published Sep. 25, 1997) and WO 96/32458 describe exemplary Fc variants, as well as interaction with the salvage receptor, and are hereby incorporated by reference. Furthermore, a native Fc comprises sites that may be removed because they provide structural features or biological activity that are not required for the fusion molecules of the present invention. Thus, in various embodiments, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by recombinant gene expression or by other means. In various embodiments, an "Fc domain" refers to a dimer of two Fc domain monomers (SEQ ID NO: 44) that generally includes full or part of the hinge region. In various embodiments, an Fc domain may be mutated to lack effector functions. In various embodiments, each of the Fc domain monomers in an Fc domain includes amino acid substitutions in the CH2 antibody constant domain to reduce the interaction or binding between the Fc domain and an Fcγ receptor. In various embodiments, each subunit of the Fc domain comprises two amino acid substitutions that reduce binding to an activating Fc receptor and/or effector function wherein said amino acid substitutions are L234A, L235A. In various embodiments, each subunit of the Fc domain comprises three amino acid substitutions that reduce binding to an activating Fc receptor and/or effector function wherein said amino acid substitutions are L234A, L235A and G237A (SEQ ID NO: 45).

In various embodiments, an Fc domain may be mutated to further extend in vivo half-life. In various embodiments, each subunit of the Fc domain comprises three amino acid substitutions that enhance binding to human FcRn wherein said amino acid substitutions are M252Y, S254T, and T256E, disclosed in U.S. Pat. Publication No. 7,658,921. In various embodiments, each subunit of the Fc domain comprises one amino acid substitution that enhanced binding to human FcRn wherein said amino acid substitution is N434A, disclosed in U.S. Pat. Publication No. 7,371,826. In various embodiments, each subunit of the Fc domain comprises one amino acid substitution that enhanced binding to human FcRn wherein said amino acid substitutions are M428L and N434S, disclosed in U.S. Pat. Publication No. 8,546,543. In various embodiments, half-life extension mutations can be combined with amino acid substitutions that reduce binding to an activating Fc receptor and/or effector function.

In various embodiments, each of the two Fc domain monomers in an Fc domain includes amino acid substitutions that promote the heterodimerization of the two monomers. In various other embodiments, heterodimerization of Fc domain monomers can be promoted by introducing different, but compatible, substitutions in the two Fc domain monomers, such as "knob-into-hole" residue pairs. The "knob-into-hole" technique is also disclosed in U.S. Pat. Publication No. 8,216,805. In yet another embodiment, one Fc domain monomer includes the knob mutation T366W and the other Fc domain monomer includes hole mutations T366S, L358A, and Y407V. In various embodiments, two Cys residues were introduced (S354C on the "knob" and Y349C on the "hole" side) that form a stabilizing disulfide bridge. The use of heterodimeric Fc may result in monovalent IL-2 variant construct.

In various embodiments, the IL-2 variant Fc-fusion protein will be monomeric, i.e., contain only a single IL-2 mutein molecule. In such embodiments, the fusion protein is co-expressed with a heterodimeric Knob-Fc linked to an IL-2 variant and the matching heterodimeric Hole Fc. When the heterodimer of the two Fc-containing polypeptides forms, the resulting protein comprises only a single IL-2 variant.

In various embodiments, the IL-2 variants are used to prepare the Fc-IL-2 fusion proteins set forth in SEQ ID NOS: 69-107, 147-189, and 198-208.

In various embodiments, the IL-2 variants of the present invention can be attached to an antibody that confers extended half-life on the fusion molecule, such as anti-keyhole limpet hemocyanin (KLH) antibody. Such an antibody recognizes a foreign antigen, confers longer half-life but have no biological function or harm in human. The IgG class could be IgG, IgA, IgE or subclass (e.g., IgG1, IgG2, IgG3, IgA1, IgA2).

In various embodiments, the heterologous protein is attached to the IL-2 variant by a linker and/or a hinge linker peptide. The linker or hinge linker may be an artificial sequence of between 5, 10, 15, 20, 30, 40 or more amino acids that are relatively free of secondary structure.

In various embodiments, the heterologous protein is attached to the IL-2 variant by a rigid linker peptide of between 10, 15, 20, 30, 40 or more amino acids that display α-helical conformation and may act as rigid spacers between protein domains.

In another aspect, IL-2 variant can be linked to various nonproteinaceous polymers, including, but not limited to, various polyols such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337. In various embodiments, amino acid substitutions may be made in various positions within the IL-2 variants to facilitate the addition of polymers such as PEG. In various embodiments, such PEGylated proteins may have increased half-life and/or reduced immunogenicity over the non-PEGylated proteins.

By "polyethylene glycol" or "PEG" is meant a polyalkylene glycol compound or a derivative thereof, with or without coupling agents or derivatization with coupling or activating moieties (e.g., with aldehyde, hydroxysuccinimidyl, hydrazide, thiol, triflate, tresylate, azirdine, oxirane, orthopyridyl disulphide, vinylsulfone, iodoacetamide or a maleimide moiety). In various embodiments, PEG includes substantially linear, straight chain PEG, branched PEG, or dendritic PEG. PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161).

In various embodiments, Il-2 variants can be linked non-covalently or covalently to an IgG Fc or other polypeptides that bind to the neonatal Fcγ/receptor, human serum albumin, or polypeptides that bind to a protein having extended serum half-life, or various nonproteinaceous polymers at either the N-terminus or C-terminus.

In another aspect, the present disclosure provides a pharmaceutical composition comprising the isolated IL-2 variants in admixture with a pharmaceutically acceptable carrier.

In another aspect, IL-2 variants can be formulated for slow release, such as covalently or non-covalently attached to hydrogels, nanoparticle, etc.

In another aspect, the present disclosure provides a method for treating an autoimmune disease in a subject, comprising administering a therapeutically effective amount of the pharmaceutical compositions of the invention to a subject in need thereof. In one embodiment, the subject is a human subject. An autoimmune disease, as pertains to the present invention, is a disease or disorder arising from and directed against an individual's own tissues or a co-segregate or manifestation thereof or resulting condition therefrom. In various embodiments, the autoimmune disease includes, but is not limited to, Graft Versus Host Disease (GvHD), Immune related adverse events (irAE), arthritis (including rheumatoid arthritis, reactive arthritis), systemic lupus erythematosus (SLE), atopic dermatitis, psoriasis and inflammatory bowel disease (IBD), encephalomyelitis, uveitis, myasthenia gravis, multiple sclerosis, insulin dependent diabetes (type 1 diabetes), various dermatitis, Addison's disease, celiac disease, chronic fatigue syndrome, autoimmune hepatitis, autoimmune alopecia, ankylosing spondylitis, ulcerative colitis, Crohn's disease, fibromyalgia, pemphigus vulgaris, Sjogren's syndrome, Kawasaki's Disease, hyperthyroidism/Graves disease, hypothyroidism/Hashimoto's disease, endometriosis, scleroderma, pernicious anemia, Goodpasture syndrome, Guillain-Barre syndrome, Wegener's disease, glomerulonephritis, aplastic anemia (including multiply transfused aplastic anemia patients), paroxysmal nocturnal hemoglobinuria, myelodysplastic syndrome, idiopathic thrombocytopenia purpura (IPT), autoimmune hemolytic anemia (AIHA), Evan's syndrome, Factor VIII inhibitor syndrome, systemic vasculitis, dermatomyositis, polymyositis and rheumatic fever, autoimmune lymphoproliferative syndrome (ALPS), autoimmune bullous pemphigoid, Parkinson's disease, sarcoidosis, vitiligo, primary biliary cirrhosis, and autoimmune myocarditis.

In another aspect, the present disclosure provides a method for treating an autoimmune disease in a subject, comprising administering a therapeutically effective amount of the pharmaceutical compositions of the invention in combination with a second therapeutic agent capable of treating an autoimmune disease.

In another aspect, the present disclosure provides a method for treating an inflammatory disease in a subject, comprising administering a therapeutically effective amount of the pharmaceutical compositions of the invention to a subject in need thereof. In one embodiment, the subject is a human subject. In various embodiments, the inflammatory disease to be treated includes, but is not limited to, Crohn's disease, colitis, dermatitis, psoriasis, diverticulitis, hepatitis, irritable bowel syndrome (IBS), lupus erythematous, nephritis, Parkinson's disease, ulcerative colitis, collagenous colitis, lymphocytic colitis, ischemic colitis, diversion colitis, Behcet's syndrome and indeterminate colitis multiple sclerosis (MS), Alzheimer's disease, arthritis, rheumatoid arthritis, asthma, and various cardiovascular diseases such as atherosclerosis and vasculitis. In various embodiments, the inflammatory disease is selected from the group consisting of rheumatoid arthritis, diabetes, gout, cryopyrin-associated periodic syndrome, and chronic obstructive pulmonary disorder.

In another aspect, the present disclosure provides a method for treating an inflammatory disease in a subject, comprising administering a therapeutically effective amount of the pharmaceutical compositions of the invention in combination with a second therapeutic agent capable of treating an inflammatory disease.

In another aspect, the present disclosure provides methods for organ transplantation or associated graft-versus-host diseasein a subject, comprising administering a therapeutically effective amount of the pharmaceutical compositions of the invention to a subject in need thereof. In one embodiment, the subject is a human subject. In various embodiments, the transplantation is selected from organ transplantations of the heart, kidneys, liver, lungs, pancreas, intestine and thymus or from tissues transplantations of the bones, tendons, cornea, skin, heart valves, nerves and veins.

In another aspect, the disclosure provides uses of the IL-2 variants for the preparation of a medicament for the treatment of an autoimmune disease.

In another aspect, the disclosure provides uses of the IL-2 variants for the preparation of a medicament for the treatment of organ transplantation and GvHD.

In another aspect, the disclosure provides uses of the IL-2 variants for the preparation of a medicament for the treatment of inflammatory disorders.

In another aspect, the present disclosure provides isolated nucleic acid molecules comprising a polynucleotide encoding an IL-2 variant of the present disclosure. In another aspect, the present disclosure provides vectors comprising the nucleic acids described herein. In various embodiments, the vector is an expression vector. In another aspect, the present disclosure provides isolated cells comprising the nucleic acids of the disclosure. In various embodiments, the cell is a host cell comprising the expression vector of the disclosure. In another aspect, methods of making the IL-2 variants are provided by culturing the host cells under conditions promoting expression of the proteins or polypeptides.

BRIEF DESCRIPTION OF THE FIGURES

FIGS. 1A-1E depicts size exclusion chromatogram of exemplary IL-2 Fc fusion proteins P-0250 (FIG. 1A), P-0318 (FIG. 1B), P-0317 (FIG. 1C), P-0447 (FIG. 1D), and P-0511 (FIG. 1E) after protein A purification. FIG. 1D (Lane 2) and FIG. 1E (Lane 3) also illustrate the SDS-PAGE of respective samples in the absence and presence of reducing agent.

FIGS. 2A-2B depicts differential effects of Fc fusion proteins of IL-2 variants with amino acid substitutions of aspartic acid at position 20 (D20X) on induction of STAT5 phosphorylation in CD4+ Treg (FIG. 2A) vs Tconv (FIG. 2B) cells in comparison with the wild type fusion protein (P-0250) in human PBMC assay.

FIGS. 3A-3B depicts differential effects of Fc fusion proteins of IL-2 variants P-0375 (N88Q) on induction of STAT5 phosphorylation in CD4+ Treg (FIG. 3A) vs Tconv (FIG. 3B) cells in comparison with the wild type (P-0250) and the benchmark proteins in human PBMC assay.

FIGS. 4A-4D depicts differential effects on STAT5 phosphorylation by Fc fusion proteins of IL-2 variants with amino acid substitutions at position 19 in comparison with the wild type (P-0250). The ability to induce STAT5 phosphorylation in CD4+ Treg (FIG. 4A and FIG. 4C) and Tconv (FIG. 4B and FIG. 4D) cells was determined in human PBMC assay by FACS analysis.

FIGS. 5A-5F depicts differential effects on STAT5 phosphorylation by Fc fusion proteins of IL-2 variants with individual amino acid substitution at either position 19 (P-0372) or position 126 (P-0303), or combination mutant (P-0419) in comparison with the wild type (P-0250) or the Benchmark-1 protein. The ability to induce STAT5 phosphorylation in CD4+ Treg (FIG. 5A, FIG. 5C, and FIG. 5E) and CD4+ Tconv (FIG. 5B, FIG. 5D & FIG. 5F) cells was determined by FACS analysis.

FIGS. 6A-6D depicts differential effects on STAT5 phosphorylation by Fc fusion proteins of IL-2 variants harboring different combination of dual amino acid substitutions (P-0419, P-0464, P-0471, P-0474, P-0417 and P-0322) in comparison with the wild type (P-0250). The biological activity of P-0417 and P-0322 was also compared to their counterparts with single amino acid substitution, P-0373 and P-0363, respectively. The ability to induce STAT5 phosphorylation in CD4+ Treg (FIG. 6A & FIG. 6C) and CD4+ Tconv (FIG. 6B & FIG. 6D) cells was determined in human PBMC assay by FACS analysis.

Figure 7A:
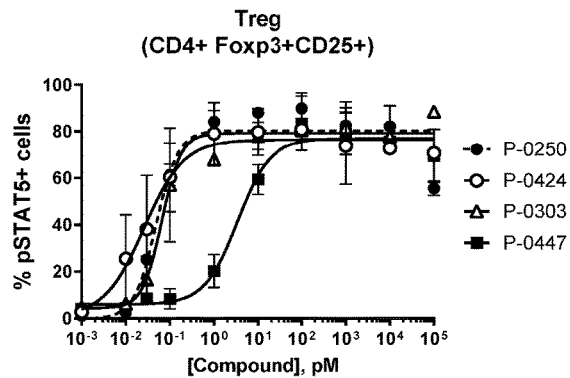
FIGS. 7A-7D depicts differential effects on STAT5 phosphorylation by Fc fusion proteins of IL-2 variants with individual amino acid substitution at either position 19

(P-0424) or position 126 (P-0303), or combination mutant (P-0447) in comparison with the wild type (P-0250), and differential effects on STAT5 phosphorylation by Fc fusion proteins of IL-2 variants harboring different combinational amino acid substitutions (P-0419, P-0447, P-0448, and P-0449) in comparison with the wild type (P-0250) and benchmark Fc fusion proteins. The ability to induce STAT5 phosphorylation in CD4+ Treg (FIG. 7A and FIG. 7C) and CD4+ Tconv (FIG. 7B and FIG. 7D) cells was determined in human PBMC assay by FACS analysis.

FIGS. 8A-8F depicts pSTAT5 stimulation activity of IL-2 fusion proteins P-0250, P-0424, and P-447 in comparison to their respective counterparts harboring S125I substitution, P-0531, P-0491, and P-0511. The ability to induce STAT5 phosphorylation in CD4+ Treg (FIG. 8A, FIG. 8C, and FIG. 8E) and CD4+ Tconv (FIG. 8B, FIG. 8D, and FIG. 8F) cells was determined in human PBMC assay by FACS analysis.

FIGS. 9A-9C depicts differential effects on STAT5 phosphorylation by IL-2 variant Fc fusions (P-0511 and P-0512) in comparison with the wild type (P-0250) and three benchmark molecules in three subsets of CD4+ T cells; CD4+ FoxP3+CD25+ Treg cells (FIG. 9A), CD4+FoxP3-CD25+ activated Tconv cells (FIG. 9B), and CD4+FoxP3-CD25- naïve Tconv cells (FIG. 9C). The ability to induce STAT5 phosphorylation was determined in human PBMC assay by FACS analysis.

FIGS. 10A-10B depicts differential effects on stimulating proliferation of CD8+ T cells (FIG. 10A) and NK cells by P-0511 and P-0512 (FIG. 10B) in comparison with the wild type (P-0250) and benchmark molecules. Cell proliferation was determined in human PBMC assay by FACS analysis of CFSE dilution and expressed as a percent of divided cells.

FIGS. 11A-11D depict differential effects on inducing STAT5 phosphorylation by IL-2 variant Fc fusion P-0511 in comparison to the wild-type equivalent P-0531 in different cells types. The ability to induce STAT5 phosphorylation in CD4+ Treg (FIG. 11A), CD4+ Tconv (FIG. 11B), CD8+ T cells (FIG. 11C), and NK cells (FIG. 11D) was determined in human PBMC assay by FACS analysis. FIG. 11E depicts binding strength of P-511 to IL-2Rβ and γc complex in comparison to P-0531 and Benchmark-1 in ELISA assay.

FIGS. 12A-12C depicts the proliferation and expansion of Treg cells in mice treated with Fc fusion proteins of IL-2 variants and the benchmarks after a single subcutaneous injection. Blood was collected at the indicated time points for measurement of proliferation and lymphocytes phenotyping. Percentage of the proliferation marker Ki67 positive Treg cells (FIG. 12A); Percentage of Treg cells in total CD4+ T cell population (FIG. 12B); Percentage of Treg cells in total blood lymphocytes (FIG. 12C). Data are expressed as mean±SEM. Statistical analysis was performed by one-way anova followed by Tukey's post hoc test. ** $p<0.0001$; * $p<0.001$ compared to PBS group at respective time point.

FIGS. 13A-13C depicts the proliferation of effector T cells and NK cells in mice treated with IL-2 mutant Fc fusion proteins and the benchmarks after a single subcutaneous injection. Blood was collected at the indicated time points for measurement of lymphocyte proliferation. Percentage of Ki67 positive CD4+T conventional (Tconv) cells (FIG. 13A); Percentage of Ki67 positive CD8+ T cells (FIG. 13B); Percentage of Ki67 positive NK cells (FIG. 13C). Data are expressed as mean±SEM. Statistical analysis was performed by one-way anova followed by Tukey's post hoc test. ** $p<0.0001$; * $p<0.001$ compared to PBS group at respective time point.

Figure 14A:
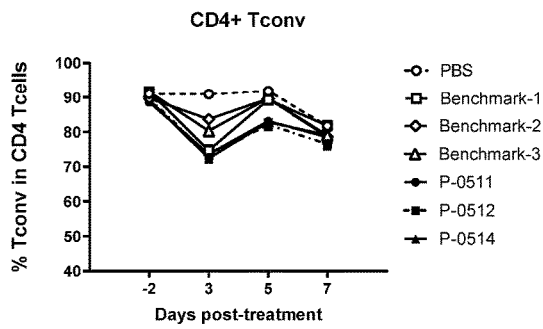
Figure 14B:
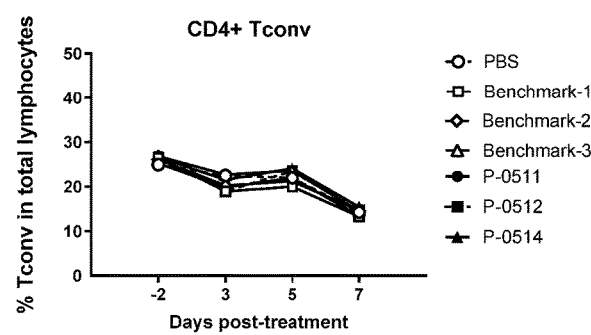
Figure 14C:
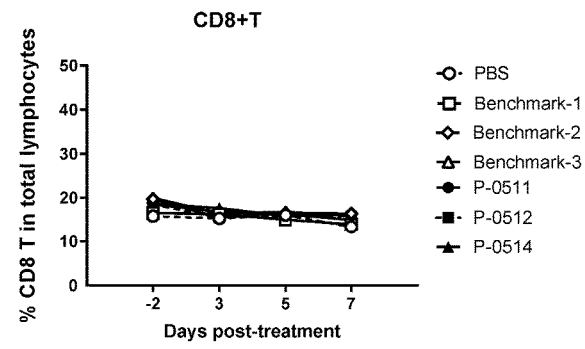
Figure 14D:
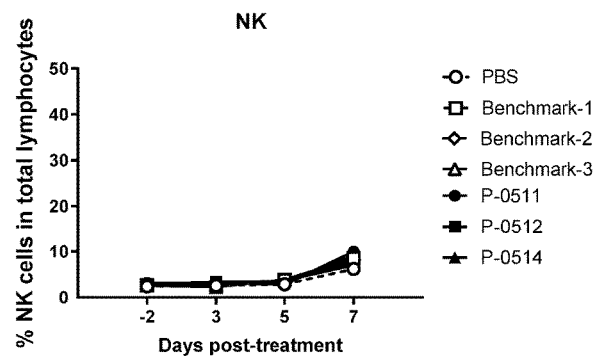

FIGS. 14A-14D depicts the expansion of effector T cells and NK cells in mice treated with IL-2 mutant Fc fusion proteins and the benchmarks after a single subcutaneous injection. Percentage of CD4+ T conventional (Tconv) cells in total CD4+ T cells (FIG. 14A) and total blood lymphocytes (FIG. 14B). Percentage of CD8+ T cells in total blood lymphocytes (FIG. 14C); Percentage of NK cells in total blood lymphocytes (FIG. 14D). Data are expressed as mean±SEM.

FIGS. 15A-15B depicts the ratio of Treg to Tconv cells based on percentage of Ki67 positive expression (FIG. 15A), and cell numbers in mice treated with IL-2 mutant Fc fusion proteins, and the benchmarks (FIG. 15B). Data were acquired with FACS and are expressed as mean±SEM. Statistical analysis was performed by one-way anova followed by Tukey's post hoc test. **** $p<0.0001$; * $p<0.05$ compared to PBS group at respective time point.

FIGS. 16A-16B depicts the expression of CD25 and Foxp3 on Treg cells in mice treated with IL-2 mutant Fc fusion proteins and the benchmarks after a single subcutaneous injection. The expression level of Foxp3 (FIG. 16A), and CD25 (FIG. 16B) was analyzed by FACS analysis and expressed as mean fluorescent intensity (MFI). Data are expressed as mean±SEM. **** $p<0.0001$, compared to PBS group at respective time point.

FIGS. 17A-17D depicts dose-dependent increases in the proliferation and expansion of Treg cells in mice following a single injection of IL-2 variant Fc fusion protein P-0511. Blood was collected at the indicated time points for lymphocyte phenotyping and measurement of Ki67 proliferation marker. Percentage of the proliferation marker Ki67 positive Treg cells (FIG. 17A); Percentage of Treg cells in total CD4+ T cells (FIG. 17B); number of Treg cells per microliter of whole blood (FIG. 17C); Fold change of Treg cell numbers from the baseline for each group (FIG. 17D). Data were expressed as mean±SEM. Statistical analysis was performed by one-way anova followed by Tukey's post hoc test. ** $p<0.0001$, * $p<0.001$, ** $p<0.01$, * $p<0.05$ compared to PBS group at respective time point.

FIGS. 18A-18D depicts dose-dependent effect of IL-2 variant Fc fusion protein P-0511 on the percentage of Treg cells (FIG. 18A), CD4+ Tconv cells (FIG. 18B), CD8 T cells (FIG. 18C), and NK cells (FIG. 18D) over total lymphocytes in mice following a single injection. Blood was collected at the indicated time points for lymphocyte phenotyping. Data were determined by FACS analysis and are expressed as mean±SEM. Statistical analysis was performed by one-way anova followed by Tukey's post hoc test. ** $p<0.0001$,  $p<0.01$, * $p<0.05$ compared to PBS group at respective time point.

Figure 19A:
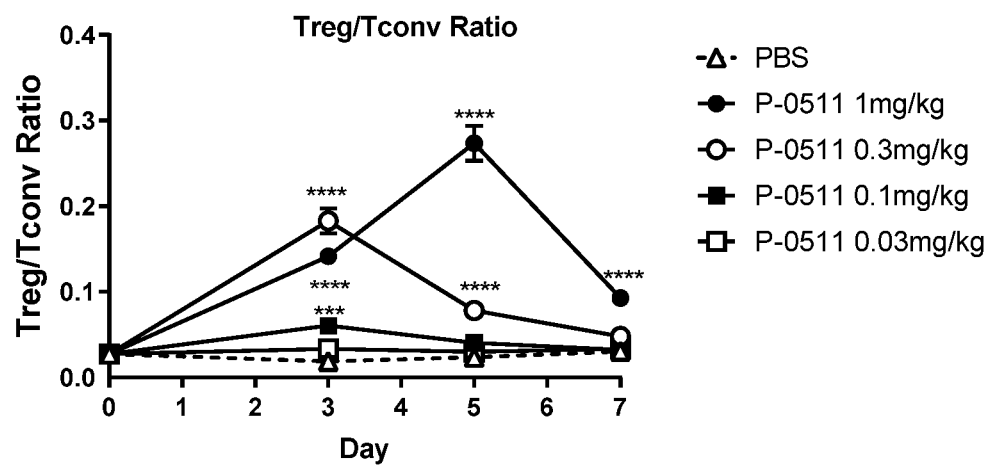

FIGS. 19A-19C depicts dose-dependent increases in ratio of Treg to T conv cell numbers (FIG. 19A), expression of CD25 on Treg cells (FIG. 19B), and expression of Foxp3 on Treg cells in mice following a single injection of P-0511 (FIG. 19C). Data were determined by FACS analysis and are expressed as mean±SEM. Statistical analysis was performed by one-way anova followed by Tukey's post hoc test. ** $p<0.0001$, * $p<0.001$, ** $p<0.01$ compared to PBS group at respective time point.

FIGS. 20A-20C depicts the sustained proliferation and expansion of Treg cells in mice receiving repeated doses of Fc fusion proteins of IL-2 variants (P-0511 and P-0512), but not the wild type (P-0531) and the benchmark. Compounds were given s.c. once every three days (Q3D) and blood was collected 3 days post the $1^{st}$ and the $3^{rd}$ injection for lymphocyte phenotyping and measurement of proliferation marker Ki67. Percentage of Ki67 positive Treg cells (FIG.

20A); Percentage of Treg cells in total CD4+ T cells (FIG. 20B); Percentage of Treg cells in total blood lymphocytes (FIG. 20C). Data were determined by FACS analysis and are expressed as mean ±SEM. Statistical analysis was performed by one-way anova followed by Tukey's post hoc test. **** p<0.0001, * p<0.05 compared to respective PBS group.

FIGS. 21A-21B depicts the sustained elevation of Treg cell counts in mice receiving repeated dosing of Fc fusion proteins of IL-2 variants (P-0511 and P-0512), but not the wild type (P-0531) and the benchmark. Compounds were given s.c. once every three days (Q3D) and blood was collected 3 days post the $1^{st}$ and the $3^{rd}$ injection for lymphocyte phenotyping and measurement of proliferation marker Ki67. Number of Treg cells per microliter of whole blood (FIG. 21A); Fold change of the Treg numbers compared to the PBS control group (FIG. 21B). Data were determined by FACS analysis and are expressed as mean±SEM. Statistical analysis was performed by one-way anova followed by Tukey's post hoc test. ** p<0.0001, * p<0.001, ** p<0.01, compared to respective PBS group.

Figure 22:
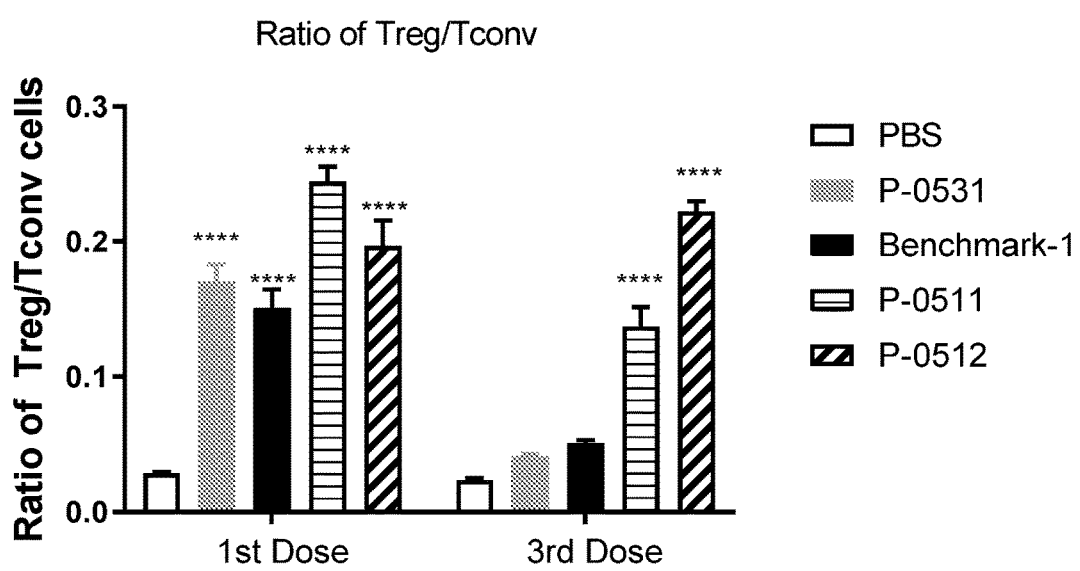

FIG. 22 depicts the retaining of the elevated ratio of Treg to Tconv in mice receiving repeated dosing of Fc fusion proteins of IL-2 variants (P-0511 and P-0512), but not the wild type (P-0531) and the benchmark. Compounds were given s.c. once every three days (Q3D) and blood was collected 3 days post the $1^{st}$ and the $3^{rd}$ injection for Treg and Tconv cell phenotyping. The ratio was calculated based on the % Treg and % Tconv in total CD4 cells. Data were determined by FACS analysis and are expressed as mean±SEM. Statistical analysis was performed by one-way anova followed by Tukey's post hoc test. **** p<0.0001, compared to respective PBS group.

FIGS. 23A-23B depicts the suppression of antigen-driven inflammation by P-0511 in a mouse model of delayed-type hypersensitivity (DTH) induced by keyhole limpet hemocyanin (KLH) antigen. Mice were KLH immunized on day 0 and re-challenged in right ear on day 5. Mice were treated with P-0511 either Q3D or Q5D starting at Day-2. Kinetics of the DTH response using the change in ear thickness relative to baseline values (Δ ear thickness) at various times after KLH challenge was illustrated for Q3D (FIG. 23A), and Q5D (FIG. 23B) dosing schedules. Data are expressed as mean±SEM. Statistical analysis was performed by one-way anova followed by Tukey's post hoc test. ** p<0.0001, * p<0.001, ** p<0.01, * p<0.05, compared to respective PBS group at respective timepoint.

Figure 24:
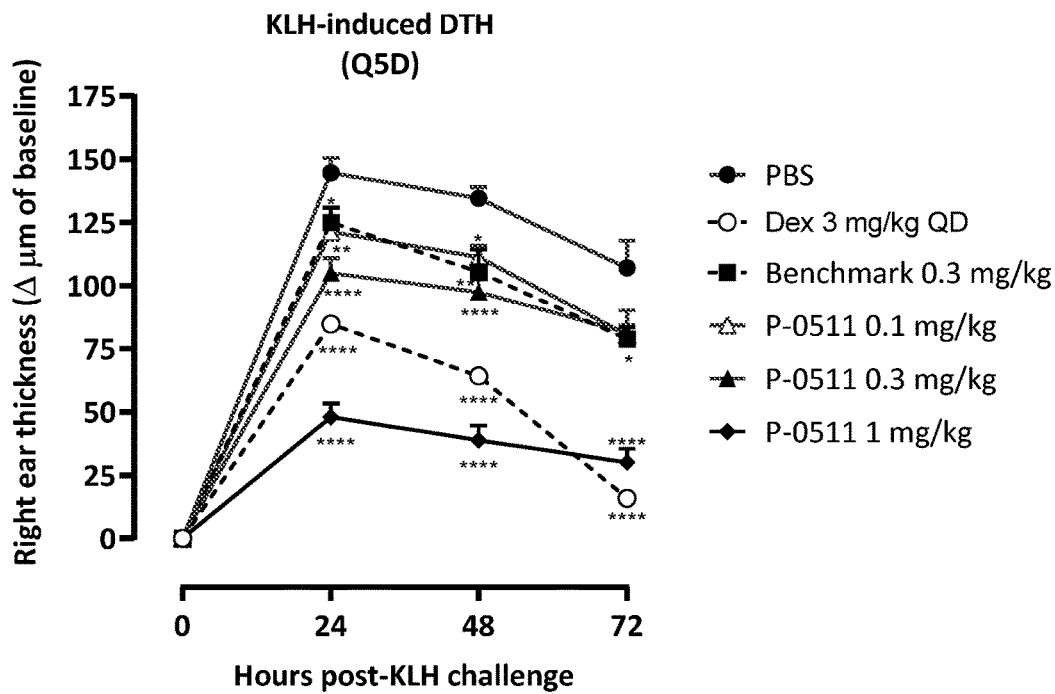

FIG. 24 depicts the suppression of antigen-driven inflammation by P-0511 in comparison with a benchmark molecule (Benchmark-1) in a mouse model of DTH induced by KLH antigen. Mice were KLH immunized on day 0 and re-challenged in right ear on day 5. Mice were treated with the compound Q5D starting on day-2. Kinetics of the DTH response using the change in ear thickness relative to baseline values (Δ ear thickness) at various times after KLH challenge was illustrated. Data are expressed as mean±SEM. Statistical analysis was performed by one-way anova followed by Tukey's post hoc test. ** p<0.0001,  p<0.01, * p<0.05, compared to respective PBS group at respective timepoint.

Mode(s) for Carrying Out the Disclosure

The present invention relates to polypeptides which share primary sequence with human IL-2, except for one to several amino acids that have been mutated. One panel of IL-2 variants comprise mutations that preferentially promotes the proliferation, survival, activation and/or function of immunosuppressive regulatory T cells ((T CD4+CD25+FoxP3+) over effector T cells and NK cells. The present invention also includes therapeutic uses of such IL-2 selective agonist, used alone, or in combination with disease tissue targeting proteins or peptides to treat autoimmune and various inflammatory disorders. Another panel of IL-2 variants comprise mutations substantially reduce the ability of these polypeptides to stimulate either Treg or Tconv cells while may having receptor binding activity and make them effective as IL-2 antagonists. In another aspect the present invention relates to pharmaceutical compositions comprising the polypeptides disclosed. Finally, the present invention relates to the therapeutic use of the polypeptides and pharmaceutical compositions disclosed due to their selective modulating effect of the immune system on diseases like autoimmune and inflammatory disorders.

Definitions

The terms "polypeptide", "peptide" and "protein" are used interchangeably herein to refer to a polymer of amino acid residues. In various embodiments, "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (Amino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to, peptide mimetics such as amino acids joined by an ether as opposed to an amide bond.

Polypeptides of the disclosure include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (5) confer or modify other physicochemical or functional properties.

An amino acid "substitution" as used herein refers to the replacement in a polypeptide of one amino acid at a particular position in a parent polypeptide sequence with a different amino acid. Amino acid substitutions can be generated using genetic or chemical methods well known in the art. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" refers to the substitution in a polypeptide of an amino acid with a functionally similar amino acid. The following six groups each contain amino acids that are conservative substitutions for one another:

---

1) Alanine (A), Serine (S), and Threonine (T)
2) Aspartic acid (D) and Glutamic acid (E)
3) Asparagine (N) and Glutamine (Q)

4) Arginine (R) and Lysine (K)
5) Isoleucine (I), Leucine (L), Methionine (M), and Valine (V)
6) Phenylalanine (F), Tyrosine (Y), and Tryptophan (W)

A "non-conservative amino acid substitution" refers to the substitution of a member of one of these classes for a member from another class. In making such changes, according to various embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in various embodiments, the substitution of amino acids whose hydropathic indices are within ±2 is included. In various embodiments, those that are within ±1 are included, and in various embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as disclosed herein. In various embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0.+−.1); glutamate (+3.0.+−.1); serine (+0.3); asparagine (+0.2); glutamine (+0.2); glycine (0); threonine (−0.4); proline (−0.5.+−.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in various embodiments, the substitution of amino acids whose hydrophilicity values are within ±2 is included, in various embodiments, those that are within ±1 are included, and in various embodiments, those within ±0.5 are included.

Exemplary amino acid substitutions are set forth in Table 1.

TABLE 1

| Original Residues | Exemplary Substitutions | Preferred Substitutions |
|---|---|---|
| Ala | Val, Leu, Ile | Val |
| Arg | Lys, Gln, Asn | Lys |
| Asn | Gln | |
| Asp | Glu | |
| Cys | Ser, Ala | Ser |
| Gln | Asn | Asn |
| Glu | Asp | Asp |

TABLE 1-continued

| Original Residues | Exemplary Substitutions | Preferred Substitutions |
|---|---|---|
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of polypeptides as set forth herein using well-known techniques. In various embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, the skilled artisan can predict the importance of amino acid residues in a polypeptide that correspond to amino acid residues important for activity or structure in similar polypeptides. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of a polypeptide with respect to its three-dimensional structure. In various embodiments, one skilled in the art may choose to not make radical changes to amino acid residues predicted to be on the surface of the polypeptide, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

The term "polypeptide fragment" and "truncated polypeptide" as used herein refers to a polypeptide that has an amino-terminal and/or carboxy-terminal deletion as compared to a corresponding full-length protein. In various embodiments, fragments can be, e.g., at least 5, at least 10, at least 25, at least 50, at least 100, at least 150, at least 200, at least 250, at least 300, at least 350, at least 400, at least 450, at least 500, at least 600, at least 700, at least 800, at least 900 or at least 1000 amino acids in length. In various embodiments, fragments can also be, e.g., at most 1000, at most 900, at most 800, at most 700, at most 600, at most 500, at most 450, at most 400, at most 350, at most 300, at most 250, at most 200, at most 150, at most 100, at most 50, at most 25, at most 10, or at most 5 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

The terms "polypeptide variant", "hybrid polypeptide" and "polypeptide mutant" as used herein refers to a polypeptide that comprises an amino acid sequence wherein one or more amino acid residues are inserted into, deleted from and/or substituted into the amino acid sequence relative to another polypeptide sequence. In various embodiments, the number of amino acid residues to be inserted, deleted, or substituted can be, e.g., at least 1, at least 2, at least 3, at least 4, at least 5, at least 10, at least 25, at least 50, at least 75, at least 100, at least 125, at least 150, at least 175, at least 200, at least 225, at least 250, at least 275, at least 300, at least 350, at least 400, at least 450 or at least 500 amino acids in length. Hybrids of the present disclosure include fusion proteins.

A "derivative" of a polypeptide is a polypeptide that has been chemically modified, e.g., conjugation to another chemical moiety such as, for example, polyethylene glycol, albumin (e.g., human serum albumin), phosphorylation, and glycosylation.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm and means that a given sequence is at least 80% identical to another length of another sequence. In various embodiments, the % identity is selected from, e.g., at least 60%, at least 65%, at least 70%, at least 75%, at least 80%, at least 85%, at least 90%, at least 95%, or at least 99% or more sequence identity to a given sequence. In various embodiments, the % identity is in the range of, e.g., about 60% to about 70%, about 70% to about 80%, about 80% to about 85%, about 85% to about 90%, about 90% to about 95%, or about 95% to about 99%.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. In various embodiments, the % homology is selected from, e.g., at least 60%, at least 65%, at least 70%, at least 75%, at least 80%, at least 85%, at least 90%, at least 95%, or at least 99% or more sequence homology to a given sequence. In various embodiments, the % homology is in the range of, e.g., about 60% to about 70%, about 70% to about 80%, about 80% to about 85%, about 85% to about 90%, about 90% to about 95%, or about 95% to about 99%.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., J. Mol. Biol. 215:403-10, 1990 (with special reference to the published default setting, i.e., parameters w=4, t=17) and Altschul et al., Nucleic Acids Res., 25:3389-3402, 1997. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix.

In addition to calculating percent sequence identity, the BLAST algorithm also performs a statistical analysis of the similarity between two sequences (see, e.g., Karlin & Altschul, Proc. Nat'l. Acad. Sci. USA, 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is, e.g., less than about 0.1, less than about 0.01, or less than about 0.001.

The term "modification" as used herein refers to any manipulation of the peptide backbone (e.g. amino acid sequence) or the post-translational modifications (e.g. glycosylation) of a polypeptide.

The term "knob-into-hole modification" as used herein refers to a modification within the interface between two immunoglobulin heavy chains in the CH3 domain. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001).

The term "fusion protein" as used herein refers to a fusion polypeptide molecule comprising two or more genes that originally coded for separate proteins, wherein the components of the fusion protein are linked to each other by peptide-bonds, either directly or through peptide linkers. The term "fused" as used herein refers to components that are linked by peptide bonds, either directly or via one or more peptide linkers.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences. A "cleavable linker" refers to a linker that can be degraded or otherwise severed to separate the two components connected by the cleavable linker. Cleavable linkers are generally cleaved by enzymes, typically peptidases, proteases, nucleases, lipases, and the like. Cleavable linkers may also be cleaved by environmental cues, such as, for example, changes in temperature, pH, salt concentration, etc.

The term "peptide linker" as used herein refers to a peptide comprising one or more amino acids, typically about 2-20 amino acids. Peptide linkers are known in the art or are described herein. Suitable, non-immunogenic linker peptides include, for example, $(G_4S)_n$, $(SG_4)_n$ or $G_4(SG_4)$ n peptide linkers. "n" is generally a number between 1 and 10, typically between 2 and 4.

"Pharmaceutical composition" refers to a composition suitable for pharmaceutical use in an animal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, vehicles, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 21$^{st}$ Ed. 2005, Mack Publishing Co, Easton. A "pharmaceutically acceptable salt" is a salt that can be formulated into a compound for pharmaceutical use including, e.g., metal salts (sodium, potassium, magnesium, calcium, etc.) and salts of ammonia or organic amines.

As used herein, "treatment" (and grammatical variations thereof such as "treat" or "treating") refers to clinical intervention in an attempt to alter the natural course of a disease in the individual being treated and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

The term "effective amount" or "therapeutically effective amount" as used herein refers to an amount of a compound or composition sufficient to treat a specified disorder, condition or disease such as ameliorate, palliate, lessen, and/or delay one or more of its symptoms. In reference to cancers or other unwanted cell proliferation, an effective amount comprises an amount sufficient to: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. An effective amount can be administered in one or more administrations.

The phrase "administering" or "cause to be administered" refers to the actions taken by a medical professional (e.g., a physician), or a person controlling medical care of a patient, that control and/or permit the administration of the agent (s)/compound(s) at issue to the patient. Causing to be administered can involve diagnosis and/or determination of an appropriate therapeutic regimen, and/or prescribing particular agent(s)/compounds for a patient. Such prescribing can include, for example, drafting a prescription form, annotating a medical record, and the like. Where administration is described herein, "causing to be administered" is also contemplated.

The terms "patient," "individual," and "subject" may be used interchangeably and refer to a mammal, preferably a human or a non-human primate, but also domesticated mammals (e.g., canine or feline), laboratory mammals (e.g., mouse, rat, rabbit, hamster, guinea pig), and agricultural mammals (e.g., equine, bovine, porcine, ovine). In various embodiments, the patient can be a human (e.g., adult male, adult female, adolescent male, adolescent female, male child, female child) under the care of a physician or other health worker in a hospital, psychiatric care facility, as an outpatient, or other clinical context. In various embodiments, the patient may be an immunocompromised patient or a patient with a weakened immune system including, but not limited to patients having primary immune deficiency, AIDS; cancer and transplant patients who are taking certain immunosuppressive drugs; and those with inherited diseases that affect the immune system (e.g., congenital agammaglobulinemia, congenital IgA deficiency). In various embodiments, the patient has an immunogenic cancer, including, but not limited to bladder cancer, lung cancer, melanoma, and other cancers reported to have a high rate of mutations (Lawrence et al., Nature, 499 (7457): 214-218, 2013).

The term "Fc domain" or "Fc region" as used herein is used to define a C-terminal region of an immunoglobulin heavy chain that contains at least a portion of the constant region. The term includes native sequence Fc regions and variant Fc regions. An IgG Fc region comprises an IgG CH2 and an IgG CH3 domain. The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical immunoglobulin heavy chains as herein described. Unless otherwise specified herein, numbering of amino acid residues in the Fc region or constant region is according to the EU numbering system.

The term "effector functions" as used herein refers to those biological activities attributable to the Fc region of an immunoglobulin, which vary with the immunoglobulin isotype. Examples of immunoglobulin effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

The term "regulatory T cell" or "Treg cell" as used herein is meant a specialized type of CD4+ T cell that can suppress the responses of other T cells (effector T cells). Treg cells are characterized by expression of CD4, the a-subunit of the IL-2 receptor (CD25), and the transcription factor forkhead box P3 (FOXP3) (Sakaguchi, Annu Rev Immunol 22, 531-62 (2004)) and play a critical role in the induction and maintenance of peripheral self-tolerance to antigens, including those expressed by tumors.

The term "conventional CD4+ T cells" as used herein is meant CD4+ T cells other than regulatory T cells.

The term "selective activation of Treg cells" as used herein is meant activation of Treg cells essentially without concomitant activation of other T cell subsets (such as CD4+T helper cells, CD8+ cytotoxic T cells) or natural killer (NK) cells. Methods for identifying and distinguishing these cell types are described in the Examples. Activation may include induction of IL-2 receptor signaling (as measured e.g. by detection of phosphorylated STAT5), induction of proliferation (as measured e.g. by detection of Ki-67), and/or up-regulation of expression of activation markers (such as e.g. CD25), and expansion of cell numbers.

As used herein, "specific binding" is meant that the binding is selective for the antigen and can be discriminated from unwanted or non-specific interactions. The ability of an immunoglobulin to bind to a specific antigen can be measured either through an enzyme-linked immunosorbent assay (ELISA) or other techniques familiar to one of skill in the art, e.g. Surface Plasmon Resonance (SPR) technique.

The terms "affinity" or "binding affinity" as used herein refers to the strength of the sum total of non-covalent interactions between a single binding site of a molecule (e.g. an antibody) and its binding partner (e.g. an antigen). The affinity of a molecule X for its partner Y can generally be represented by the dissociation constant (KD), which is the ratio of dissociation and association rate constants (koff and kon, respectively). A particular method for measuring affinity is Surface Plasmon Resonance (SPR).

The term "reduced binding", as used herein refers to a decrease in affinity for the respective interaction, as measured for example by SPR. Conversely, "increased binding" refers to an increase in binding affinity for the respective interaction.

The term "polymer" as used herein generally includes, but is not limited to, homopolymers; copolymers, such as, for example, block, graft, random and alternating copolymers; and terpolymers; and blends and modifications thereof. Furthermore, unless otherwise specifically limited, the term "polymer" shall include all possible geometrical configurations of the material. These configurations include, but are not limited to isotactic, syndiotactic, and random symmetries.

"Polynucleotide" refers to a polymer composed of nucleotide units.

Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is substantially identical to the nucleotide sequence of the polynucleotide binding partner of the second polynucleotide, or if the first polynucleotide can hybridize to the second polynucleotide under stringent hybridization conditions.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA. The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence-dependent and are different under different environmental parameters. An extensive guide to the hybridization of nucleic acids can be found in Tijssen, 1993, Laboratory Techniques in Biochemistry and Molecular Biology—Hybridization with Nucleic Acid Probes, part I, chapter 2, "Overview of principles of hybridization and the strategy of nucleic acid probe assays", Elsevier, N.Y.; Sambrook et al., 2001, Molecular Cloning: A Laboratory Manual, Cold Spring Harbor Laboratory, 3.sup.rd ed., NY; and Ausubel et al., eds., Current Edition, Current Protocols in Molecular Biology, Greene Publishing Associates and Wiley Interscience, NY.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than about 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes. See Sambrook et al. for a description of SSC buffer. A high stringency wash can be preceded by a low stringency wash to remove background probe signal. An exemplary medium stringency wash for a duplex of, e.g., more than about 100 nucleotides, is 1×SSC at 45° C. for 15 minutes. An exemplary low stringency wash for a duplex of, e.g., more than about 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties. In instances where a probe provides a point of initiation for synthesis of a complementary polynucleotide, a probe can also be a primer.

A "vector" is a polynucleotide that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06. A nucleotide sequence is "operably linked" to a regulatory sequence if the regulatory sequence affects the expression (e.g., the level, timing, or location of expression) of the nucleotide sequence.

A "host cell" is a cell that can be used to express a polynucleotide of the disclosure. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The term "isolated molecule" (where the molecule is, for example, a polypeptide or a polynucleotide) is a molecule that by virtue of its origin or source of derivation (1) is not associated with naturally associated components that accompany it in its native state, (2) is substantially free of other molecules from the same species, (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

A protein or polypeptide is "substantially pure," "substantially homogeneous," or "substantially purified" when at least about 60% to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The terms "label" or "labeled" as used herein refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In various embodiments, labels are attached by spacer arms of various lengths to reduce potential steric hindrance.

The term "heterologous" as used herein refers to a composition or state that is not native or naturally found, for example, that may be achieved by replacing an existing natural composition or state with one that is derived from another source. Similarly, the expression of a protein in an organism other than the organism in which that protein is naturally expressed constitutes a heterologous expression system and a heterologous protein.

It is understood that aspect and embodiments of the disclosure described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the disclosure described herein include "consisting" and/or "consisting essentially of" aspects and variations.

IL-2

Interleukin-2 (IL-2), a classic Th1 cytokine, is produced by T cells after activation through the T-cell antigen receptor and the co-stimulatory molecule CD28. The regulation of IL-2 occurs through activation of signaling pathways and transcription factors that act on the IL-2 promoter to generate new gene transcription, but also involves modulation of the stability of IL-2 mRNA. IL-2 binds to a multichain receptor, including a highly regulated a chain and β and γ chains that mediate signaling through the Jak-STAT pathway. IL-2 delivers activation, growth, and differentiation signals to T cells, B cells, and NK cells. IL-2 is also important in mediating activation-induced cell death of T cells, a function that provides an essential mechanism for terminating immune responses. A commercially available unglycosylated human recombinant IL-2 product, aldesleukin (available as the PROLEUKIN® brand of desalanyl-1, serine-125 human interleukin-2 from Prometheus Laboratories Inc., San Diego Calif.), has been approved for administration to patients suffering from metastatic renal cell carcinoma and metastatic melanoma. IL-2 has also been suggested for administration in patients suffering from or infected with hepatitis C virus (HCV), human immunodeficiency virus (HIV), acute myeloid leukemia, non-Hodgkin's lymphoma, cutaneous T-cell lymphoma, juvenile rheumatoid arthritis, atopic dermatitis, breast cancer and bladder cancer. Unfortunately, short half-life and severe toxicity limits the optimal dosing of IL-2.

As used herein, the terms "native IL-2" and "native interleukin-2" in the context of proteins or polypeptides refer to any naturally occurring mammalian interleukin-2 amino acid sequences, including immature or precursor and mature forms. Non-limiting examples of GenBank Accession Nos. for the amino acid sequence of various species of native mammalian interleukin-2 include NP_032392.1 (*Mus musculus*, immature form), NP_001040595.1 (*macaca mulatta*, immature form), NP_000577.2 (human, precursor form), CAA01199.1 (human, immature form), AAD48509.1 (human, immature form), and AAB20900.1 (human). In various embodiments of the present invention, native IL-2 is the immature or precursor form of a naturally occurring mammalian IL-2. In other embodiments, native IL-2 is the mature form of a naturally occurring mammalian IL-2. In various embodiments, native IL-2 is the precursor form of naturally occurring human IL-2. In various embodiments, native IL-2 is the mature form of naturally occurring human IL-2. In various embodiments, IL-2 is derived from the amino acid sequence of the human IL-2 precursor sequence set forth in SEQ ID NO: 1:

```
                                        (SEQ ID NO: 1)
MYRMQLLSCIALSLALVTNSAPTSSSTKKTQLQLEHLLLD

LQMILNGINNYKNPKLTRMLTFKFYMPKKATELKHLQCLE

EELKPLEEVLNLAQSKNFHLRPRDLISNINVIVLELKGSE

TTFMCEYADETATIVEFLNRWITFCQSIISTLT
```

In various embodiments, IL-2 comprises the amino acid sequence of the human IL-2 mature form wild type sequence set forth in SEQ ID NO: 3, which contains substitution of cysteine at position 125 to serine, but does not alter IL-2 receptor binding compared to the naturally occurring IL-2:

```
                                        (SEQ ID NO: 3)
APTSSSTKKTQLQLEHLLLDLQMILNGINNYKNPKLTRML

TFKFYMPKKATELKHLQCLEEELKPLEEVLNLAQSKNFHL

RPRDLISNINVIVLELKGSETTFMCEYADETATIVEFLNR

WITFSQSIISTLT
```

IL-2 Variants

The present invention relates to polypeptides which share primary sequence with human IL-2, except for one to several amino acids that have been mutated. One panel of IL-2 variants comprise mutations that preferentially promotes the proliferation, survival, activation and/or function of immunosuppressive regulatory T cells ((T CD4+CD25+FoxP3+) over effector T cells and NK cells. Also includes therapeutic uses of such IL-2 selective agonist, used alone, or in combination with disease tissue targeting protein or peptide to treat Treg cell-deficient autoimmune and various inflammatory disorders. In another aspect the present invention relates to pharmaceutical compositions comprising the polypeptides disclosed. Finally, the present invention relates to the therapeutic use of the polypeptides and pharmaceutical compositions disclosed due to their selective modulating effect of the immune system on diseases like autoimmune and inflammatory disorders or cancer and various infectious diseases.

The present invention relates to polypeptides of 100 to 500 amino acids in length, preferably of 140 residues size whose apparent molecular weight is at least 15 kD. These polypeptides maintain high sequence identity, more than 90%, with native IL-2. In these positions, these polypeptides are mutated introducing amino acid residues different from those in the same position in the native IL-2.

The polypeptides of the present invention may be referred to as immunomodulatory polypeptides, IL-2 analogs or IL-2 variants, among other names. These polypeptides are designed based on the 3D structure of the IL-2 receptor complex (available in PDB public database), introducing mutations mainly in the positions of the IL-2 corresponding to amino acids interacting with receptor subunit(s) β or γ or βγ.

In various embodiments, the IL-2 variant (or mutant) comprises a sequence derived from the sequence of the mature human IL-2 polypeptide as set forth in SEQ ID NO: 3. In various embodiments, the IL-2 variant comprises a different amino acid sequence than the native (or wild type) IL-2 protein. In various embodiments, the IL-2 variant binds the IL-2Rα polypeptide and functions as an IL-2 agonist or antagonist. In various embodiments, the IL-2 variants with agonist activity have super agonist activity. In various embodiments, the IL-2 variant can function as an IL-2 agonist or antagonist independent of its association with IL-2Rα. IL-2 agonists are exemplified by comparable or increased biological activity compared to wild type IL-2. IL-2 antagonists are exemplified by decreased biological activity compared to wild type IL-2 or by the ability to inhibit IL-2-mediated responses. In various embodiments, the sequence of the IL-2 variant has at least one amino acid change, e.g. substitution or deletion, compared to the native IL-2 sequence, such changes resulting in IL-2 agonist or antagonist activity. In various embodiments, the IL-2 variants as Fc fusion protein have the amino acid sequence set forth in SEQ ID NOs: 4-43, 108-146, and 193-197 with reduced binding to IL-2Rβ and/or $\gamma_C$ and enhanced selectivity in activating and proliferating regulatory T cells (Treg).

Exemplary IL-2 variants are provided in Table 2A-2F:

TABLE 2A

IL-2 single mutations targeting both IL-2Rβ interface and the proposed toxic motif

| | | Fc fusion protein | |
|---|---|---|---|
| Mutation | SEQ ID: NO | Protein ID | SEQ ID: NO |
| D20T | 5 | P-0363 | 72 |
| D20E | 6 | P-0364 | 73 |
| | | P-0412 | 105 |
| D20N | 7 | P-0365 | 74 |
| D20Q | 8 | P-0366 | 75 |
| D20S | 9 | P-0367 | 76 |
| D20Y | 10 | P-0368 | 77 |
| D20I | 11 | P-0252 | 78 |
| | | P-0306 | 106 |

TABLE 2A-continued

IL-2 single mutations targeting both IL-2Rβ interface and the proposed toxic motif

| | | Fc fusion protein | |
|---|---|---|---|
| Mutation | SEQ ID: NO | Protein ID | SEQ ID: NO |
| L19Y | 12 | P-0372 | 79 |
| L19N | 13 | P-0373 | 80 |
| | | P-0416 | 104 |
| L19R | 14 | P-0374 | 81 |
| L19Q | 37 | P-0423 | 147 |
| L19H | 38 | P-0424 | 148 |
| L19D | 39 | P-0425 | 149 |
| L19P | 40 | P-0426 | 150 |
| L19S | 108 | P-0427 | 151 |
| L21S | 109 | P-0428 | 152 |
| L21N | 110 | P-0429 | 153 |
| L21R | 111 | P-0430 | 154 |

TABLE 2B

IL-2 single Mutations targeting IL-2Rβ interface

| | | Fc fusion protein | |
|---|---|---|---|
| Mutation | SEQ ID: NO | Protein ID | SEQ ID: NO |
| N88R | 4 | P-0254 | 71 |
| | | P-0496 | 190 |
| N88G | 15 | P-0253 | 82 |
| N88I | 16 | P-0302 | 83 |
| N88Q | 17 | P-0375 | 84 |
| N88E | 18 | P-0376 | 85 |
| N88T | 19 | P-0377 | 86 |
| N88M | 20 | P-0378 | 87 |

TABLE 2C

IL-2 single mutations targeting γc receptor interface

| | | Fc fusion protein | |
|---|---|---|---|
| Mutation | SEQ ID: NO | Protein ID | SEQ ID: NO |
| Q126E | 21 | P-0303 | 88 |
| Q126L | 22 | P-0304 | 89 |
| Q126N | 23 | P-0369 | 90 |
| Q126D | 24 | P-0370 | 91 |
| Q126M | 25 | P-0371 | 92 |
| Q126K | 112 | P-0497 | 155 |
| Q126H | 113 | P-0498 | 156 |
| Q126Y | 114 | P-0499 | 157 |
| S125E | 115 | P-0500 | 158 |
| S125K | 116 | P-0501 | 159 |
| S125H | 117 | P-0502 | 160 |
| S125W | 118 | P-0503 | 161 |
| S125I | 119 | P-0531 | 162 |
| Q22N | 120 | P-0505 | 163 |
| Q22H | 121 | P-0506 | 164 |
| Q22K | 122 | P-0507 | 165 |
| Q22Y | 123 | P-0508 | 166 |
| Q22I | 124 | P-0509 | 167 |

TABLE 2D

IL-2 mutation combinations targeting both IL-2Rβ interface and the proposed toxic motif

| | | Fc fusion protein | |
|---|---|---|---|
| Mutation | SEQ ID: NO | Protein ID | SEQ ID: NO |
| D20I/N88G | 26 | P-0251 | 93 |
| D20I/N88R | 27 | P-0317 | 94 |
| | | P-0319 | 107 |
| D20T/N88R | 28 | P-0324 | 96 |
| D20I/N88I | 29 | P-0318 | 95 |

TABLE 2E

IL-2 mutation combinations targeting IL-2Rβ, γc interfaces and the proposed toxic motif

| | | Fc fusion protein | |
|---|---|---|---|
| Mutation | SEQ ID: NO | Protein ID | SEQ ID: NO |
| D20T/Q126E | 30 | P-0322 | 97 |
| D20T/N88R/Q126E | 31 | P-0325 | 99 |
| D20T/Q126L | 32 | P-0323 | 98 |
| D20T/N88R/Q126L | 33 | P-0326 | 100 |
| L19N/Q126E | 34 | P-0417 | 101 |
| L19R/Q126E | 35 | P-0418 | 102 |
| L19Y/Q126E | 36 | P-0419 | 103 |
| D20T/S125I/Q126K | 41 | P-0582 | 203 |
| L19N/S125I/Q126K | 42 | P-0583 | 204 |
| L19R/S125I/Q126K | 43 | P-0584 | 205 |
| L19H/Q126E | 125 | P-0447 | 168 |
| L19Q/Q126E | 126 | P-0448 | 169 |
| L19S/Q126E | 127 | P-0449 | 170 |
| L19Y/Q126K | 128 | P-0464 | 171 |
| L19Y/Q126H | 129 | P-0465 | 172 |
| L19Y/Q126Y | 130 | P-0466 | 173 |
| L19Y/S125E | 131 | P-0467 | 174 |
| L19Y/S125K | 132 | P-0468 | 175 |
| L19Y/S125H | 133 | P-0469 | 176 |
| L19Y/S125W | 134 | P-0470 | 177 |
| L19Y/S125I | 135 | P-0471 | 178 |
| L19Y/Q22N | 136 | P-0472 | 179 |
| L19Y/Q22H | 137 | P-0473 | 180 |
| L19Y/Q22K | 138 | P-0474 | 181 |
| L19Y/Q22Y | 139 | P-0475 | 182 |
| L19Y/Q22I | 140 | P-0476 | 183 |
| L19H/Q126K | 141 | P-0480 | 184 |
| L19H/S125I | 142 | P-0491 | 185 |
| L19D/S125I | 143 | P-0492 | 186 |
| D20E/S125I | 144 | P-0493 | 187 |
| D20T/S125I | 145 | P-0494 | 188 |
| L19Y/S125I/Q126E | 146 | P-0495 | 189 |
| L19H/S125I/Q126E | 193 | P-0511 | 198 |
| | | P-0585 | 206 |
| | | P-0616 | 208 |
| | | P-0672 | 209 + 213 |
| | | P-0673 | 210 + 213 |
| | | P-0674 | 211 |
| L19H/S125I/Q126K | 194 | P-0512 | 199 |
| | | P-0586 | 207 |
| L19Q/Q126K | 195 | P-0513 | 200 |
| L19Q/S125I/Q126E | 196 | P-0514 | 201 |
| L19Q/S125I/Q126K | 197 | P-0515 | 202 |

TABLE 2F

Single or combination IL-2 mutations to improve fusion protein manufacturability and targeting IL-2Rβ and/or γc interfaces and the proposed toxic motif

| | | Fc fusion protein | |
|---|---|---|---|
| Mutation | SEQ ID: NO | Protein ID | SEQ ID: NO |
| S125I | 119 | P-0531 | 162 |
| L19H/S125I | 142 | P-0491 | 185 |
| L19D/S125I | 143 | P-0492 | 186 |
| D20E/S125I | 144 | P-0493 | 187 |
| D20T/S125I | 145 | P-0494 | 188 |
| L19Y/S125I/Q126E | 146 | P-0495 | 189 |
| L19H/S125I/Q126E | 193 | P-0511 | 198 |
| | | P-0585 | 206 |
| | | P-0616 | 208 |
| | | P-0672 | 209 + 213 |
| | | P-0673 | 210 + 213 |
| | | P-0674 | 211 |
| L19H/S125I/Q126K | 194 | P-0512 | 199 |
| | | P-0586 | 207 |
| L19Q/S125I/Q126E | 196 | P-0514 | 201 |
| L19Q/S125I/Q126K | 197 | P-0515 | 202 |
| D20T/S125I/Q126K | 41 | P-0582 | 203 |
| L19N/S125I/Q126K | 42 | P-0583 | 204 |
| L19R/S125I/Q126K | 43 | P-0584 | 205 |

The present invention also includes additional modifications to the class of IL-2 variants mentioned above and especially to those described in Tables 2A-2F. As can be appreciated by skilled artisan, additional combination mutants combining the preferred mutations described in Table 2A-2F may result in more Treg cell-selective IL-2 agonists. Any further combination mutants come with the spirit and scope of the present invention whether it is to increase their affinity to specific components of the IL-2 receptor, or to improve their in vivo pharmacodynamics: increase half-life or reduce their internalization by T cells. These additional mutations may be obtained by rational design with bioinformatics tools, or by using combinatorial molecular libraries of different nature (phage libraries, libraries of gene expression in yeast or bacteria). In another aspect the present invention relates to a fusion protein comprising any of the immunomodulatory polypeptides described above, coupled to a carrier protein. The carrier protein can be Albumin or the Fc region of human immunoglobulins.

Fc Domains

Immunoglobulins of IgG class are among the most abundant proteins in human blood. Their circulation half-lives can reach as long as 21 days. Fusion proteins have been reported to combine the Fc regions of IgG with the domains of another protein, such as various cytokines and receptors (see, for example, Capon et al., Nature, 337:525-531, 1989; Chamow et al., Trends Biotechnol., 14:52-60, 1996); U.S. Pat. Nos. 5,116,964 and 5,541,087). The prototype fusion protein is a homodimer protein linked through cysteine residues in the hinge region of IgG Fc, resulting in a molecule similar to an IgG molecule without the heavy chain variable and CH1 domains and light chains. The dimer nature of fusion proteins comprising the Fc domain may be advantageous in providing higher order interactions (i.e. bivalent or bispecific binding) with other molecules. Due to the structural homology, Fc fusion proteins exhibit in vivo pharmacokinetic profile comparable to that of human IgG with a similar isotype.

The term "Fc" refers to molecule or sequence comprising the sequence of a non-antigen-binding fragment of whole antibody, whether in monomeric or multimeric form. The original immunoglobulin source of the native Fc is preferably of human origin and may be any of the immunoglobulins, although IgG1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), Nucleic Acids Res. 10:4071-9). The term "native Fc" as used herein is generic to the monomeric, dimeric, and multimeric forms. Fc domains containing binding sites for Protein A, Protein G, various Fc receptors and complement proteins.

In various embodiments, the term "Fc variant" refers to a molecule or sequence that is modified from a native Fc but still comprises a binding site for the salvage receptor, FcRn. International applications WO 97/34631 (published Sep. 25, 1997) and WO 96/32478 describe exemplary Fc variants, as well as interaction with the salvage receptor, and are hereby incorporated by reference. Furthermore, a native Fc comprises sites that may be removed because they provide structural features or biological activity that are not required for the fusion molecules of the present invention. Thus, in various embodiments, the term "Fc variant" comprises a molecule or sequence that lacks one or more native Fc sites or residues that affect or are involved in (1) disulfide bond formation, (2) incompatibility with a selected host cell (3)N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by recombinant gene expression or by other means. In various embodiments, an "Fc domain" refers to a dimer of two Fc domain monomers (SEQ ID NO: 44) that generally includes full or part of the hinge region. In various embodiments, an Fc domain may be mutated to lack effector functions. In various embodiments, each of the Fc domain monomers in an Fc domain includes amino acid substitutions in the CH2 antibody constant domain to reduce the interaction or binding between the Fc domain and an Fcγ receptor. In various embodiments, each subunit of the Fc domain comprises two amino acid substitutions that reduce binding to an activating Fc receptor and/or effector function wherein said amino acid substitutions are L234A and L235A. In various embodiments, each subunit of the Fc domain comprises three amino acid substitutions that reduce binding to an activating Fc receptor and/or effector function wherein said amino acid substitutions are L234A, L235A and G237A (SEQ ID NO: 45).

In various embodiments, each of the two Fc domain monomers in an Fc domain includes amino acid substitutions that promote the heterodimerization of the two monomers. In various other embodiments, heterodimerization of Fc domain monomers can be promoted by introducing different, but compatible, substitutions in the two Fc domain monomers, such as "knob-into-hole" residue pairs. The "knob-into-hole" technique is also disclosed in U.S. Pat. Publication No. 8,216,805. In yet another embodiment, one Fc domain monomer includes the knob mutation T366W and the other Fc domain monomer includes hole mutations T366S, L358A, and Y407V. In various embodiments, two Cys residues were introduced (S354C on the "knob" and Y349C on the "hole" side) that form a stabilizing disulfide bridge. The use of heterodimeric Fc may result in monovalent IL-2 variant.

In various embodiments, an Fc domain may be mutated to further extend in vivo half-life. In various embodiments, each subunit of the Fc domain comprises three amino acid substitutions that enhance binding to human FcRn wherein said amino acid substitutions are M252Y, S254T, and T256E, disclosed in U.S. Pat. Publication No. 7,658,921. In various embodiments, each subunit of the Fc domain comprises one amino acid substitution that enhanced binding to human FcRn wherein said amino acid substitution is N434A, disclosed in U.S. Pat. Publication No. 7,371,826. In various embodiments, each subunit of the Fc domain comprises one amino acid substitution that enhanced binding to human FcRn wherein said amino acid substitutions are M428L and N434S, disclosed in U.S. Pat. Publication No. 8,546,543. In various embodiments, half-life extension mutations can be combined with amino acid substitutions that reduce binding to an activating Fc receptor and/or effector function.

In various embodiments, the Fc domain sequence used to make IL-2 variant Fc-fusions is the human IgG1-Fc domain sequence with reduced/abolished effector function set forth in SEQ ID NO: 45:

```
                                            (SEQ ID NO: 45)
DKTHTCPPCPAPEAAGAPSVFLFPPKPKDTLMISRTPEVT

CVVVDVSHEDPEVKFNWYVDGVEVHNAKTKPREEQYNSTY

RVVSVLTVLHQDWLNGKEYKCKVSNKALPAPIEKTISKAK

GQPREPQVYTLPPSRDELTKNQVSLTCLVKGFYPSDIAVE

WESNGQPENNYKTTPPVLDSDGSFFLYSKLTVDKSRWQQG

NVFSCSVMHEALHNHYTQKSLSLSPG
``` wherein SEQ ID NO: 45 contains amino acid substitutions (underlined) that ablate FcγR and C1q binding.

In various embodiments, the Fc domain sequence used to make IL-2 variant Fc-fusions is the IgG1-Fc domain with extended half-life and reduced/abolished effector function set forth in SEQ ID NO: 46

```
                                            (SEQ ID NO: 46)
DKTHTCPPCPAPEAAGGPSVFLFPPKPKDTLYITREPEVT

CVVVDVSHEDPEVKFNWYVDGVEVHNAKTKPREEQYNSTY

RVVSVLTVLHQDWLNGKEYKCKVSNKALPAPIEKTISKAK

GQPREPQVYTLPPSRDELTKNQVSLTCLVKGFYPSDIAVE

WESNGQPENNYKTTPPVLDSDGSFFLYSKLTVDKSRWQQG

NVFSCSVMHEALHNHYTQKSLSLSPG
``` wherein SEQ ID NO: 46 contains amino acid substitutions (underlined) that ablate FcγR and C1q binding and substitutions (bold) that extend fusion protein serum half-life.

In various embodiments, the Fc domain sequence used to make IL-2 variant Fc-fusions is the IgG1-Fc domain with reduced/abolished effector function and extended half-life and having the amino acid sequence set forth in SEQ ID NO: 47

```
                                          (SEQ ID NO: 47)
DKTHTCPPCPAPEAAGAPSVFLFPPKPKDTLMISRTPEVT

CVVVDVSHEDPEVKFNWYVDGVEVHNAKTKPREEQYNSTY

RVVSVLTVLHQDWLNGKEYKCKVSNKALPAPIEKTISKAK

GQPREPQVYTLPPSRDELTKNQVSLTCLVKGFYPSDIAVE

WESNGQPENNYKTTPPVLDSDGSFFLYSKLTVDKSRWQQG

NVFSCSVMHEALHAHYTQKSLSLSPG
``` wherein SEQ ID NO: 47 contains amino acid substitutions (underlined) that ablate FcγR and C1q binding and substitution (bold) that extends fusion protein serum half-life.

In various embodiments, the heterodimeric Fc domain sequence used to make the IL-2 variant Fc-fusions is the Knob-Fc domain with extended in vivo half-life sequence set forth in SEQ ID NO: 212:

```
                                         (SEQ ID NO: 212)
DKTHTCPPCPAPEAAGAPSVFLFPPKPKDTLMISRTPEVT

CVVVDVSHEDPEVKFNWYVDGVEVHNAKTKPREEQYNSTY

RVVSVLTVLHQDWLNGKEYKCKVSNKALPAPIEKTISKAK

GQPREPQVCTLPPSREEMTKNQVSLWCLVKGFYPSDIAVE

WESNGQPENNYKTTPPVLDSDGSFFLYSKLTVDKSRWQQG

NVFSCSVMHEALHAHYTQKSLSLSPG
``` wherein SEQ ID NO: 212 contains amino acid substitutions (underlined) that ablate FcγR and C1q binding and amino acid substitution (bold) to extend half-life.

In various embodiments, the heterodimeric Fc domain sequence used to make the IL-2 variant Fc-fusions is the Hole-Fc domain with extended in vivo half-life sequence set forth in SEQ ID NO: 213:

```
                                         (SEQ ID NO: 213)
DKTHTCPPCPAPEAAGAPSVFLFPPKPKDTLMISRTPEVT

CVVVDVSHEDPEVKFNWYVDGVEVHNAKTKPREEQYNSTY

RVVSVLTVLHQDWLNGKEYKCKVSNKALPAPIEKTISKAK

GQPREPQVYTLPPCREEMTKNQVSLSCAVKGFYPSDIAVE

WESNGQPENNYKTTPPVLDSDGSFFLVSKLTVDKSRWQQG

NVFSCSVMHEALHAHYTQKSLSLSPG
``` wherein SEQ ID NO: 213 contains amino acid substitutions (underlined) that ablate FcγR and C1q binding and amino acid substitution (bold) to extend half-life.

Linkers

In various embodiments, the heterologous protein is attached to the IL-2 variant by a linker and/or a hinge linker peptide. The linker or hinge linker may be an artificial sequence of between 5, 10, 15, 20, 30, 40 or more amino acids that are relatively free of secondary structure or display a-helical conformation.

Peptide linker provides covalent linkage and additional structural and/or spatial flexibility between protein domains. As known in the art, peptide linkers contain flexible amino acid residues, such as glycine and serine. In various embodiments, peptide linker may include 1-100 amino acids. In various embodiments, a spacer can contain motif of GGGSGGGS (SEQ ID NO: 55). In other embodiments, a linker can contain motif of (GGGGS)n, wherein n is an integer from 1 to 10. In other embodiments, a linker can also contain amino acids other than glycine and serine. In another embodiment, a linker can contain other protein motifs, including but not limited to, sequences of a-helical conformation such as AEAAAKEAAAKEAAAKA (SEQ ID NO: 53). In various embodiments, linker length and composition can be tuned to optimize activity or developability, including but not limited to, expression level and aggregation propensity. In another embodiment, the peptide linker can be a simple chemical bond, e.g., an amide bond (e.g., by chemical conjugation of PEG).

Exemplary peptide linkers are provided in Table 3:

TABLE 3

| Linker sequence | SEQ ID NO: |
|---|---|
| GGGSGGGSGGGS | 48 |
| GGGS | 49 |
| GSSGGSGGSGGSG | 50 |
| GSSGT | 51 |
| GGGGSGGGGSGGGS | 52 |
| AEAAAKEAAAKEAAAKA | 53 |
| GGGGSGGGGSGGGGSGGGGS | 54 |
| GGGSGGGS | 55 |
| GS | 56 |
| GGS | 57 |
| GGGGS | 58 |
| GGSG | 59 |
| SGGG | 60 |
| GSGS | 61 |
| GSGSGS | 62 |
| GSGSGSGS | 63 |
| GSGSGSGSGS | 64 |
| GSGSGSGSGSGS | 65 |
| GGGGSGGGGS | 66 |
| GGGGSGGGGSGGGGS | 67 |

Polynucleotides

In another aspect, the present disclosure provides isolated nucleic acid molecules comprising a polynucleotide encoding IL-2, an IL-2 variant, an IL-2 fusion protein, or an IL-2 variant fusion protein of the present disclosure. The subject nucleic acids may be single-stranded or double stranded. Such nucleic acids may be DNA or RNA molecules. DNA includes, for example, cDNA, genomic DNA, synthetic DNA, DNA amplified by PCR, and combinations thereof. Genomic DNA encoding IL-2 polypeptides is obtained from genomic libraries which are available for a number of species. Synthetic DNA is available from chemical synthesis of overlapping oligonucleotide fragments followed by assembly of the fragments to reconstitute part or all of the coding regions and flanking sequences. RNA may be obtained from prokaryotic expression vectors which direct high-level synthesis of mRNA, such as vectors using T7 promoters and RNA polymerase. cDNA is obtained from libraries prepared from mRNA isolated from various tissues that express IL-2. The DNA molecules of the disclosure include full-length genes as well as polynucleotides and fragments thereof. The full-length gene may also include sequences encoding the N-terminal signal sequence. Such nucleic acids may be used, for example, in methods for making the novel IL-2 variants.

In various embodiments, the isolated nucleic acid molecules comprise the polynucleotides described herein, and further comprise a polynucleotide encoding at least one heterologous protein described herein. In various embodiments, the nucleic acid molecules further comprise polynucleotides encoding the linkers or hinge linkers described herein.

In various embodiments, the recombinant nucleic acids of the present disclosure may be operably linked to one or more regulatory nucleotide sequences in an expression construct. Regulatory sequences are art-recognized and are selected to direct expression of the IL-2 variant. Accordingly, the term regulatory sequence includes promoters, enhancers, and other expression control elements. Exemplary regulatory sequences are described in Goeddel; Gene Expression Technology: Methods in Enzymology, Academic Press, San Diego, Calif. (1990). Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the present disclosure. The promoters may be either naturally occurring promoters, or hybrid promoters that combine elements of more than one promoter. An expression construct may be present in a cell on an episome, such as a plasmid, or the expression construct may be inserted in a chromosome. In various embodiments, the expression vector contains a selectable marker gene to allow the selection of transformed host cells. Selectable marker genes are well known in the art and will vary with the host cell used.

In another aspect of the present disclosure, the subject nucleic acid is provided in an expression vector comprising a nucleotide sequence encoding an IL-2 variant and operably linked to at least one regulatory sequence. The term "expression vector" refers to a plasmid, phage, virus or vector for expressing a polypeptide from a polynucleotide sequence. Vectors suitable for expression in host cells are readily available and the nucleic acid molecules are inserted into the vectors using standard recombinant DNA techniques. Such vectors can include a wide variety of expression control sequences that control the expression of a DNA sequence when operatively linked to it may be used in these vectors to express DNA sequences encoding an IL-2 variant. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., PhoS, the promoters of the yeast a-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered. An exemplary expression vector suitable for expression of vIL-2 is the pDSRa, (described in WO 90/14363, herein incorporated by reference) and its derivatives, containing vIL-2 polynucleotides, as well as any additional suitable vectors known in the art or described below.

A recombinant nucleic acid of the present disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant IL-2 polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press, 1989) Chapters 16 and 17. In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the B-gal containing pBlueBac III).

In various embodiments, a vector will be designed for production of the subject IL-2 variants in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject IL-2 variants in cells propagated in culture, e.g., to produce proteins, including fusion proteins or variant proteins, for purification.

This present disclosure also pertains to a host cell transfected with a recombinant gene including a nucleotide sequence coding an amino acid sequence for one or more of the subject IL-2 variant. The host cell may be any prokaryotic or eukaryotic cell. For example, an IL-2 variant of the present disclosure may be expressed in bacterial cells such as *E. coli*, insect cells (e.g., using a baculovirus expression system), yeast, or mammalian cells. Other suitable host cells are known to those skilled in the art.

Accordingly, the present disclosure further pertains to methods of producing the subject IL-2 variants. For example, a host cell transfected with an expression vector encoding an IL-2 variant can be cultured under appropriate conditions to allow expression of the IL-2 variant to occur. The IL-2 variant may be secreted and isolated from a mixture of cells and medium containing the IL-2 variant. Alternatively, the IL-2 variant may be retained cytoplasmically or in a membrane fraction and the cells harvested, lysed and the protein isolated. A cell culture includes host cells, media and other byproducts. Suitable media for cell culture is well known in the art.

The polypeptides and proteins of the present disclosure can be purified according to protein purification techniques are well known to those of skill in the art. These techniques involve, at one level, the crude fractionation of the proteinaceous and non-proteinaceous fractions. Having separated the peptide polypeptides from other proteins, the peptide or polypeptide of interest can be further purified using chromatographic and electrophoretic techniques to achieve partial or complete purification (or purification to homogeneity). The term "isolated polypeptide" or "purified polypeptide" as used herein, is intended to refer to a composition, isolatable from other components, wherein the polypeptide is purified to any degree relative to its naturally-obtainable state. A purified polypeptide therefore also refers to a polypeptide that is free from the environment in which it may naturally occur. Generally, "purified" will refer to a polypeptide composition that has been subjected to fractionation to remove various other components, and which composition substantially retains its expressed biological activity. Where the term "substantially purified" is used, this designation will refer to a peptide or polypeptide composition in which the polypeptide or peptide forms the major component of the composition, such as constituting about 50%, about 60%, about 70%, about 80%, about 85%, or about 90% or more of the proteins in the composition.

Various techniques suitable for use in purification will be well known to those of skill in the art. These include, for example, precipitation with ammonium sulphate, PEG, antibodies (immunoprecipitation) and the like or by heat denaturation, followed by centrifugation; chromatography such as affinity chromatography (Protein-A columns), ion exchange, gel filtration, reverse phase, hydroxyapatite, hydrophobic interaction chromatography; isoelectric focusing; gel electrophoresis; and combinations of these techniques. As is generally known in the art, it is believed that the order of conducting the various purification steps may be changed, or that certain steps may be omitted, and still result in a suitable method for the preparation of a substantially purified polypeptide.

Pharmaceutical Compositions

In another aspect, the present disclosure provides a pharmaceutical composition comprising the IL-2 variants, or IL-2 variant fusion proteins, in admixture with a pharmaceutically acceptable carrier. Such pharmaceutically acceptable carriers are well known and understood by those of ordinary skill and have been extensively described (see, e.g., Remington's Pharmaceutical Sciences, 18th Edition, A. R. Gennaro, ed., Mack Publishing Company, 1990). The pharmaceutically acceptable carriers may be included for purposes of modifying, maintaining or preserving, for example, the pH, osmolarity, viscosity, clarity, color, isotonicity, odor, sterility, stability, rate of dissolution or release, adsorption or penetration of the composition. Such pharmaceutical compositions may influence the physical state, stability, rate of in vivo release, and rate of in vivo clearance of the polypeptide. Suitable pharmaceutically acceptable carriers include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute thereof. In one embodiment of the present disclosure, compositions may be prepared for storage by mixing the selected composition having the desired degree of purity with optional formulation agents (Remington's Pharmaceutical Sciences, supra) in the form of a lyophilized cake or an aqueous solution. Further, the therapeutic composition may be formulated as a lyophilizate using appropriate excipients such as sucrose. The optimal pharmaceutical composition will be determined by one of ordinary skill in the art depending upon, for example, the intended route of administration, delivery format, and desired dosage.

When parenteral administration is contemplated, the therapeutic pharmaceutical compositions may be in the form of a pyrogen-free, parenterally acceptable aqueous solution comprising the desired IL-2 polypeptide or IL-2 polypeptide fusion protein, in a pharmaceutically acceptable vehicle. A particularly suitable vehicle for parenteral injection is sterile distilled water in which a polypeptide is formulated as a sterile, isotonic solution, properly preserved. In various embodiments, pharmaceutical formulations suitable for injectable administration may be formulated in aqueous solutions, preferably in physiologically compatible buffers such as Hanks' solution, Ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Optionally, the suspension may also contain suitable stabilizers or agents to increase the solubility of the compounds and allow for the preparation of highly concentrated solutions.

In various embodiments, the therapeutic pharmaceutical compositions may be formulated for targeted delivery using a colloidal dispersion system. Colloidal dispersion systems include macromolecule complexes, nanocapsules, microspheres, beads, and lipid-based systems including oil-in-water emulsions, micelles, mixed micelles, and liposomes. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

In various embodiments, oral administration of the pharmaceutical compositions is contemplated. Pharmaceutical compositions that are administered in this fashion can be formulated with or without those carriers customarily used in the compounding of solid dosage forms such as tablets and capsules. In solid dosage forms for oral administration (capsules, tablets, pills, dragees, powders, granules, and the like), one or more therapeutic compounds of the present disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof Besides inert diluents, the oral compositions can also include adjuvants such as wetting agents, emulsifying and suspending agents, sweetening, flavoring, coloring, perfuming, and preservative agents.

In various embodiments, topical administration of the pharmaceutical compositions, either to skin or to mucosal membranes, is contemplated. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface-active agents. Keratolytic agents such as those known in the art may also be included. Examples are salicylic acid and sulfur. Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required. The ointments, pastes, creams and gels may contain, in addition to a subject compound of the disclosure (e.g., a IL-2 variant), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Additional pharmaceutical compositions contemplated for use herein include formulations involving polypeptides in sustained- or controlled-delivery formulations. Techniques for formulating a variety of other sustained- or controlled-delivery means, such as liposome carriers, bioerodible microparticles or porous beads and depot injections, are also known to those skilled in the art.

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the polypeptide is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.001 mg/kg to up to about 100 mg/kg or more, depending on the factors mentioned above. Polypeptide compositions may be preferably injected or administered intravenously. Long-acting pharmaceutical compositions may be administered every three to four days, every week, or biweekly depending on the half-life and clearance rate of the particular formulation. The frequency of dosing will depend upon the pharmacokinetic parameters of the polypeptide in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

The route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, intralesional routes, intramedullary, intrathecal, intraventricular, transdermal, subcutaneous, or intraperitoneal or intratumorally; as well as intranasal, enteral, topical, sublingual, urethral, vaginal, or rectal means, by sustained release systems or by implantation devices. Where desired, the compositions may be administered by bolus injection or continuously by infusion, or by implantation device. Alternatively, or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

Therapeutic Uses

The present disclosure provides for a method of treating an autoimmune disease in a subject, comprising administering to said subject a therapeutically effective amount (either as monotherapy or in a combination therapy regimen) of an IL-2 variant, or IL-2 variant fusion protein, of the present disclosure in pharmaceutically acceptable carrier. An autoimmune disease, as pertains to the present invention, is a disease or disorder arising from and directed against an individual's own tissues or a co-segregate or manifestation thereof or resulting condition therefrom. In various embodiments, the autoimmune disease includes, but is not limited to, arthritis (including rheumatoid arthritis, reactive arthritis), systemic lupus erythematosus (SLE), psoriasis and inflammatory bowel disease (IBD), encephalomyelitis, uveitis, myasthenia gravis, multiple sclerosis, insulin dependent diabetes, Addison's disease, celiac disease, chronic fatigue syndrome, autoimmune hepatitis, autoimmune alopecia, ankylosing spondylitis, ulcerative colitis, Crohn's disease, fibromyalgia, pemphigus vulgaris, Sjogren's syndrome, Kawasaki's Disease, hyperthyroidism/Graves disease, hypothyroidism/Hashimoto's disease, endometriosis, scleroderma, pernicious anemia, Goodpasture syndrome, Guillain-Barre syndrome, Wegener's disease, glomerulonephritis, aplastic anemia (including multiply transfused aplastic anemia patients), paroxysmal nocturnal hemoglobinuria, myelodysplastic syndrome, idiopathic thrombocytopenia purpura, autoimmune hemolytic anemia, Evan's syndrome, Factor VIII inhibitor syndrome, systemic vasculitis, dermatomyositis, polymyositis and rheumatic fever, autoimmune lymphoproliferative syndrome (ALPS), autoimmune bullous pemphigoid, Parkinson's disease, sarcoidosis, vitiligo, primary biliary cirrhosis, and autoimmune myocarditis.

In another aspect, the present disclosure provides for a method of treating an inflammatory disease in a subject, comprising administering to said subject a therapeutically effective amount (either as monotherapy or in a combination therapy regimen) of an IL-2 variant, or IL-2 variant fusion protein, of the present disclosure in pharmaceutically acceptable carrier. "Inflammatory diseases" include all diseases associated with acute or various inflammation. Acute inflammation is the initial response of the body to harmful stimuli and results from an increased movement of plasma and leukocytes (such as e.g. granulocytes) from the blood into the injured tissues. A number of biochemical events propagates and matures the inflammatory response, involving the local vascular system, the immune system, and various cells within the injured tissue. Prolonged inflammation is referred to as various inflammation, which leads to a progressive shift in the type of cells present at the site of inflammation and is characterized by simultaneous destruction and healing of the tissue from the inflammatory process.

In another aspect, the present disclosure provides a method for treating an inflammatory disease in a subject, comprising administering a therapeutically effective amount of the pharmaceutical compositions of the invention to a subject in need thereof. In one embodiment, the subject is a human subject. In various embodiments, the inflammatory disease to be treated includes, but is not limited to, Crohn's disease, colitis, dermatitis, psoriasis, diverticulitis, hepatitis, irritable bowel syndrome (IBS), lupus erythematous, nephritis, Parkinson's disease, ulcerative colitis, collagenous colitis, lymphocytic colitis, ischemic colitis, diversion colitis, Behcet's syndrome and indeterminate colitis multiple sclerosis (MS), Alzheimer's disease, arthritis, rheumatoid arthritis, asthma, and various cardiovascular diseases such as atherosclerosis and vasculitis. In various embodiments, the inflammatory disease is selected from the group consisting of rheumatoid arthritis, diabetes, gout, cryopyrin-associated periodic syndrome, and chronic obstructive pulmonary disorder.

In another aspect, the present disclosure provides methods for organ transplantation or associated graft-versus-host diseasein a subject, comprising administering a therapeutically effective amount of the pharmaceutical compositions of the invention to a subject in need thereof. In one embodiment, the subject is a human subject. In various embodiments, the transplantation is selected from organ transplantations of the heart, kidneys, liver, lungs, pancreas, intestine and thymus or from tissues transplantations of the bones, tendons, cornea, skin, heart valves, nerves and veins. As used herein, the term "graft vs. host disease" or "GvHD" refers to a condition, including acute and chronic, resulting from transplanted (graft) cell effects on host cells and tissues resulting from GVH. In other words, donor immune cells infused within the graft or donor immune cells that develop from the stem cells, may see the patient's (host) cells as foreign and turn against them with an immune response. Acute graft-versus-host disease (GvHD) is specifically a disorder caused by donor immune cells in patients who have had an allogeneic marrow or blood cell transplantation. The most commonly affected tissues are skin intestine and liver. In severe cases, GvHD can cause blistering in the skin or excessive diarrhea and wasting. Prednisone and/or other immunosuppressive medications are used to treat acute graft-versus-host disease.

A therapeutically effective dose can be estimated initially from cell culture assays by determining an $EC_{50}$. A dose can then be formulated in animal models to achieve a circulating plasma concentration range that includes the $EC_{50}$ as determined in cell culture. Such information can be used to more accurately determine useful doses in humans. Levels in plasma may be measured, for example, by HPLC. The exact composition, route of administration and dosage can be chosen by the individual physician in view of the subject's condition.

Dosage regimens can be adjusted to provide the optimum desired response (e.g., a therapeutic or prophylactic response). For example, a single bolus can be administered, several divided doses (multiple or repeat or maintenance) can be administered over time and the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the present disclosure will be dictated primarily by the unique characteristics of the antibody and the particular therapeutic or prophylactic effect to be achieved.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a subject may also be determined, as can the temporal requirements for administering each agent to provide a detectable therapeutic benefit to the subject. Accordingly, while certain dose and administration regimens are exemplified herein, these examples in no way limit the dose and administration regimen that may be provided to a subject in practicing the present disclosure.

It is to be noted that dosage values may vary with the type and severity of the condition to be alleviated and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this disclosure may be based on a variety of factors, including the type of disease, the age, weight, sex, medical condition of the subject, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present disclosure encompasses intra-subject dose-escalation as determined by the skilled artisan. Determining appropriate dosages and regimens are well-known in the relevant art and would be understood to be encompassed by the skilled artisan once provided the teachings disclosed herein.

An exemplary, non-limiting daily dosing range for a therapeutically or prophylactically effective amount of an IL-2 variant, or IL-2 variant fusion protein, of the disclosure can be range from about 0.1 µg/kg to 100 mg/kg or more, depending on the factors mentioned above. For repeated administrations over several days or longer, depending on the condition, the treatment would generally be sustained until a desired suppression of disease symptoms occurs. In various embodiments, the dosage would be in the range from about 0.0001 to 100 mg/kg, 0.0001 to 90 mg/kg, 0.0001 to 80 mg/kg, 0.0001 to 70 mg/kg, 0.0001 to 60 mg/kg, 0.0001 to 50 mg/kg, 0.0001 to 40 mg/kg, 0.0001 to 30 mg/kg, 0.0001 to 20 mg/kg, 0.0001 to 10 mg/kg, 0.0001 to 5 mg/kg, 0.0001 to 4 mg/kg, 0.0001 to 3 mg/kg, 0.0001 to 2 mg/kg, 0.0001 to 1 mg/kg, 0.001 to 50 mg/kg, 0.001 to 40 mg/kg, 0.001 to 30 mg/kg, 0.001 to 20 mg/kg, 0.001 to 10 mg/kg, 0.001 to 5 mg/kg, 0.001 to 4 mg/kg, 0.001 to 3 mg/kg, 0.001 to 2 mg/kg, 0.001 to 1 mg/kg, 0.010 to 50 mg/kg, 0.010 to 40 mg/kg, 0.010 to 30 mg/kg, 0.010 to 20 mg/kg, 0.010 to 10 mg/kg, 0.010 to 5 mg/kg, 0.010 to 4 mg/kg, 0.010 to 3 mg/kg, 0.010 to 2 mg/kg, 0.010 to 1 mg/kg, 0.1 to 50 mg/kg, 0.1 to 40 mg/kg, 0.1 to 30 mg/kg, 0.1 to 20 mg/kg, 0.1 to 10 mg/kg, 0.1 to 5 mg/kg, 0.1 to 4 mg/kg, 0.1 to 3 mg/kg, 0.1 to 2 mg/kg, 0.1 to 1 mg/kg, 1 to 50 mg/kg, 1 to 40 mg/kg, 1 to 30 mg/kg, 1 to 20 mg/kg, 1 to 10 mg/kg, 1 to 5 mg/kg, 1 to 4 mg/kg, 1 to 3 mg/kg, 1 to 2 mg/kg, or 1 to 1 mg/kg body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. It is to be noted that dosage values may vary with the type and severity of the conditions to be alleviated. It is to be further understood that for any particular subject, the specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Toxicity and therapeutic index of the pharmaceutical compositions of the disclosure can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effective dose is the therapeutic index and it can be expressed as the ratio $LD_{50}/ED_{50}$. Compositions that exhibit large therapeutic indices are generally preferred.

The dosing frequency of the administration of the IL-2 variant, or IL-2 variant fusion protein pharmaceutical composition depends on the nature of the therapy and the particular disease being treated. The subject can be treated at regular intervals, such as twice weekly, weekly or monthly, until a desired therapeutic result is achieved. Exemplary dosing frequencies include but are not limited to once weekly without break; once every 2 weeks; once every 3 weeks; weakly without break for 2 weeks, then monthly; weakly without break for 3 weeks, then monthly; monthly; once every other month; once every three months; once every four months; once every five months; or once every six months, or yearly.

Combination Therapy

As used herein, the terms "co-administration", "co-administered" and "in combination with", referring to the a IL-2 variant, or IL-2 variant fusion protein, of the disclosure and one or more other therapeutic agents, is intended to mean, and does refer to and include the following: simultaneous administration of such combination of a IL-2 variant, or IL-2 variant fusion protein, of the disclosure and therapeutic agent(s) to a subject in need of treatment, when such components are formulated together into a single dosage form which releases said components at substantially the same time to said subject; substantially simultaneous administration of such combination of a IL-2 variant, or IL-2 variant fusion protein, of the disclosure and therapeutic agent(s) to a subject in need of treatment, when such components are formulated apart from each other into separate dosage forms which are taken at substantially the same time by said subject, whereupon said components are released at substantially the same time to said subject; sequential administration of such combination of a IL-2 variant, or IL-2 variant fusion protein, of the disclosure and therapeutic agent(s) to a subject in need of treatment, when such components are formulated apart from each other into separate dosage forms which are taken at consecutive times by said subject with a significant time interval between each administration, whereupon said components are released at substantially different times to said subject; and sequential administration of such combination of a IL-2 variant, or IL-2 variant fusion protein, of the disclosure and therapeutic agent(s) to a subject in need of treatment, when such components are formulated together into a single dosage form which releases said components in a controlled manner whereupon they are concurrently, consecutively, and/or overlappingly released at the same and/or different times to said subject, where each part may be administered by either the same or a different route.

In another aspect, the present disclosure provides a method for treating an autoimmune disease in a subject, comprising administering a therapeutically effective amount of the pharmaceutical compositions of the invention in combination with a second therapeutic agent capable of treating an autoimmune disease. In various embodiments, the second therapeutic agent is selected from the group consisting of: immunosuppressants such as corticosteroids, cyclosporin, cyclophosphamide, prednisone, azathioprine, methotrexate, rapamycin, tacrolimus, biological agents such as TNF-alpha blockers or antagonists, IL-10 agonist or long half-life extended IL-10 (PEGylated, antibody or Fc fusion IL-10); immunosuppressive agents (e.g., antibodies against other lymphocyte surface markers (e.g., CD40, alpha-4 integrin) or against cytokines), other fusion proteins (e.g., CTLA-4-Ig (ORENCIA®), TNFR-Ig (ENBREL®)), TNF-alpha blockers such as ENBREL®, REMICADE®, CIMZIA® and HUMIRA®, cyclophosphamide (CTX) (i.e. ENDOXAN®, CYTOXAN®, NEOSAR®, PROCYTOX®, REVIMMUNE®), methotrexate (MTX) (i.e. RHEUMA-TREX®, TREXALL®), rituximab, belimumab (i.e. BEN-LYSTA®), anti-IL-6 antibodies (such as Sarilumab), or anti-IL-6 receptor antibodies (such as Tocilizumab), or other immunosuppressive drugs (e.g., cyclosporin A, FK506-like compounds, rapamycin compounds, or steroids), anti-proliferatives, cytotoxic agents, or other compounds that may assist in immunosuppression. or any other biological agent targeting any inflammatory cytokine, nonsteroidal anti-inflammatory drugs/Cox-2 inhibitors, hydroxychloroquine, sulphasalazopryine, gold salts, etanercept, infliximab, mycophenolate mofetil, basiliximab, atacicept, rituximab, cytoxan, interferon beta-1a, interferon beta-1b, glatiramer acetate, mitoxantrone hydrochloride, anakinra and/or other biologics and/or intravenous immunoglobulin (IVIG). Non-limiting examples of such known therapeutics include interferons, such as IFN-beta-1a (REBIF®. AVONEX® and CINNOVEX®) and IFN-beta-1b (BETASERON®, EXTAVIA®, BETAFERON®, ZIFERON®); glatiramer acetate (COPAXONE®), a polypeptide; natalizumab (TYSABRI®); and mitoxantrone (NOVANTRONE®), a cytotoxic agent.

In another aspect, the present disclosure provides a method for treating an inflammatory disease in a subject, comprising administering a therapeutically effective amount of the pharmaceutical compositions of the invention in combination with a second therapeutic agent capable of inhibiting or reducing differentiation of Th1, Th17, Th22, and/or other cells that secrete, or cause other cells to secrete, inflammatory molecules, including, but not limited to, IL-1beta, TNF-alpha, TGF-beta, IFN-gamma, IL-17, IL-6, IL-23, IL-22, IL-21, and MMPs; inhibiting or reducing activity of Th1, Th 17, Th22, and/or other cells that secrete, or cause other cells to secrete, inflammatory molecules, including, but not limited to, IL-1beta, TNF-alpha, TGF-beta, IFN-gamma, IL-17, IL-6, IL-23, IL-22, IL-21, and MMPs; inhibiting or reducing the Th1 and/or Th17 pathways; inhibiting or reducing cytokine production and/or secretion by Th1, Th17, Th22, and/or other cells that secrete, or cause other cells to secrete, inflammatory molecules, including, but not limited to, IL-1beta, TNF-alpha, TGF-beta, IFN-gamma, IL-17, IL-6, IL-23, IL-22, IL-21, and MMPs; inhibiting or reducing proliferation of Th1, Th17, Th22, and/or other cells that secrete, or cause other cells to secrete, inflammatory molecules, including, but not limited to, IL-1beta, TNF-alpha, TGF-beta, IFN-gamma, IL-17, IL-6, IL-23, IL-22, IL-21, and MMPs. In various embodiments the second therapeutic agent is a non-steroidal anti-inflammatory agents including, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clmdanac, oxepinac, felbmac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed. In various embodiments the second therapeutic agent is a steroidal anti-inflammatory drugs including, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fiuosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolones prednisone, beclomethasone dipropionate, triamcinolone, and mixtures thereof.

In various embodiments, the combination therapy comprises administering an IL-2 variant and the second agent composition simultaneously, either in the same pharmaceutical composition or in separate pharmaceutical composition. In various embodiments, an IL-2 variant composition and the second agent composition are administered sequentially, i.e., an IL-2 variant composition is administered either prior to or after the administration of the second agent composition. In various embodiments, the administrations of an IL-2 variant composition and the second agent composition are concurrent, i.e., the administration period of an IL-2 variant composition and the second agent composition overlap with each other. In various embodiments, the administrations of an IL-2 variant composition and the second agent composition are non-concurrent. For example, in various embodiments, the administration of an IL-2 variant composition is terminated before the second agent composition is administered. In various embodiments, the administration second agent composition is terminated before an IL-2 variant composition is administered.

The following examples are offered to more fully illustrate the disclosure but are not construed as limiting the scope thereof.

Example 1

Design of the IL-2 Variants to Selectively Targeting Treg Cells

In one aspect the current invention is directed one or more mutations to attenuate the affinity of IL-2 for the IL-2Rβ and/or γc receptor subunits. In the context of weakened IL-2Rβγ interaction, the enhanced IL-2 sensitivity of Tregs conferred by IL-2Rα expression may result in a pronounced growth advantage for this cell subset. As a result, these mutants could serve as Treg promoters in autoimmune and inflammatory diseases.

The variants were designed computationally based on the reported structure of human IL-2 in Protein Data Bank (PDB code 2B5I). A panel of variants were designed including 1 to 3 mutations (introducing conservative and non-conservative amino acid substitutions) in residues that are at or near the interface that make direct contact with IL-2Rβ or γc receptor subunits. For example, D20 is engaged in an extensive network of hydrogen bonds to receptor subunit side chains at the IL-2Rβ interface. Similarly, N88 is an energetic hot spot for the IL-2/IL-2Rβ interaction, engaging in critical hydrogen bonds with the receptor chain. Q126 is integral to the γc interaction, and Q22 is similarly at the γc interface. The present inventors postulated that mutations at the above-mentioned sites or neighboring residues may result in a defect in their ability to interact with the IL-2 intermediate affinity receptor IL-2Rβγ.

Interestingly, the proposed '$^{19}$LDL' motif resembling a component of bacterial toxins (Baluna R, Rizo et. al., Proc Natl Acad Sci 1999; 96:3957-62) overlaps with the IL-2Rβ interface. This 'toxic motif' is responsible, in part, for direct vascular toxicity of IL-2. As a result, replacement of the critical toxic motif residue D20, or mutations introduced to substitute the flanking residues, L19 and L21 with non-aliphatic residues, was expected to also eliminate the toxic motif and prevent endothelial cell damage and significantly reduce VLS as well.

In the present invention, a panel of IL-2 variants (SEQ ID NOs: 4-43, 108-146, and 193-197) with the following 1-3 amino acid substitutions (D20T, D20E, D20N, D20Q, D20S, D20Y, D20I , L19Y, L19N, L19R, L19Q, L19H, L19D, L19P, L19S, L21S, L21N, L21R, N88R, N88G, N88I , N88Q, N88E, N88T, N88M, Q126E, Q126L, Q126N, Q126D, Q126M, Q126K, Q126H, Q126Y, Q125E, S125K, S125H, S125W, S125I, Q22N, Q22H, Q22K, Q22Y, Q221, D20I /N88G, D20I/N88R, D20T/N88R, D20I/N88I , D20T/Q126E, D20T/N88R/Q126E, D20T/Q126L, D20T/N88R/Q126L, L19N/Q126E, L19R/Q126E, L19Y/Q126E, L19H/Q126E, L19Q/Q126E, L19S/Q126E, L19Y/Q126K, L19Y/Q126H, L19Y/Q126Y, L19Y/S125E, L19Y/S125K, L19Y/S125H, L19Y/S125W, L19Y/S125I , L19Y/Q22N, L19Y/Q22H, L19Y/Q22K, L19Y/Q22Y, L19Y/Q221, L19H/Q126K, L19H/S125I , L19D/S125I , D20E/S251, D20T/S125I , L19Y/S125l/Q126E, L19H/S125l/Q126E, L19H/S125l/Q126K, L19Q/S125I/Q126E, L19Q/Q126K, L19Q/S125l/Q126K, D20T/S125l/Q126K, L19N/S125l/Q126K, and L19R/S125l/Q126K) were expressed as C-terminal fusions to the Fc homodimer via a "GGGSGGGS" linker (SEQ ID NO: 55). IL-2 variants with D20I , D20I/N88G, D20E, or L19N amino acid substitutions were also expressed as N-terminal fusions to the Fc homodimer via a rigid "AEAAAKEAAAKEAAAKA" linker (SEQ ID NO: 53). Collectively, the sequences of these IL-2 variants Fc fusion constructs are listed with SEQ ID NOS: 73-107, 147-189 and 198-211. Constructs with wild-type IL-2 in the same Fc fusion formats (both C- and N-terminal) were also made (SEQ ID NOS: 71 and 72).

All of the above IL-2 variant Fc fusion molecules are designed to afford a growth advantage to cells that highly express IL-2Rα, leading to the preference for Treg cells versus other lymphocytes proliferation, including CD4+ conventional T cells, CD8+ T cells, and NK cells. Further, the mutations at position 19, 20, or 21 are expected to eliminate the toxic motif responsible for vascular toxicity, so the resulting molecules may have two beneficial properties, including enhanced selectivity for Treg activation and reduced endothelial cell damage. Nevertheless, optimal mutation or mutation combination is critical to tune the level of impairment on activation of effector T and NK cells while maintaining high enough potency on activation of Treg cells and thus maximize the window for selective targeting of Treg subset.

Moreover, a single point mutation has been identified and led to improved protein stability, higher expression level, and lower aggregation propensity. Combination of aggregation-reducing and Treg-targeting mutations resulted in superior protein developability as well as Treg cell growth advantages.

Example 2

Construction and Production of IL-2 Fc Fusion Constructs

All genes were codon optimized for expression in mammalian cells, which were synthesized and subcloned into the recipient mammalian expression vector (GenScript). Protein expression is driven by an CMV promoter and a synthetic SV40 polyA signal sequence is present at the 3' end of the CDS. A leader sequence has been engineered at the N-terminus of the constructs to ensure appropriate signaling and processing for secretion.

The constructs were produced by co-transfecting HEK293-F cells growing in suspension with the mammalian expression vectors using polyethylenimine (PEI, 25,000 MW linear, Polysciences). If there were two or more expression vectors, the vectors were transfected in a 1:1 ratio. For transfection, HEK293 cells were cultivated in serum free FreeStyle™ 293 Expression Medium (ThermoFisher). For production in 1000 ml shaking flasks (working volume 330 mL), HEK293 cells were seeded at a density of $0.8\times10^6$ cells/ml 24 hours before transfection. A total of 330 μg of DNA expression vectors were mixed with 16.7 ml Opti-Mem™ Medium (ThermoFisher). After addition of 0.33 mg PEI diluted in 16.7 ml Opti-Mem™ Medium, the mixture was vortexed for 15 sec and subsequently incubated for 10 min at room temperature. The DNA/PEI solution was then added to the cells and incubated at 37° C. in an incubator with 8% $CO_2$. Sodium butyrate (Millipore Sigma) was added to the cells at day 4 at a final concentration of 2 mg/L to help sustain protein expression. After 6 days cultivation, supernatant was collected for purification by centrifugation for 20 min at 2200 rpm. The solution was sterile filtered (0.22 μm filter, Corning). The secreted protein was purified from cell culture supernatants using Protein A affinity chromatography.

For affinity chromatography each supernatant was loaded on a HiTrap™ MabSelectSure™ column (CV=5 mL, GE Healthcare) equilibrated with 25 ml phosphate buffered saline, pH 7.2 (ThermoFisher). Unbound protein was removed by washing with 5 column volumes PBS, pH 7.2 and target protein was eluted with 25 mM sodium citrate, 25 mM sodium chloride, pH 3.2. Protein solution was neutralized by adding 3% of 1 M Tris pH 10.2. Ion exchange chromatography or mix-mode chromatography, including but not limited to CaptoTYMMC (GE Healthcare), ceramic hydroxyapatite, or ceramic fluoroapatite (Bio-Rad) was also utilized to polish the Protein A material as needed. Target protein was concentrated with an Amicon®Ultra-15 concentrator 10 KDa NMWC (Merck Millipore Ltd.).

The purity and molecular weight of the purified constructs were analyzed by SDS-PAGE with and in the absence of a reducing agent and staining with Coomassie (Imperial® Stain). The NuPAGE® Pre-Cast gel system (4-12% or 8-16% Bis-Tris, ThermoFisher) was used according to the manufacturer's instructions. The protein concentration of purified protein samples was determined by measuring the UV absorbance at 280 nm (Nanodrop Spectrophotometer, ThermoFisher) divided by the molar extinction coefficient calculated on the basis of the amino acid sequence. The aggregate content of the constructs was analyzed on an Agilent 1200 high-performance liquid chromatography (HPLC) system. Samples were injected onto an AdvanceBio size-exclusion column (300 Å, 4.6×150 mm, 2.7 µm, LC column, Agilent) using 150 mM sodium phosphate, pH 7.0 as the mobile phase at 25° C.

It is worth noting that the expression profiles and aggregation propensities of IL-2 variant Fc fusions vary significantly between constructs with different mutation sites or mutants sharing the same mutation site but different residue substitutions.

Example 3

A Single Amino Acid Substitution in IL-2 Results in Universal Improvement in the Developability of the Fusion Compounds The engineering approach to find a combination of mutations that result in a variant protein with the desired biological properties encountered significant challenges when applied to IL-2. It is known in the field that naturally occurring IL-2 protein tends not to be very stable and is prone to aggregate. This was demonstrated in our experiments that the wild-type IL-2 Fc fusion protein (P-0250) expressed at a low level (around 3 mg/L transiently in HEK-293F cells) with high aggregation propensity, exemplified by SEC chromatogram depicted in FIG. 1A. The engineering efforts floundered as amino acid substitutions in IL-2 aimed at the desired biological activity typically resulted in mutant proteins that are even less stable. A significant portion of IL-2 variants of the current work expressed at extremely low level, and some variants were significantly more aggregation prone, exemplified by SEC chromatogram of P-0318 (SEQ ID NO: 95) depicted in FIG. 1B. This is problematic for the manufacture and storage of a therapeutic agent.

It was also observed that the expression profiles and aggregation propensities of IL-2 variant fusions vary significantly among constructs with different mutation sites or mutants sharing the same mutation site but different residue substitutions. This observation is exemplified by P-0317 (SEQ ID NO: 94) and P-0318 (SEQ ID NO: 95). Both variant fusions share the same mutation sites at residues 20 and 88 and differ only by one amino acid. P-0317 harbors amino acid substitutions of D20I and N88R while P-0318 contains D20I and N88I mutations. Both variant fusions expressed at similarly low level. As can be seen in FIG. 1B, P-0318 is very aggregation prone: 65% high-molecular weight species, which makes the expected peak as the minor species in the chromatogram and was marked with an arrow. In contrast, P-0317 is relatively pure with 7.5% aggregates (FIG. 1C). It would be deduced that N88R mutation may reduce aggregation propensity of the resulting fusion proteins. However, IL-2 with N88R single mutation, or D20T/N88R dual mutations, the resulting fusion proteins, P-0254 (SEQ ID NO: 71) and P-0324 (SEQ ID NO: 96), respectively, were aggregation prone with 30-40% aggregates. So, the contributions of individual amino acid substitution to the protein stability seem to be context dependent.

The fact that amino acid substitutions to IL-2 typically result in less stable protein was further compounded by the unpredictable contributions of different residue substitutions to the protein stability. It is thus very desirable to find residue substitution(s) that can universally enhance protein developability, including improved stability, higher expression level, and lower aggregation propensity.

Amino acid substitutions at position 125 was originally aimed at tuning IL-2 selectivity as the residue is in immediate proximity to Q126, which is integral to the γc interaction. Naturally occurring IL-2 contains an unpaired cysteine at position 125, which was replaced by a serine in Proleukin, and S125 is considered as wild type IL-2 residue in the present invention. IL-2 containing alanine substitution at position 125 is also widely used. As substitution of serine or alanine for cysteine at position 125 retained full biological activity, bulky charged or hydrophobic residues, including Glu, Lys, Try, His, and Ile, were introduced at position 125 to replace Ser of P-0372 (SEQ ID NO: 79) aiming to interfere the interaction of Q126 with γc so as to achieve altered biological activity. All the resulting fusion molecules but P-0471 (SEQ ID NO: 178) expressed at too low level to be characterized. P-0471, on the contrary, when compared to its S125 counterpart (P-0372), expressed at a significantly higher level (19.3 mg/L vs 4.0 mg/L titer) with greatly reduced aggregation propensity (1% vs 21.7% aggregation). The impressive improvement in developability, especially on the product purity prompted us to evaluate whether such enhancement by isoleucine substitution at position 125 can be recapitulated in different mutational context.

S125I substitution was thus introduced into a number of IL-2 variant Fc fusion molecules. The constructs harboring Ile-125 substitution in IL-2 were expressed using the same vector and in the same culturing conditions as their Ser-125 counterparts and purified using MabSelectSure. The expression level in mg/L and purity assessed by SEC chromatography in aggregation % of exemplary molecules are summarized in Table 4. The two molecules in the same row of Table 4 share the same other amino acid substitution(s) and differ only at residue 125 with either serine or isoleucine. As an example, the SEC chromatogram and SDS-PAGE pictures of P-0447 (SEQ ID NO: 168) and its Ile-125 counterpart P-0511 (SEQ ID NO: 198) were further illustrated in FIGS. 1D and 1E. It is clear from Table 4 that isoleucine substitution at position 125 resulted in 4 to 11-fold enhanced expression level and uniformly low aggregation propensity.

TABLE 4

The 125I substitution reduced aggregation and increased expression of various IL-2 fusion proteins

| Serine-125 | | | Isoleucine-125 | | | expression |
|---|---|---|---|---|---|---|
| Protein ID: | Aggregation % (SEC) | Expression (mg/L) | Protein ID: | Aggregation % (SEC) | Expression (mg/L) | fold↑ by S125I substitution |
| P-0250 | 25.7 | 3.1 | P-0531 | 0.7 | 29.5 | 9.6 |
| P-0424 | 21.4 | 7.7 | P-0491 | 0.6 | 36.7 | 4.8 |
| P-0425 | 32.6 | 2.6 | P-0492 | 0 | 13.6 | 5.2 |
| P-0372 | 21.7 | 4.0 | P-0471 | 1.0 | 19.3 | 4.8 |
| P-0363 | 29.4 | 1.4 | P-0494 | 0.5 | 11.7 | 8.4 |
| P-0364 | 21.1 | 0.7 | P-0493 | 1.7 | 7.9 | 11.3 |
| P-0447 | 23.7 | 7.3 | P-0511 | 0.7 | 26.6 | 3.6 |
| P-0419 | 33.8 | 6.7 | P-0495 | 0.8 | 23.5 | 3.5 |

It is evident from current invention that isoleucine substitution at position 125 resulted in universal improvement in developability of the IL-2 fusion constructs with full retaining of biological activity. Ile substitution at position 125 of wild type IL-2 and IL-2 variants with different mutational context in Fc fusion format all resulted in 4 to 11-fold enhanced expression level and uniformly low aggregation propensity. The expression level in mg/L and purity of protein A purified material assessed by SEC chromatography in % of aggregation of exemplary molecules are summarized in Table 4. This finding is especially valuable as engineering of IL-2 for desired biological properties had been hindered by the fact that altering marginally stable wild-type IL-2 typically results in even less stale mutant proteins. The inherent challenges of IL-2 engineering can be mitigated by a single amino acid substitution at position 125 with isoleucine. In summary, isoleucine substitution at position 125 of IL-2 or IL-2 variant significantly improved protein developability profile, which was demonstrated by the protein expression increase and substantial reduction of aggregation propensity of the IL-2 constructs.

Example 4

Identification of IL-2 Variants of Single Amino Acid Substitutions Demonstrating Differential Selectivity Towards Treg Lymphocytes Single amino acid substitutions were introduced to IL-2 at positions corresponding to amino acids interacting with receptor subunit(s) β or γ or βγ. These substitutions were aimed to reduce IL-2 signaling capacity through the intermediate affinity IL-2Rβγ complex and confer signaling specificity from the high affinity IL-2Rαβγ. IL-2 variants containing single amino acid substitutions were examined for their ability to differentially stimulate STAT5 phosphorylation in CD4 positive Treg and Tconv cells. STAT5 is known to be involved in the downstream signaling cascade upon IL-2 binding to the transmembrane IL-2 receptors. The phosphorylation of STAT5 in defined lymphocyte subpopulations was measured using fresh human peripheral blood mononuclear cells (PBMC) and the forkhead transcription factor FOXP3 was used to identify the Treg population in FACS analysis.

Briefly, human PBMC were isolated by Ficoll-Hypaque centrifugation from the buffy coat of a healthy donor. PBMC were starved in serum-free MACS buffer at 4° C. for 1 hour. $2\times10^5$ PBMC were then treated with serial dilutions of test compounds for 30 min at 37° C. Cells were fixed and permeabilized with Foxp3/Transcription Factor Staining Buffer Set (EBIO) by incubating with 1× Foxp3 fixation/permeabilization working solution for 30 minutes and washing with 1× permeabilization buffer. Cells were additionally fixed with Cytofix buffer and permeabilized with Perm Buffer III (BD Biosciences) and then washed. After blocking Fc receptors by adding human TruStain™ FcX (1:50 dilution), cells were stained with a mixture of anti-CD25-PE, anti-FOXP3-APC, anti-pSTAT5-FITC, and anti-CD4-PerCP-Cy5.5 antibodies at concentrations recommended by the manufacturer for 45 minutes at room temperature. Cells were collected by centrifugation, washed, resuspended in FACS buffer, and analyzed by flow cytometry. The flow cytometry data was gated into CD4+/Foxp3+/CD25$^{high}$ and CD4+/Foxp3−/CD25$^{low}$ groups for the Treg and CD4 conventional T cell subsets, respectively. Data are expressed as a percent of pStat5 positive cells in gated population.

FIG. 2 shows the dose-response effects of exemplary Fc fusion proteins of IL-2 variants on STAT5 phosphorylation in CD4 positive Treg and Tconv cells in comparison with the wild type fusion protein. The wild type IL-2 Fc fusion protein (P-0250) induced STAT5 phosphorylation in both Treg and Teff cells with $EC_{50}$ values of 0.1 pM and 25.4 pM, respectively. The potency of wild type IL-2 was about 250-fold greater in Treg cells than in CD4+ Tconv cells, coinciding with the higher expression levels of the high affinity trimeric receptors in Treg cells.

Various substitutions of the aspartic acid at position 20, P-0364 (D20E), P-0363 (D20T), P-0365 (D20N), P-0366 (D20Q) & P-0367 (D20S) demonstrated the ability to induce STAT5 phosphorylation in Treg cells while such activity was largely diminished or abolished in CD4+ Tconv cells (FIG. 2A & 2B). These variants are potentially Treg-biased IL-2 agents to activate Treg cells for the treatment of autoimmune disease. Furthermore, a mutation at D20, the critical residue of the proposed toxin-like motif, is expected to eliminate the toxic motif and prevent endothelial cell damage. Therefore, these variants are expected to have Treg selective activity with improved safety profile on VLS. Additionally, P-0368 showed no biological activity (FIG. 2A & 2B).

FIG. 3 shows the ability of IL-2 variant P-0375 (N88Q) to induce STAT5 phosphorylation in CD4 positive Treg and CD4+ Tconv cells in comparison with Benchmark-1 and Benchmark-2 compounds harboring V91K and N88R mutations, respectively. The activity profile of the N88Q variant was similar to that of the Benchmark-2.

FIG. 4 shows the biological activity of IL-2 variants harboring various mutations at position 19 in comparison with the wild type. Variants P-0372 (L19Y), P-0373 (L19N), P-0374 (L19R), P-0423 (L19Q), P-0424 (L19H), and P-0427 (L19S) demonstrated similar activity as the wild type in inducing STAT5 phosphorylation in Treg cells (FIGS. 4A and 4C). Variants P-0372, P-0374, P-0423, and P-0427 also largely retained the biological activity in CD4+ Tconv cells (FIGS. 4B and 4D) while such activity was reduced in CD4+ Tconv for variants P-0373 and P-0424. Mutant P-0425 (L19D) demonstrated slightly reduced potency in inducing STAT5 phosphorylation in Treg cells while such activity was significantly impaired in CD4+ Tconv cells (FIGS. 4C & 4D). The demonstrated selective activation of Treg cells over CD4+ Tconv cells by mutants P-0373, P-0424, and P-0425, especially the wide window for selective targeting of Treg subset of P-0373 and P-0425, make them potential Treg-biased IL-2 agents to activate Treg cells for the treatment of autoimmune disease. Importantly, L19 is part of the proposed toxin-like motif, and mutations at this site is also expected to have improved safety profile with reduced VLS.

Example 5

Combination of IL-2Rβ and $\gamma_c$-Targeting Amino Acid Substitutions in IL-2 for Differential Selectivity Towards Treg Lymphocytes It was demonstrated in Example 4 that directed mutations aimed to attenuate the affinity of IL-2 for either IL-2Rβ or γc receptor subunit can result in IL-2 mutants with differential selectivity towards Treg lymphocytes. It was then reasoned that modulation of the affinity of IL-2 for both IL-2Rβ and γc receptor subunits via combining one amino acid substitution(s) targeting β receptor and the other substitution(s) targeting γ receptor may yield desired potency and a selectivity window for Treg lymphocytes.

Such rationale is demonstrated in FIG. 5. FIGS. 5A and 5B show the effect of IL-2Rβ-targeting variant P-0372 (L19Y) on STAT5 phosphorylation in Treg and CD4+ Tconv cells in comparison with the wild type IL-2 fusion protein P-0250. Similarly, FIGS. 5C and 5D show the STAT5 phosphorylation activity for P-0303 (Q126E) harboring an amino acid substitution targeting to disturb the interaction with the γ receptor. The data suggested that each single amino substitution minimally impacted the pSTAT5 activation potency but also only showed a modestly improved selective window for Treg lymphocyte subset relative to the wild type. The window for selective activation of Treg cells was significantly widened by combining L19Y and Q126E mutations in P-0419 as demonstrated in FIGS. 5E and 5F. Treg activation potency was mainly reserved in P-0419, and the activity profile of the P-0419 variant was very comparable to that of the Benchmark-1 molecule that contains a V91K mutation. This strategy is particularly attractive as 19L is also part of the proposed toxin-like motif, and mutations at this site are also expected to have an improved safety profile with reduced VLS.

However, combining one amino acid substitution targeting β receptor and the other substitution targeting γ receptor may not always yield desired potency and selectivity window. It requires the right amount of activity modulation for each aspect. The four IL-2 variants in FIGS. 6A and 6B share the same L19Y substitution targeting the beta receptor, and the additional mutation designed to target the γc receptor is Q126E in P-0419, Q126K in P-0464, S125I in P-0471, and Q22K in P-0474, respectively. While all mutants retained comparable potency in inducing STAT5 phosphorylation in Treg cells (FIG. 6A), such activity varied significantly in CD4+ Tconv cells (FIG. 6B), demonstrating differential ability in tuning selectivity of Treg activation via combining amino acid substitutions.

However, compounding additional receptor attenuation by combining Q126E substitution to IL-2 variants that already demonstrated biased specificity for Treg subset may result in significantly diminished or ablated activity for Treg cells. As demonstrated in (FIGS. 6C and 6D), both variants P-0373 (L19N) and P-0363 (D20T) already showed some or significant biased selective window for Treg cells (FIGS. 6C and 6D). Their respective counterparts with an additional Q126E substitution, P-0417 and P-0322, showed a pronounced reduced potency in Treg cell activation. Thus, it is critical to find the right residue substitution combinations to tune the activity to the desired potency and biased specificity for Treg cells.

Figure 7B:
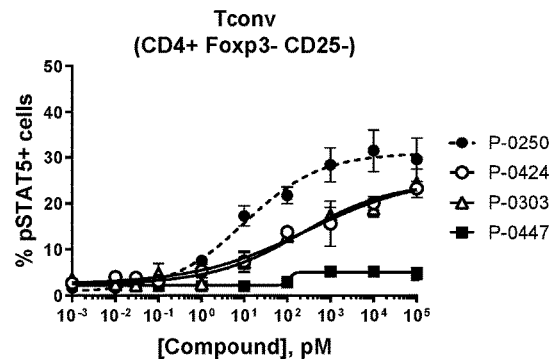
Figure 7C:
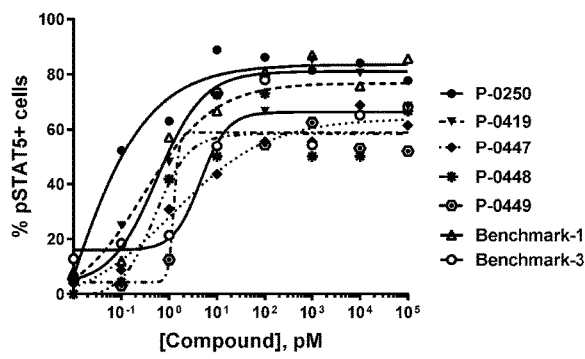
Figure 7D:
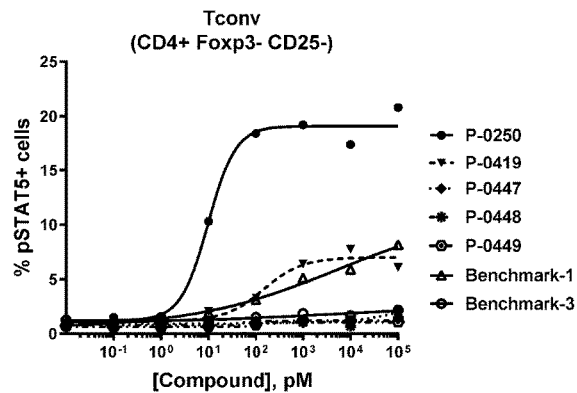

Additional variants harboring double amino acid substitutions at sites L19 and Q126, including P-0447 (L19H/Q126E), P-0448 (L19Q/Q126E), and P-0449 (L19S/Q126E) were evaluated, and the activity was shown in FIGS. 7A-7D. Compared to IL-2 variants each containing one single amino acid substitution P-0424 (L19H) and P-0303 (Q126E), the variant harboring the combination of the two amino acid substitutions P-0447 (L19H, Q126E) demonstrated robust biological activity in stimulation of STAT5 phosphorylation in Treg cells while such activity was nearly completely abolished in Tconv cells (FIGS. 7A and 7B). In a separate study evaluating P-0419, P-0447, P-0448 and P-0449 in comparison with two benchmark compounds, all four variants demonstrated significant potency in inducing STAT5 phosphorylation in Treg cells, while such activity was largely abolished in CD4+ Tconv cells (FIGS. 7C and 7D). P-0419 has a comparable activity profile to Benchmark-1, which was similarly demonstrated in FIGS. 5E and 5F, while P-0447, P-0448 and P-0449 are on par with Benchmark-3 in terms of potency and selectivity window for Treg cells.

All these mutants are potentially Treg-biased IL-2 agents to activate Treg cells for the treatment of autoimmune disease. Additionally, these mutants are also expected to have an improved safety profile with reduced VLS due to the elimination of the potentially toxic motif.

Example 6

IL-2 Variants with Isoleucine Substitution at Position 125 Retain Full Biological Activity It was shown in Example 3 that isoleucine substitution at position 125 resulted in universal improvement in developability of the IL-2 fusion constructs. To make S125I substitution a viable approach to mitigate the developability challenges of IL-2 engineering, it is important to demonstrate that such amino acid replacement does not compromise the biological activity of resulting fusion proteins in comparison to their Ser-125 counterparts.

The S125I substitution was then introduced into wild-type IL-2 or IL-2 variants that already harbored 1 or 2 mutations targeting receptor subunit(s) β or γ or βγ. The resulting IL-2 variants containing isoleucine at position 125 were tested for their ability to stimulate STAT5 phosphorylation in Treg and Tconv cells in comparison with their respective serine counterparts at position 125. Table 5 lists the potency and selectivity of IL-2 variants in Treg cells. The two molecules in the same row of Table 5 share the same other amino acid substitution(s) and differ only at position 125 with either serine or isoleucine. The data demonstrated that the S125I substitution fully retained or slightly improved the biological activity of various tested IL-2 variants without altering the Treg specificity.

TABLE 5

IL-2 variants containing S125I substitution retained the biological activity and Treg selectivity

| Serine-125 | | | Isoleucine-125 | | |
|---|---|---|---|---|---|
| Protein ID: | Treg $EC_{50}$ (pM) | Treg Selectivity | Protein ID: | Treg $EC_{50}$ (pM) | Treg Selectivity |
| P-0250 | 0.049 | Yes | P-0531 | 0.012 | Yes |
| P-0424 | 0.026 | Yes | P-0491 | 0.029 | Yes |
| P-0425 | 1 | Yes | P-0492 | ~0.10 | Yes |
| P-0372 | 0.05 | Yes | P-0471 | 0.09 | Yes |
| P-0364 | 3.61 | Yes | P-0493 | 0.08 | Yes |
| P-0447 | 1.71 | Yes | P-0511 | 0.76 | Yes |
| P-0419 | 0.56 | Yes | P-0495 | ~0.33 | Yes |
| P-0480 | 0.24 | Yes | P-0512 | 0.35 | Yes |

Data from three exemplary constructs, P-0250, P-0424, and P-0447, and their S125I equivalents: P-0531, P-0491, and P-0511, respectively, were shown in FIG. 8. P-0250 is the wild-type IL-2 Fc fusion molecule, P-0424 contains one amino acid substitution L19H, and P-0447 comprise two amino acid substitutions L19H/Q126E. Their dose-dependent effect on STAT5 phosphorylation in Treg and CD4+ Tconv cells is illustrated in FIG. 8. As shown in FIGS. 8A-8F, S125I substitution slightly increased potency of the three tested compounds without altering Treg selectivity for P-0531 and P-0491; for P-0511, S125I substitution further widened the Treg selectivity window.

The data thus demonstrated that the S125I substitution in IL-2 retains the IL-2 activity profile of the IL-2 fusion proteins of different mutational context. In summary, isoleucine substitution at position 125 of IL-2 resulted in universal developability improvement (increased production yield, reduced aggregation, lowered immunogenicity potential) for IL-2, IL-2 fusions, IL-2 variants and IL-2 variant fusions and full retention of the biological activity and selectivity. This specific amino acid substitution represents a viable mitigation strategy to address the inherent IL-2 engineering challenges.

Example 7

Effects of IL-2 Variants on CD25+CD4+ T Cells, CD8 Cytotoxic T Cells and NK Cells In addition to being assessed for their ability to differentially stimulate STAT5 phosphorylation in CD4 positive Treg (CD4+/Foxp3+/CD25$^{high}$) versus Tconv (CD4+/Foxp3−/CD25$^{low}$) cells, two variants, P-0511 and P-0512, were further assayed for their ability to stimulate other effector T and NK cells, including CD4 positive Teff (CD4+/Foxp3−/CD25+), CD8 cytotoxic T effector and NK cells in comparison to wild-type IL-2 (P-0250) and three IL-2 benchmark molecules containing V91K, N88R, N88D respectively.

IL-2 variants of the current invention have weakened IL-2Rβγ interaction, and the pronounced growth advantage of Treg versus CD4+ Tconv by these variants was conferred by the high constitutive IL-2R☐☐☐CD25) expression in Treg. CD25 expression can be induced in CD4+T effector cells after immune stimulation. It is thus desirable to confirm that IL-2 variants retain Treg specificity over other CD25+ lymphocyte subsets. Exemplary lymphocyte subset with medium to high expression level of CD25 includes CD4+ effector T cells (Teff).

After human PBMC Cells were treated with serial dilutions of test compounds, fixed and permeabilized, washed, and stained with a mixture of anti-CD25-PE, anti-FOXP3-APC, anti-pSTAT5-FITC, and anti-CD4-PerCP-Cy5.5 antibodies, the flow cytometry analysis was gated into CD4+/Foxp3+/CD25+, CD4+/Foxp3−/CD25+, CD4+/Foxp3−/CD25− groups for the Treg, CD4 effector, and CD4 naive T cell subsets, respectively. Data are expressed as a percent of pSTAT5 positive cells in gated population and illustrated in FIG. 9. P-0512 has a comparable activity profile to Benchmark-1 for all the three T cell subsets, while P-511 is superior to both Benchmark-2 and -3 in terms of potency and selectivity window for Treg cells versus both Teff and naïve CD4 T cells. Benchmark-2 showed much weaker potency in activating each of the three subsets. Despite the expression of CD25 at medium to high level on Teff, the preferential activation of Treg over Teff by IL-2 variants with attenuated IL-2Rβγ interaction, especially P-0511, was clearly demonstrated in FIGS. 9A and 9B.

Further, P-0511 and P-0512 were tested for their ability to stimulate NK and CD8+ T cells proliferation in comparison with the wild type and benchmark molecules. Intracellular fluorescent label carboxyfluorescein diacetate succinimidyl ester (CFSE) method was utilized. Briefly, human PBMC ($1 \times 10^5$ cells/well) were labeled with CFSE, plated onto 96-well plates, and incubated with increasing concentrations of different IL-2 compounds. Cells were then harvested after 5 or 7 days of incubation and stained with either anti-CD56-APC antibody for NK cells or anti-CD8-APC antibody for CD8+ T cells and analyzed by flow cytometry. Data are expressed as a percent of divided cells and illustrated in FIG. 10A for CD8+ T cell proliferation and FIG. 10B for NK cell proliferation.

As expected, all IL-2 variants showed weakened potency in stimulating both CD8+ T and NK cells compared to P-0250, the wild-type IL-2 fusion molecules. In corroboration with the observation in STAT5 phosphorylation assay (FIG. 9), P-0512 has a comparable activity profile to Benchmark-1, and P-0511 is on par with Benchmark-3 in terms of potency for both lymphocyte subsets, while Benchmark-2 exhibited much weaker potency.

The STAT5 phosphorylation activity on other responder cells than CD4+ T cell subsets, including CD8+ T and NK, by P-0511 was compared to P-0531, the S125I equivalent of wild-type P-0250. P-0511 exhibited profound activity in stimulation of STAT5 phosphorylation in Treg cells similar as P-0531 (FIG. 11A), while such activity was nearly completely abolished in CD4+ Tconv (FIG. 11B), CD8+T (FIG. 11C), and NK (FIG. 11D) cells. IL-2 receptors expressed on CD4+ Tconv, CD8+T and NK cells are primarily dimeric IL-2Rs, comprising IL-2Rβ and γc. To confirm that the significantly diminished pSTAT5 signaling by P-0511 on CD8+T and NK cell was due to its impaired interaction with IL-2Rβ and γc, an ELISA assay was developed.

Briefly, non-covalent complex of IL-2Rβ-ECD (NP_000869) and γc-ECD (NP_000197) through heterodimeric Fc chains was coated onto the wells of Nunc Maxisorp 96-well microplates at 2 µg/well. After overnight incubation at 4° C. and blocking with superblock (ThermoFisher), 3-fold serial dilutions of IL-2 Fc fusion proteins starting at either 100 or 270 nM were added to each well at 100 µl/well. Following a one-hour incubation at room temperature, biotin mouse anti-human IL-2 Ab (BD BioSciences) at 1 µg/ml was added to each well followed by incubation with HRP-Avidin (ThermoFisher) at 1 µg/ml for 1 hour. Wells were thoroughly aspirated and washed three times with PBS/0.05% Tween-20 following each step. Finally, 100 µl TMB substrate was added to each well; the plate was developed at room temperature in the dark for 10 minutes, and 100 μl/well of stop solution (2N Sulfuric acid, Ricca Chemical) was added. Absorbance was determined at 450 nm; curves were fit using Prism software (GraphPad) and illustrated in FIG. 11E.

Figure 11E:
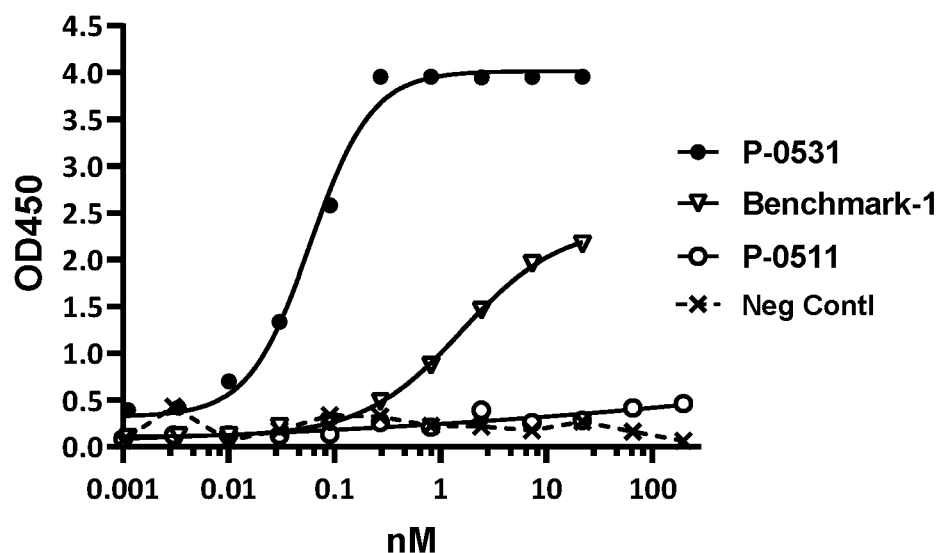

As shown in FIG. 11E, the developability-improved wild-type IL-2 fusion protein, P-0531, bound to the IL-2 dimeric receptor complex with sub-nanomolar affinity ($EC_{50}$=0.06 nM); Benchmark-1 molecule showed reduced binding ($EC_{50}$=1.6 nM), which agreed with its accordingly diminished potency in stimulating STAT5 phosphorylation in CD8+T and NK cells (FIGS. 10A-B). In contrast, P-0511 did not show appreciable binding to IL-2Rβ and γc complex, indicating that the two IL-2 mutations of P-0511 at the interfaces with both β and γc receptor subunits dramatically impaired its interaction with the complex. With virtually abolished binding to the dimeric IL-2 receptor complex, it is striking that P-0511 exhibited only slightly reduced activity on Treg compared to wild-type IL-2 fusion. P-0511 exemplifies IL-2 variant with desired potency and selectivity window for Treg lymphocytes.

In summary, a spectrum of IL-2 variants listed in Table 2A-2F was constructed, expressed, and tested in in vitro assays. Biological activities of exemplary IL-2 variants in Treg vs other lymphocyte subsets, including CD4+ Tconv, CD4+ Teff, CD8+T and NK cells, were demonstrated in FIGS. 2-11. Many variants retained high potency for Treg cells with reduced or abolished activity for Tconv cells and other lymphocyte subsets. Some variants have a similar activity profile as Benchmark-1 while others resemble the activity feature of Benchmark-2 or Benchmark-3. Further, majority of the IL-2 variants had the proposed toxin-like motif eliminated aiming to reduce VLS. Importantly, the incorporation of S125I amino acid substitution yielded IL-2 variant fusions with superior developability profiles while retaining biological activity and selectivity in Treg cells. These variants are potentially Treg-biased IL-2 agents for the treatment of autoimmune disease with an improved safety profile.

Example 8

Fc Fusion Proteins of IL-2 Variants Preferentially Proliferate and Expand Treg Cells in Mice IL-2 variant Fc fusion proteins were administered to mice and their ability to preferentially proliferate and expand regulatory T cells (CD4+CD25+FoxP3+ T cells) over effector T cells and NK cells were determined in vivo.

Female C57/BL6 mice (7-week old) were received from Charles River Laboratory and acclimated in house for at least 7 days before the study. Vehicle (PBS), 0.3 mg/kg of each test compounds, or IL-2 benchmark compounds were subcutaneously administered to mice on day 0. Peripheral blood samples were collected into heparin-treated tubes on days 3, 5 and 7 post-treatment. Each group contained 6 mice and baseline blood was collected 2 days prior to the treatment (day-2). After red blood cell lysis, total viable mononuclear blood cells were counted by trypan blue dead cell exclusion method and proceeded to intracellular staining for immune cell phenotype and Ki67 proliferation markers using flow cytometric analysis. Cells were stained separately with two panels of antibodies as listed: 1) anti-mouse Foxp3-FITC, Ki67-PE, anti-mouse CD25-APC and anti-mouse CD4-Percpcy5.5 (1:50 dilution) for CD4+T-regulatory cells (Treg); 2) anti-mouse CD3-FITC, Ki67-PE, anti-mouse CD335-APC and anti-mouse CD8-Percpcy5.5 (1:50 dilution) for CD8+T and NK cells.

All tested IL-2 compounds stimulated Treg cell proliferation and expansion as demonstrated by increased Ki67 positive Treg cells and elevated percentage of Treg over total CD4+ T cells or total lymphocytes (FIGS. 12A-12C). The effect was observed 3 days post injection and persisted to day 5 or day 7 following one single injection. In contrast to ex vivo observations that Benchmark-1 consistently exhibited highest potency among IL-2 variants in inducing Treg phosphorylation, all three tested variants, P-0511, P-0512 and P-0514, demonstrated stronger in vivo efficacy in stimulation of Treg cell proliferation and expansion than benchmark molecules in mice. P-0511, P-0512 and P-0514 exhibited comparable activity. The relative in vivo potency ranking between the three benchmarks agreed with the ex vivo human PBMC cell assay, namely Benchmark-1 was of the highest potency, followed by Benchmark-3. Benchmark-2 is much weaker in proliferating and expanding Treg cells. (FIG. 12A-12C).

On T effector and NK cells, Benchmark-1 showed strong Ki67 stimulation on cytotoxic CD8 T cells and NK cells, while Benchmarks-2 and -3 showed low effects on CD8 T cells and NK cells (FIG. 13A-13C). Variant P-0514 showed similar Ki67 stimulation on CD8+ T cells as Benchmark-1, while variants P-0511 and P-0512 showed mild Ki67 stimulation on CD8 T cells and NK cells as Benchmark-2 and 3 (FIG. 13A-13C). Data suggest variants P-0511 and P-0512 demonstrate superior biological activity and selectivity on Treg compared to Benchmarks 1 & 2. Benchmark-3 was not efficacious to stimulate and expand both Treg and effector cells.

The percentage of CD4+ T conventional cells was reduced in all IL-2 variant-treated groups due to increased Treg population (FIG. 14A). No significant expansion of CD4+ Tconv cells, CD8 T cells or NK cells was observed in mice treated with any of Treg biased IL-2 variants (P-0511, P-0512 and P-0514) nor the three benchmarks (FIG. 14B-14D).

Compared to the three benchmarks, all three variants, P-0511, P-0512, and P-0514, also exhibited the most beneficial Treg/Tconv ratio both in terms of Ki67 stimulation and cell expansion based on the cell counts at all measured time points (FIGS. 15A and 15B).

The expression of Foxp3 increased on Treg cells by all tested IL-2 compounds 3 days post injection (FIG. 16A), and all three variants exhibited comparably higher expression of CD25 and Foxp3 markers than the three benchmarks (FIGS. 16A and 16B), suggesting superior Treg activation and functionality.

Body weights were monitored prior to and during the treatment. No significant weight changes were observed (Data not shown).

Overall, the data demonstrated that variants P-0511, P-0512 and P-0514 exhibit the ability to promote activation, proliferation and expansion of immunosuppressive Treg cells while sparing CD4+ conventional cells, cytotoxic effector T cells and NK cells. The data also evidenced the superiority of these three variants over benchmark molecules in terms of both efficacy and selectivity on Treg proliferation and expansion. These variants may serve as therapeutic agents to combat autoimmune and inflammatory diseases as well as rejection of organ transplantation.

Example 9

A Dose-Response Pharmacodynamics Study with IL-2 Variant Fc Fusion Protein in Mice Following a Single Injection Following a single subcutaneous administration of vehicle (PBS) or P-0511 (1, 0.3, 0.1, or 0.03 mg/kg) to female Balb/C mice (n=5/group), peripheral blood was collected on day-2 as baseline, and post dose on days 3, 5, and 7. On day 7, mice were sacrificed, and spleens were harvested. Blood lymphocyte phenotyping, proliferation and expansion were measured by flow cytometry at each timepoint using fresh whole blood.

No significant changes in body weight or spleen weight in any treatment groups (data not shown)

As illustrated in FIG. 17, dose-dependent increases in the proliferation of Treg cells as reflected by increased percentage of Ki67 positive cells (FIG. 17A) were observed in mice treated with P-0511 at 1, 0.3, or 0.1 mg/kg dosing levels. Treatment at 0.03 mg/kg had minimal effect. Stimulation of Ki67 expression in Treg cells peaked on day 3 at the three higher dose levels and plateaued till day 5 before decline. As a result, P-0511 treatment resulted in elevations in the percentage of Treg over total CD4+ T cells (FIG. 17B), absolute Treg cell numbers (FIG. 17C) and fold change of cell counts from baseline (FIG. 17D) in a dose-dependent manner. The increases in Treg cell expansion followed a similar kinetic pattern as the proliferation/activation Ki67 markers (FIG. 17), namely culmination on day 3 and further extension to day 5. Dosing at 1 mg/kg stimulated a greater magnitude and duration of Treg and the signals sustained to day 5.

Treatment of P-0511 also resulted in a dose-dependent and statistically significant elevation of percentage of Treg over total lymphocytes (FIG. 18A), while no statistically significant changes in the percentages of CD4+ Tconv cells (FIG. 18B), CD8 Teff (FIG. 18C) or NK (FIG. 18D) cells over the total lymphocytes were observed. At the peak, Treg accounted for 4.5% of total lymphocytes with 1 mg/kg single dose treatment versus 3.1% at 0.3 mg/kg dosing and 1.4% at 0.1 mg/kg. In the vehicle control group, Treg represented 0.5% of the total lymphocytes (FIG. 18A).

The Treg/Tconv ratio was calculated based on cell count (FIG. 19A). The Treg/Tconv ratio peaked at 0.27 for treatment at 1 mg/kg, 0.18 for 0.3 mg/kg, and 0.06 for 0.1 mg/kg versus 0.027 untreated (FIG. 19A), suggesting preferential expansion of Treg cells over Tconv cells by P-0511. Additionally, expression of Treg cell functional markers, including CD25 (FIG. 19B), and FoxP3 (FIG. 19C), increased dose-dependently. Increases in the mean fluorescence intensity (MFI) of CD25 and FoxP3 peaked on day 3 and diminished to a lower level on day 5.

Overall, the data demonstrated that P-0511 exhibit potent and preferential Treg activation and expansion in a dose-dependent manner. It requires careful considerations to achieve optimized dosing strategy for maximal potency to promote activation, proliferation and expansion of immunosuppressive Treg cells while sparing cytotoxic effector T cells and NK cells.

Example 10

A Pharmacodynamics Study in Mice Following Repeated Administration of IL-2 Variant Fc Fusion Proteins Female Balb/C mice (7-week old) were acclimated in house for 5-7 days before the study. Vehicle (PBS), 0.3 mg/kg of P-0511, P-0512, P-0531, or Benchmark-1 compound were subcutaneously administered to mice (n=5/group) on days 0, 3, and 6. On days 3 and 9, three days after the first injection and multiple (3) injections, respectively, peripheral blood was collected. Based on earlier in vivo experiments, Treg cell activation, proliferation, and expansion were expected to peak on day 3, and thus three days post injection was selected for data collection and analysis. Changes in blood lymphocyte activation, proliferation, and expansion were measured by flow cytometry. P-0531 is the S125I equivalent of the wild type IL-2 fusion protein. The Benchmark-1 contains V91K mutation.

Three days following a single subcutaneous administration of IL-2 fusion proteins, near 90% of Treg cells showed positive Ki67 expression in all tested groups and the Ki67 positive cells remained significantly high after receiving the $3^{rd}$ dose of all tested compounds (FIG. 20A). Intriguingly, Treg cells, as expressed by % Treg over total CD4 T cells or over total lymphocytes, declined drastically to near control levels in mice treated with P-0531 and Benchmark-1, while sustained at significantly high levels in mice treated with P-0511 and P-0512 after three consecutive Q3D treatments in comparison with one treatment (FIGS. 20B-20C). Data suggest that wild type IL-2 or Benchmark-1 may accelerate the exhaustion of Treg cells or precipitate desensitization of Treg due to stronger potency on Treg stimulation. Additional explanations may also include differences in half-life or "receptor sink" on non-lymphocytes leading to altered drug exposure for non- or less-Treg selective wild type IL-2 or Benchmark-1.

Similar observations were also obtained for Treg cell counts and fold changes relative to PBS control (FIGS. 21A-21B), as well as Treg/Tconv ratio (FIG. 22). P-0511 and P-0512 demonstrated superior capabilities to sustain Treg pool and maintain Treg selectivity compared to P-0531 and Benchmark-1.

Overall the data illustrated that P-0511 and P-0512 are superior IL-2 molecules that show preferential and sustained in vivo Treg expansion after multiple doses. Tuning the dosing regimen of IL-2 variant Fc fusions, e.g., dosing amount and frequency, may further optimize the desired potency and selectivity on Treg over proinflammatory immune activation.

Example 11

Suppression of Antigen-Driven Inflammation by IL-2 Variant Fc Fusion Protein in a Delayed-Type Hypersensitivity (DTH) Mouse Model The ability of Treg cells induced by IL-2 variants to suppress T cell antigen-driven inflammation in vivo was assessed in a model of delayed-type hypersensitivity (DTH). Female Balb/C mice (7-week old) were acclimated in house for 7 days and randomized into groups. Subcutaneous administration of vehicle (PBS), P-0511 at either 0.1 mg/kg or 0.3 mg/kg was initiated on day-2 and was given either once every 3 days (Q3D) for three injections or once every 5 days (Q5D) for two injections. Mice were then sensitized with a subcutaneous administration of 100 μg keyhole limpet hemocyanin (KLH) in 200 μl saline on day 0. For Q3D dosing, two more subcutaneous injections of PBS or P-0511 (0.1 or 0.3 mg/kg) were administered on days 1 and 4; for Q5D dosing, one additional s.c. injection of PBS, 0.1 or 0.3 mg/kg P-0511 was administered on day 3. Mice received an intradermal challenge of KLH (5 μg in 10 μl saline) in right ear on day 5. Right ear thickness was measured using a caliper on day 5 prior KLH challenge and daily from day 6 to day 8 corresponding to 24 h, 48h, and 72 h post KLH challenge. One group of mice also received 5 mg/kg daily i.p. treatment of dexamethasone from day 5 to day 8 as a positive control.

Kinetics of the DTH response using the change in ear thickness relative to baseline values (Δ ear thickness) at various times after KLH challenge was illustrated in FIG. 23.

A pronounced ear inflammation and swelling was peaked 24 post intradermal KLH challenge of the ear pinna following subcutaneous KLH antigen sensitization and the ear swelling prolonged for 72 hours in PBS group. It is evident that the immune suppressive steroid dexamethasone is potent in inhibiting KLH-induced inflammatory response, reaching ~85% inhibition 72 hours after KLH challenge with 4 consecutive daily dosing at 5 mg/kg. Suppression of antigen-driven inflammation by Treg cells induced by P-0511 was also evident in mice treated with 0.3 mg/kg P-0511 either Q3D or Q5D at all time points post KLH challenge (FIGS. 23A-23B). At 0.1 mg/kg dosing, a similar trend of alleviating the DTH inflammatory response was observed for both Q3D and Q5D administration, but the effect did not reach statistical significance at most of the time points. Both Q3D and Q5D dosing schedules were effective.

In a separate study, dose-dependent response of P-0511 (0.1, 0.3 and 1 mg/kg, Q5D) on suppression of KLH-induced DTH was determined and compared with Benchmark-1 (0.3 mg/kg, Q5D). As illustrated in FIG. 24, P-0511 demonstrated dose-dependent inhibition of ear inflammation. Mice receiving 1 mg/kg P-0511 demonstrated strong resistance to KLH-induced DTH and minimal ear swelling was observed following KLH challenge. Intermediate and mild inhibitory effect was observed for 0.3 mg/kg and 0.1 mg/kg of P-0511, respectively. Benchmark-1 showed mild inhibition of ear swelling and the effect of 0.3 mg/kg Benchmark-1 was similar to that achieved by 0.1 mg/kg P-0511 (FIG. 24).

In summary, Treg cells induced by P-0511 administration was efficacious in suppressing T cell antigen-driven inflammation in a DTH model. Additionally, Treg suppression was sustained without repeated dosing after KLH challenge. It was also evident from the example that it is critical to tune the dosing regimen to achieve optimal efficacy.

Example 12

Pharmacodynamics/Pharmacokinetics Effects of P-0511 in Cynomolgus Monkey

PK/PD properties of P-0511, an IL-2 variant Fc fusion protein, in cynomolgus monkey will be evaluated following a Q14D×3 dosing schedule. Drug-naïve cynomolgus monkeys will be acclimated for 3-4 weeks and randomized in 4 groups (n=3-4/group), which will be followed by a pre-dose baseline week. On days 1, 15, and 29, one group will receive subcutaneous administration of vehicle (PBS), and the other three groups will be dosed subcutaneously with P-0511 at either 100 μg/kg, 30 μg/kg, or 10 μg/kg.

Blood is collected on days −7, −3, 2, 4, 6, 8, 11, 14, 18, 21, 28, 32, 35, 43, 50, 57. Whole blood is used for FACS immunophenotyping of peripheral blood Treg, non-regulatory CD4 T cells, CD8 T cells, and NK cells, naïve and memory, to determine pharmacodynamics. Cell activation and proliferation will also be monitored by measuring CD69 and Ki67. Whole blood is also used for complete blood count (CBC) with 5-part differential: neutrophil, lymphocytes, monocytes, eosinophil, and basophil.

PK properties of P-0511 will be assessed in the cynomolgus plasma samples by measuring full-length intact P-0511 using mouse anti-human IL-2 mAb (BD Pharmingen) to coat 96-well plates in order to capture P-0511. P-0511 will be detected using goat anti-human Fc polyclonal-HRP (ThermoFisher) and its plasma concentration will be subsequently quantified. In addition to the plasma samples collected on days −7, −3, 2, 4, 6, 8, 11, 14, 18, 21, 28, 32, 35, 43, 50, 57, three more plasma samples were collected on day 1 at 0.5 hour, 3 hours, and 6 hours post the first administration of the P-0511.

Plasma samples from days −8, 8, 21, 35, 43, 57 will also be used to evaluate the following clinical chemistry parameters: aspartate aminotransferase, alanine aminotransferase, alkaline phosphatase, gamma glutamyl transferase, albumin, total bilirubin, creatinine, blood urea nitrogen, and C-reactive protein.

Further, body weight and body temperature of each animal will be monitored weekly or twice weekly during the whole study period.

All of the articles and methods disclosed and claimed herein can be made and executed without undue experimentation in light of the present disclosure. While the articles and methods of this disclosure have been described in terms of preferred embodiments, it will be apparent to those of skill in the art that variations may be applied to the articles and methods without departing from the spirit and scope of the disclosure. All such variations and equivalents apparent to those skilled in the art, whether now existing or later developed, are deemed to be within the spirit and scope of the disclosure as defined by the appended claims. All patents, patent applications, and publications mentioned in the specification are indicative of the levels of those of ordinary skill in the art to which the disclosure pertains. All patents, patent applications, and publications are herein incorporated by reference in their entirety for all purposes and to the same extent as if each individual publication was specifically and individually indicated to be incorporated by reference in its entirety for any and all purposes. The disclosure illustratively described herein suitably may be practiced in the absence of any element(s) not specifically disclosed herein. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

Sequence Listings

The nucleic and amino acid sequences listed in the accompanying sequence listing are shown using standard letter abbreviations for nucleotide bases and one letter codes for amino acids, as defined in 37 C.F.R. 1.822.

SEQ ID NO: 1 is a human IL-2 precursor amino acid sequence.

SEQ ID NO: 2 is a human IL-2 mature form naturally occurring amino acid sequence.

SEQ ID NO: 3 is a human IL-2 mature form wild type amino acid sequence.

SEQ ID NOS: 4-43, 108-146 and 193-197 are the amino acid sequences of various IL-2 variants.

SEQ ID NO: 44 is a human IgG1-Fc amino acid sequence.

SEQ ID NO: 45 is a human IgG1-Fc with reduced/abolished effector function amino acid sequence.

SEQ ID NOS: 46 and 47 and 212-213 are human IgG1-Fc with reduced/abolished effector function and extended half-life amino acid sequences.

SEQ ID NOS: 48-67 are the amino acid sequences of various peptide linker sequences.

SEQ ID NO: 68 is a human IL-2 receptor alpha Sushi domain amino acid sequence.

SEQ ID NOS: 69-107, 147-189 and 198-211 are the amino acid sequences of various Fc-IL-2 fusion proteins.

SEQ ID NOS: 190-192 are the amino acid sequences of benchmark Fc-IL-2 variant fusion proteins.

SEQ ID NOS: 214-222 are the nucleotide sequences of various Fc-IL-2 fusion proteins.

```
Human IL-2 precursor sequence
                                                            (SEQ ID NO: 1)
MYRMQLLSCIALSLALVTNSAPTSSSTKKTQLQLEHLLLDLQMIL

NGINNYKNPKLTRMLTFKFYMPKKATELKHLQCLEEELKPLEEVL

NLAQSKNFHLRPRDLISNINVIVLELKGSETTFMCEYADETATIV

EFLNRWITFCQSIISTLT

Human IL-2 mature form naturally occurring
sequence
                                                            (SEQ ID NO: 2)
APTSSSTKKTQLQLEHLLLDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFCQSIISTLT

Human IL-2 mature form wild-type sequence
                                                            (SEQ ID NO: 3)
APTSSSTKKTQLQLEHLLLDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSQSIISTLT

IL-2 N88R variant sequence
                                                            (SEQ ID NO: 4)
APTSSSTKKTQLQLEHLLLDLQMILNGINNYKNPKLTRMLTFKFY

MPKKATELKHLQCLEEELKPLEEVLNLAQSKNFHLRPRDLISRIN

VIVLELKGSETTFMCEYADETATIVEFLNRWITFSQSIISTLT

IL-2 D20T variant sequence
                                                            (SEQ ID NO: 5)
APTSSSTKKTQLQLEHLLLTLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSQSIISTLT

IL-2 D20E variant sequence
                                                            (SEQ ID NO: 6)
APTSSSTKKTQLQLEHLLLELQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSQSIISTLT

IL-2 D20N variant sequence
                                                            (SEQ ID NO: 7)
APTSSSTKKTQLQLEHLLLNLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSQSIISTLT

IL-2 D20Q variant sequence
                                                            (SEQ ID NO: 8)
APTSSSTKKTQLQLEHLLLQLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSQSIISTLT
```

-continued

IL-2 D20S variant sequence
(SEQ ID NO: 9)
APTSSSTKKTQLQLEHLLLSLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSQSIISTLT IL-2 D20Y variant sequence
(SEQ ID NO: 10)
APTSSSTKKTQLQLEHLLLYLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSQSIISTLT IL-2 D20I variant sequence
(SEQ ID NO: 11)
APTSSSTKKTQLQLEHLLLILQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSQSIISTLT IL-2 L19Y variant sequence
(SEQ ID NO: 12)
APTSSSTKKTQLQLEHLLYDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSQSIISTLT IL-2 L19N variant sequence
(SEQ ID NO: 13)
APTSSSTKKTQLQLEHLLNDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSQSIISTLT IL-2 L19R variant sequence
(SEQ ID NO: 14)
APTSSSTKKTQLQLEHLLRDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSQSIISTLT IL-2 N88G variant sequence
(SEQ ID NO: 15)
APTSSSTKKTQLQLEHLLLDLQMILNGINNYKNPKLTRMLTFKFY
MPKKATELKHLQCLEEELKPLEEVLNLAQSKNFHLRPRDLISGIN
VIVLELKGSETTFMCEYADETATIVEFLNRWITFSQSIISTLT IL-2 N88I variant sequence
(SEQ ID NO: 16)
APTSSSTKKTQLQLEHLLLDLQMILNGINNYKNPKLTRMLTFKFY
MPKKATELKHLQCLEEELKPLEEVLNLAQSKNFHLRPRDLISIIN
VIVLELKGSETTFMCEYADETATIVEFLNRWITFSQSIISTLT IL-2 N88Q variant sequence
(SEQ ID NO: 17)
APTSSSTKKTQLQLEHLLLDLQMILNGINNYKNPKLTRMLTFKFY
MPKKATELKHLQCLEEELKPLEEVLNLAQSKNFHLRPRDLISQIN
VIVLELKGSETTFMCEYADETATIVEFLNRWITFSQSIISTLT IL-2 N88E variant sequence
(SEQ ID NO: 18)
APTSSSTKKTQLQLEHLLLDLQMILNGINNYKNPKLTRMLTFKFY
MPKKATELKHLQCLEEELKPLEEVLNLAQSKNFHLRPRDLISEIN
VIVLELKGSETTFMCEYADETATIVEFLNRWITFSQSIISTLT -continued IL-2 N88T variant sequence (SEQ ID NO: 19)

APTSSSTKKTQLQLEHLLLDLQMILNGINNYKNPKLTRMLTFKFY
MPKKATELKHLQCLEEELKPLEEVLNLAQSKNFHLRPRDLISTIN
VIVLELKGSETTFMCEYADETATIVEFLNRWITFSQSIISTLT

IL-2 N88M variant sequence (SEQ ID NO: 20)

APTSSSTKKTQLQLEHLLLDLQMILNGINNYKNPKLTRMLTFKFY
MPKKATELKHLQCLEEELKPLEEVLNLAQSKNFHLRPRDLISMIN
VIVLELKGSETTFMCEYADETATIVEFLNRWITFSQSIISTLT

IL-2 Q126E variant sequence (SEQ ID NO: 21)

APTSSSTKKTQLQLEHLLLDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSESIISTLT

IL-2 Q126L variant sequence (SEQ ID NO: 22)

APTSSSTKKTQLQLEHLLLDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSLSIISTLT

IL-2 Q126N variant sequence (SEQ ID NO: 23)

APTSSSTKKTQLQLEHLLLDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSNSIISTLT

IL-2 Q126D variant sequence (SEQ ID NO: 24)

APTSSSTKKTQLQLEHLLLDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSDSIISTLT

IL-2 Q126M variant sequence (SEQ ID NO: 25)

APTSSSTKKTQLQLEHLLLDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSMSIISTLT

IL-2 D201/N88G variant sequence (SEQ ID NO: 26)

APTSSSTKKTQLQLEHLLLILQMILNGINNYKNPKLTRMLTFKFY
MPKKATELKHLQCLEEELKPLEEVLNLAQSKNFHLRPRDLISGIN
VIVLELKGSETTFMCEYADETATIVEFLNRWITFSQSIISTLT

IL-2 D201/N88R variant sequence (SEQ ID NO: 27)

APTSSSTKKTQLQLEHLLLILQMILNGINNYKNPKLTRMLTFKFY
MPKKATELKHLQCLEEELKPLEEVLNLAQSKNFHLRPRDLISRIN
VIVLELKGSETTFMCEYADETATIVEFLNRWITFSQSIISTLT

IL-2 D20T/N88R variant sequence (SEQ ID NO: 28)

APTSSSTKKTQLQLEHLLLTLQMILNGINNYKNPKLTRMLTFKFY
MPKKATELKHLQCLEEELKPLEEVLNLAQSKNFHLRPRDLISRIN
VIVLELKGSETTFMCEYADETATIVEFLNRWITFSQSIISTLT

```
IL-2 D20T/N88I variant sequence
                                                      (SEQ ID NO: 29)
APTSSSTKKTQLQLEHLLLILQMILNGINNYKNPKLTRMLTFKFY

MPKKATELKHLQCLEEELKPLEEVLNLAQSKNFHLRPRDLISIIN

VIVLELKGSETTFMCEYADETATIVEFLNRWITFSQSIISTLT

IL-2 D20T/Q126E variant sequence
                                                      (SEQ ID NO: 30)
APTSSSTKKTQLQLEHLLLTLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSESIISTLT

IL-2 D20T/N88R/Q126E variant sequence
                                                      (SEQ ID NO: 31)
APTSSSTKKTQLQLEHLLLTLQMILNGINNYKNPKLTRMLTFKFY

MPKKATELKHLQCLEEELKPLEEVLNLAQSKNFHLRPRDLISRIN

VIVLELKGSETTFMCEYADETATIVEFLNRWITFSESIISTLT

IL-2 D20T/Q126L variant sequence
                                                      (SEQ ID NO: 32)
APTSSSTKKTQLQLEHLLLTLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSLSIISTLT

IL-2 D20T/N88R/Q126L variant sequence
                                                      (SEQ ID NO: 33)
APTSSSTKKTQLQLEHLLLTLQMILNGINNYKNPKLTRMLTFKFY

MPKKATELKHLQCLEEELKPLEEVLNLAQSKNFHLRPRDLISRIN

VIVLELKGSETTFMCEYADETATIVEFLNRWITFSLSIISTLT

IL-2 L19N/Q126E variant sequence
                                                      (SEQ ID NO: 34)
APTSSSTKKTQLQLEHLLNDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSESIISTLT

IL-2 L19R/Q126E variant sequence
                                                      (SEQ ID NO: 35)
APTSSSTKKTQLQLEHLLRDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSESIISTLT

IL-2 L19Y/Q126E variant sequence
                                                      (SEQ ID NO: 36)
APTSSSTKKTQLQLEHLLYDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSESIISTLT

IL-2 L19Q variant sequence
                                                      (SEQ ID NO: 37)
APTSSSTKKTQLQLEHLLQDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSQSIISTLT

IL-2 L19H variant sequence
                                                      (SEQ ID NO: 38)
APTSSSTKKTQLQLEHLLHDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSQSIISTLT
```

-continued

IL-2 L19D variant sequence (SEQ ID NO: 39)

APTSSSTKKTQLQLEHLLDDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSQSIISTLT

IL-2 L19P variant sequence (SEQ ID NO: 40)

APTSSSTKKTQLQLEHLLPDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSQSIISTLT

IL-2 D20T/S125I/Q126K variant sequence (SEQ ID NO: 41)

APTSSSTKKTQLQLEHLLLTLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFIKSIISTLT

IL-2 L19N/S125I/Q126K variant sequence (SEQ ID NO: 42)

APTSSSTKKTQLQLEHLLNDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFIKSIISTLT

IL-2 L19R/S125I/Q126K variant sequence (SEQ ID NO: 43)

APTSSSTKKTQLQLEHLLRDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFIKSIISTLT

Human IgG1-Fc (SEQ ID NO: 44)

DKTHTCPPCPAPELLGGPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
DELTKNQVSLTCLVKGFYPSDIAVEWESNGQPENNYKTTPPVLDS
DGSFFLYSKLTVDKSRWQQGNVFSCSVMHEALHNHYTQKSLSLSP
G

Human IgG1-Fc with reduced/abolished
effector function (SEQ ID NO: 45)

DKTHTCPPCPAPEAAGAPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
DELTKNQVSLTCLVKGFYPSDIAVEWESNGQPENNYKTTPPVLDS
DGSFFLYSKLTVDKSRWQQGNVFSCSVMHEALHNHYTQKSLSLSP
G

Human IgG1-Fc reduced/abolished effector
function and with extended half-life (SEQ ID NO: 46)

DKTHTCPPCPAPEAAGGPSVFLFPPKPKDTLYITREPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR

-continued

```
EEMTKNQVSLTCLVKGFYPSDIAVEWESNGQPENNYKTTPPVLDS

DGSFFLYSKLTVDKSRWQQGNVFSCSVMHEALHNHYTQKSLSLSP

G
```

Human IgG1-Fc with reduced/abolished
effector function and extended half-life
(SEQ ID NO: 47)

```
DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHAHYTQKSLSLSP

G
```

Peptide linker sequence
(SEQ ID NO: 48)

GGGSGGGSGGGS

Peptide linker sequence
(SEQ ID NO: 49)

GGGS

Peptide linker sequence
(SEQ ID NO: 50)

GSSGGSGGSGGSG

Peptide linker sequence
(SEQ ID NO: 51)

GSSGT

Peptide linker sequence
(SEQ ID NO: 52)

GGGGSGGGGSGGGS

Peptide linker sequence
(SEQ ID NO: 53)

AEAAAKEAAAKEAAAKA

Peptide linker sequence
(SEQ ID NO: 54)

GGGGSGGGGSGGGGSGGGGS

Peptide linker sequence
(SEQ ID NO: 55)

GGGSGGGS

Peptide linker sequence
(SEQ ID NO: 56)

GS

Peptide linker sequence
(SEQ ID NO: 57)

GGS

Peptide linker sequence
(SEQ ID NO: 58)

GGGGS

Peptide linker sequence
(SEQ ID NO: 59)

GGSG

Peptide linker sequence
(SEQ ID NO: 60)

SGGG

Peptide linker sequence
(SEQ ID NO: 61)

GSGS

Peptide linker sequence
(SEQ ID NO: 62)

GSGSGS

-continued

Peptide linker sequence (SEQ ID NO: 63)
GSGSGSGS

Peptide linker sequence (SEQ ID NO: 64)
GSGSGSGSGS

Peptide linker sequence (SEQ ID NO: 65)
GSGSGSGSGSGS

Peptide linker sequence (SEQ ID NO: 66)
GGGGSGGGGS

Peptide linker sequence (SEQ ID NO: 67)
GGGGSGGGGSGGGGS

Human IL-2Rα sushi domains sequence (SEQ ID NO: 68)
ELCDDDPPEIPHATFKAMAYKEGTMLNCECKRGFRRIKSGSLYML
CTGNSSHSSWDNQCQCTSSATRNTTKQVTPQPEEQKERKTTEMQS
PMQPVDQASLPGHCREPPPWENEATERIYHFVVGQMVYYQCVQGY
RALHRGPAESVCKMTHGKTRWTQPQLICTG P-0250 (SEQ ID NO: 69)
DKTHTCPPCPAPEAAGAPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
DELTKNQVSLTCLVKGFYPSDIAVEWESNGQPENNYKTTPPVLDS
DGSFFLYSKLTVDKSRWQQGNVFSCSVMHEALHNHYTQKSLSLSP
GGGGSGGGSAPTSSSTKKTQLQLEHLLLDLQMILNGINNYKNPKL
TRMLTFKFYMPKKATELKHLQCLEEELKPLEEVLNLAQSKNFHLR
PRDLISNINVIVLELKGSETTFMCEYADETATIVEFLNRWITFSQ
SIISTLT P-0305 (SEQ ID NO: 70)
APTSSSTKKTQLQLEHLLLDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSQSIISTLTAE
AAAKEAAAKEAAAKACPPCPAPEAAGAPSVFLFPPKPKDTLMISR
TPEVTCVVVDVSHEDPEVKFNWYVDGVEVHNAKTKPREEQYNSTY
RVVSVLTVLHQDWLNGKEYKCKVSNKALPAPIEKTISKAKGQPRE
PQVYTLPPSRDELTKNQVSLTCLVKGFYPSDIAVEWESNGQPENN
YKTTPPVLDSDGSFFLYSKLTVDKSRWQQGNVFSCSVMHEALHNH
YTQKSLSLSPG P-0254 (SEQ ID NO: 71)
DKTHTCPPCPAPEAAGAPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
DELTKNQVSLTCLVKGFYPSDIAVEWESNGQPENNYKTTPPVLDS -continued

DGSFFLYSKLTVDKSRWQQGNVFSCSVMHEALHNHYTQKSLSLSP

GGGGSGGGSAPTSSSTKKTQLQLEHLLLDLQMILNGINNYKNPKL

TRMLTFKFYMPKKATELKHLQCLEEELKPLEEVLNLAQSKNFHLR

PRDLISRINVIVLELKGSETTFMCEYADETATIVEFLNRWITFSQ

SIISTLT

P-0363 (SEQ ID NO: 72)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLTLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSQ

SIISTLT

P-0364 (SEQ ID NO: 73)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLELQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSQ

SIISTLT

P-0365 (SEQ ID NO: 74)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLNLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSQ

SIISTLT

P-0366 (SEQ ID NO: 75)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

```
GGGGSGGGSAPTSSSTKKTQLQLEHLLLQLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSQ

SIISTLT
```

P-0367 (SEQ ID NO: 76)
```
DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLSLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSQ

SIISTLT
```

P-0368 (SEQ ID NO: 77)
```
DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLYLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSQ

SIISTLT
```

P-0252 (SEQ ID NO: 78)
```
DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLILQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSQ

SIISTLT
```

P-0372 (SEQ ID NO: 79)
```
DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP
```

```
                          -continued
GGGGSGGGSAPTSSSTKKTQLQLEHLLYDLQMILNGINNYKNPKL
TRMLTFKFYMPKKATELKHLQCLEEELKPLEEVLNLAQSKNFHLR
PRDLISNINVIVLELKGSETTFMCEYADETATIVEFLNRWITFSQ
SIISTLT P-0373                                              (SEQ ID NO: 80)
DKTHTCPPCPAPEAAGAPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
DELTKNQVSLTCLVKGFYPSDIAVEWESNGQPENNYKTTPPVLDS
DGSFFLYSKLTVDKSRWQQGNVFSCSVMHEALHNHYTQKSLSLSP
GGGGSGGGSAPTSSSTKKTQLQLEHLLNDLQMILNGINNYKNPKL
TRMLTFKFYMPKKATELKHLQCLEEELKPLEEVLNLAQSKNFHLR
PRDLISNINVIVLELKGSETTFMCEYADETATIVEFLNRWITFSQ
SIISTLT P-0374                                              (SEQ ID NO: 81)
DKTHTCPPCPAPEAAGAPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
DELTKNQVSLTCLVKGFYPSDIAVEWESNGQPENNYKTTPPVLDS
DGSFFLYSKLTVDKSRWQQGNVFSCSVMHEALHNHYTQKSLSLSP
GGGGSGGGSAPTSSSTKKTQLQLEHLLRDLQMILNGINNYKNPKL
TRMLTFKFYMPKKATELKHLQCLEEELKPLEEVLNLAQSKNFHLR
PRDLISNINVIVLELKGSETTFMCEYADETATIVEFLNRWITFSQ
SIISTLT P-0253                                              (SEQ ID NO: 82)
DKTHTCPPCPAPEAAGAPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
DELTKNQVSLTCLVKGFYPSDIAVEWESNGQPENNYKTTPPVLDS
DGSFFLYSKLTVDKSRWQQGNVFSCSVMHEALHNHYTQKSLSLSP
GGGGSGGGSAPTSSSTKKTQLQLEHLLLDLQMILNGINNYKNPKL
TRMLTFKFYMPKKATELKHLQCLEEELKPLEEVLNLAQSKNFHLR
PRDLISGINVIVLELKGSETTFMCEYADETATIVEFLNRWITFSQ
SIISTLT P-0302                                              (SEQ ID NO: 83)
DKTHTCPPCPAPEAAGAPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
DELTKNQVSLTCLVKGFYPSDIAVEWESNGQPENNYKTTPPVLDS
DGSFFLYSKLTVDKSRWQQGNVFSCSVMHEALHNHYTQKSLSLSP
GGGGSGGGSAPTSSSTKKTQLQLEHLLLDLQMILNGINNYKNPKL
```

```
TRMLTFKFYMPKKATELKHLQCLEEELKPLEEVLNLAQSKNFHLR

PRDLISIINVIVLELKGSETTFMCEYADETATIVEFLNRWITFSQ

SIISTLT
```

P-0375                                          (SEQ ID NO: 84)

```
DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLQMILNGINNYKNPKL

TRMLTFKFYMPKKATELKHLQCLEEELKPLEEVLNLAQSKNFHLR

PRDLISQINVIVLELKGSETTFMCEYADETATIVEFLNRWITFSQ

SIISTLT
```

P-0376                                          (SEQ ID NO: 85)

```
DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLQMILNGINNYKNPKL

TRMLTFKFYMPKKATELKHLQCLEEELKPLEEVLNLAQSKNFHLR

PRDLISEINVIVLELKGSETTFMCEYADETATIVEFLNRWITFSQ

SIISTLT
```

P-0377                                          (SEQ ID NO: 86)

```
DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLQMILNGINNYKNPKL

TRMLTFKFYMPKKATELKHLQCLEEELKPLEEVLNLAQSKNFHLR

PRDLISTINVIVLELKGSETTFMCEYADETATIVEFLNRWITFSQ

SIISTLT
```

P-0378                                          (SEQ ID NO: 87)

```
DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLQMILNGINNYKNPKL
```

-continued

TRMLTFKFYMPKKATELKHLQCLEEELKPLEEVLNLAQSKNFHLR

PRDLISMINVIVLELKGSETTFMCEYADETATIVEFLNRWITFSQ

SIISTLT

P-0303 (SEQ ID NO: 88)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSE

SIISTLT

P-0304 (SEQ ID NO: 89)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSL

SIISTLT

P-0369 (SEQ ID NO: 90)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSN

SIISTLT

P-0370 (SEQ ID NO: 91)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLQMILNGINNYKNPKL

TRMLTFKFYMPKKATELKHLQCLEEELKPLEEVLNLAQSKNFHLR

```
PRDLISNINVIVLELKGSETTFMCEYADETATIVEFLNRWITFSD

SIISTLT

P-0371                                          (SEQ ID NO: 92)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSM

SIISTLT

P-0251                                          (SEQ ID NO: 93)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLILQMILNGINNYKNPKL

TRMLTFKFYMPKKATELKHLQCLEEELKPLEEVLNLAQSKNFHLR

PRDLISGINVIVLELKGSETTFMCEYADETATIVEFLNRWITFSQ

SIISTLT

P-0317                                          (SEQ ID NO: 94)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLILQMILNGINNYKNPKL

TRMLTFKFYMPKKATELKHLQCLEEELKPLEEVLNLAQSKNFHLR

PRDLISRINVIVLELKGSETTFMCEYADETATIVEFLNRWITFSQ

SIISTLT

P-0318                                          (SEQ ID NO: 95)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLILQMILNGINNYKNPKL

TRMLTFKFYMPKKATELKHLQCLEEELKPLEEVLNLAQSKNFHLR
```

-continued

PRDLISIINVIVLELKGSETTFMCEYADETATIVEFLNRWITFSQ

SIISTLT

P-0324 (SEQ ID NO: 96)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLTLQMILNGINNYKNPKL

TRMLTFKFYMPKKATELKHLQCLEEELKPLEEVLNLAQSKNFHLR

PRDLISRINVIVLELKGSETTFMCEYADETATIVEFLNRWITFSQ

SIISTLT

P-0322 (SEQ ID NO: 97)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLTLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSE

SIISTLT

P-0323 (SEQ ID NO: 98)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLTLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSL

SIISTLT

P-0325 (SEQ ID NO: 99)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLTLQMILNGINNYKNPKL

```
TRMLTFKFYMPKKATELKHLQCLEEELKPLEEVLNLAQSKNFHLR

PRDLISRINVIVLELKGSETTFMCEYADETATIVEFLNRWITFSE

SIISTLT

P-0326                                              (SEQ ID NO: 100)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLTLQMILNGINNYKNPKL

TRMLTFKFYMPKKATELKHLQCLEEELKPLEEVLNLAQSKNFHLR

PRDLISRINVIVLELKGSETTFMCEYADETATIVEFLNRWITFSL

SIISTLT

P-0417                                              (SEQ ID NO: 101)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLNDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSE

SIISTLT

P-0418                                              (SEQ ID NO: 102)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLRDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSE

SIISTLT

P-0419                                              (SEQ ID NO: 103)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLYDLQMILNGINNYKNPKL
```

-continued

```
TRMLTFKFYMPKKATELKHLQCLEEELKPLEEVLNLAQSKNFHLR

PRDLISNINVIVLELKGSETTFMCEYADETATIVEFLNRWITFSE

SIISTLT

P-0416                                              (SEQ ID NO: 104)
APTSSSTKKTQLQLEHLLNDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSQSIISTLTAE

AAAKEAAAKEAAAKACPPCPAPEAAGAPSVFLFPPKPKDTLMISR

TPEVTCVVVDVSHEDPEVKFNWYVDGVEVHNAKTKPREEQYNSTY

RVVSVLTVLHQDWLNGKEYKCKVSNKALPAPIEKTISKAKGQPRE

PQVYTLPPSRDELTKNQVSLTCLVKGFYPSDIAVEWESNGQPENN

YKTTPPVLDSDGSFFLYSKLTVDKSRWQQGNVFSCSVMHEALHNH

YTQKSLSLSPG

P-0412                                              (SEQ ID NO: 105)
APTSSSTKKTQLQLEHLLLELQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSQSIISTLTAE

AAAKEAAAKEAAAKACPPCPAPEAAGAPSVFLFPPKPKDTLMISR

TPEVTCVVVDVSHEDPEVKFNWYVDGVEVHNAKTKPREEQYNSTY

RVVSVLTVLHQDWLNGKEYKCKVSNKALPAPIEKTISKAKGQPRE

PQVYTLPPSRDELTKNQVSLTCLVKGFYPSDIAVEWESNGQPENN

YKTTPPVLDSDGSFFLYSKLTVDKSRWQQGNVFSCSVMHEALHNH

YTQKSLSLSPG

P-0306                                              (SEQ ID NO: 106)
APTSSSTKKTQLQLEHLLLILQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSQSIISTLTAE

AAAKEAAAKEAAAKACPPCPAPEAAGAPSVFLFPPKPKDTLMISR

TPEVTCVVVDVSHEDPEVKFNWYVDGVEVHNAKTKPREEQYNSTY

RVVSVLTVLHQDWLNGKEYKCKVSNKALPAPIEKTISKAKGQPRE

PQVYTLPPSRDELTKNQVSLTCLVKGFYPSDIAVEWESNGQPENN

YKTTPPVLDSDGSFFLYSKLTVDKSRWQQGNVFSCSVMHEALHNH

YTQKSLSLSPG

P-0319                                              (SEQ ID NO: 107)
APTSSSTKKTQLQLEHLLLILQMILNGINNYKNPKLTRMLTFKFY

MPKKATELKHLQCLEEELKPLEEVLNLAQSKNFHLRPRDLISRIN

VIVLELKGSETTFMCEYADETATIVEFLNRWITFSQSIISTLTAE

AAAKEAAAKEAAAKACPPCPAPEAAGAPSVFLFPPKPKDTLMISR

TPEVTCVVVDVSHEDPEVKFNWYVDGVEVHNAKTKPREEQYNSTY

RVVSVLTVLHQDWLNGKEYKCKVSNKALPAPIEKTISKAKGQPRE

PQVYTLPPSRDELTKNQVSLTCLVKGFYPSDIAVEWESNGQPENN
```

-continued

```
YKTTPPVLDSDGSFFLYSKLTVDKSRWQQGNVFSCSVMHEALHNH

YTQKSLSLSPG

IL-2 L19S variant sequence                                  (SEQ ID NO: 108)

APTSSSTKKTQLQLEHLLSDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSQSIISTLT

IL-2 L21S variant sequence                                  (SEQ ID NO: 109)

APTSSSTKKTQLQLEHLLLDSQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSQSIISTLT

IL-2 L21N variant sequence                                  (SEQ ID NO: 110)

APTSSSTKKTQLQLEHLLLDNQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSQSIISTLT

IL-2 L21R variant sequence                                  (SEQ ID NO: 111)

APTSSSTKKTQLQLEHLLLDRQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSQSIISTLT

IL-2 Q126K variant sequence                                 (SEQ ID NO: 112)

APTSSSTKKTQLQLEHLLLDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSKSIISTLT

IL-2 Q126H variant sequence                                 (SEQ ID NO: 113)

APTSSSTKKTQLQLEHLLLDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSHSIISTLT

IL-2 Q126Y variant sequence                                 (SEQ ID NO: 114)

APTSSSTKKTQLQLEHLLLDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSYSIISTLT

IL-2 S125E variant sequence                                 (SEQ ID NO: 115)

APTSSSTKKTQLQLEHLLLDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFEQSIISTLT

IL-2 S125K variant sequence                                 (SEQ ID NO: 116)

APTSSSTKKTQLQLEHLLLDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFKQSIISTLT
```

-continued

IL-2 S125H variant sequence
(SEQ ID NO: 117)
APTSSSTKKTQLQLEHLLLDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFHQSIISTLT IL-2 S125W variant sequence
(SEQ ID NO: 118)
APTSSSTKKTQLQLEHLLLDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFWQSIISTLT IL-2 S125I variant sequence
(SEQ ID NO: 119)
APTSSSTKKTQLQLEHLLLDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFIQSIISTLT IL-2 Q22N variant sequence
(SEQ ID NO: 120)
APTSSSTKKTQLQLEHLLLDLNMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSQSIISTLT IL-2 Q22H variant sequence
(SEQ ID NO: 121)
APTSSSTKKTQLQLEHLLLDLHMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSQSIISTLT IL-2 Q22K variant sequence
(SEQ ID NO: 122)
APTSSSTKKTQLQLEHLLLDLKMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSQSIISTLT IL-2 Q22Y variant sequence
(SEQ ID NO: 123)
APTSSSTKKTQLQLEHLLLDLYMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSQSIISTLT IL-2 Q22I variant sequence
(SEQ ID NO: 124)
APTSSSTKKTQLQLEHLLLDLIMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSQSIISTLT IL-2 L19H/Q126E variant sequence
(SEQ ID NO: 125)
APTSSSTKKTQLQLEHLLHDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSESIISTLT IL-2 L19Q/Q126E variant sequence
(SEQ ID NO: 126)
APTSSSTKKTQLQLEHLLQDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSESIISTLT -continued IL-2 L19S/Q126E variant sequence  (SEQ ID NO: 127)
APTSSSTKKTQLQLEHLLSDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSESIISTLT IL-2 L19Y/Q126K variant sequence  (SEQ ID NO: 128)
APTSSSTKKTQLQLEHLLYDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSKSIISTLT IL-2 L19Y/Q126H variant sequence  (SEQ ID NO: 129)
APTSSSTKKTQLQLEHLLYDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSHSIISTLT IL-2 L19Y/Q126Y variant sequence  (SEQ ID NO: 130)
APTSSSTKKTQLQLEHLLYDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSYSIISTLT IL-2 L19Y/S125E variant sequence  (SEQ ID NO: 131)
APTSSSTKKTQLQLEHLLYDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFEQSIISTLT IL-2 L19Y/S125K variant sequence  (SEQ ID NO: 132)
APTSSSTKKTQLQLEHLLYDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFKQSIISTLT IL-2 L19Y/S125H variant sequence  (SEQ ID NO: 133)
APTSSSTKKTQLQLEHLLYDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFHQSIISTLT IL-2 L19Y/S125W variant sequence  (SEQ ID NO: 134)
APTSSSTKKTQLQLEHLLYDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFWQSIISTLT IL-2 L19Y/S125I variant sequence  (SEQ ID NO: 135)
APTSSSTKKTQLQLEHLLYDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFIQSIISTLT IL-2 L19Y/Q22N variant sequence  (SEQ ID NO: 136)
APTSSSTKKTQLQLEHLLYDLNMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSQSIISTLT -continued IL-2 L19Y/Q22H variant sequence (SEQ ID NO: 137)
APTSSSTKKTQLQLEHLLYDLHMILNGINNYK
NPKLTRMLTFKFYMPKKATELKHLQCLEEELKPLEEVLNLAQSKN
FHLRPRDLISNINVIVLELKGSETTFMCEYADETATIVEFLNRWI
TFSQSIISTLT IL-2 L19Y/Q22K variant sequence (SEQ ID NO: 138)
APTSSSTKKTQLQLEHLLYDLKMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSQSIISTLT IL-2 L19Y/Q22Y variant sequence (SEQ ID NO: 139)
APTSSSTKKTQLQLEHLLYDLYMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSQSIISTLT IL-2 L19Y/Q22I variant sequence (SEQ ID NO: 140)
APTSSSTKKTQLQLEHLLYDLIMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSQSIISTLT IL-2 L19H/Q126K variant sequence (SEQ ID NO: 141)
APTSSSTKKTQLQLEHLLHDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFSKSIISTLT IL-2 L19H/S125I variant sequence (SEQ ID NO: 142)
APTSSSTKKTQLQLEHLLHDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFIQSIISTLT IL-2 L19D/S125I variant sequence (SEQ ID NO: 143)
APTSSSTKKTQLQLEHLLDDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFIQSIISTLT IL-2 D20E/S125I variant sequence (SEQ ID NO: 144)
APTSSSTKKTQLQLEHLLLELQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFIQSIISTLT IL-2 D20T/S125I variant sequence (SEQ ID NO: 145)
APTSSSTKKTQLQLEHLLLTLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFIQSIISTLT -continued IL-2 L19Y/S125L/Q126E variant sequence (SEQ ID NO: 146)
APTSSSTKKTQLQLEHLLYDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFIESIISTLT P-0423 (SEQ ID NO: 147)
DKTHTCPPCPAPEAAGAPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
DELTKNQVSLTCLVKGFYPSDIAVEWESNGQPENNYKTTPPVLDS
DGSFFLYSKLTVDKSRWQQGNVFSCSVMHEALHNHYTQKSLSLSP
GGGGSGGGSAPTSSSTKKTQLQLEHLLQDLQMILNGINNYKNPKL
TRMLTFKFYMPKKATELKHLQCLEEELKPLEEVLNLAQSKNFHLR
PRDLISNINVIVLELKGSETTFMCEYADETATIVEFLNRWITFSQ
SIISTLT P-0424 (SEQ ID NO: 148)
DKTHTCPPCPAPEAAGAPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
DELTKNQVSLTCLVKGFYPSDIAVEWESNGQPENNYKTTPPVLDS
DGSFFLYSKLTVDKSRWQQGNVFSCSVMHEALHNHYTQKSLSLSP
GGGGSGGGSAPTSSSTKKTQLQLEHLLHDLQMILNGINNYKNPKL
TRMLTFKFYMPKKATELKHLQCLEEELKPLEEVLNLAQSKNFHLR
PRDLISNINVIVLELKGSETTFMCEYADETATIVEFLNRWITFSQ
SIISTLT P-0425 (SEQ ID NO: 149)
DKTHTCPPCPAPEAAGAPSVFLFPPKPKDTLM
ISRTPEVTCVVVDVSHEDPEVKFNWYVDGVEVHNAKTKPREEQYN
STYRVVSVLTVLHQDWLNGKEYKCKVSNKALPAPIEKTISKAKGQ
PREPQVYTLPPSRDELTKNQVSLTCLVKGFYPSDIAVEWESNGQP
ENNYKTTPPVLDSDGSFFLYSKLTVDKSRWQQGNVFSCSVMHEAL
HNHYTQKSLSLSPGGGGSGGGSAPTSSSTKKTQLQLEHLLDDLQM
ILNGINNYKNPKLTRMLTFKFYMPKKATELKHLQCLEEELKPLEE
VLNLAQSKNFHLRPRDLISNINVIVLELKGSETTFMCEYADETAT
IVEFLNRWITFSQSIISTLT P-0426 (SEQ ID NO: 150)
DKTHTCPPCPAPEAAGAPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
DELTKNQVSLTCLVKGFYPSDIAVEWESNGQPENNYKTTPPVLDS
DGSFFLYSKLTVDKSRWQQGNVFSCSVMHEALHNHYTQKSLSLSP

```
                                                -continued
GGGGSGGGSAPTSSSTKKTQLQLEHLLPDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSQ

SIISTLT

P-0427                                          (SEQ ID NO: 151)
DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLSDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSQ

SIISTLT

P-0428                                          (SEQ ID NO: 152)
DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDSQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSQ

SIISTLT

P-0429                                          (SEQ ID NO: 153)
DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDNQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSQ

SIISTLT

P-0430                                          (SEQ ID NO: 154)
DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDRQMILNGINNYKNPKL
```

-continued

TRMLTFKFYMPKKATELKHLQCLEEELKPLEEVLNLAQSKNFHLR

PRDLISNINVIVLELKGSETTFMCEYADETATIVEFLNRWITFSQ

SIISTLT

P-0497                                                      (SEQ ID NO: 155)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSK

SIISTLT

P-0498                                                      (SEQ ID NO: 156)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSH

SIISTLT

P-0499                                                      (SEQ ID NO: 157)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSY

SIISTLT

P-0500                                                      (SEQ ID NO: 158)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLQMILNGINNYKNPKL

-continued

TRMLTFKFYMPKKATELKHLQCLEEELKPLEEVLNLAQSKNFHLR

PRDLISNINVIVLELKGSETTFMCEYADETATIVEFLNRWITFEQ

SIISTLT

P-0501 (SEQ ID NO: 159)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFKQ

SIISTLT

P-0502 (SEQ ID NO: 160)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFHQ

SIISTLT

P-0503 (SEQ ID NO: 161)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFWQ

SIISTLT

P-0531 (SEQ ID NO: 162)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLQMILNGINNYKNPKL

TRMLTFKFYMPKKATELKHLQCLEEELKPLEEVLNLAQSKNFHLR

-continued

PRDLISNINVIVLELKGSETTFMCEYADETATIVEFLNRWITFIQ

SIISTLT

P-0505 (SEQ ID NO: 163)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLNMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSQ

SIISTLT

P-0506 (SEQ ID NO: 164)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLHMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSQ

SIISTLT

P-0507 (SEQ ID NO: 165)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLKMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSQ

SIISTLT

P-0508 (SEQ ID NO: 166)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLYMILNGINNYKNPKL

TRMLTFKFYMPKKATELKHLQCLEEELKPLEEVLNLAQSKNFHLR

-continued

PRDLISNINVIVLELKGSETTFMCEYADETATIVEFLNRWITFSQ

SIISTLT

P-0509 (SEQ ID NO: 167)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLIMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSQ

SIISTLT

P-0447 (SEQ ID NO: 168)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLHDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSE

SIISTLT

P-0448 (SEQ ID NO: 169)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLQDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSE

SIISTLT

P-0449 (SEQ ID NO: 170)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLSDLQMILNGINNYKNPKL

```
TRMLTFKFYMPKKATELKHLQCLEEELKPLEEVLNLAQSKNFHLR

PRDLISNINVIVLELKGSETTFMCEYADETATIVEFLNRWITFSE

SIISTLT

P-0464                                          (SEQ ID NO: 171)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLYDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSK

SIISTLT

P-0465                                          (SEQ ID NO: 172)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLYDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSH

SIISTLT

P-0466                                          (SEQ ID NO: 173)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLYDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSY

SIISTLT

P-0467                                          (SEQ ID NO: 174)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLYDLQMILNGINNYKNPKL
```

P-0468 (SEQ ID NO: 175)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLYDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFEQ

SIISTLT

P-0468 (SEQ ID NO: 175)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLYDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFKQ

SIISTLT

P-0469 (SEQ ID NO: 176)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLYDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFHQ

SIISTLT

P-0470 (SEQ ID NO: 177)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLYDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFWQ

SIISTLT

P-0471 (SEQ ID NO: 178)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLYDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFIQ

SIISTLT

P-0472 (SEQ ID NO: 179)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLYDLNMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSQ

SIISTLT

P-0473 (SEQ ID NO: 180)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLYDLHMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSQ

SIISTLT

P-0474 (SEQ ID NO: 181)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLYDLKMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSQ

SIISTLT

P-0475 (SEQ ID NO: 182)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLYDLYMILNGINNYKNPKL

TRMLTFKFYMPKKATELKHLQCLEEELKPLEEVLNLAQSKNFHLR

-continued

PRDLISNINVIVLELKGSETTFMCEYADETATIVEFLNRWITFSQ

SIISTLT

P-0476 (SEQ ID NO: 183)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLYDLIMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSQ

SIISTLT

P-0480 (SEQ ID NO: 184)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLHDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFSK

SIISTLT

P-0491 (SEQ ID NO: 185)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLHDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFIQ

SIISTLT

P-0492 (SEQ ID NO: 186)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLDDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFIQ

SIISTLT

P-0493 (SEQ ID NO: 187)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLELQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFIQ

SIISTLT

P-0494 (SEQ ID NO: 188)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLTLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFIQ

SIISTLT

P-0495 (SEQ ID NO: 189)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLYDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFIE

SIISTLT

P-0496 (Benchmark-2) (SEQ ID NO: 190)

APTSSSTKKTQLQLEHLLLDLQMILNGINNYKNPKLTRMLTFKFY

MPKKATELKHLQCLEEELKPLEEVLNLAQSKNFHLRPRDLISRIN

VIVLELKGSETTFMCEYADETATIVEFLNRWITFSQSIISTLTGG

GGSGGGGSGGGGSGGGGSCPPCPAPEAAGAPSVFLFPPKPKDTLM

ISRTPEVTCVVVDVSHEDPEVKFNWYVDGVEVHNAKTKPREEQYN

STYRVVSVLTVLHQDWLNGKEYKCKVSNKALPAPIEKTISKAKGQ

```
                                                      -continued
PREPQVYTLPPSRDELTKNQVSLTCLVKGFYPSDIAVEWESNGQP

ENNYKTTPPVLDSDGSFFLYSKLTVDKSRWQQGNVFSCSVMHEAL

HNHYTQKSLSLSPG

Benchmark-1
                                                                        (SEQ ID NO: 191)
DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLQMILNGINNYKNPKL

TRMLTFKFYMPKKATELKHLQCLEEELKPLEEVLNLAQSKNFHLR

PRDLISNINKIVLELKGSETTFMCEYADETATIVEFLNRWITFSQ

SIISTLT

Benchmark-3
                                                                        (SEQ ID NO: 192)
DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLLDLQMILNGINNYKNPKL

TRMLTFKFYMPKKATELKHLQCLEEELKPLEEVLNLAQSKNFHLR

PRDLISDINVIVLELKGSETTFMCEYADETATIVEFLNRWITFSQ

SIISTLT

IL-2 L19H/S125l/Q126E variant sequence
                                                                        (SEQ ID NO: 193)
APTSSSTKKTQLQLEHLLHDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFIESIISTLT

IL-2 L19H/S125l/Q126K variant sequence
                                                                        (SEQ ID NO: 194)
APTSSSTKKTQLQLEHLLHDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFIKSIISTLT

IL-2 L19Q/Q126K variant sequence
                                                                        (SEQ ID NO: 195)
APTSSSTKKTQLQLEHLLQDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFSKSIISTLT

IL-2 L19Q/S125l/Q126E variant sequence
                                                                        (SEQ ID NO: 196)
APTSSSTKKTQLQLEHLLQDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFIESIISTLT
```

IL-2 L19Q/S125I/Q126K variant sequence (SEQ ID NO: 197)
APTSSSTKKTQLQLEHLLQDLQMILNGINNYKNPKLTRMLTFKFY
MPKKATELKHLQCLEEELKPLEEVLNLAQSKNFHLRPRDLISNIN
VIVLELKGSETTFMCEYADETATIVEFLNRWITFIKSIISTLT P-0511 (SEQ ID NO: 198)
DKTHTCPPCPAPEAAGAPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
DELTKNQVSLTCLVKGFYPSDIAVEWESNGQPENNYKTTPPVLDS
DGSFFLYSKLTVDKSRWQQGNVFSCSVMHEALHNHYTQKSLSLSP
GGGGSGGGSAPTSSSTKKTQLQLEHLLHDLQMILNGINNYKNPKL
TRMLTFKFYMPKKATELKHLQCLEEELKPLEEVLNLAQSKNFHLR
PRDLISNINVIVLELKGSETTFMCEYADETATIVEFLNRWITFIE
SIISTLT P-0512 (SEQ ID NO: 199)
DKTHTCPPCPAPEAAGAPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
DELTKNQVSLTCLVKGFYPSDIAVEWESNGQPENNYKTTPPVLDS
DGSFFLYSKLTVDKSRWQQGNVFSCSVMHEALHNHYTQKSLSLSP
GGGGSGGGSAPTSSSTKKTQLQLEHLLHDLQMILNGINNYKNPKL
TRMLTFKFYMPKKATELKHLQCLEEELKPLEEVLNLAQSKNFHLR
PRDLISNINVIVLELKGSETTFMCEYADETATIVEFLNRWITFIK
SIISTLT P-0513 (SEQ ID NO: 200)
DKTHTCPPCPAPEAAGAPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
DELTKNQVSLTCLVKGFYPSDIAVEWESNGQPENNYKTTPPVLDS
DGSFFLYSKLTVDKSRWQQGNVFSCSVMHEALHNHYTQKSLSLSP
GGGGSGGGSAPTSSSTKKTQLQLEHLLQDLQMILNGINNYKNPKL
TRMLTFKFYMPKKATELKHLQCLEEELKPLEEVLNLAQSKNFHLR
PRDLISNINVIVLELKGSETTFMCEYADETATIVEFLNRWITFSK
SIISTLT P-0514 (SEQ ID NO: 201)
DKTHTCPPCPAPEAAGAPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
DELTKNQVSLTCLVKGFYPSDIAVEWESNGQPENNYKTTPPVLDS
DGSFFLYSKLTVDKSRWQQGNVFSCSVMHEALHNHYTQKSLSLSP

```
GGGGSGGGSAPTSSSTKKTQLQLEHLLQDLQMILNGINNYKNPKL
TRMLTFKFYMPKKATELKHLQCLEEELKPLEEVLNLAQSKNFHLR
PRDLISNINVIVLELKGSETTFMCEYADETATIVEFLNRWITFIE
SIISTLT
```

P-0515 (SEQ ID NO: 202)

```
DKTHTCPPCPAPEAAGAPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
DELTKNQVSLTCLVKGFYPSDIAVEWESNGQPENNYKTTPPVLDS
DGSFFLYSKLTVDKSRWQQGNVFSCSVMHEALHNHYTQKSLSLSP
GGGGSGGGSAPTSSSTKKTQLQLEHLLQDLQMILNGINNYKNPKL
TRMLTFKFYMPKKATELKHLQCLEEELKPLEEVLNLAQSKNFHLR
PRDLISNINVIVLELKGSETTFMCEYADETATIVEFLNRWITFIK
SIISTLT
```

P-0582 (SEQ ID NO: 203)

```
DKTHTCPPCPAPEAAGAPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
DELTKNQVSLTCLVKGFYPSDIAVEWESNGQPENNYKTTPPVLDS
DGSFFLYSKLTVDKSRWQQGNVFSCSVMHEALHNHYTQKSLSLSP
GGGGSGGGSAPTSSSTKKTQLQLEHLLLTLQMILNGINNYKNPKL
TRMLTFKFYMPKKATELKHLQCLEEELKPLEEVLNLAQSKNFHLR
PRDLISNINVIVLELKGSETTFMCEYADETATIVEFLNRWITFIK
SIISTLT
```

P-0583 (SEQ ID NO: 204)

```
DKTHTCPPCPAPEAAGAPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
DELTKNQVSLTCLVKGFYPSDIAVEWESNGQPENNYKTTPPVLDS
DGSFFLYSKLTVDKSRWQQGNVFSCSVMHEALHNHYTQKSLSLSP
GGGGSGGGSAPTSSSTKKTQLQLEHLLNDLQMILNGINNYKNPKL
TRMLTFKFYMPKKATELKHLQCLEEELKPLEEVLNLAQSKNFHLR
PRDLISNINVIVLELKGSETTFMCEYADETATIVEFLNRWITFIK
SIISTLT
```

P-0584 (SEQ ID NO: 205)

```
DKTHTCPPCPAPEAAGAPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
DELTKNQVSLTCLVKGFYPSDIAVEWESNGQPENNYKTTPPVLDS
DGSFFLYSKLTVDKSRWQQGNVFSCSVMHEALHNHYTQKSLSLSP
GGGGSGGGSAPTSSSTKKTQLQLEHLLRDLQMILNGINNYKNPKL
```

TRMLTFKFYMPKKATELKHLQCLEEELKPLEEVLNLAQSKNFHLR

PRDLISNINVIVLELKGSETTFMCEYADETATIVEFLNRWITFIK

SIISTLT

P-0585 (SEQ ID NO: 206)

DKTHTCPPCPAPEAAGGPSVFLFPPKPKDTLYITREPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

EEMTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLHDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFIE

SIISTLT

P-0586 (SEQ ID NO: 207)

DKTHTCPPCPAPEAAGGPSVFLFPPKPKDTLYITREPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

EEMTKNQVSLTCLVKGFYPSDIAVEWESNGQPENNYKTTPPVLDS

DGSFFLYSKLTVDKSRWQQGNVFSCSVMHEALHNHYTQKSLSLSP

GGGGSGGGSAPTSSSTKKTQLQLEHLLHDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFIK

SIISTLT

P-0616 (SEQ ID NO: 208)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHAHYTQKSLSLSP

GGGGSGGGSAPTSSSTKKTQLQLEHLLHDLQMILNGINNYKNPKL

TRMLTFKFYMPKKATELKHLQCLEEELKPLEEVLNLAQSKNFHLR

PRDLISNINVIVLELKGSETTFMCEYADETATIVEFLNRWITFIE

SIISTLT

P-0672 Knob-Fc chain (SEQ ID NO: 209)

DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVCTLPPSR

EEMTKNQVSLWCLVKGFYPSDIAVEWESNGQPENNYKTTPPVLDS

DGSFFLYSKLTVDKSRWQQGNVFSCSVMHEALHAHYTQKSLSLSP

GGGGSGGGSAPTSSSTKKTQLQLEHLLHDLQMILNGINNYKNPKL

```
                                                           -continued
TRMLTFKFYMPKKATELKHLQCLEEELKPLEEVLNLAQSKNFHLR

PRDLISNINVIVLELKGSETTFMCEYADETATIVEFLNRWITFIE

SIISTLT
```

P-0673 Knob-Fc chain                                       (SEQ ID NO: 210)

```
APTSSSTKKTQLQLEHLLHDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFIESIISTLTGG

GGSGGGGSGGGGSGGGGSCPPCPAPEAAGAPSVFLFPPKPKDTLM

ISRTPEVTCVVVDVSHEDPEVKFNWYVDGVEVHNAKTKPREEQYN

STYRVVSVLTVLHQDWLNGKEYKCKVSNKALPAPIEKTISKAKGQ

PREPQVCTLPPSREEMTKNQVSLWCLVKGFYPSDIAVEWESNGQP

ENNYKTTPPVLDSDGSFFLYSKLTVDKSRWQQGNVFSCSVMHEAL

HAHYTQKSLSLSPG
```

P-0674                                                     (SEQ ID NO: 211)

```
APTSSSTKKTQLQLEHLLHDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFIESIISTLTGG

GGSGGGGSGGGGSGGGGSCPPCPAPEAAGAPSVFLFPPKPKDTLM

ISRTPEVTCVVVDVSHEDPEVKFNWYVDGVEVHNAKTKPREEQYN

STYRVVSVLTVLHQDWLNGKEYKCKVSNKALPAPIEKTISKAKGQ

PREPQVYTLPPSRDELTKNQVSLTCLVKGFYPSDIAVEWESNGQP

ENNYKTTPPVLDSDGSFFLYSKLTVDKSRWQQGNVFSCSVMHEAL

HAHYTQKSLSLSPG
```

Knob-Fc domain with extended in vivo half-life             (SEQ ID NO: 212)

```
DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVCTLPPSR

EEMTKNQVSLWCLVKGFYPSDIAVEWESNGQPENNYKTTPPVLDS

DGSFFLYSKLTVDKSRWQQGNVFSCSVMHEALHAHYTQKSLSLSP

G
```

Hole-Fc domain with extended in vivo half-life             (SEQ ID NO: 213)

```
DKTHTCPPCPAPEAAGAPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPCR

EEMTKNQVSLSCAVKGFYPSDIAVEWESNGQPENNYKTTPPVLDS

DGSFFLVSKLTVDKSRWQQGNVFSCSVMHEALHAHYTQKSLSLSP

G
```

P-0511                                                     (SEQ ID NO: 214)

```
atggagtttgggctgagctggcttttcttgtggctattttaaaa ggtgtccagtgtgataagactcacacttgccctccatgcccagct ccagaggccgctggcgctccttccgtcttttctgttcccacctaag
```

```
ccaaaggacactctcatgatctctaggacaccagaggtcacatgc
gtcgtggtggatgtgagccacgaggacccagaggtgaaattcaac
tggtacgtggatggagtcgaggtccacaacgccaagacaaagcca
agagaggaacagtacaattccacatacagagtggtgtccgtgctg
actgtgctgcatcaagactggctgaacggcaaggagtacaaatgc
aaggtcagcaacaaggccctcccagccccaatcgagaagacaatt
tccaaggccaagggccagcctagggagccacaagtgtatactctg
cctccttctagggacgagctgacaaagaaccaagtgtctctgact
tgtctggtgaagggcttctaccctagcgacatcgccgtggaatgg
gagtccaatggacagccagagaataactataagactacacctcca
gtcctcgactccgacggaagcttctttctgtactccaagctcact
gtggataagtctaggtggcaacaaggcaacgtcttcagctgtagc
gtcatgcatgaggctctccacaaccactacactcagaagtctctg
tctctgtccccggcggaggaggctccggaggaggatccgctcct
acttcctcctccactaagaagacacagctccaactggagcatctg
ctccatgatctgcagatgattctgaacggcattaacaactataaa
aatccaaagctgactaggatgctgacttttaagttctacatgcca
aagaaagccacagagctgaaacacctccagtgcctcgaggaagaa
ctgaagccactcgaggaggtgctgaacctcgcccagtccaagaat
ttccatctgaggccaagggatctgatcagcaacatcaacgtcatt
gtgctggagctgaaaggcagcgagactactttcatgtgcgagtac
gccgatgagacagctacaatcgtggagttcctcaataggtggatc
acattcatcgaaagcatcattagcacactgaca
```

P-0512 (SEQ ID NO: 215)

<u>atggagtttgggctgagctggcttttttcttgtggctatttt aaaa</u>
<u>ggtgtccagtgtg</u>ataagactcacacttgccctccatgcccagct
ccagaggccgctggcgctccttccgtctttctgttcccacctaag
ccaaaggacactctcatgatctctaggacaccagaggtcacatgc
gtcgtggtggatgtgagccacgaggacccagaggtgaaattcaac
tggtacgtggatggagtcgaggtccacaacgccaagacaaagcca
agagaggaacagtacaattccacatacagagtggtgtccgtgctg
actgtgctgcatcaagactggctgaacggcaaggagtacaaatgc
aaggtcagcaacaaggccctcccagccccaatcgagaagacaatt
tccaaggccaagggccagcctagggagccacaagtgtatactctg
cctccttctagggacgagctgacaaagaaccaagtgtctctgact
tgtctggtgaagggcttctaccctagcgacatcgccgtggaatgg
gagtccaatggacagccagagaataactataagactacacctcca
gtcctcgactccgacggaagcttctttctgtactccaagctcact
gtggataagtctaggtggcaacaaggcaacgtcttcagctgtagc
gtcatgcatgaggctctccacaaccactacactcagaagtctctg -continued

```
tctctgtccccggcggaggaggctccggaggaggatccgctcct acttcctcctccactaagaagacacagctccaactggagcatctg ctccatgatctgcagatgattctgaacggcattaacaactataaa aatccaaagctgactaggatgctgacttttaagttctacatgcca aagaaagccacagagctgaaacacctccagtgcctcgaggaagaa ctgaagccactcgaggaggtgctgaacctcgcccagtccaagaat ttccatctgaggccaagggatctgatcagcaacatcaacgtcatt gtgctggagctgaaaggcagcgagactactttcatgtgcgagtac gccgatgagacagctacaatcgtggagttcctcaataggtggatc acattcatcaagagcatcattagcacactgaca
```

P-0514 (SEQ ID NO: 216)

```
atggagtttgggctgagctggcttttcttgtggctattttaaaa ggtgtccagtgtgataagactcacacttgccctccatgcccagct ccagaggccgctggcgctccttccgtctttctgttcccacctaag ccaaaggacactctcatgatctctaggacaccagaggtcacatgc gtcgtggtggatgtgagccacgaggacccagaggtgaaattcaac tggtacgtggatggagtcgaggtccacaacgccaagacaaagcca agagaggaacagtacaattccacatacagagtggtgtccgtgctg actgtgctgcatcaagactggctgaacggcaaggagtacaaatgc aaggtcagcaacaaggccctcccagcccccaatcgagaagacaatt tccaaggccaagggccagcctagggagccacaagtgtatactctg cctccttctagggacgagctgacaaagaaccaagtgtctctgact tgtctggtgaagggcttctaccctagcgacatcgccgtggaatgg gagtccaatggacagccagagaataactataagactacacctcca gtcctcgactccgacggaagcttcttttctgtactccaagctcact gtggataagtctaggtggcaacaaggcaacgtcttcagctgtagc gtcatgcatgaggctctccacaaccactacactcagaagtctctg tctctgtccccggcggaggaggctccggaggaggatccgctcct acttcctcctccactaagaagacacagctccaactggagcatctg ctccaggatctgcagatgattctgaacggcattaacaactataaa aatccaaagctgactaggatgctgacttttaagttctacatgcca aagaaagccacagagctgaaacacctccagtgcctcgaggaagaa ctgaagccactcgaggaggtgctgaacctcgcccagtccaagaat ttccatctgaggccaagggatctgatcagcaacatcaacgtcatt gtgctggagctgaaaggcagcgagactactttcatgtgcgagtac gccgatgagacagctacaatcgtggagttcctcaataggtggatc acattcatcgaaagcatcattagcacactgaca
```

P-0582 (SEQ ID NO: 217)

```
atggagtttgggctgagctggcttttcttgtggctattttaaaa ggtgtccagtgtgataagactcacacttgccctccatgcccagct ccagaggccgctggcgctccttccgtctttctgttcccacctaag
```

-continued ccaaaggacactctcatgatctctaggacaccagaggtcacatgc
gtcgtggtggatgtgagccacgaggacccagaggtgaaattcaac
tggtacgtggatggagtcgaggtccacaacgccaagacaaagcca
agagaggaacagtacaattccacatacagagtggtgtccgtgctg
actgtgctgcatcaagactggctgaacggcaaggagtacaaatgc
aaggtcagcaacaaggccctcccagccccaatcgagaagacaatt
tccaaggccaagggccagcctagggagccacaagtgtatactctg
cctccttctagggacgagctgacaaagaaccaagtgtctctgact
tgtctggtgaagggcttctaccctagcgacatcgccgtggaatgg
gagtccaatggacagccagagaataactataagactacacctcca
gtcctcgactccgacggaagcttctttctgtactccaagctcact
gtggataagtctaggtggcaacaaggcaacgtcttcagctgtagc
gtcatgcatgaggctctccacaaccactacactcagaagtctctg
tctctgtccccggcggaggaggctccggaggaggatccgctcct
acttcctcctccactaagaagacacagctccaactggagcatctg
ctcctgactctgcagatgattctgaacggcattaacaactataaa
aatccaaagctgactaggatgctgacttttaagttctacatgcca
aagaaagccacagagctgaaacacctccagtgcctcgaggaagaa
ctgaagccactcgaggaggtgctgaacctcgcccagtccaagaat
ttccatctgagggccaagggatctgatcagcaacatcaacgtcatt
gtgctggagctgaaaggcagcgagactactttcatgtgcgagtac
gccgatgagacagctacaatcgtggagttcctcaataggtggatc
acattcatcaagagcatcattagcacactgaca

P-0583

<u>atggagtttgggctgagctggcttttttcttgtggctattttaaaa</u>
<u>ggtgtccagtgtgat</u>aagactcacacttgccctccatgcccagct
ccagaggccgctggcgctccttccgtctttctgttcccacctaag
ccaaaggacactctcatgatctctaggacaccagaggtcacatgc
gtcgtggtggatgtgagccacgaggacccagaggtgaaattcaac
tggtacgtggatggagtcgaggtccacaacgccaagacaaagcca
agagaggaacagtacaattccacatacagagtggtgtccgtgctg
actgtgctgcatcaagactggctgaacggcaaggagtacaaatgc
aaggtcagcaacaaggccctcccagccccaatcgagaagacaatt
tccaaggccaagggccagcctagggagccacaagtgtatactctg
cctccttctagggacgagctgacaaagaaccaagtgtctctgact
tgtctggtgaagggcttctaccctagcgacatcgccgtggaatgg
gagtccaatggacagccagagaataactataagactacacctcca
gtcctcgactccgacggaagcttctttctgtactccaagctcact
gtggataagtctaggtggcaacaaggcaacgtcttcagctgtagc
gtcatgcatgaggctctccacaaccactacactcagaagtctctg (SEQ ID NO: 218)

```
                              -continued
tctctgtccccggcggaggaggctccggaggaggatccgctcct acttcctcctccactaagaagacacagctccaactggagcatctg ctcaacgatctgcagatgattctgaacggcattaacaactataaa aatccaaagctgactaggatgctgacttttaagttctacatgcca aagaaagccacagagctgaaacacctccagtgcctcgaggaagaa ctgaagccactcgaggaggtgctgaacctcgcccagtccaagaat ttccatctgaggccaagggatctgatcagcaacatcaacgtcatt gtgctggagctgaaaggcagcgagactactttcatgtgcgagtac gccgatgagacagctacaatcgtggagttcctcaataggtggatc acattcatcaagagcatcattagcacactgaca
```

P-0584                                                              (SEQ ID NO: 219)

```
atggagtttgggctgagctggcttttcttgtggctattttaaaa ggtgtccagtgtgataagactcacacttgccctccatgcccagct ccagaggccgctggcgctccttccgtctttctgttcccacctaag ccaaaggacactctcatgatctctaggacaccagaggtcacatgc gtcgtggtggatgtgagccacgaggacccagaggtgaaattcaac tggtacgtggatggagtcgaggtccacaacgccaagacaaagcca agagaggaacagtacaattccacatacagagtggtgtccgtgctg actgtgctgcatcaagactggctgaacggcaaggagtacaaatgc aaggtcagcaacaaggccctcccagcccaatcgagaagacaatt tccaaggccaagggccagcctagggagccacaagtgtatactctg cctccttctagggacgagctgacaaagaaccaagtgtctctgact tgtctggtgaagggcttctaccctagcgacatcgccgtggaatgg gagtccaatggacagccagagaataactataagactacacctcca gtcctcgactccgacggaagcttcttttctgtactccaagctcact gtggataagtctaggtggcaacaaggcaacgtcttcagctgtagc gtcatgcatgaggctctccacaaccactacactcagaagtctctg tctctgtccccggcggaggaggctccggaggaggatccgctcct acttcctcctccactaagaagacacagctccaactggagcatctg ctcagggatctgcagatgattctgaacggcattaacaactataaa aatccaaagctgactaggatgctgacttttaagttctacatgcca aagaaagccacagagctgaaacacctccagtgcctcgaggaagaa ctgaagccactcgaggaggtgctgaacctcgcccagtccaagaat ttccatctgaggccaagggatctgatcagcaacatcaacgtcatt gtgctggagctgaaaggcagcgagactactttcatgtgcgagtac gccgatgagacagctacaatcgtggagttcctcaataggtggatc acattcatcaagagcatcattagcacactgaca
```

P-0585                                                              (SEQ ID NO: 220)

<u>atggagtttgggctgagctggcttttcttgtggctattttaaaa</u>

<u>ggtgtccagtgt</u>gataagactcacacttgccctccatgcccagct ccagaggccgctggcggaccttccgtctttctgttcccacctaag -continued

```
ccaaaggacactctctacatcacaagggaaccagaggtcacatgc
gtcgtggtggatgtgagccacgaggacccagaggtgaaattcaac
tggtacgtggatggagtcgaggtccacaacgccaagacaaagcca
agagaggaacagtacaattccacatacagagtggtgtccgtgctg
actgtgctgcatcaagactggctgaacggcaaggagtacaaatgc
aaggtcagcaacaaggccctcccagccccaatcgagaagacaatt
tccaaggccaagggccagcctagggagccacaagtgtatactctg
cctccttctagggacgagctgacaaagaaccaagtgtctctgact
tgtctggtgaagggcttctaccctagcgacatcgccgtggaatgg
gagtccaatggacagccagagaataactataagactacacctcca
gtcctcgactccgacggaagcttctttctgtactccaagctcact
gtggataagtctaggtggcaacaaggcaacgtcttcagctgtagc
gtcatgcatgaggctctccacaaccactacactcagaagtctctg
tctctgtccccggcggaggaggctccggaggaggatccgctcct
acttcctcctccactaagaagacacagctccaactggagcatctg
ctccatgatctgcagatgattctgaacggcattaacaactataaa
aatccaaagctgactaggatgctgacttttaagttctacatgcca
aagaaagccacagagctgaaacacctccagtgcctcgaggaagaa
ctgaagccactcgaggaggtgctgaacctcgcccagtccaagaat
ttccatctgagggccaagggatctgatcagcaacatcaacgtcatt
gtgctggagctgaaaggcagcgagactactttcatgtgcgagtac
gccgatgagacagctacaatcgtggagttcctcaataggtggatc
acattcatcgaaagcatcattagcacactgaca
```

P-0586   (SEQ ID NO: 221)

```
atggagtttgggctgagctggcttttttcttgtggctattttaaaa
ggtgtccagtgtgataagactcacacttgccctccatgcccagct
ccagaggccgctggcggaccttccgtctttctgttcccacctaag
ccaaaggacactctctacatcacaagggaaccagaggtcacatgc
gtcgtggtggatgtgagccacgaggacccagaggtgaaattcaac
tggtacgtggatggagtcgaggtccacaacgccaagacaaagcca
agagaggaacagtacaattccacatacagagtggtgtccgtgctg
actgtgctgcatcaagactggctgaacggcaaggagtacaaatgc
aaggtcagcaacaaggccctcccagccccaatcgagaagacaatt
tccaaggccaagggccagcctagggagccacaagtgtatactctg
cctccttctagggacgagctgacaaagaaccaagtgtctctgact
tgtctggtgaagggcttctaccctagcgacatcgccgtggaatgg
gagtccaatggacagccagagaataactataagactacacctcca
gtcctcgactccgacggaagcttctttctgtactccaagctcact
gtggataagtctaggtggcaacaaggcaacgtcttcagctgtagc
gtcatgcatgaggctctccacaaccactacactcagaagtctctg
```

-continued tctctgtccccggcggaggaggctccggaggaggatccgctcct acttcctcctccactaagaagacacagctccaactggagcatctg ctccatgatctgcagatgattctgaacggcattaacaactataaa aatccaaagctgactaggatgctgacttttaagttctacatgcca aagaaagccacagagctgaaacacctccagtgcctcgaggaagaa ctgaagccactcgaggaggtgctgaacctcgcccagtccaagaat ttccatctgaggccaagggatctgatcagcaacatcaacgtcatt gtgctggagctgaaaggcagcgagactactttcatgtgcgagtac gccgatgagacagctacaatcgtggagttcctcaataggtggatc acattcatcaagagcatcattagcacactgaca

P-0616

<u>atggagtttgggctgagctggcttttcttgtggctattttaaaa</u>

<u>ggtgtccagtgt</u>gataagactcacacttgccctccatgcccagct ccagaggccgctggcgctccttccgtctttctgttcccacctaag ccaaaggacactctcatgatctctaggacaccagaggtcacatgc gtcgtggtggatgtgagccacgaggacccagaggtgaaattcaac tggtacgtggatggagtcgaggtccacaacgccaagacaaagcca agagaggaacagtacaattccacatacagagtggtgtccgtgctg actgtgctgcatcaagactggctgaacggcaaggagtacaaatgc aaggtcagcaacaaggccctcccagccccaatcgagaagacaatt tccaaggccaagggccagcctagggagccacaagtgtatactctg cctccttctagggacgagctgacaaagaaccaagtgtctctgact tgtctggtgaagggcttctaccctagcgacatcgccgtggaatgg gagtccaatggacagccagagaataactataagactacacctcca gtcctcgactccgacggaagcttctttctgtactccaagctcact gtggataagtctaggtggcaacaaggcaacgtcttcagctgtagc gtcatgcatgaggctctccacgctcactacactcagaagtctctg tctctgtccccggcggaggaggctccggaggaggatccgctcct acttcctcctccactaagaagacacagctccaactggagcatctg ctccatgatctgcagatgattctgaacggcattaacaactataaa aatccaaagctgactaggatgctgacttttaagttctacatgcca aagaaagccacagagctgaaacacctccagtgcctcgaggaagaa ctgaagccactcgaggaggtgctgaacctcgcccagtccaagaat ttccatctgaggccaagggatctgatcagcaacatcaacgtcatt gtgctggagctgaaaggcagcgagactactttcatgtgcgagtac gccgatgagacagctacaatcgtggagttcctcaataggtggatc acattcatcgaaagcatcattagcacactgaca (SEQ ID NO: 222)

What is claimed is:

1. An isolated fusion protein comprising an interleukin-2 (IL-2) variant polypeptide comprising the amino acid sequence set forth in SEQ ID NO: 193, fused to an Fc domain comprising the amino acid sequence set forth in SEQ ID NO: 45; wherein the IL-2 variant polypeptide is fused to the Fc domain by a peptide linker having the amino acid sequence set forth in SEQ ID NO: 55.

2. The isolated fusion protein according to claim 1, wherein the isolated fusion protein comprises the amino acid sequence set forth in SEQ ID NO: 198.

3. The isolated fusion protein according to claim 2, wherein the isolated fusion protein comprises two polypeptide chains, wherein each of the polypeptide chains consists of the amino acid sequence set forth in SEQ ID NO: 198.

4. The isolated fusion protein according to claim 3, wherein the two polypeptide chains are connected by at least one interchain disulfide bond.

5. The isolated fusion protein according to claim 4, wherein the two polypeptide chains are connected by two interchain disulfide bonds.

6. A pharmaceutical composition comprising an isolated fusion protein comprising the amino acid sequence set forth in SEQ ID NO: 198 in admixture with a pharmaceutically acceptable carrier.

* * * * *